(12) United States Patent
Catlett et al.

(10) Patent No.: US 12,410,451 B2
(45) Date of Patent: Sep. 9, 2025

(54) YEAST EXPRESSING A HETEROLOGOUS TREHALASE FOR ETHANOL PRODUCTION

(71) Applicant: Novozymes A/S, Bagsvaerd (DK)

(72) Inventors: Michael Glenn Catlett, West Sacramento, CA (US); Monica Tassone, West Sacramento, CA (US); Paul Vincent Harris, Carnation, WA (US); Robert Lyle Osborne, Raleigh, NC (US); Shiro Fukuyama, Chiba (JP); Tomoko Matsui, Chiba (JP); Ryoko Kataoka, Longmont, CO (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 18/516,805

(22) Filed: Nov. 21, 2023

(65) Prior Publication Data

US 2024/0124902 A1   Apr. 18, 2024

Related U.S. Application Data

(62) Division of application No. 17/260,516, filed as application No. PCT/US2019/042870 on Jul. 22, 2019, now Pat. No. 11,866,751.

(60) Provisional application No. 62/703,103, filed on Jul. 25, 2018.

(51) Int. Cl.
   *C12P 7/06* (2006.01)

(52) U.S. Cl.
   CPC .............. *C12P 7/06* (2013.01); *C12P 2203/00* (2013.01); *C12Y 302/01001* (2013.01); *C12Y 302/01093* (2013.01)

(58) Field of Classification Search
   None
   See application file for complete search history.

(56) References Cited

U.S. PATENT DOCUMENTS

| | | | |
|---|---|---|---|
| 8,076,109 B2 * | 12/2011 | Allain | C12P 7/06 435/71.1 |
| 9,206,444 B2 * | 12/2015 | Brevnova | C12Y 302/01021 |
| 11,584,783 B2 * | 2/2023 | Morant | C12N 9/2402 |
| 11,807,889 B2 * | 11/2023 | Tassone | C12Y 301/00 |
| 11,866,751 B2 * | 1/2024 | Catlett | C12N 9/242 |
| 2018/0155744 A1 | 6/2018 | Cripwell et al. | |
| 2020/0140495 A1 * | 5/2020 | Morant | C12P 19/14 |

FOREIGN PATENT DOCUMENTS

| | | |
|---|---|---|
| WO | 2011049945 A2 | 4/2011 |
| WO | 2011128712 A1 | 10/2011 |
| WO | 2011153516 A2 | 12/2011 |
| WO | 2015065871 A1 | 5/2015 |
| WO | 2016205127 A1 | 12/2016 |
| WO | 2017037614 A1 | 3/2017 |
| WO | 2017077504 A1 | 5/2017 |
| WO | 2017087330 A1 | 5/2017 |
| WO | 2018098381 A1 | 5/2018 |
| WO | 2018222990 A1 | 12/2018 |

OTHER PUBLICATIONS

Anonymous, 2011, Alignment SEQ ID No. 41 of U.S. Pat. No. 8,076,109 to SEQ ID No. 126126.
Chica et al., 2005, Curr Op Biotechnol, 16(4), 378-384.
Haan et al., 2013, J Chem Tech Biotechnol, 88, 983-991.
Matsuura et al., 1984, J Biochem, 95(3), 697-702.
Moore et al., 2017, TREMBL Accession No. A0A1F7ZUG0.
Singh et al., 2017, Current Protein and Peptide Science, 18, 1-11.

* cited by examiner

*Primary Examiner* — Christian L Fronda
(74) *Attorney, Agent, or Firm* — Eric J. Fechter

(57) ABSTRACT

Described herein are recombinant fermenting organisms having a heterologous polynucleotide encoding an alpha-amylase and/or a heterologous polynucleotide encoding a trehalase. Also described are processes for producing a fermentation product, such as ethanol, from starch or cellulosic-containing material with the recombinant fermenting organisms.

13 Claims, 3 Drawing Sheets

Specification includes a Sequence Listing.

YEAST EXPRESSING A HETEROLOGOUS TREHALASE FOR ETHANOL PRODUCTION

CROSS-REFERENCE TO RELATED APPLICATIONS

This application is a divisional of U.S. patent application Ser. No. 17/260,516, which is a 35 U.S.C. 371 national application of PCT/US2019/042870, filed Jul. 22, 2019, which claims priority or the benefit from U.S. Provisional Application Ser. No. 62/703,103, filed Jul. 25, 2018, The contents of these applications are fully incorporated herein by reference.

REFERENCE TO A SEQUENCE LISTING

This application contains a Sequence Listing in computer readable form created on Nov. 21, 2023, named SQ_ST26.xml and 335 KB in size, which is incorporated herein by reference.

BACKGROUND

Production of ethanol from starch and cellulosic containing materials is well-known in the art.

The most commonly industrially used commercial process for starch-containing material, often referred to as a "conventional process", includes liquefying gelatinized starch at high temperature (about 85° C.) using typically a bacterial alpha-amylase, followed by simultaneous saccharification and fermentation (SSF) carried out anaerobically in the presence of typically a glucoamylase and a *Saccharomyces cerevisae* yeast.

Yeasts which are used for production of ethanol for use as fuel, such as in the corn ethanol industry, require several characteristics to ensure cost effective production of the ethanol. These characteristics include ethanol tolerance, low by-product yield, rapid fermentation, and the ability to limit the amount of residual sugars remaining in the ferment. Such characteristics have a marked effect on the viability of the industrial process.

Yeast of the genus *Saccharomyces* exhibits many of the characteristics required for production of ethanol. In particular, strains of *Saccharomyces cerevisiae* are widely used for the production of ethanol in the fuel ethanol industry. Strains of *Saccharomyces cerevisiae* that are widely used in the fuel ethanol industry have the ability to produce high yields of ethanol under fermentation conditions found in, for example, the fermentation of corn mash. An example of such a strain is the yeast used in commercially available ethanol yeast product called ETHANOL RED®.

*Saccharomyces cerevisae* yeast have been genetically engineered to express alpha-amylase and/or glucoamylase to improve yield and decrease the amount of exogenously added enzymes necessary during SSF (e.g., WO2018/098381, WO2017/087330, WO2017/037614, WO2011/128712, WO2011/153516, US2018/0155744). Yeast have also been engineered to express trehalase in an attempt to increase fermentation yield by breaking down residual trehalose (e.g., WO2017/077504).

Despite significant improvement of ethanol production processes over the past decade there is still a desire and need for providing improved processes of ethanol fermentation from starch and cellulosic containing material in an economically and commercially relevant scale.

SUMMARY

Described herein are, inter alia, methods for producing a fermentation product, such as ethanol, from starch or cellulosic-containing material, and yeast suitable for use in such processes. The Applicant has surprisingly found that yeast expressing certain alpha-amylases and/or trehalases provide beneficial properties that may be useful for ethanol fermentation.

A first aspect relates to methods of producing a fermentation product from a starch-containing or cellulosic-containing material comprising: (a) saccharifying the starch-containing or cellulosic-containing material; and (b) fermenting the saccharified material of step (a) with a fermenting organism; wherein the fermenting organism comprises a heterologous polynucleotide encoding an alpha-amylase or a heterologous polynucleotide encoding a trehalase.

In some embodiments of the methods, fermentation and saccharification are performed simultaneously in a simultaneous saccharification and fermentation (SSF). In other embodiments, fermentation and saccharification are performed sequentially (SHF).

In some embodiments of the methods, the method comprises recovering the fermentation product from the from the fermentation (e.g., by distillation).

In some embodiments of the methods, the fermentation product is ethanol.

In some embodiments of the methods, fermentation is performed under reduced nitrogen conditions (e.g., less than 1000 ppm urea or ammonium hydroxide, such as less than 750 ppm, less than 500 ppm, less than 400 ppm, less than 300 ppm, less than 250 ppm, less than 200 ppm, less than 150 ppm, less than 100 ppm, less than 75 ppm, less than 50 ppm, less than 25 ppm, or less than 10 ppm).

In some embodiments of the methods, the alpha-amylase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 76-101, 121-174 and 231. In some embodiments of the methods, the heterologous polynucleotide encodes an alpha-amylase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 76-101, 121-174 and 231. In some embodiments of the methods, the heterologous polynucleotide encodes an alpha-amylase having a mature polypeptide sequence comprising or consisting of the amino acid sequence of any one of SEQ ID NOs: SEQ ID NOs: 76-101, 121-174 and 231.

In some embodiments of the methods, the trehalase has mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 175-226. In some embodiments of the methods, the heterologous polynucleotide encodes a trehalase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 175-226. In some embodiments of the methods, the heterologous polynucleotide encodes a trehalase having a mature polypeptide sequence comprising or consisting of the amino acid sequence of any one of SEQ ID NOs: SEQ ID NOs: 175-226.

In some embodiments of the methods, saccharification of step (a) occurs on a starch-containing material, and wherein the starch-containing material is either gelatinized or ungelatinized starch.

In some embodiments of the methods, the method comprises liquefying the starch-containing material by contacting the material with an alpha-amylase prior to saccharification.

In some embodiments of the methods, liquefying the starch-containing material and/or saccharifying the starch-containing material is conducted in presence of exogenously added protease.

In some embodiments of the methods, the fermenting organism comprises a heterologous polynucleotide encoding a glucoamylase, such as a glucoamylase having a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus* glycoamylase (e.g., a *Pycnoporus sanguineus* glucoamylase of SEQ ID NO: 229), a *Gloeophyllum* glucoamylase (e.g. a *Gloeophyllum sepiarium* of SEQ ID NO: 8), or a glucoamylase of any one of SEQ ID NOs: 102-113 (e.g., a *Saccharomycopsis fibuligera* glucoamylase of SEQ ID NO: 103 or 104, or a *Trichoderma reesei* glucoamylase of SEQ ID NO: 230).

In some embodiments of the methods, the fermenting organism comprises a heterologous polynucleotide encoding a protease, such as a protease having a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69).

In some embodiments of the methods, saccharification of step (a) occurs on a cellulosic-containing material, and wherein the cellulosic-containing material is pretreated (e.g. a dilute acid pretreatment).

In some embodiments of the methods, saccharification occurs on a cellulosic-containing material, and wherein the enzyme composition comprises one or more enzymes selected from a cellulase (e.g., endoglucanase, a cellobiohydrolase, or a beta-glucosidase), an AA9 polypeptide, a hemicellulase (e.g., a xylanase, an acetylxylan esterase, a feruloyl esterase, an arabinofuranosidase, a xylosidase, or a glucuronidase), a CIP, an esterase, an expansin, a ligninolytic enzyme, an oxidoreductase, a pectinase, a protease, and a swollenin.

In some embodiments of the methods, the fermenting organism is a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell. In some embodiments, the fermenting organism is a *Saccharomyces cerevisiae* cell.

Another aspect relates to a recombinant yeast cell comprising a heterologous polynucleotide encoding an alpha-amylase or a heterologous polynucleotide encoding a trehalase.

In some embodiments, the recombinant yeast cell is a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell. In some embodiments, the recombinant yeast cell is a *Saccharomyces cerevisiae* cell.

In some embodiments of the yeast cell, the alpha-amylase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 76-101, 121-174 and 231. In some embodiments of the methods, the heterologous polynucleotide encodes an alpha-amylase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 76-101, 121-174 and 231. In some embodiments of the methods, the heterologous polynucleotide encodes an alpha-amylase having a mature polypeptide sequence comprising or consisting of the amino acid sequence of any one of SEQ ID NOs: SEQ ID NOs: 76-101, 121-174 and 231.

In some embodiments of the yeast cell, the trehalase has mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 175-226. In some embodiments of the methods, the heterologous polynucleotide encodes a trehalase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 175-226. In some embodiments of the methods, the heterologous polynucleotide encodes a trehalase having a mature polypeptide sequence comprising or consisting of the amino acid sequence of any one of SEQ ID NOs: SEQ ID NOs: 175-226.

In some embodiments of the yeast cell, the fermenting organism comprises a heterologous polynucleotide encoding a glucoamylase, such as a glucoamylase having a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus* glycoamylase (e.g., a *Pycnoporus sanguineus* glucoamylase of SEQ ID NO: 229), a *Gloeophyllum* glucoamylase (e.g. a *Gloeophyllum sepiarium* of SEQ ID NO: 8), or a glucoamylase of any one of SEQ ID NOs: 102-113 (e.g., a *Saccharomycopsis fibuligera* glucoamylase of SEQ ID NO: 103 or 104, or a *Trichoderma reesei* glucoamylase of SEQ ID NO: 230).

In some embodiments of the yeast cell, the fermenting organism comprises a heterologous polynucleotide encoding a protease, such as a protease having a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69).

DEFINITIONS

Figure 1:
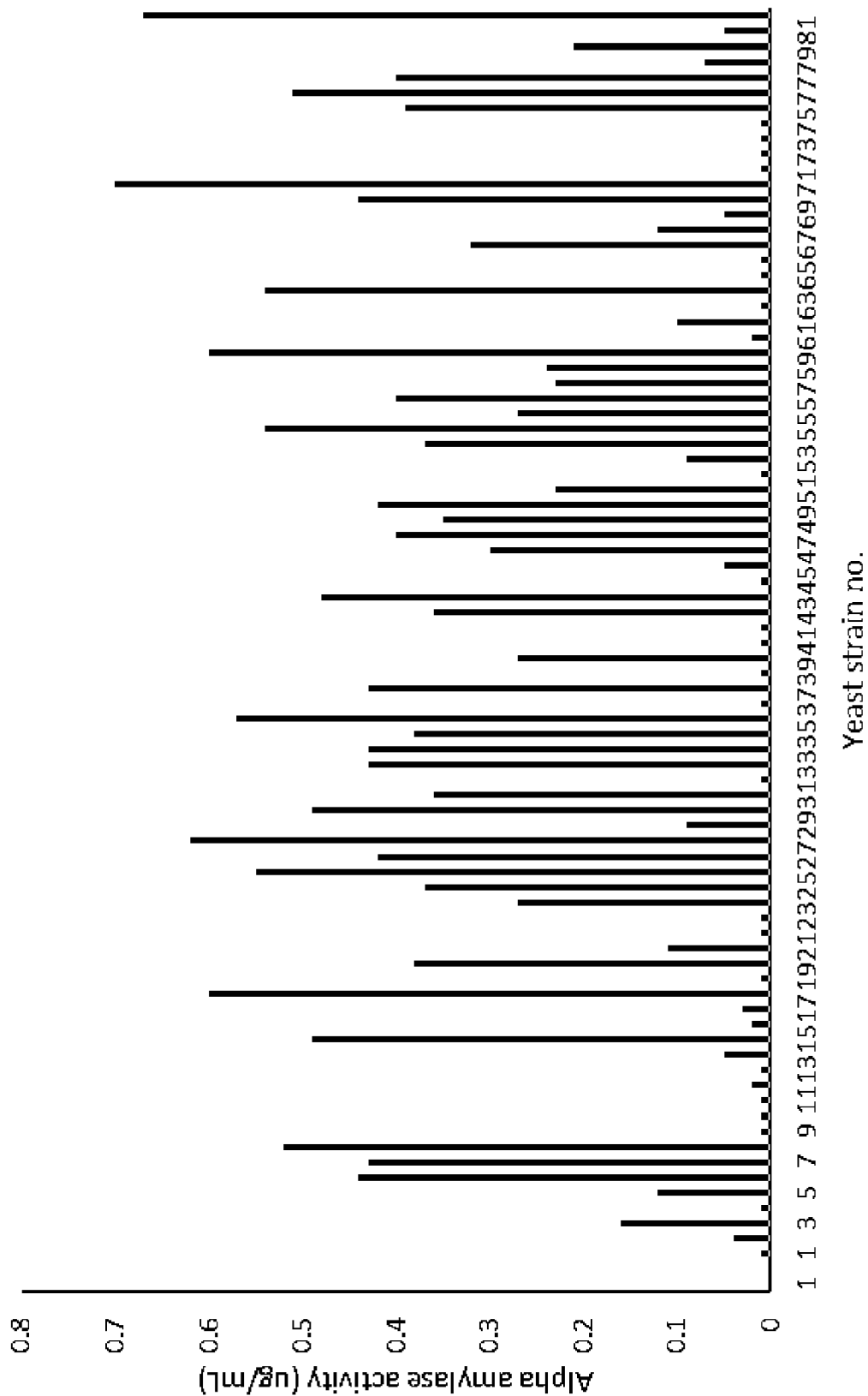
FIG. 1 shows alpha-amylase activity for strains constructed in Example 1.

Unless defined otherwise or clearly indicated by context, all technical and scientific terms used herein have the same meaning as commonly understood by one of ordinary skill in the art.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-amylase: The term "alpha amylase" means an 1,4-alpha-D-glucan glucanohydrolase, EC. 3.2.1.1, which catalyze hydrolysis of starch and other linear and branched 1,4-glucosidic oligo- and polysaccharides. For purposes of the present invention, alpha amylase activity can be determined using an alpha amylase assay described in the examples section below.

Auxiliary Activity 9: The term "Auxiliary Activity 9" or "AA9" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic-containing material by an enzyme having cellulolytic activity. Cellulolytic enhancing activity can be determined by measuring the increase in reducing sugars or the increase of the total of cellobiose and glucose from the hydrolysis of a cellulosic-containing material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40 C-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one embodiment, the beta-glucosidase is an *Aspergillus oryzae* beta-glucosidase (e.g., recombinantly produced in *Aspergillus oryzae* according to WO02/095014). In another embodiment, the beta-glucosidase is an *Aspergillus fumigatus* beta-glucosidase (e.g., recombinantly produced in *Aspergillus oryzae* as described in WO02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASO.

AA9 polypeptide enhancing activity can also be determined according to WO2013/028928 for high temperature compositions.

AA9 polypeptides enhance the hydrolysis of a cellulosic-containing material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside in 100 mM sodium citrate containing 0.01% TWEEN® 20.

Catalase: The term "catalase" means a hydrogen-peroxide:hydrogen-peroxide oxidoreductase (EC 1.11.1.6) that catalyzes the conversion of 2 $H_2O_2$ to $O_2+2$ $H_2O$. For purposes of the present invention, catalase activity is determined according to U.S. Pat. No. 5,646,025. One unit of catalase activity equals the amount of enzyme that catalyzes the oxidation of 1 µmole of hydrogen peroxide under the assay conditions.

Catalytic domain: The term "catalytic domain" means the region of an enzyme containing the catalytic machinery of the enzyme.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic-containing material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic-containing material by cellulolytic enzyme(s) under the following conditions: 1-50 mg of cellulolytic enzyme protein/g of cellulose in pretreated corn stover (PCS) (or other pretreated cellulosic-containing material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, CA, USA).

Coding sequence: The term "coding sequence" or "coding region" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Disruption: The term "disruption" means that a coding region and/or control sequence of a referenced gene is partially or entirely modified (such as by deletion, insertion, and/or substitution of one or more nucleotides) resulting in the absence (inactivation) or decrease in expression, and/or the absence or decrease of enzyme activity of the encoded polypeptide. The effects of disruption can be measured using techniques known in the art such as detecting the absence or decrease of enzyme activity using from cell-free extract measurements referenced herein; or by the absence or decrease of corresponding mRNA (e.g., at least 25% decrease, at least 50% decrease, at least 60% decrease, at least 70% decrease, at least 80% decrease, or at least 90% decrease); the absence or decrease in the amount of corresponding polypeptide having enzyme activity (e.g., at least 25% decrease, at least 50% decrease, at least 60% decrease, at least 70% decrease, at least 80% decrease, or at least 90% decrease); or the absence or decrease of the specific activity of the corresponding polypeptide having enzyme activity (e.g., at least 25% decrease, at least 50% decrease, at least 60% decrease, at least 70% decrease, at least 80% decrease, or at least 90% decrease). Disruptions of a particular gene of interest can be generated by methods known in the art, e.g., by directed homologous recombination (see *Methods in Yeast Genetics* (1997 edition), Adams, Gottschling, Kaiser, and Sterns, Cold Spring Harbor Press (1998)).

Endogenous gene: The term "endogenous gene" means a gene that is native to the referenced host cell. "Endogenous gene expression" means expression of an endogenous gene.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of the polypeptide including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Expression vector: The term "expression vector" means a linear or circular DNA molecule that comprises a polynucleotide encoding a polypeptide and is operably linked to control sequences that provide for its expression.

Fermentable medium: The term "fermentable medium" or "fermentation medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as ethanol. In some instances, the fermentation medium is derived from a natural source, such as sugar cane, starch, or cellulose, and may be the result of pretreating the source by enzymatic hydrolysis (saccharification). The term fermentation medium is understood herein to refer to a medium before the fermenting organism is added, such as, a medium resulting from a saccharification process, as well as a medium used in a simultaneous saccharification and fermentation process (SSF).

Glucoamylase: The term "glucoamylase" (1,4-alpha-D-glucan glucohydrolase, EC 3.2.1.3) is defined as an enzyme that catalyzes the release of D-glucose from the non-reducing ends of starch or related oligo- and polysaccharide molecules. For purposes of the present invention, glucoamylase activity may be determined according to the procedure described in the Examples herein.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0. Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide in a host cell having one or more extra copies of the polynucleotide to quantitatively alter expression. A "heterologous gene" is a gene comprising a heterologous polynucleotide.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, and the like with a nucleic acid construct or expression vector comprising a polynucleotide described herein (e.g., a polynucleotide encoding an alpha-amylase and/or trehalase). The term "host cell" encompasses any progeny of a parent cell that is not identical to the parent cell due to mutations that occur during replication. The term "recombinant cell" is defined herein as a non-naturally occurring host cell comprising one or more (e.g., two, several) heterologous polynucleotides.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" is defined herein as a polypeptide having biological activity that is in its final form following translation and any post-translational modifications, such as N-terminal processing, C-terminal truncation, glycosylation, phosphorylation, etc. The mature polypeptide sequence lacks a signal sequence, which may be determined using techniques known in the art (See, e.g., Zhang and Henzel, 2004, *Protein Science* 13: 2819-2824).

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Nucleic acid construct: The term "nucleic acid construct" means a polynucleotide comprises one or more (e.g., two, several) control sequences. The polynucleotide may be single-stranded or double-stranded, and may be isolated from a naturally occurring gene, modified to contain segments of nucleic acids in a manner that would not otherwise exist in nature, or synthetic.

Operably linked: The term "operably linked" means a configuration in which a control sequence is placed at an appropriate position relative to the coding sequence of a polynucleotide such that the control sequence directs expression of the coding sequence.

Pretreated corn stover: The term "Pretreated Corn Stover" or "PCS" means a cellulosic-containing material derived from corn stover by treatment with heat and dilute sulfuric acid, alkaline pretreatment, neutral pretreatment, or any pretreatment known in the art.

Protease: The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in *Eur. J. Biochem.* 223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J. Biochem.* 264: 610-650 (1999); respectively. The term "subtilases" refer to a sub-group of serine protease according to Siezen et al., 1991, *Protein Engng.* 4: 719-737 and Siezen et al., 1997, *Protein Science* 6: 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Protease activity may be determined using methods described in the art (e.g., US 2015/0125925) or using commercially available assay kits (e.g., Sigma-Aldrich).

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to a PHADEBAS assay or the sweet potato starch assay described in WO2016/087237.

Sequence Identity: The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, J. Mol. Biol. 1970, 48, 443-453) as implemented in the Needle program of the EMBOSS package (EMBOSS: The European Molecular Biology Open Software Suite, Rice et al., Trends Genet 2000, 16, 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of the Referenced Sequence−Total Number of Gaps in Alignment)

For purposes described herein, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Referenced Sequence−Total Number of Gaps in Alignment)

Signal peptide: The term "signal peptide" is defined herein as a peptide linked (fused) in frame to the amino terminus of a polypeptide having biological activity and directs the polypeptide into the cell's secretory pathway. Signal sequences may be determined using techniques known in the art (See, e.g., Zhang and Henzel, 2004, Protein Science 13: 2819-2824). The polypeptides described herein may comprise any suitable signal peptide known in the art, or any signal peptide described herein (e.g., the S. cerevisiae MFα1 signal peptide of SEQ ID NO: 7, the S. cerevisiae EXG1 signal peptide of SEQ ID NO: 227, or the S. cerevisiae AG2 signal peptide of SEQ ID NO: 234, or a signal peptide having at least 80%, 85%, 90%, 95%, 96%, 97%, 98% or 99% sequence identity thereof).

Trehalase: The term "trehalase" means an enzyme which degrades trehalose into its unit monosaccharides (i.e., glucose). Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on "http://www.expasy.org/enzyme/". Trehalases are enzymes that catalyze the following reactions:

EC 3.2.1.28: Alpha,alpha-trehalose+$H_2O$⇌2 D-glucose;
EC 3.2.1.93: Alpha,alpha-trehalose 6-phosphate+$H_2O$⇌D-glucose+D-glucose 6-phosphate.

For purposes of the present invention, trehalase activity may be determined according to the trehalase activity assay described herein in the experimental section.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylose Isomerase: The term "Xylose Isomerase" or "XI" means an enzyme which can catalyze D-xylose into D-xylulose in vivo, and convert D-glucose into D-fructose in vitro. Xylose isomerase is also known as "glucose isomerase" and is classified as E.C. 5.3.1.5. As the structure of the enzyme is very stable, the xylose isomerase is a good model for studying the relationships between protein structure and functions (Karimaki et al., Protein Eng Des Sel, 12004, 17 (12):861-869). Xylose Isomerase activity may be determined using techniques known in the art (e.g., a coupled enzyme assay using D-sorbitol dehydrogenase, as described by Verhoeven et. al., 2017, Sci Rep 7, 46155).

Reference to "about" a value or parameter herein includes embodiments that are directed to that value or parameter per se. For example, description referring to "about X" includes the embodiment "X". When used in combination with measured values, "about" includes a range that encompasses at least the uncertainty associated with the method of measuring the particular value, and can include a range of plus or minus two standard deviations around the stated value.

Likewise, reference to a gene or polypeptide that is "derived from" another gene or polypeptide X, includes the gene or polypeptide X.

As used herein and in the appended claims, the singular forms "a," "or," and "the" include plural referents unless the context clearly dictates otherwise.

It is understood that the embodiments described herein include "consisting" and/or "consisting essentially of" embodiments. As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

DETAILED DESCRIPTION

Described herein, inter alia, are methods for producing a fermentation product, such as ethanol, from starch or cellulosic containing material.

During industrial scale fermentation, yeast encounter various physiological challenges including variable concentrations of sugars, high concentrations of yeast metabolites such as ethanol, glycerol, organic acids, osmotic stress, as well as potential competition from contaminating microbes such as wild yeasts and bacteria. As a consequence, many yeasts are not suitable for use in industrial fermentation. The most widely used commercially available industrial strain of *Saccharomyces* (i.e. for industrial scale fermentation) is the *Saccharomyces cerevisiae* strain used, for example, in the product ETHANOL RED®. This strain is well suited to industrial ethanol production; however, it remains unclear how modifications to the yeast will impact performance. In particular, the functional expression of heterologous enzymes by an industrially-relevant *Saccharomyces cerevisiae* yeast is uncertain (See, for example U.S. Pat. No. 9,206,444 where the applicant was unable to functionally express numerous enzymes/enzyme classes).

The Applicant has surprisingly found that yeast expressing certain alpha-amylases and/or trehalases provide beneficial properties that may be useful for ethanol fermentation.

In one aspect is a method of producing a fermentation product from a starch-containing or cellulosic-containing material comprising:
  (a) saccharifying the starch-containing or cellulosic-containing material; and
  (b) fermenting the saccharified material of step (a) with a fermenting organism;
  wherein the fermenting organism comprises a heterologous polynucleotide encoding an alpha-amylase or a heterologous polynucleotide encoding a trehalase.

Steps of saccharifying and fermenting are carried out either sequentially or simultaneously (SSF). In one embodiment, steps of saccharifying and fermenting are carried out simultaneously (SSF). In another embodiment, steps of saccharifying and fermenting are carried out sequentially.

Fermenting Organism

The fermenting organism described herein may be derived from any host cell known to the skilled artisan capable of producing a fermentation product, such as ethanol. As used herein, a "derivative" of strain is derived from a referenced strain, such as through mutagenesis, recombinant DNA technology, mating, cell fusion, or cytoduction between yeast strains. Those skilled in the art will understand that the genetic alterations, including metabolic modifications exemplified herein, may be described with reference to a suitable host organism and their corresponding metabolic reactions or a suitable source organism for desired genetic material such as genes for a desired metabolic pathway. However, given the complete genome sequencing of a wide variety of organisms and the high level of skill in the area of genomics, those skilled in the art can apply the teachings and guidance provided herein to other organisms. For example, the metabolic alterations exemplified herein can readily be applied to other species by incorporating the same or analogous encoding nucleic acid from species other than the referenced species.

The host cells for preparing the recombinant cells described herein can be from any suitable host, such as a yeast strain, including, but not limited to, a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell. In particular, *Saccharomyces* host cells are contemplated, such as *Saccharomyces cerevisiae, bayanus* or *carlsbergensis* cells. Preferably, the yeast cell is a *Saccharomyces cerevisiae* cell.

Suitable cells can, for example, be derived from commercially available strains and polyploid or aneuploid industrial strains, including but not limited to those from Superstart™, THERMOSACC®, C5 FUEL™, XyloFerm®, etc. (Lallemand); RED STAR and ETHANOL RED® (Fermentis/Lesaffre); FALI (AB Mauri); Baker's Best Yeast, Baker's Compressed Yeast, etc. (Fleishmann's Yeast); BIOFERM AFT, XP, CF, and XR (North American Bioproducts Corp.); Turbo Yeast (Gert Strand AB); and FERMIOL® (DSM Specialties). Other useful yeast strains are available from biological depositories such as the American Type Culture Collection (ATCC) or the Deutsche Sammlung von Mikroorganismen and Zellkulturen GmbH (DSMZ), such as, e.g., BY4741 (e.g., ATCC 201388); Y108-1 (ATCC PTA. 10567) and NRRL YB-1952 (ARS Culture Collection). Still other *S. cerevisiae* strains suitable as host cells DBY746, [Alpha][Eta]22, 5150-2B, GPY55-15Ba, CEN.PK, USM21, TMB3500, TMB3400, VTT-A-63015, VTT-A-85068, VTT-c-79093 and their derivatives as well as *Saccharomyces* sp. 1400, 424A (LNH-ST), 259A (LNH-ST) and derivatives thereof. In one embodiment, the recombinant cell is a derivative of a strain *Saccharomyces cerevisiae* CIBTS1260 (deposited under Accession No. NRRL Y-50973 at the Agricultural Research Service Culture Collection (NRRL), Illinois 61604 U.S.A.).

The fermenting organism may be *Saccharomyces* strain, e.g., *Saccharomyces cerevisiae* strain produced using the method described and concerned in U.S. Pat. No. 8,257,959-BB.

The strain may also be a derivative of *Saccharomyces cerevisiae* strain NMI V14/004037 (See, WO2015/143324 and WO2015/143317 each incorporated herein by reference), strain nos. V15/004035, V15/004036, and V15/004037 (See, WO2016/153924 incorporated herein by reference), strain nos. V15/001459, V15/001460, V15/001461 (See, WO2016/138437 incorporated herein by reference), strain no. NRRL Y67342 (See, WO2017/063159 incorporated herein by reference), or any strain described in WO2017/087330 (incorporated herein by reference).

The fermenting organisms according to the invention have been generated in order to improve fermentation yield and to improve process economy by cutting enzyme costs since part or all of the necessary enzymes needed to improve method performance are be produced by the fermenting organism.

The fermenting organisms described herein may utilize expression vectors comprising the coding sequence of one or more (e.g., two, several) heterologous genes linked to one or more control sequences that direct expression in a suitable cell under conditions compatible with the control sequence(s). Such expression vectors may be used in any of the cells and methods described herein. The polynucleotides described herein may be manipulated in a variety of ways to provide for expression of a desired polypeptide. Manipulation of the polynucleotide prior to its insertion into a vector may be desirable or necessary depending on the expression vector. The techniques for modifying polynucleotides utilizing recombinant DNA methods are well known in the art.

A construct or vector (or multiple constructs or vectors) comprising the one or more (e.g., two, several) heterologous genes may be introduced into a cell so that the construct or vector is maintained as a chromosomal integrant or as a self-replicating extra-chromosomal vector as described earlier.

The various nucleotide and control sequences may be joined together to produce a recombinant expression vector that may include one or more (e.g., two, several) convenient restriction sites to allow for insertion or substitution of the polynucleotide at such sites. Alternatively, the polynucleotide(s) may be expressed by inserting the polynucleotide(s) or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the cell, or a transposon, may be used.

The expression vector may contain any suitable promoter sequence that is recognized by a cell for expression of a gene described herein. The promoter sequence contains transcriptional control sequences that mediate the expression of the polypeptide. The promoter may be any polynucleotide that shows transcriptional activity in the cell of choice including mutant, truncated, and hybrid promoters, and may be obtained from genes encoding extracellular or intracellular polypeptides either homologous or heterologous to the cell.

Each heterologous polynucleotide described herein may be operably linked to a promoter that is foreign to the polynucleotide. For example, in one embodiment, the heterologous polynucleotide encoding the hexose transporter is operably linked to a promoter foreign to the polynucleotide. The promoters may be identical to or share a high degree of sequence identity (e.g., at least about 80%, at least about 85%, at least about 90%, at least about 95%, at least about 96%, at least about 97%, at least about 98%, or at least about 99%) with a selected native promoter.

Examples of suitable promoters for directing the transcription of the nucleic acid constructs in a yeast cells, include, but are not limited to, the promoters obtained from the genes for enolase, (e.g., *S. cerevisiae* enolase or *I. orientalis* enolase (ENO1)), galactokinase (e.g., *S. cerevisiae* galactokinase or *I. orientalis* galactokinase (GAL1)), alcohol dehydrogenase/glyceraldehyde-3-phosphate dehydrogenase (e.g., *S. cerevisiae* alcohol dehydrogenase/glyceraldehyde-3-phosphate dehydrogenase or *I. orientalis* alcohol dehydrogenase/glyceraldehyde-3-phosphate dehydrogenase (ADH1, ADH2/GAP)), triose phosphate isomerase (e.g., *S. cerevisiae* triose phosphate isomerase or *I. orientalis* triose phosphate isomerase (TPI)), metallothionein (e.g., *S. cerevisiae* metallothionein or *I. orientalis* metallothionein (CUP1)), 3-phosphoglycerate kinase (e.g., *S. cerevisiae* 3-phosphoglycerate kinase or *I. orientalis* 3-phosphoglycerate kinase (PGK)), PDC1, xylose reductase (XR), xylitol dehydrogenase (XDH), L-(+)-lactate-cytochrome c oxidoreductase (CYB2), translation elongation factor-1 (TEF1), translation elongation factor-2 (TEF2), glyceraldehyde-3-phosphate dehydrogenase (GAPDH), and orotidine 5'-phosphate decarboxylase (URA3) genes. Other suitable promoters may be obtained from *S. cerevisiae* TDH3, HXT7, PGK1, RPL18B and CCW12 genes. Additional useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the yeast cell of choice may be used. The terminator may be identical to or share a high degree of sequence identity (e.g., at least about 80%, at least about 85%, at least about 90%, at least about 95%, at least about 96%, at least about 97%, at least about 98%, or at least about 99%) with the selected native terminator.

Suitable terminators for yeast host cells may be obtained from the genes for enolase (e.g., *S. cerevisiae* or *I. orientalis* enolase cytochrome C (e.g., *S. cerevisiae* or *I. orientalis* cytochrome (CYC1)), glyceraldehyde-3-phosphate dehydrogenase (e.g., *S. cerevisiae* or *I. orientalis* glyceraldehyde-3-phosphate dehydrogenase (gpd)), PDC1, XR, XDH, transaldolase (TAL), transketolase (TKL), ribose 5-phosphate ketol-isomerase (RKI), CYB2, and the galactose family of genes (especially the GAL10 terminator). Other suitable terminators may be obtained from *S. cerevisiae* ENO2 or TEF1 genes. Additional useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO94/25612) and a *Bacillus subtilis* SP82 gene (Hue et al., 1995, Journal of Bacteriology 177: 3465-3471).

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the yeast cell of choice may be used.

Suitable leaders for yeast host cells are obtained from the genes for enolase (e.g., *S. cerevisiae* or *I. orientalis* enolase (ENO-1)), 3-phosphoglycerate kinase (e.g., *S. cerevisiae* or *I. orientalis* 3-phosphoglycerate kinase), alpha-factor (e.g., *S. cerevisiae* or *I. orientalis* alpha-factor), and alcohol dehydrogenase/glyceraldehyde-3-phosphate dehydrogenase (e.g., *S. cerevisiae* or *I. orientalis* alcohol dehydrogenase/glyceraldehyde-3-phosphate dehydrogenase (ADH2/GAP)).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used. Useful polyadenylation sequences for yeast cells are described by Guo and Sherman, 1995, *Mol. Cellular Biol.* 15: 5983-5990.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound.

Regulatory systems in prokaryotic systems include the lac, tac, and trp operator systems. In yeast, the ADH2 system or GAL1 system may be used.

The vectors may contain one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3.

The vectors may contain one or more (e.g., two, several) elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination. Potential integration loci include those described in the art (e.g., See US2012/0135481).

For autonomous replication, the vector may further comprise an origin of replication enabling the vector to replicate autonomously in the yeast cell. The origin of replication may be any plasmid replicator mediating autonomous replication that functions in a cell. The term "origin of replication" or "plasmid replicator" means a polynucleotide that enables a plasmid or vector to replicate in vivo. Examples of origins of replication for use in a yeast host cell are the 2 micron origin of replication, ARS1, ARS4, the combination of ARS1 and CEN3, and the combination of ARS4 and CEN6.

More than one copy of a polynucleotide described herein may be inserted into a host cell to increase production of a polypeptide. An increase in the copy number of the polynucleotide can be obtained by integrating at least one additional copy of the sequence into the yeast cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors described herein are well known to one skilled in the art (see, e.g., Sambrook et al., 1989, *Molecular Cloning, A Laboratory Manual*, 2d edition, Cold Spring Harbor, New York).

Additional procedures and techniques known in the art for the preparation of recombinant cells for ethanol fermentation, are described in, e.g., WO2016/045569, the content of which is hereby incorporated by reference.

The fermenting organism may be in the form of a composition comprising a fermenting organism (e.g., a yeast strain described herein) and a naturally occurring and/or a nonnaturally occurring component.

The fermenting organism described herein may be in any viable form, including crumbled, dry, including active dry and instant, compressed, cream (liquid) form etc. In one embodiment, the fermenting organism (e.g., a *Saccharomyces cerevisiae* yeast strain) is dry yeast, such as active dry yeast or instant yeast. In one embodiment, the fermenting organism (e.g., a *Saccharomyces cerevisiae* yeast strain) is crumbled yeast. In one embodiment, the fermenting organism (e.g., a *Saccharomyces cerevisiae* yeast strain) is compressed yeast. In one embodiment, the fermenting organism (e.g., a *Saccharomyces cerevisiae* yeast strain) is cream yeast.

In one embodiment is a composition comprising a fermenting organism described herein (e.g., a *Saccharomyces cerevisiae* yeast strain), and one or more of the component selected from the group consisting of: surfactants, emulsifiers, gums, swelling agent, and antioxidants and other processing aids.

The compositions described herein may comprise a fermenting organism described herein (e.g., a *Saccharomyces cerevisiae* yeast strain) and any suitable surfactants. In one embodiment, the surfactant(s) is/are an anionic surfactant, cationic surfactant, and/or nonionic surfactant.

The compositions described herein may comprise a fermenting organism described herein (e.g., a *Saccharomyces cerevisiae* yeast strain) and any suitable emulsifier. In one embodiment, the emulsifier is a fatty-acid ester of sorbitan. In one embodiment, the emulsifier is selected from the group of sorbitan monostearate (SMS), citric acid esters of monodiglycerides, polyglycerolester, fatty acid esters of propylene glycol.

In one embodiment, the composition comprises a fermenting organism described herein (e.g., a *Saccharomyces cerevisiae* yeast strain), and Olindronal SMS, Olindronal SK, or Olindronal SPL including composition concerned in European Patent No. 1,724,336 (hereby incorporated by reference). These products are commercially available from Bussetti, Austria, for active dry yeast.

The compositions described herein may comprise a fermenting organism described herein (e.g., a *Saccharomyces cerevisiae* yeast strain) and any suitable gum. In one embodiment, the gum is selected from the group of carob, guar, tragacanth, arabic, xanthan and acacia gum, in particular for cream, compressed and dry yeast.

The compositions described herein may comprise a fermenting organism described herein (e.g., a *Saccharomyces cerevisiae* yeast strain) and any suitable swelling agent. In one embodiment, the swelling agent is methyl cellulose or carboxymethyl cellulose.

The compositions described herein may comprise a fermenting organism described herein (e.g., a *Saccharomyces cerevisiae* yeast strain) and any suitable anti-oxidant. In one embodiment, the antioxidant is butylated hydroxyanisol (BHA) and/or butylated hydroxytoluene (BHT), or ascorbic acid (vitamin C), particular for active dry yeast.

Gene Disruptions

The fermenting organisms described herein may also comprise one or more (e.g., two, several) gene disruptions, e.g., to divert sugar metabolism from undesired products to ethanol. In some aspects, the recombinant host cells produce a greater amount of ethanol compared to the cell without the one or more disruptions when cultivated under identical conditions. In some aspects, one or more of the disrupted endogenous genes is inactivated.

In certain embodiments, the fermenting organism provided herein comprises a disruption of one or more endogenous genes encoding enzymes involved in producing alternate fermentative products such as glycerol or other byproducts such as acetate or diols. For example, the cells provided herein may comprise a disruption of one or more of glycerol 3-phosphate dehydrogenase (GPD, catalyzes reaction of dihydroxyacetone phosphate to glycerol 3-phosphate), glycerol 3-phosphatase (GPP, catalyzes conversion of glycerol-3 phosphate to glycerol), glycerol kinase (catalyzes conversion of glycerol 3-phosphate to glycerol), dihydroxyacetone kinase (catalyzes conversion of dihydroxyacetone phosphate to dihydroxyacetone), glycerol dehydrogenase (catalyzes conversion of dihydroxyacetone to glycerol), and aldehyde dehydrogenase (ALD, e.g., converts acetaldehyde to acetate).

Modeling analysis can be used to design gene disruptions that additionally optimize utilization of the pathway. One exemplary computational method for identifying and designing metabolic alterations favoring biosynthesis of a desired product is the OptKnock computational framework, Burgard et al., 2003, *Biotechnol. Bioeng.* 84: 647-657.

The fermenting organisms comprising a gene disruption may be constructed using methods well known in the art, including those methods described herein. A portion of the gene can be disrupted such as the coding region or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The fermenting organisms comprising a gene disruption may be constructed by gene deletion techniques to eliminate or reduce expression of the gene. Gene deletion techniques enable the partial or complete removal of the gene thereby eliminating their expression. In such methods, deletion of the gene is accomplished by homologous recombination using a plasmid that has been constructed to contiguously contain the 5' and 3' regions flanking the gene.

The fermenting organisms comprising a gene disruption may also be constructed by introducing, substituting, and/or removing one or more (e.g., two, several) nucleotides in the gene or a control sequence thereof required for the transcription or translation thereof. For example, nucleotides may be inserted or removed for the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229: 4719; Lo et al., 1985, *Proc. Natl. Acad. Sci. U.S.A.* 81: 2285; Higuchi et al., 1988, *Nucleic Acids Res* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *BioTechniques* 8: 404.

The fermenting organisms comprising a gene disruption may also be constructed by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The fermenting organisms comprising a gene disruption may also be constructed by the process of gene conversion (see, for example, Iglesias and Trautner, 1983, *Molecular General Genetics* 189: 73-76). For example, in the gene conversion method, a nucleotide sequence corresponding to the gene is mutagenized in vitro to produce a defective nucleotide sequence, which is then transformed into the recombinant strain to produce a defective gene. By homologous recombination, the defective nucleotide sequence replaces the endogenous gene. It may be desirable that the defective nucleotide sequence also comprises a marker for selection of transformants containing the defective gene.

The fermenting organisms comprising a gene disruption may be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp. 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of the gene.

A nucleotide sequence homologous or complementary to a gene described herein may be used from other microbial sources to disrupt the corresponding gene in a recombinant strain of choice.

In one aspect, the modification of a gene in the recombinant cell is unmarked with a selectable marker. Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

Methods Using a Starch-Containing Material

In some aspects, the methods described herein produce a fermentation product from a starch-containing material. Starch-containing material is well-known in the art, containing two types of homopolysaccharides (amylose and amylopectin) and is linked by alpha-(1-4)-D-glycosidic bonds. Any suitable starch-containing starting material may be used. The starting material is generally selected based on the desired fermentation product, such as ethanol. Examples of starch-containing starting materials include cereal, tubers or grains. Specifically, the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In one embodiment, the starch-containing starting material is corn. In one embodiment, the starch-containing starting material is wheat. In one embodiment, the starch-containing starting material is barley. In one embodiment, the starch-containing starting material is rye. In one embodiment, the starch-containing starting material is milo. In one embodiment, the starch-containing starting material is sago. In one embodiment, the starch-containing starting material is cassava. In one embodiment, the starch-containing starting material is tapioca. In one embodiment, the starch-containing starting material is sorghum. In one embodiment, the starch-containing starting material is rice. In one embodiment, the starch-containing starting material is peas. In one embodiment, the starch-containing starting material is beans. In one embodiment, the starch-containing starting material is sweet potatoes. In one embodiment, the starch-containing starting material is oats.

The methods using a starch-containing material may include a conventional process (e.g., including a liquefaction step described in more detail below) or a raw starch hydrolysis process. In some embodiments using a starch-containing material, saccharification of the starch-containing material is at a temperature above the initial gelatinization temperature. In some embodiments using a starch-containing material, saccharification of the starch-containing material is at a temperature below the initial gelatinization temperature.

Liquefaction

In aspects using a starch-containing material, the methods may further comprise a liquefaction step carried out by subjecting the starch-containing material at a temperature above the initial gelatinization temperature to an alpha-amylase and optionally a protease and/or a glucoamylase. Other enzymes such as a pullulanase and phytase may also be present and/or added in liquefaction. In some embodiments, the liquefaction step is carried out prior to steps a) and b) of the described methods.

Liquefaction step may be carried out for 0.5-5 hours, such as 1-3 hours, such as typically about 2 hours.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. The initial gelatinization temperature of a given starch-containing material may be determined as the temperature at which birefringence is lost in 5% of the starch granules using the method described by Gorinstein and Lii, 1992, *Starch/Stärke* 44(12): 461-466.

Liquefaction is typically carried out at a temperature in the range from 70-100° C. In one embodiment, the temperature in liquefaction is between 75-95° C., such as between 75-90° C., between 80-90° C., or between 82-88° C., such as about 85° C.

A jet-cooking step may be carried out prior to liquefaction in step, for example, at a temperature between 110-145° C., 120-140° C., 125-135° C., or about 130° C. for about 1-15 minutes, for about 3-10 minutes, or about 5 minutes.

The pH during liquefaction may be between 4 and 7, such as pH 4.5-6.5, pH 5.0-6.5, pH 5.0-6.0, pH 5.2-6.2, or about 5.2, about 5.4, about 5.6, or about 5.8.

In one embodiment, the process further comprises, prior to liquefaction, the steps of:
  i) reducing the particle size of the starch-containing material, preferably by dry milling;
  ii) forming a slurry comprising the starch-containing material and water.

The starch-containing starting material, such as whole grains, may be reduced in particle size, e.g., by milling, in order to open up the structure, to increase surface area, and allowing for further processing. Generally, there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. In one embodiment the starch-containing material is subjected to dry milling. In one embodiment, the particle size is reduced to between 0.05 to 3.0 mm, e.g., 0.1-0.5 mm, or so that at least 30%, at least 50%, at least 70%, or at least 90% of the starch-containing material fit through a sieve with a 0.05 to 3.0 mm screen, e.g., 0.1-0.5 mm screen. In another embodiment, at least 50%, e.g., at least 70%, at least 80%, or at least 90% of the starch-containing material fit through a sieve with #6 screen.

The aqueous slurry may contain from 10-55 w/w-% dry solids (DS), e.g., 25-45 w/w-% dry solids (DS), or 30-40 w/w-% dry solids (DS) of starch-containing material.

The alpha-amylase, optionally a protease, and optionally a glucoamylase may initially be added to the aqueous slurry to initiate liquefaction (thinning). In one embodiment, only a portion of the enzymes (e.g., about ⅓) is added to the aqueous slurry, while the rest of the enzymes (e.g., about ⅔) are added during liquefaction step.

A non-exhaustive list of alpha-amylases used in liquefaction can be found below in the "Alpha-Amylases" section. Examples of suitable proteases used in liquefaction include any protease described supra in the "Proteases" section. Examples of suitable glucoamylases used in liquefaction include any glucoamylase found in the "Glucoamylases" section.

Saccharification and Fermentation of Starch-Containing Material

In aspects using a starch-containing material, a glucoamylase may be present and/or added in saccharification step a) and/or fermentation step b) or simultaneous saccharification and fermentation (SSF). The glucoamylase of the saccharification step a) and/or fermentation step b) or simultaneous saccharification and fermentation (SSF) is typically different from the glucoamylase optionally added to any liquefaction step described supra. In one embodiment, the glucoamylase is present and/or added together with a fungal alpha-amylase.

In some aspects, the fermenting organism comprises a heterologous polynucleotide encoding a glucoamylase, for example, as described in WO2017/087330, the content of which is hereby incorporated by reference.

Examples of glucoamylases can be found in the "Glucoamylases" section below.

When doing sequential saccharification and fermentation, saccharification step a) may be carried out under conditions well-known in the art. For instance, saccharification step a) may last up to from about 24 to about 72 hours. In one embodiment, pre-saccharification is done. Pre-saccharification is typically done for 40-90 minutes at a temperature between 30-65° C., typically about 60° C. Pre-saccharification is, in one embodiment, followed by saccharification during fermentation in simultaneous saccharification and fermentation (SSF). Saccharification is typically carried out at temperatures from 20-75° C., preferably from 40-70° C., typically about 60° C., and typically at a pH between 4 and 5, such as about pH 4.5.

Fermentation is carried out in a fermentation medium, as known in the art and, e.g., as described herein. The fermentation medium includes the fermentation substrate, that is, the carbohydrate source that is metabolized by the fermenting organism. With the processes described herein, the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Generally, fermenting organisms such as yeast, including *Saccharomyces cerevisiae* yeast, require an adequate source of nitrogen for propagation and fermentation. Many sources of supplemental nitrogen, if necessary, can be used and such sources of nitrogen are well known in the art. The nitrogen source may be organic, such as urea, DDGs, wet cake or corn mash, or inorganic, such as ammonia or ammonium hydroxide. In one embodiment, the nitrogen source is urea.

Fermentation can be carried out under low nitrogen conditions, e.g., when using a protease-expressing yeast. In some embodiments, the fermentation step is conducted with less than 1000 ppm supplemental nitrogen (e.g., urea or ammonium hydroxide), such as less than 750 ppm, less than 500 ppm, less than 400 ppm, less than 300 ppm, less than 250 ppm, less than 200 ppm, less than 150 ppm, less than 100 ppm, less than 75 ppm, less than 50 ppm, less than 25 ppm, or less than 10 ppm, supplemental nitrogen. In some embodiments, the fermentation step is conducted with no supplemental nitrogen.

Simultaneous saccharification and fermentation ("SSF") is widely used in industrial scale fermentation product production processes, especially ethanol production processes. When doing SSF the saccharification step a) and the fermentation step b) are carried out simultaneously. There is no holding stage for the saccharification, meaning that a fermenting organism, such as yeast, and enzyme(s), may be added together. However, it is also contemplated to add the fermenting organism and enzyme(s) separately. SSF is typically carried out at a temperature from 25° C. to 40° C., such as from 28° C. to 35° C., such as from 30° C. to 34° C., or about 32° C. In one embodiment, fermentation is ongoing for 6 to 120 hours, in particular 24 to 96 hours. In one embodiment, the pH is between 4-5.

In one embodiment, a cellulolytic enzyme composition is present and/or added in saccharification, fermentation or simultaneous saccharification and fermentation (SSF). Examples of such cellulolytic enzyme compositions can be found in the "Cellulolytic Enzymes and Compositions" section below. The cellulolytic enzyme composition may be present and/or added together with a glucoamylase, such as one disclosed in the "Glucoamylases" section below.

Alpha-Amylases

The expressed and/or exogenous alpha-amylase may be any alpha-amylase that is suitable for the host cells and/or the methods described herein, such as a naturally occurring alpha-amylase (e.g., a native alpha-amylase from another species or an endogenous alpha-amylase expressed from a modified expression vector) or a variant thereof that retains alpha-amylase activity. Any alpha-amylase contemplated for expression by a fermenting organism described below is also contemplated for aspects of the invention involving exogenous addition of an alpha-amylase.

In some embodiments, the fermenting organism comprises a heterologous polynucleotide encoding an alpha-amylase, for example, as described in WO2017/087330, the content of which is hereby incorporated by reference. Any alpha-amylase described or referenced herein is contemplated for expression in the fermenting organism.

In some embodiments, the fermenting organism comprising a heterologous polynucleotide encoding an alpha-amylase has an increased level of alpha-amylase activity compared to the host cells without the heterologous polynucleotide encoding the alpha-amylase, when cultivated under the same conditions. In some embodiments, the fermenting organism has an increased level of alpha-amylase activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the alpha-amylase, when cultivated under the same conditions.

Exemplary alpha-amylases that can be used with the host cells and/or the methods described herein include bacterial, yeast, or filamentous fungal alpha-amylases, e.g., derived from any of the microorganisms described or referenced herein.

The term "bacterial alpha-amylase" means any bacterial alpha-amylase classified under EC 3.2.1.1. A bacterial alpha-amylase used herein may, e.g., be derived from a strain of the genus *Bacillus*, which is sometimes also referred to as the genus *Geobacillus*. In one embodiment, the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of bacterial alpha-amylases include the *Bacillus stearothermophilus* alpha-amylase (BSG) of SEQ ID NO: 3 in WO99/19467, the *Bacillus amyloliquefaciens* alpha-amylase (BAN) of SEQ ID NO: 5 in WO99/19467, and the *Bacillus licheniformis* alpha-amylase (BLA) of SEQ ID NO: 4 in WO99/19467 (all sequences are hereby incorporated by reference). In one embodiment, the alpha-amylase may be an enzyme having a mature polypeptide sequence with a degree of identity of at least 60%, e.g., at least 70%, at least 80%, at least 90%, at least 95%, at least 96%, at least 97%, at least 98% or at least 99% to any of the sequences shown in SEQ ID NOs: 3, 4 or 5, in WO99/19467.

In one embodiment, the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated at the C-terminal, so that it is from 480-495 amino acids long, such as about 491 amino acids long, e.g., so that it lacks a functional starch binding domain (compared to SEQ ID NO: 3 in WO99/19467).

The *Bacillus* alpha-amylase may also be a variant and/or hybrid. Examples of such a variant can be found in any of WO96/23873, WO96/23874, WO97/41213, WO99/19467, WO00/60059, and WO02/10355 (each hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO96/23873—see, e.g., page 20, lines 1-10 (hereby incorporated by reference), such as corresponding to deletion of positions I181 and G182 compared to the amino acid sequence of *Bacillus stearothermophilus* alpha-amylase set forth in SEQ ID NO: 3 disclosed in WO99/19467 or the deletion of amino acids R179 and G180 using SEQ ID NO: 3 in WO99/19467 for numbering (which reference is hereby incorporated by reference). In some embodiments, the *Bacillus* alpha-amylases, such as *Bacillus stearothermophilus* alpha-amylases, have a double deletion corresponding to a deletion of positions 181 and 182 and further optionally comprise a N193F substitution (also denoted I181*+G182*+N193F) compared to the wild-type BSG alpha-amylase amino acid sequence set forth in SEQ ID NO: 3 disclosed in WO99/19467. The bacterial alpha-amylase may also have a substitution in a position corresponding to S239 in the *Bacillus licheniformis* alpha-amylase shown in SEQ ID NO: 4 in WO99/19467, or a S242 and/or E188P variant of the *Bacillus stearothermophilus* alpha-amylase of SEQ ID NO: 3 in WO99/19467.

In one embodiment, the variant is a S242A, E or Q variant, e.g., a S242Q variant, of the *Bacillus stearothermophilus* alpha-amylase.

In one embodiment, the variant is a position E188 variant, e.g., E188P variant of the *Bacillus stearothermophilus* alpha-amylase.

The bacterial alpha-amylase may, in one embodiment, be a truncated *Bacillus* alpha-amylase. In one embodiment, the truncation is so that, e.g., the *Bacillus stearothermophilus* alpha-amylase shown in SEQ ID NO: 3 in WO99/19467, is about 491 amino acids long, such as from 480 to 495 amino acids long, or so it lacks a functional starch bind domain. The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO99/19467) and the 37 N-terminal amino acid residues of the alpha-amylase derived from *Bacillus amyloliquefaciens* (shown in SEQ ID NO: 5 of WO99/19467). In one embodiment, this hybrid has one or more, especially all, of the following substitutions: G48A+T49I+G107A+H156Y+A181T+N190F+I201F+A209V+Q264S (using the *Bacillus licheniformis* numbering in SEQ ID NO: 4 of WO99/19467). In some embodiments, the variants have one or more of the following mutations (or corresponding mutations in other *Bacillus* alpha-amylases): H154Y, A181T, N190F, A209V and Q264S and/or the deletion of two residues between positions 176 and 179, e.g., deletion of E178 and G179 (using SEQ ID NO: 5 of WO99/19467 for position numbering).

In one embodiment, the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO2007/134207. The mature enzyme sequence starts after the initial "Met" amino acid in position 1.

The alpha-amylase may be a thermostable alpha-amylase, such as a thermostable bacterial alpha-amylase, e.g., from *Bacillus stearothermophilus*. In one embodiment, the alpha-amylase used in a process described herein has a T½ (min) at pH 4.5, 85° C., 0.12 mM $CaCl_2$ of at least 10 determined as described in Example 1 of WO2018/098381.

In one embodiment, the thermostable alpha-amylase has a T½ (min) at pH 4.5, 85° C., 0.12 mM $CaCl_2$, of at least 15. In one embodiment, the thermostable alpha-amylase has a T½ (min) at pH 4.5, 85° C., 0.12 mM $CaCl_2$, of as at least 20. In one embodiment, the thermostable alpha-amylase has a T½ (min) at pH 4.5, 85° C., 0.12 mM $CaCl_2$, of as at least 25. In one embodiment, the thermostable alpha-amylase has a T½ (min) at pH 4.5, 85° C., 0.12 mM $CaCl_2$, of as at least 30. In one embodiment, the thermostable alpha-amylase has a T½ (min) at pH 4.5, 85° C., 0.12 mM $CaCl_2$, of as at least 40.

In one embodiment, the thermostable alpha-amylase has a T½ (min) at pH 4.5, 85° C., 0.12 mM $CaCl_2$, of at least 50. In one embodiment, the thermostable alpha-amylase has a T½ (min) at pH 4.5, 85° C., 0.12 mM $CaCl_2$, of at least 60. In one embodiment, the thermostable alpha-amylase has a T½ (min) at pH 4.5, 85° C., 0.12 mM $CaCl_2$, between 10-70. In one embodiment, the thermostable alpha-amylase has a T½ (min) at pH 4.5, 85° C., 0.12 mM $CaCl_2$, between 15-70. In one embodiment, the thermostable alpha-amylase has a T½ (min) at pH 4.5, 85° C., 0.12 mM $CaCl_2$, between 20-70. In one embodiment, the thermostable alpha-amylase has a T½ (min) at pH 4.5, 85° C., 0.12 mM $CaCl_2$, between 25-70. In one embodiment, the thermostable alpha-amylase has a T½ (min) at pH 4.5, 85° C., 0.12 mM $CaCl_2$, between 30-70. In one embodiment, the thermostable alpha-amylase has a T½ (min) at pH 4.5, 85° C., 0.12 mM $CaCl_2$, between 40-70. In one embodiment, the thermostable alpha-amylase has a T½ (min) at pH 4.5, 85° C., 0.12 mM $CaCl_2$, between 50-70. In one embodiment, the thermostable alpha-amylase has a T½ (min) at pH 4.5, 85° C., 0.12 mM $CaCl_2$, between 60-70.

In one embodiment, the alpha-amylase is a bacterial alpha-amylase, e.g., derived from the genus *Bacillus*, such as a strain of *Bacillus stearothermophilus*, e.g., the *Bacillus stearothermophilus* as disclosed in WO99/019467 as SEQ ID NO: 3 with one or two amino acids deleted at positions R179, G180, I181 and/or G182, in particular with R179 and G180 deleted, or with I181 and G182 deleted, with mutations in below list of mutations.

In some embodiment, the *Bacillus stearothermophilus* alpha-amylases have double deletion I181+G182, and optional substitution N193F, further comprising one of the following substitutions or combinations of substitutions:
 V59A+Q89R+G112D+E129V+K177L+R179E+K220P+N224L+Q254S;
 V59A+Q89R+E129V+K177L+R179E+H208Y+K220P+N224L+Q254S;
 V59A+Q89R+E129V+K177L+R179E+K220P+N224L+Q254S+D269E+D281N;
 V59A+Q89R+E129V+K177L+R179E+K220P+N224L+Q254S+I270L;
 V59A+Q89R+E129V+K177L+R179E+K220P+N224L+Q254S+H274K;

V59A+Q89R+E129V+K177L+R179E+K220P+N224L+ Q254S+Y276F;
V59A+E129V+R157Y+K177L+R179E+K220P+ N224L+S242Q+Q254S;
V59A+E129V+K177L+R179E+H208Y+K220P+ N224L+S242Q+Q254S;
V59A+E129V+K177L+R179E+K220P+N224L+ S242Q+Q254S;
V59A+E129V+K177L+R179E+K220P+N224L+ S242Q+Q254S+H274K;
V59A+E129V+K177L+R179E+K220P+N224L+ S242Q+Q254S+Y276F;
V59A+E129V+K177L+R179E+K220P+N224L+ S242Q+Q254S+D281N;
V59A+E129V+K177L+R179E+K220P+N224L+ S242Q+Q254S+M284T;
V59A+E129V+K177L+R179E+K220P+N224L+ S242Q+Q254S+G416V;
V59A+E129V+K177L+R179E+K220P+N224L+Q254S;
V59A+E129V+K177L+R179E+K220P+N224L+ Q254S+M284T;
A91L+M96I+E129V+K177L+R179E+K220P+N224L+ S242Q+Q254S;
E129V+K177L+R179E;
E129V+K177L+R179E+K220P+N224L+S242Q+ Q254S;
E129V+K177L+R179E+K220P+N224L+S242Q+ Q254S+Y276F+L427M;
E129V+K177L+R179E+K220P+N224L+S242Q+ Q254S+M284T;
E129V+K177L+R179E+K220P+N224L+S242Q+ Q254S+N376*+I377*;
E129V+K177L+R179E+K220P+N224L+Q254S;
E129V+K177L+R179E+K220P+N224L+Q254S+ M284T;
E129V+K177L+R179E+S242Q;
E129V+K177L+R179V+K220P+N224L+S242Q+ Q254S;
K220P+N224L+S242Q+Q254S;
M284V;
V59A+Q89R+E129V+K177L+R179E+Q254S+M284V; and
V59A+E129V+K177L+R179E+Q254S+M284V;

In one embodiment, the alpha-amylase is selected from the group of Bacillus stearothermophilus alpha-amylase variants with double deletion I181*+G182*, and optionally substitution N193F, and further one of the following substitutions or combinations of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 1 herein for numbering).

It should be understood that when referring to Bacillus stearothermophilus alpha-amylase and variants thereof they are normally produced in truncated form. In particular, the truncation may be so that the Bacillus stearothermophilus alpha-amylase shown in SEQ ID NO: 3 in WO99/19467, or variants thereof, are truncated in the C-terminal and are typically from 480-495 amino acids long, such as about 491 amino acids long, e.g., so that it lacks a functional starch binding domain.

In one embodiment, the alpha-amylase variant may be an enzyme having a mature polypeptide sequence with a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO99/19467.

In one embodiment, the bacterial alpha-amylase, e.g., Bacillus alpha-amylase, such as especially Bacillus stearothermophilus alpha-amylase, or variant thereof, is dosed to liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS. In one embodiment, the bacterial alpha-amylase, e.g., Bacillus alpha-amylase, such as especially Bacillus stearothermophilus alpha-amylases, or variant thereof, is dosed to liquefaction in a concentration of between 0.0001-1 mg EP (Enzyme Protein)/g DS, e.g., 0.0005-0.5 mg EP/g DS, such as 0.001-0.1 mg EP/g DS.

In one embodiment, the bacterial alpha-amylase is derived from the Bacillus subtilis alpha-amylase of SEQ ID NO: 76, the Bacillus subtilis alpha-amylase of SEQ ID NO: 82, the Bacillus subtilis alpha-amylase of SEQ ID NO: 83, the Bacillus subtilis alpha-amylase of SEQ ID NO: 84, or the Bacillus licheniformis alpha-amylase of SEQ ID NO: 85, the Clostridium phytofermentans alpha-amylase of SEQ ID NO: 89, the Clostridium phytofermentans alpha-amylase of SEQ ID NO: 90, the Clostridium phytofermentans alpha-amylase of SEQ ID NO: 91, the Clostridium phytofermentans alpha-amylase of SEQ ID NO: 92, the Clostridium phytofermentans alpha-amylase of SEQ ID NO: 93, the Clostridium phytofermentans alpha-amylase of SEQ ID NO: 94, the Clostridium thermocellum alpha-amylase of SEQ ID NO: 95, the Thermobifida fusca alpha-amylase of SEQ ID NO: 96, the Thermobifida fusca alpha-amylase of SEQ ID NO: 97, the Anaerocellum thermophilum of SEQ ID NO: 98, the Anaerocellum thermophilum of SEQ ID NO: 99, the Anaerocellum thermophilum of SEQ ID NO: 100, the Streptomyces avermitilis of SEQ ID NO: 101, or the Streptomyces avermitilis of SEQ ID NO: 88.

In one embodiment, the alpha-amylase is derived from Bacillus amyloliquefaciens, such as the Bacillus amyloliquefaciens alpha-amylase of SEQ ID NO: 231 (e.g., as described in WO2018/002360, or variants thereof as described in WO2017/037614).

In one embodiment, the alpha-amylase is derived from a yeast alpha-amylase, such as the Saccharomycopsis fibuligera alpha-amylase of SEQ ID NO: 77, the Debaryomyces occidentalis alpha-amylase of SEQ ID NO: 78, the Debaryomyces occidentalis alpha-amylase of SEQ ID NO: 79, the Lipomyces kononenkoae alpha-amylase of SEQ ID NO: 80, the Lipomyces kononenkoae alpha-amylase of SEQ ID NO: 81.

In one embodiment, the alpha-amylase is derived from a filamentous fungal alpha-amylase, such as the Aspergillus niger alpha-amylase of SEQ ID NO: 86, or the Aspergillus niger alpha-amylase of SEQ ID NO: 87.

Additional alpha-amylases that may be expressed with the fermenting organisms and used with the methods described herein are described in the examples, and include, but are not limited to alpha-amylases shown in Table 1 (or derivatives thereof).

TABLE 1

| Donor Organism (catalytic domain) | SEQ ID NO: (mature polypeptide) |
|---|---|
| Rhizomucor pusillus | 121 |
| Bacillus licheniformis | 122 |

TABLE 1-continued

| Donor Organism (catalytic domain) | SEQ ID NO: (mature polypeptide) |
|---|---|
| Aspergillus niger | 123 |
| Aspergillus tamarii | 124 |
| Acidomyces richmondensis | 125 |
| Aspergillus bombycis | 126 |
| Alternaria sp | 127 |
| Rhizopus microsporus | 128 |
| Syncephalastrum racemosum | 129 |
| Rhizomucor pusillus | 130 |
| Dichotomocladium hesseltinei | 131 |
| Lichtheimia ramosa | 132 |
| Penicillium aethiopicum | 133 |
| Subulispora sp | 134 |
| Trichoderma paraviridescens | 135 |
| Byssoascus striatosporus | 136 |
| Aspergillus brasiliensis | 137 |
| Penicillium subspinulosum | 138 |
| Penicillium antarcticum | 139 |
| Penicillium coprophilum | 140 |
| Penicillium olsonii | 141 |
| Penicillium vasconiae | 142 |
| Penicillium sp | 143 |
| Heterocephalum aurantiacum | 144 |
| Neosartorya massa | 145 |
| Penicillium janthinellum | 146 |
| Aspergillus brasiliensis | 147 |
| Aspergillus westerdijkiae | 148 |
| Hamigera avellanea | 149 |
| Hamigera avellanea | 150 |
| Meripilus giganteus | 151 |
| Cerrena unicolor | 152 |
| Physalacria cryptomeriae | 153 |
| Lenzites betulinus | 154 |
| Trametes ljubarskyi | 155 |
| Bacillus subtilis | 156 |
| Bacillus subtilis subsp. subtilis | 157 |
| Schwanniomyces occidentalis | 158 |
| Rhizomucor pusillus | 159 |
| Aspergillus niger | 160 |
| Bacillus stearothermophilus | 161 |
| Bacillus halmapalus | 162 |
| Aspergillus oryzae | 163 |
| Bacillus amyloliquefaciens | 164 |
| Rhizomucor pusillus | 165 |
| Kionochaeta ivoriensis | 166 |
| Aspergillus niger | 167 |
| Aspergillus oryzae | 168 |
| Penicillium canescens | 169 |
| Acidomyces acidothermus | 170 |
| Kinochaeta ivoriensis | 171 |
| Aspergillus terreus | 172 |
| Thamnidium elegans | 173 |
| Meripilus giganteus | 174 |

Additional alpha-amylases contemplated for use with the present invention can be found in WO2011/153516 (the content of which is incorporated herein).

Additional polynucleotides encoding suitable alpha-amylases may be obtained from microorganisms of any genus, including those readily available within the UniProtKB database (www.uniprot.org).

As described supra, the alpha-amylase may be a bacterial alpha-amylase. For example, the alpha-amylase may be derived from a Gram-positive bacterium such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces*, or a Gram-negative bacterium such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma*.

In one embodiment, the alpha-amylase is derived from *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis*.

In another embodiment, the alpha-amylase is derived from *Streptococcus equisimilis*, *Streptococcus pyogenes*, *Streptococcus uberis*, or *Streptococcus equi* subsp. *Zooepidemicus*.

In another embodiment, the alpha-amylase is derived from *Streptomyces achromogenes*, *Streptomyces avermitilis*, *Streptomyces coelicolor*, *Streptomyces griseus*, or *Streptomyces lividans*.

The alpha-amylase may be a fungal alpha-amylase. For example, the alpha-amylase may be derived from a yeast such as a *Candida*, *Kluyveromyces*, *Pichia*, *Saccharomyces*, *Schizosaccharomyces*, *Yarrowia* or *Issatchenkia*; or derived from a filamentous fungus such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria*.

In another embodiment, the alpha-amylase is derived from *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis*.

In another embodiment, the alpha-amylase is derived from *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The alpha-amylase coding sequences described or referenced herein, or a subsequence thereof, as well as the alpha-amylases described or referenced herein, or a fragment thereof, may be used to design nucleic acid probes to identify and clone DNA encoding an alpha-amylase from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with a coding sequence, or a subsequence thereof, the carrier material is used in a Southern blot.

In one embodiment, the nucleic acid probe is a polynucleotide, or subsequence thereof, that encodes the alpha-amylase of any one of SEQ ID NOs: 76-101, 121-174 and 231, or a fragment thereof.

For purposes of the probes described above, hybridization indicates that the polynucleotide hybridizes to a labeled nucleic acid probe, or the full-length complementary strand thereof, or a subsequence of the foregoing; under very low to very high stringency conditions. Molecules to which the nucleic acid probe hybridizes under these conditions can be detected using, for example, X-ray film. Stringency and washing conditions are defined as described supra.

In one embodiment, the alpha-amylase is encoded by a polynucleotide that hybridizes under at least low stringency conditions, e.g., medium stringency conditions, medium-high stringency conditions, high stringency conditions, or very high stringency conditions with the full-length complementary strand of the coding sequence for any one of the alpha-amylases described or referenced herein (e.g., the coding sequence that encodes any one of SEQ ID NOs: 76-101, 121-174 and 231). (Sambrook et al., 1989, *Molecular Cloning, A Laboratory Manual*, 2d edition, Cold Spring Harbor, New York).

The alpha-amylase may also be identified and obtained from other sources including microorganisms isolated from nature (e.g., soil, composts, water, silage, etc.) or DNA samples obtained directly from natural materials (e.g., soil, composts, water, silage, etc.) using the above-mentioned probes. Techniques for isolating microorganisms and DNA directly from natural habitats are well known in the art. The polynucleotide encoding a alpha-amylase may then be derived by similarly screening a genomic or cDNA library of another microorganism or mixed DNA sample.

Once a polynucleotide encoding an alpha-amylase has been detected with a suitable probe as described herein, the sequence may be isolated or cloned by utilizing techniques that are known to those of ordinary skill in the art (see, e.g., Sambrook et al., 1989, *Molecular Cloning, A Laboratory Manual*, 2d edition, Cold Spring Harbor, New York). Techniques used to isolate or clone polynucleotides encoding alpha-amylases include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shares structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used.

In one embodiment, the alpha-amylase has a mature polypeptide sequence that comprises or consists of the amino acid sequence of any one of the alpha-amylases described or referenced herein (e.g., any one of SEQ ID NOs: 76-101, 121-174 and 231). In another embodiment, the alpha-amylase has a mature polypeptide sequence that is a fragment of the any one of the alpha-amylases described or referenced herein (e.g., any one of SEQ ID NOs: 76-101, 121-174 and 231). In one embodiment, the number of amino acid residues in the fragment is at least 75%, e.g., at least 80%, 85%, 90%, or 95% of the number of amino acid residues in referenced full length alpha-amylase (e.g. any one of SEQ ID NOs: 76-101, 121-174 and 231). In other embodiments, the alpha-amylase may comprise the catalytic domain of any alpha-amylase described or referenced herein (e.g., the catalytic domain of any one of SEQ ID NOs: 76-101, 121-174 and 231).

The alpha-amylase may be a variant of any one of the alpha-amylases described supra (e.g., any one of SEQ ID NOs: 76-101, 121-174 and 231). In one embodiment, the alpha-amylase has a mature polypeptide sequence of at least 60%, e.g., at least 65%, 70%, 75%, 80%, 85%, 90%, 95%, 97%, 98%, 99%, or 100% sequence identity to any one of the alpha-amylases described supra (e.g., any one of SEQ ID NOs: 76-101, 121-174 and 231).

In one embodiment, the alpha-amylase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the alpha-amylases described supra (e.g., any one of SEQ ID NOs: 76-101, 121-174 and 231). In one embodiment, the alpha-amylase has an amino acid substitution, deletion, and/or insertion of one or more (e.g., two, several) of amino acid sequence of any one of the alpha-amylases described supra (e.g., any one of SEQ ID NOs: 76-101, 121-174 and 231). In some embodiments, the total number of amino acid substitutions, deletions and/or insertions is not more than 10, e.g., not more than 9, 8, 7, 6, 5, 4, 3, 2, or 1.

The amino acid changes are generally of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the alpha-amylase, alter the substrate specificity, change the pH optimum, and the like.

Essential amino acids can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for activity to identify amino acid residues that are critical to the activity of the molecule. See also, Hilton et al., 1996, *J. Biol. Chem.* 271: 4699-4708. The active site or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Led.* 309: 59-64. The identities of essential amino acids can also be inferred from analysis of identities with other alpha-amylases that are related to the referenced alpha-amylase.

Additional guidance on the structure-activity relationship of the polypeptides herein can be determined using multiple sequence alignment (MSA) techniques well-known in the art. Based on the teachings herein, the skilled artisan could make similar alignments with any number of alpha-amylases described herein or known in the art. Such alignments aid the skilled artisan to determine potentially relevant domains (e.g., binding domains or catalytic domains), as well as which amino acid residues are conserved and not conserved among the different alpha-amylase sequences. It is appreciated in the art that changing an amino acid that is conserved at a particular position between disclosed polypeptides will more likely result in a change in biological activity (Bowie et al., 1990, Science 247: 1306-1310: "Residues that are directly involved in protein functions such as binding or catalysis will certainly be among the most conserved"). In contrast, substituting an amino acid that is not highly conserved among the polypeptides will not likely or significantly alter the biological activity.

Even further guidance on the structure-activity relationship for the skilled artisan can be found in published x-ray crystallography studies known in the art.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO95/17413; or WO95/22625. Other methods that can be used include error-prone PCR, phage display (e.g., Lowman et al., 1991, *Biochemistry* 30: 10832-10837; U.S. Pat. No. 5,223,409; WO92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active alpha-amylases can be recovered from the host cells and rapidly sequenced using standard methods in the art. These methods allow the rapid determination of the importance of individual amino acid residues in a polypeptide.

In some embodiments, the alpha-amylase has at least 20%, e.g., at least 40%, at least 50%, at least 60%, at least 70%, at least 80%, at least 90%, at least 95%, at least 96%, at least 97%, at least 98%, at least 99%, or 100% of the alpha-amylase activity of any alpha-amylase described or referenced herein (e.g., any one of SEQ ID NOs: 76-101, 121-174 and 231) under the same conditions.

In one embodiment, the alpha-amylase coding sequence hybridizes under at least low stringency conditions, e.g., medium stringency conditions, medium-high stringency conditions, high stringency conditions, or very high stringency conditions with the full-length complementary strand of the coding sequence from any alpha-amylase described or referenced herein (e.g., any one of SEQ ID NOs: 76-101, 121-174 and 231). In one embodiment, the alpha-amylase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any alpha-amylase described or referenced herein (e.g., any one of SEQ ID NOs: 76-101, 121-174 and 231).

In one embodiment, the alpha-amylase comprises the coding sequence of any alpha-amylase described or referenced herein (any one of SEQ ID NOs: 76-101, 121-174 and 231). In one embodiment, the alpha-amylase comprises a coding sequence that is a subsequence of the coding sequence from any alpha-amylase described or referenced herein, wherein the subsequence encodes a polypeptide having alpha-amylase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The alpha-amylase may be a fused polypeptide or cleavable fusion polypeptide in which another polypeptide is fused at the N-terminus or the C-terminus of the alpha-amylase. A fused polypeptide may be produced by fusing a polynucleotide encoding another polypeptide to a polynucleotide encoding the alpha-amylase. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

Trehalases

The expressed and/or exogenous trehalase can be any trehalase that is suitable for the fermenting organisms and/or their methods of use described herein, such as a naturally occurring trehalase or a variant thereof that retains trehalase activity. Any trehalase contemplated for expression by a fermenting organism described below is also contemplated for aspects of the invention involving exogenous addition of a trehalase (e.g., added before, during or after liquefaction and/or saccharification).

In some embodiments, the fermenting organism comprising a heterologous polynucleotide encoding a trehalase has an increased level of trehalase activity compared to the host cells without the heterologous polynucleotide encoding the trehalase, when cultivated under the same conditions. In some embodiments, the fermenting organism has an increased level of trehalase activity of at least 5%, e.g., at least 10%, at least 15%, at least 20%, at least 25%, at least 50%, at least 100%, at least 150%, at least 200%, at least 300%, or at least 500% compared to the fermenting organism without the heterologous polynucleotide encoding the trehalase, when cultivated under the same conditions.

Trehalases that may be expressed with the fermenting organisms and used with the methods described herein include, but are not limited to, trehalases shown in Table 2 (or derivatives thereof).

TABLE 2

| Donor Organism (catalytic domain) | SEQ ID NO: (mature polypeptide) |
|---|---|
| Chaetomium megalocarpum | 175 |
| Lecanicillium psalliotae | 176 |
| Doratomyces sp | 177 |
| Mucor moelleri | 178 |
| Phialophora cyclaminis | 179 |
| Thielavia arenaria | 180 |
| Thielavia antarctica | 181 |
| Chaetomium sp | 182 |
| Chaetomium nigricolor | 183 |
| Chaetomium jodhpurense | 184 |
| Chaetomium piluliferum | 185 |
| Myceliophthora hinnulea | 186 |
| Chloridium virescens | 187 |
| Gelasinospora cratophora | 188 |
| Acidobacteriaceae bacterium | 189 |
| Acidobacterium capsulatum | 190 |
| Acidovorax wautersii | 191 |
| Xanthomonas arboricola | 192 |
| Kosakonia sacchari | 193 |
| Enterobacter sp | 194 |
| Saitozyma flava | 195 |
| Phaeotremella skinneri | 196 |
| Trichoderma asperellum | 197 |
| Corynascus sepedonium | 198 |
| Myceliophthora thermophila | 199 |
| Trichoderma reesei | 200 |
| Chaetomium virescens | 201 |
| Rhodothermus marinus | 202 |

TABLE 2-continued

| Donor Organism (catalytic domain) | SEQ ID NO: (mature polypeptide) |
|---|---|
| Myceliophthora sepedonium | 203 |
| Moelleriella libera | 204 |
| Acremonium dichromosporum | 205 |
| Fusarium sambucinum | 206 |
| Phoma sp | 207 |
| Lentinus similis | 208 |
| Diaporthe nobilis | 209 |
| Solicoccozyma terricola | 210 |
| Dioszegia cryoxerica | 211 |
| Talaromyces funiculosus | 212 |
| Hamigera avellanea | 213 |
| Talaromyces ruber | 214 |
| Trichoderma lixii | 215 |
| Aspergillus cervinus | 216 |
| Rasamsonia brevistipitata | 217 |
| Acremonium curvulum | 218 |
| Talaromyces piceae | 219 |
| Penicillium sp | 220 |
| Talaromyces aurantiacus | 221 |
| Talaromyces pinophilus | 222 |
| Talaromyces leycettanus | 223 |
| Talaromyces variabilis | 224 |
| Aspergillus niger | 225 |
| Trichoderma reesei | 226 |

Additional polynucleotides encoding suitable trehalases may be derived from microorganisms of any suitable genus, including those readily available within the UniProtKB database (www.uniprot.org).

The trehalase coding sequences can also be used to design nucleic acid probes to identify and clone DNA encoding trehalases from strains of different genera or species, as described supra.

The polynucleotides encoding trehalases may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding trehalases are described supra.

In one embodiment, the trehalase has a mature polypeptide sequence that comprises or consists of the amino acid sequence of any one of the trehalases described or referenced herein (e.g., any one of SEQ ID NOs: 175-226). In another embodiment, the trehalase has a mature polypeptide sequence that is a fragment of the any one of the trehalases described or referenced herein (e.g., any one of SEQ ID NOs: 175-226). In one embodiment, the number of amino acid residues in the fragment is at least 75%, e.g., at least 80%, 85%, 90%, or 95% of the number of amino acid residues in referenced full length trehalase (e.g. any one of SEQ ID NOs: 175-226). In other embodiments, the trehalase may comprise the catalytic domain of any trehalase described or referenced herein (e.g., the catalytic domain of any one of SEQ ID NOs: 175-226).

The trehalase may be a variant of any one of the trehalases described supra (e.g., any one of SEQ ID NOs: 175-226). In one embodiment, the trehalase has a mature polypeptide sequence of at least 60%, e.g., at least 65%, 70%, 75%, 80%, 85%, 90%, 95%, 97%, 98%, 99%, or 100% sequence identity to any one of the trehalases described supra (e.g., any one of SEQ ID NOs: 175-226).

In one embodiment, the trehalase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the trehalases described supra (e.g., any one of SEQ ID NOs: 175-226). In one embodiment, the trehalase has an amino acid substitution, deletion, and/or insertion of one or more (e.g., two, several) of amino acid sequence of any one of the trehalases described supra (e.g., any one of SEQ ID NOs: 175-226). In some embodiments, the total number of amino acid substitutions, deletions and/or insertions is not more than 10, e.g., not more than 9, 8, 7, 6, 5, 4, 3, 2, or 1.

In some embodiments, the trehalase has at least 20%, e.g., at least 40%, at least 50%, at least 60%, at least 70%, at least 80%, at least 90%, at least 95%, at least 96%, at least 97%, at least 98%, at least 99%, or 100% of the trehalase activity of any trehalase described or referenced herein (e.g., any one of SEQ ID NOs: 175-226) under the same conditions.

In one embodiment, the trehalase coding sequence hybridizes under at least low stringency conditions, e.g., medium stringency conditions, medium-high stringency conditions, high stringency conditions, or very high stringency conditions with the full-length complementary strand of the coding sequence from any trehalase described or referenced herein (e.g., any one of SEQ ID NOs: 175-226). In one embodiment, the trehalase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any trehalase described or referenced herein (e.g., any one of SEQ ID NOs: 175-226).

In one embodiment, the trehalase comprises the coding sequence of any trehalase described or referenced herein (any one of SEQ ID NOs: 175-226). In one embodiment, the trehalase comprises a coding sequence that is a subsequence of the coding sequence from any trehalase described or referenced herein, wherein the subsequence encodes a polypeptide having trehalase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The trehalase can also include fused polypeptides or cleavable fusion polypeptides, as described supra.

Glucoamylases

The expressed and/or exogenous glucoamylase can be any glucoamylase that is suitable for the fermenting organisms and/or their methods of use described herein, such as a naturally occurring glucoamylase or a variant thereof that retains glucoamylase activity. Any glucoamylase contemplated for expression by a fermenting organism described below is also contemplated for aspects of the invention involving exogenous addition of a glucoamylase (e.g., added before, during or after liquefaction and/or saccharification).

In some embodiments, the fermenting organism comprises a heterologous polynucleotide encoding a glucoamylase, for example, as described in WO2017/087330, the content of which is hereby incorporated by reference. Any glucoamylase described or referenced herein is contemplated for expression in the fermenting organism.

In some embodiments, the fermenting organism comprising a heterologous polynucleotide encoding an glucoamylase has an increased level of glucoamylase activity compared to the host cells without the heterologous polynucleotide encoding the glucoamylase, when cultivated under the same conditions. In some embodiments, the fermenting organism has an increased level of glucoamylase activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the glucoamylase, when cultivated under the same conditions.

Exemplary glucoamylases that can be used with the host cells and/or the methods described herein include bacterial, yeast, or filamentous fungal glucoamylases, e.g., obtained from any of the microorganisms described or referenced herein, as described supra under the sections related to alpha-amylases.

The glucoamylase may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO92/00381, WO00/04136 and WO01/04273 (from Novozymes, Denmark); the *A. awamori* glucoamylase disclosed in WO84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO99/28448), *Talaromyces leycettanus* (U.S. Pat. No. Re. 32,153), *Talaromyces duponti, Talaromyces thermophilus* (U.S. Pat. No. 4,587,215). In one embodiment, the glucoamylase used during saccharification and/or fermentation is the *Talaromyces emersonii* glucoamylase disclosed in WO99/28448.

Bacterial glucoamylases contemplated include glucoamylases from the genus *Clostridium*, in particular *C. thermoamylolyticum* (EP 135,138), and *C. thermohydrosulfuricum* (WO86/01831).

Contemplated fungal glucoamylases include *Trametes cingulate, Pachykytospora papyracea*; and *Leucopaxillus giganteus* all disclosed in WO2006/069289; or *Peniophora rufomarginata* disclosed in WO2007/124285; or a mixture thereof. Also hybrid glucoamylase are contemplated. Examples include the hybrid glucoamylases disclosed in WO2005/045018.

In one embodiment, the glucoamylase is derived from a strain of the genus *Pycnoporus*, in particular a strain of *Pycnoporus* as described in WO2011/066576 (SEQ ID NO: 2, 4 or 6 therein), including the *Pycnoporus sanguineus* glucoamylase, or from a strain of the genus *Gloeophyllum*, such as a strain of *Gloeophyllum sepiarium* or *Gloeophyllum trabeum*, in particular a strain of *Gloeophyllum* as described in WO2011/068803 (SEQ ID NO: 2, 4, 6, 8, 10, 12, 14 or 16 therein). In one embodiment, the glucoamylase is SEQ ID NO: 2 in WO2011/068803 (i.e. *Gloeophyllum sepiarium* glucoamylase). In one embodiment, the glucoamylase is the *Gloeophyllum sepiarium* glucoamylase of SEQ ID NO: 8. In one embodiment, the glucoamylase is the *Pycnoporus sanguineus* glucoamylase of SEQ ID NO: 229.

In one embodiment, the glucoamylase is a *Gloeophyllum trabeum* glucoamylase (disclosed as SEQ ID NO: 3 in WO2014/177546). In another embodiment, the glucoamylase is derived from a strain of the genus *Nigrofomes*, in particular a strain of *Nigrofomes* sp. disclosed in WO2012/064351 (disclosed as SEQ ID NO: 2 therein).

Also contemplated are glucoamylases with a mature polypeptide sequence which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature polypeptide sequences mentioned above.

Glucoamylases may be added to the saccharification and/or fermentation in an amount of 0.0001-20 AGU/g DS, such as 0.001-10 AGU/g DS, 0.01-5 AGU/g DS, or 0.1-2 AGU/g DS.

Glucoamylases may be added to the saccharification and/or fermentation in an amount of 1-1,000 µg EP/g DS, such as 10-500 µg/g DS, or 25-250 µg/g DS.

Glucoamylases may be added to liquefaction in an amount of 0.1-100 µg EP/g DS, such as 0.5-50 µg EP/g DS, 1-25 µg EP/g DS, or 2-12 µg EP/g DS.

In one embodiment, the glucoamylase is added as a blend further comprising an alpha-amylase (e.g., any alpha-amylase described herein). In one embodiment, the alpha-amylase is a fungal alpha-amylase, especially an acid fungal alpha-amylase. The alpha-amylase is typically a side activity.

In one embodiment, the glucoamylase is a blend comprising *Talaromyces emersonii* glucoamylase disclosed in WO99/28448 as SEQ ID NO: 34 and *Trametes cingulata* glucoamylase disclosed as SEQ ID NO: 2 in WO06/069289.

In one embodiment, the glucoamylase is a blend comprising *Talaromyces emersonii* glucoamylase disclosed in WO99/28448, *Trametes cingulata* glucoamylase disclosed as SEQ ID NO: 2 in WO06/69289, and an alpha-amylase.

In one embodiment, the glucoamylase is a blend comprising *Talaromyces emersonii* glucoamylase disclosed in WO99/28448, *Trametes cingulata* glucoamylase disclosed in WO06/69289, and *Rhizomucor pusillus* alpha-amylase with *Aspergillus niger* glucoamylase linker and SBD disclosed as V039 in Table 5 in WO2006/069290.

In one embodiment, the glucoamylase is a blend comprising *Gloeophyllum sepiarium* glucoamylase shown as SEQ ID NO: 2 in WO2011/068803 and an alpha-amylase, in particular *Rhizomucor pusillus* alpha-amylase with an *Aspergillus niger* glucoamylase linker and starch-binding domain (SBD), disclosed SEQ ID NO: 3 in WO2013/006756, in particular with the following substitutions: G128D+D143N.

In one embodiment, the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In one embodiment, the alpha-amylase is derived from a *Rhizomucor pusillus* with an *Aspergillus niger* glucoamylase linker and starch-binding domain (SBD), disclosed as V039 in Table 5 in WO2006/069290.

In one embodiment, the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; and G128D+Y141W+D143N+K192R; or G128D+Y141W+D143N+K192R+P219C (using SEQ ID NO: 3 in WO2013/006756 for numbering).

In one embodiment, the glucoamylase blend comprises *Gloeophyllum sepiarium* glucoamylase (e.g., SEQ ID NO: 2 in WO2011/068803) and *Rhizomucor pusillus* alpha-amylase.

In one embodiment, the glucoamylase blend comprises *Gloeophyllum sepiarium* glucoamylase shown as SEQ ID NO: 2 in WO2011/068803 and *Rhizomucor pusillus* with an *Aspergillus niger* glucoamylase linker and starch-binding domain (SBD), disclosed SEQ ID NO: 3 in WO2013/006756 with the following substitutions: G128D+D143N.

Commercially available compositions comprising glucoamylase include AMG 200L; AMG 300 L; SAN™ SUPER, SAN™ EXTRA L, SPIRIZYME® PLUS, SPIRIZYME® FUEL, SPIRIZYME® B4U, SPIRIZYME® ULTRA, SPIRIZYME® EXCEL, SPIRIZYME ACHIEVE®, and AMG® E (from Novozymes A/S); OPTIDEX™ 300, GC480, GC417 (from DuPont-Danisco); AMIGASE™ and AMIGASE™ PLUS (from DSM); G-ZYME™ G900, G-ZYME™ and G990 ZR (from DuPont-Danisco).

In one embodiment, the glucoamylase is derived from the *Debaryomyces occidentalis* glucoamylase of SEQ ID NO: 102. In one embodiment, the glucoamylase is derived from the *Saccharomycopsis fibuligera* glucoamylase of SEQ ID NO: 103. In one embodiment, the glucoamylase is derived from the *Saccharomycopsis fibuligera* glucoamylase of SEQ ID NO: 104. In one embodiment, the glucoamylase is derived from the *Saccharomyces cerevisiae* glucoamylase of SEQ ID NO: 105. In one embodiment, the glucoamylase is derived from the *Aspergillus niger* glucoamylase of SEQ ID NO: 106. In one embodiment, the glucoamylase is derived from the *Aspergillus oryzae* glucoamylase of SEQ ID NO: 107. In one embodiment, the glucoamylase is derived from the *Rhizopus oryzae* glucoamylase of SEQ ID NO: 108. In one embodiment, the glucoamylase is derived from the *Clostridium thermocellum* glucoamylase of SEQ ID NO: 109. In one embodiment, the glucoamylase is derived from the *Clostridium thermocellum* glucoamylase of SEQ ID NO: 110. In one embodiment, the glucoamylase is derived from the Arxula adeninivorans glucoamylase of SEQ ID NO: 111. In one embodiment, the glucoamylase is derived from the *Hormoconis resinae* glucoamylase of SEQ ID NO: 112. In one embodiment, the glucoamylase is derived from the *Aureobasidium pullulans* glucoamylase of SEQ ID NO: 113.

In one embodiment, the glucoamylase is a *Trichoderma reesei* glucoamylase, such as the *Trichoderma reesei* glucoamylase of SEQ ID NO: 230.

In one embodiment, the glucoamylase has a Relative Activity heat stability at 85° C. of at least 20%, at least 30%, or at least 35% determined as described in Example 4 of WO2018/098381 (heat stability).

In one embodiment, the glucoamylase has a relative activity pH optimum at pH 5.0 of at least 90%, e.g., at least 95%, at least 97%, or 100% determined as described in Example 4 of WO2018/098381 (pH optimum).

In one embodiment, the glucoamylase has a pH stability at pH 5.0 of at least 80%, at least 85%, at least 90% determined as described in Example 4 of WO2018/098381 (pH stability).

In one embodiment, the glucoamylase used in liquefaction, such as a *Penicillium oxalicum* glucoamylase variant, has a thermostability determined as DSC Td at pH 4.0 as described in Example 15 of WO2018/098381 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C. In one embodiment, the glucoamylase, such as a *Penicillium oxalicum* glucoamylase variant, has a thermostability determined as DSC Td at pH 4.0 as described in Example 15 of WO2018/098381 in the range between 70° C. and 95° C., such as between 80° C. and 90° C.

In one embodiment, the glucoamylase, such as a *Penicillium oxalicum* glucoamylase variant, used in liquefaction has a thermostability determined as DSC Td at pH 4.8 as described in Example 15 of WO2018/098381 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C., such as at least 91° C. In one embodiment, the glucoamylase, such as a *Penicillium oxalicum* glucoamylase variant, has a thermostability determined as DSC Td at pH 4.8 as described in Example 15 of WO2018/098381 in the range between 70° C. and 95° C., such as between 80° C. and 90° C.

In one embodiment, the glucoamylase, such as a *Penicillium oxalicum* glucoamylase variant, used in liquefaction has a residual activity determined as described in Example 16 of WO2018/098381, of at least 100% such as at least 105%, such as at least 110%, such as at least 115%, such as at least 120%, such as at least 125%. In one embodiment, the glucoamylase, such as a *Penicillium oxalicum* glucoamylase variant, has a thermostability determined as residual activity as described in Example 16 of WO2018/098381, in the range between 100% and 130%.

In one embodiment, the glucoamylase, e.g., of fungal origin such as a filamentous fungi, from a strain of the genus *Penicillium*, e.g., a strain of *Penicillium oxalicum*, in particular the *Penicillium oxalicum* glucoamylase disclosed as SEQ ID NO: 2 in WO2011/127802 (which is hereby incorporated by reference).

In one embodiment, the glucoamylase has a mature polypeptide sequence of at least 80%, e.g., at least 85%, at least 90%, at least 91%, at least 92%, at least 93%, at least 94%, at least 95%, at least 96%, at least 97%, at least 98%, at least 99% or 100% identity to the mature polypeptide shown in SEQ ID NO: 2 in WO2011/127802.

In one embodiment, the glucoamylase is a variant of the *Penicillium oxalicum* glucoamylase disclosed as SEQ ID NO: 2 in WO2011/127802, having a K79V substitution. The K79V glucoamylase variant has reduced sensitivity to protease degradation relative to the parent as disclosed in WO2013/036526 (which is hereby incorporated by reference).

In one embodiment, the glucoamylase is derived from *Penicillium oxalicum.*

In one embodiment, the glucoamylase is a variant of the *Penicillium oxalicum* glucoamylase disclosed as SEQ ID NO: 2 in WO2011/127802. In one embodiment, the *Penicillium oxalicum* glucoamylase is the one disclosed as SEQ ID NO: 2 in WO2011/127802 having Val (V) in position 79.

Contemplated *Penicillium oxalicum* glucoamylase variants are disclosed in WO2013/053801 which is hereby incorporated by reference.

In one embodiment, these variants have reduced sensitivity to protease degradation.

In one embodiment, these variant have improved thermostability compared to the parent.

In one embodiment, the glucoamylase has a K79V substitution (using SEQ ID NO: 2 of WO2011/127802 for numbering), corresponding to the PE001 variant, and further comprises one of the following alterations or combinations of alterations T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K33C+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+D26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+

Q327F+E501V+Y504T; P2N+P4S+P11F+T65A+
Q327F+E501V+Y504T+T516P+K524T+G526A;
P2N+P4S+P11F+T65A+Q327F+E501V+N502T+
Y504*; P2N+P4S+P11F+T65A+Q327F+E501V+
Y504T; P2N+P4S+P11F+T65A+S103N+Q327F+
E501V+Y504T; K5A+P11F+T65A+Q327F+E501V+
Y504T; P2N+P4S+P11F+T65A+Q327F+E501V+
Y504T+T516P+K524T+G526A; P2N+P4S+P11F+
T65A+V79A+Q327F+E501V+Y504T; P2N+P4S+
P11F+T65A+V79G+Q327F+E501V+Y504T; P2N+
P4S+P11F+T65A+V79I+Q327F+E501V+Y504T;
P2N+P4S+P11F+T65A+V79L+Q327F+E501V+
Y504T; P2N+P4S+P11F+T65A+V79S+Q327F+
E501V+Y504T; P2N+P4S+P11F+T65A+L72V+
Q327F+E501V+Y504T; S255N+Q327F+E501V+
Y504T; P2N+P4S+P11F+T65A+E74N+V79K+
Q327F+E501V+Y504T; P2N+P4S+P11F+T65A+
G220N+Q327F+E501V+Y504T; P2N+P4S+P11F+
T65A+Y245N+Q327F+E501V+Y504T; P2N+P4S+
P11F+T65A+Q253N+Q327F+E501V+Y504T; P2N+
P4S+P11F+T65A+D279N+Q327F+E501V+Y504T;
P2N+P4S+P11F+T65A+Q327F+S359N+E501V+
Y504T; P2N+P4S+P11F+T65A+Q327F+D370N+
E501V+Y504T; P2N+P4S+P11F+T65A+Q327F+
V460S+E501V+Y504T; P2N+P4S+P11F+T65A+
Q327F+V460T+P468T+E501V+Y504T; P2N+P4S+
P11F+T65A+Q327F+T463N+E501V+Y504T; P2N+
P4S+P11F+T65A+Q327F+S465N+E501V+Y504T;
and P2N+P4S+P11F+T65A+Q327F+T477N+E501V+
Y504T.

In one embodiment, the *Penicillium oxalicum* glucoamylase variant has a K79V substitution (using SEQ ID NO: 2 of WO2011/127802 for numbering), corresponding to the PE001 variant, and further comprises one of the following substitutions or combinations of substitutions:

P11F+T65A+Q327F;
P2N+P4S+P11F+T65A+Q327F;
P11F+D26C+K33C+T65A+Q327F;
P2N+P4S+P11F+T65A+Q327W+E501V+Y504T;
P2N+P4S+P11F+T65A+Q327F+E501V+Y504T; and
P11F+T65A+Q327W+E501V+Y504T.

Additional glucoamylases contemplated for use with the present invention can be found in WO2011/153516 (the content of which is incorporated herein).

Additional polynucleotides encoding suitable glucoamylases may be obtained from microorganisms of any genus, including those readily available within the UniProtKB database (www.uniprot.org).

The glucoamylase coding sequences can also be used to design nucleic acid probes to identify and clone DNA encoding glucoamylases from strains of different genera or species, as described supra.

The polynucleotides encoding glucoamylases may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding glucoamylases are described supra.

In one embodiment, the glucoamylase has a mature polypeptide sequence that comprises or consists of the amino acid sequence of any one of the glucoamylases described or referenced herein (e.g., any one of SEQ ID NOs: 8, 102-113, 229 and 230). In another embodiment, the glucoamylase has a mature polypeptide sequence that is a fragment of the any one of the glucoamylases described or referenced herein (e.g., any one of SEQ ID NOs: 8, 102-113, 229 and 230). In one embodiment, the number of amino acid residues in the fragment is at least 75%, e.g., at least 80%, 85%, 90%, or 95% of the number of amino acid residues in referenced full length glucoamylase (e.g. any one of SEQ ID NOs: 8, 102-113, 229 and 230). In other embodiments, the glucoamylase may comprise the catalytic domain of any glucoamylase described or referenced herein (e.g., the catalytic domain of any of SEQ ID NOs: 8, 102-113, 229 and 230).

The glucoamylase may be a variant of any one of the glucoamylases described supra (e.g., any one of SEQ ID NOs: 8, 102-113, 229 and 230). In one embodiment, the glucoamylase has a mature polypeptide sequence of at least 60%, e.g., at least 65%, 70%, 75%, 80%, 85%, 90%, 95%, 97%, 98%, 99%, or 100% sequence identity to any one of the glucoamylases described supra (e.g., any one of SEQ ID NOs: 8, 102-113, 229 and 230).

In one embodiment, the glucoamylase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the glucoamylases described supra (e.g., any one of SEQ ID NOs: 8, 102-113, 229 and 230). In one embodiment, the glucoamylase has an amino acid substitution, deletion, and/or insertion of one or more (e.g., two, several) of amino acid sequence of any one of the glucoamylases described supra (e.g., any one of SEQ ID NOs: 8, 102-113, 229 and 230). In some embodiments, the total number of amino acid substitutions, deletions and/or insertions is not more than 10, e.g., not more than 9, 8, 7, 6, 5, 4, 3, 2, or 1.

In some embodiments, the glucoamylase has at least 20%, e.g., at least 40%, at least 50%, at least 60%, at least 70%, at least 80%, at least 90%, at least 95%, at least 96%, at least 97%, at least 98%, at least 99%, or 100% of the glucoamylase activity of any glucoamylase described or referenced herein (e.g., any one of SEQ ID NOs: 8, 102-113, 229 and 230) under the same conditions.

In one embodiment, the glucoamylase coding sequence hybridizes under at least low stringency conditions, e.g., medium stringency conditions, medium-high stringency conditions, high stringency conditions, or very high stringency conditions with the full-length complementary strand of the coding sequence from any glucoamylase described or referenced herein (e.g., any one of SEQ ID NOs: 8, 102-113, 229 and 230). In one embodiment, the glucoamylase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any glucoamylase described or referenced herein (e.g., any one of SEQ ID NOs: 8, 102-113, 229 and 230).

In one embodiment, the glucoamylase comprises the coding sequence of any glucoamylase described or referenced herein (any one of SEQ ID NOs: 8, 102-113, 229 and 230). In one embodiment, the glucoamylase comprises a coding sequence that is a subsequence of the coding sequence from any glucoamylase described or referenced herein, wherein the subsequence encodes a polypeptide having glucoamylase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The glucoamylase can also include fused polypeptides or cleavable fusion polypeptides, as described supra.

Proteases

The expressed and/or exogenous protease can be any protease that is suitable for the fermenting organisms and/or their methods of use described herein, such as a naturally occurring protease or a variant thereof that retains protease activity. Any protease contemplated for expression by a fermenting organism described below is also contemplated for aspects of the invention involving exogenous addition of a protease.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

In some aspects, the fermenting organism comprising a heterologous polynucleotide encoding a protease has an increased level of protease activity compared to the fermenting organism without the heterologous polynucleotide encoding the protease, when cultivated under the same conditions. In some aspects, the fermenting organism has an increased level of protease activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the protease, when cultivated under the same conditions.

Exemplary proteases that may be expressed with the fermenting organisms and used with the methods described herein include, but are not limited to, proteases shown in Table 3 (or derivatives thereof).

TABLE 3

| Donor Organism (catalytic domain) | SEQ ID NO: (mature polypeptide) | Family |
|---|---|---|
| *Aspergillus niger* | 9 | A1 |
| *Trichoderma reesei* | 10 | |
| *Thermoascus aurantiacus* | 11 | M35 |
| *Dichomitus squalens* | 12 | S53 |
| *Nocardiopsis prasina* | 13 | S1 |
| *Penicillium simplicissimum* | 14 | S10 |
| *Aspergillus niger* | 15 | |
| *Meriphilus giganteus* | 16 | S53 |
| *Lecanicillium* sp. WMM742 | 17 | S53 |
| *Talaromyces proteolyticus* | 18 | S53 |
| *Penicillium ranomafanaense* | 19 | A1A |
| *Aspergillus oryzae* | 20 | S53 |
| *Talaromyces liani* | 21 | S10 |

TABLE 3-continued

| Donor Organism (catalytic domain) | SEQ ID NO: (mature polypeptide) | Family |
|---|---|---|
| *Thermoascus thermophilus* | 22 | S53 |
| *Pyrococcus furiosus* | 23 | |
| *Trichoderma reesei* | 24 | |
| *Rhizomucor miehei* | 25 | |
| *Lenzites betulinus* | 26 | S53 |
| *Neolentinus lepideus* | 27 | S53 |
| *Thermococcus* sp. | 28 | S8 |
| *Thermococcus* sp. | 29 | S8 |
| *Thermomyces lanuginosus* | 30 | S53 |
| *Thermococcus thioreducens* | 31 | S53 |
| *Polyporus arcularius* | 32 | S53 |
| *Ganoderma lucidum* | 33 | S53 |
| *Ganoderma lucidum* | 34 | S53 |
| *Ganoderma lucidum* | 35 | S53 |
| *Trametes* sp. AH28-2 | 36 | S53 |
| *Cinereomyces lindbladii* | 37 | S53 |
| *Trametes versicolor* O82DDP | 38 | S53 |
| *Paecilomyces hepiali* | 39 | S53 |
| *Isaria tenuipes* | 40 | S53 |
| *Aspergillus tamarii* | 41 | S53 |
| *Aspergillus brasiliensis* | 42 | S53 |
| *Aspergillus iizukae* | 43 | S53 |
| *Penicillium sp-72364* | 44 | S10 |
| *Aspergillus denticulatus* | 45 | S10 |
| *Hamigera* sp. t184-6 | 46 | S10 |
| *Penicillium janthinellum* | 47 | S10 |
| *Penicillium vasconiae* | 48 | S10 |
| *Hamigera paravellanea* | 49 | S10 |
| *Talaromyces variabilis* | 50 | S10 |
| *Penicillium arenicola* | 51 | S10 |
| *Nocardiopsis kunsanensis* | 52 | S1 |
| *Streptomyces parvulus* | 53 | S1 |
| *Saccharopolyspora endophytica* | 54 | S1 |
| *luteus* cellwall enrichments K | 55 | S1 |
| *Saccharothrix australiensis* | 56 | S1 |
| *Nocardiopsis baichengensis* | 57 | S1 |
| *Streptomyces* sp. SM15 | 58 | S1 |
| *Actinoalloteichus spitiensis* | 59 | S1 |
| *Byssochlamys verrucosa* | 60 | M35 |
| *Hamigera terricola* | 61 | M35 |
| *Aspergillus tamarii* | 62 | M35 |
| *Aspergillus niveus* | 63 | M35 |
| *Penicillium sclerotiorum* | 64 | A1 |
| *Penicillium bilaiae* | 65 | A1 |
| *Penicillium antarcticum* | 66 | A1 |
| *Penicillium sumatrense* | 67 | A1 |
| *Trichoderma lixii* | 68 | A1 |
| *Trichoderma brevicompactum* | 69 | A1 |
| *Penicillium cinnamopurpureum* | 70 | A1 |
| *Bacillus licheniformis* | 71 | S8 |
| *Bacillus subtilis* | 72 | S8 |
| *Trametes cf versicol* | 73 | S53 |

Additional polynucleotides encoding suitable proteases may be derived from microorganisms of any suitable genus, including those readily available within the UniProtKB database (www.uniprot.org).

In one embodiment, the protease is derived from *Aspergillus*, such as the *Aspergillus niger* protease of SEQ ID NO: 9, the *Aspergillus tamarii* protease of SEQ ID NO: 41, or the *Aspergillus denticulatus* protease of SEQ ID NO: 45. In one embodiment, the protease is derived from *Dichomitus*, such as the *Dichomitus squalens* protease of SEQ ID NO: 12. In one embodiment, the protease is derived from *Penicillium*, such as the *Penicillium simplicissimum* protease of SEQ ID NO: 14, the *Penicillium antarcticum* protease of SEQ ID NO: 66, or the *Penicillium sumatrense* protease of SEQ ID NO: 67. In one aspect, the protease is derived from *Meriphilus*, such as the *Meriphilus giganteus* protease of SEQ ID NO: 16. In one aspect, the protease is derived from *Talaromyces*, such as the *Talaromyces liani* protease of SEQ ID NO: 21. In one aspect, the protease is derived from *Thermoascus*, such as the *Thermoascus thermophilus* protease of SEQ ID NO: 22. In one aspect, the protease is derived from *Ganoderma*, such as the *Ganoderma lucidum* protease of SEQ ID NO: 33. In one aspect, the protease is derived from *Hamigera*, such as the *Hamigera terricola* protease of SEQ ID NO: 61. In one aspect, the protease is derived from *Trichoderma*, such as the *Trichoderma brevicompactum* protease of SEQ ID NO: 69.

The protease coding sequences can also be used to design nucleic acid probes to identify and clone DNA encoding proteases from strains of different genera or species, as described supra.

The polynucleotides encoding proteases may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding proteases are described supra.

In one embodiment, the protease has a mature polypeptide sequence that comprises or consists of the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69). In another embodiment, the protease has a mature polypeptide sequence that is a fragment of the protease of any one of SEQ ID NOs: 9-73 (e.g., wherein the fragment has protease activity). In one embodiment, the number of amino acid residues in the fragment is at least 75%, e.g., at least 80%, 85%, 90%, or 95% of the number of amino acid residues in referenced full length protease (e.g. any one of SEQ ID NOs: 9-73). In other embodiments, the protease may comprise the catalytic domain of any protease described or referenced herein (e.g., the catalytic domain of any one of SEQ ID NOs: 9-73).

The protease may be a variant of any one of the proteases described supra (e.g., any one of SEQ ID NOs: 9-73. In one embodiment, the protease has a mature polypeptide sequence of at least 60%, e.g., at least 65%, 70%, 75%, 80%, 85%, 90%, 95%, 97%, 98%, 99%, or 100% sequence identity to any one of the proteases described supra (e.g., any one of SEQ ID NOs: 9-73).

In one embodiment, the protease has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the proteases described supra (e.g., any one of SEQ ID NOs: 9-73). In one embodiment, the protease has an amino acid substitution, deletion, and/or insertion of one or more (e.g., two, several) of amino acid sequence of any one of the proteases described supra (e.g., any one of SEQ ID NOs: 9-73). In some embodiments, the total number of amino acid substitutions, deletions and/or insertions is not more than 10, e.g., not more than 9, 8, 7, 6, 5, 4, 3, 2, or 1.

In one embodiment, the protease coding sequence hybridizes under at least low stringency conditions, e.g., medium stringency conditions, medium-high stringency conditions, high stringency conditions, or very high stringency conditions with the full-length complementary strand of the coding sequence from any protease described or referenced herein (e.g., any one of SEQ ID NOs: 9-73). In one embodiment, the protease coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any protease described or referenced herein (e.g., any one of SEQ ID NOs: 9-73).

In one embodiment, the protease comprises the coding sequence of any protease described or referenced herein (any one of SEQ ID NOs: 9-73). In one embodiment, the protease comprises a coding sequence that is a subsequence of the coding sequence from any protease described or referenced herein, wherein the subsequence encodes a polypeptide having protease activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The protease can also include fused polypeptides or cleavable fusion polypeptides, as described supra.

In one embodiment, the protease used according to a process described herein is a Serine proteases. In one particular embodiment, the protease is a serine protease belonging to the family 53, e.g., an endo-protease, such as S53 protease from *Meripilus giganteus, Dichomitus squalens Trametes versicolor, Polyporus arcularius, Lenzites betulinus, Ganoderma lucidum, Neolentinus lepideus*, or *Bacillus* sp. 19138, in a process for producing ethanol from a starch-containing material, the ethanol yield was improved, when the S53 protease was present/or added during saccharification and/or fermentation of either gelatinized or un-gelatinized starch. In one embodiment, the proteases is selected from: (a) proteases belonging to the EC 3.4.21 enzyme group; and/or (b) proteases belonging to the EC 3.4.14 enzyme group; and/or (c) Serine proteases of the peptidase family S53 that comprises two different types of peptidases: tripeptidyl aminopeptidases (exo-type) and endo-peptidases; as described in 1993, *Biochem. J.* 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Peptidase family S53 contains acid-acting endopeptidases and tripeptidyl-peptidases. The residues of the catalytic triad are Glu, Asp, Ser, and there is an additional acidic residue, Asp, in the oxyanion hole. The order of the residues is Glu, Asp, Asp, Ser. The Ser residue is the nucleophile equivalent to Ser in the Asp, His, Ser triad of subtilisin, and the Glu of the triad is a substitute for the general base, His, in subtilisin.

The peptidases of the S53 family tend to be most active at acidic pH (unlike the homologous subtilisins), and this can be attributed to the functional importance of carboxylic residues, notably Asp in the oxyanion hole. The amino acid sequences are not closely similar to those in family S8 (i.e. serine endopeptidase subtilisins and homologues), and this, taken together with the quite different active site residues and the resulting lower pH for maximal activity, provides for a substantial difference to that family. Protein folding of the peptidase unit for members of this family resembles that of subtilisin, having the clan type SB.

In one embodiment, the protease used according to a process described herein is a Cysteine proteases.

In one embodiment, the protease used according to a process described herein is a Aspartic proteases. Aspartic acid proteases are described in, for example, Hand-book of Proteolytic Enzymes, Edited by A. J. Barrett, N. D. Rawlings and J. F. Woessner, Academic Press, San Diego, 1998, Chapter 270). Suitable examples of aspartic acid protease include, e.g., those disclosed in R. M. Berka et al. Gene, 96, 313 (1990)); (R. M. Berka et al. Gene, 125, 195-198 (1993)); and Gomi et al. Biosci. Biotech. Biochem. 57, 1095-1100 (1993), which are hereby incorporated by reference.

The protease also may be a metalloprotease, which is defined as a protease selected from the group consisting of:
  (a) proteases belonging to EC 3.4.24 (metalloendopeptidases); preferably EC 3.4.24.39 (acid metallo proteinases);
  (b) metalloproteases belonging to the M group of the above Handbook;
  (c) metalloproteases not yet assigned to clans (designation: Clan MX), or belonging to either one of clans MA, MB, MC, MD, ME, MF, MG, MH (as defined at pp. 989-991 of the above Handbook);
  (d) other families of metalloproteases (as defined at pp. 1448-1452 of the above Handbook);
  (e) metalloproteases with a HEXXH motif;
  (f) metalloproteases with an HEFTH motif;
  (g) metalloproteases belonging to either one of families M3, M26, M27, M32, M34, M35, M36, M41, M43, or M47 (as defined at pp. 1448-1452 of the above Handbook);
  (h) metalloproteases belonging to the M28E family; and
  (i) metalloproteases belonging to family M35 (as defined at pp. 1492-1495 of the above Handbook).

In other particular embodiments, metalloproteases are hydrolases in which the nucleophilic attack on a peptide bond is mediated by a water molecule, which is activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

There are no limitations on the origin of the metalloprotease used in a process of the invention. In an embodiment the metalloprotease is classified as EC 3.4.24, preferably EC 3.4.24.39. In one embodiment, the metalloprotease is an acid-stable metalloprotease, e.g., a fungal acid-stable metalloprotease, such as a metalloprotease derived from a strain of the genus *Thermoascus*, preferably a strain of *Thermoascus aurantiacus*, especially *Thermoascus aurantiacus* CGMCC No. 0670 (classified as EC 3.4.24.39). In another embodiment, the metalloprotease is derived from a strain of the genus *Aspergillus*, preferably a strain of *Aspergillus oryzae*.

In one embodiment the metalloprotease has a degree of sequence identity to amino acids −178 to 177, −159 to 177, or preferably amino acids 1 to 177 (the mature polypeptide) of SEQ ID NO: 1 of WO2010/008841 (a *Thermoascus aurantiacus* metalloprotease) of at least 80%, at least 82%, at least 85%, at least 90%, at least 95%, or at least 97%; and which have metalloprotease activity. In particular embodiments, the metalloprotease consists of an amino acid sequence with a degree of identity to SEQ ID NO: 1 as mentioned above.

The *Thermoascus aurantiacus* metalloprotease is a preferred example of a metalloprotease suitable for use in a process of the invention. Another metalloprotease is derived from *Aspergillus oryzae* and comprises the sequence of SEQ ID NO: 11 disclosed in WO2003/048353, or amino acids −23-353; −23-374; −23-397; 1-353; 1-374; 1-397; 177-353; 177-374; or 177-397 thereof, and SEQ ID NO: 10 disclosed in WO2003/048353.

Another metalloprotease suitable for use in a process of the invention is the *Aspergillus oryzae* metalloprotease comprising SEQ ID NO: 5 of WO2010/008841, or a metalloprotease is an isolated polypeptide which has a degree of identity to SEQ ID NO: 5 of at least about 80%, at least 82%, at least 85%, at least 90%, at least 95%, or at least 97%; and which have metalloprotease activity. In particular embodiments, the metalloprotease consists of the amino acid sequence of SEQ ID NO: 5 of WO2010/008841.

In a particular embodiment, a metalloprotease has an amino acid sequence that differs by forty, thirty-five, thirty, twenty-five, twenty, or by fifteen amino acids from amino acids −178 to 177, −159 to 177, or +1 to 177 of the amino acid sequences of the *Thermoascus aurantiacus* or *Aspergillus oryzae* metalloprotease.

In another embodiment, a metalloprotease has an amino acid sequence that differs by ten, or by nine, or by eight, or by seven, or by six, or by five amino acids from amino acids −178 to 177, −159 to 177, or +1 to 177 of the amino acid sequences of these metalloproteases, e.g., by four, by three, by two, or by one amino acid.

In particular embodiments, the metalloprotease a) comprises or b) consists of
  i) the amino acid sequence of amino acids −178 to 177, −159 to 177, or +1 to 177 of SEQ ID NO:1 of WO2010/008841;
  ii) the amino acid sequence of amino acids −23-353, −23-374, −23-397, 1-353, 1-374, 1-397, 177-353, 177-374, or 177-397 of SEQ ID NO: 3 of WO2010/008841;
  iii) the amino acid sequence of SEQ ID NO: 5 of WO2010/008841; or allelic variants, or fragments, of the sequences of i), ii), and iii) that have protease activity.

A fragment of amino acids −178 to 177, −159 to 177, or +1 to 177 of SEQ ID NO: 1 of WO2010/008841 or of amino acids −23-353, −23-374, −23-397, 1-353, 1-374, 1-397, 177-353, 177-374, or 177-397 of SEQ ID NO: 3 of WO2010/008841; is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

The protease may be a variant of, e.g., a wild-type protease, having thermostability properties defined herein. In one embodiment, the thermostable protease is a variant of a metallo protease. In one embodiment, the thermostable protease used in a process described herein is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In one embodiment, the thermostable protease is a variant of the mature part of the metallo protease shown in SEQ ID NO: 2 disclosed in WO2003/048353 or the mature part of SEQ ID NO: 1 in WO2010/008841 further with one of the following substitutions or combinations of substitutions:

S5*+D79L+S87P+A112P+D142 L;
D79L+S87P+A112P+T124V+D142 L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L; and
D79L+S87P+D142L.

In one embodiment, the thermostable protease is a variant of the metallo protease disclosed as the mature part of SEQ ID NO: 2 disclosed in WO2003/048353 or the mature part of SEQ ID NO: 1 in WO2010/008841 with one of the following substitutions or combinations of substitutions:

D79L+S87P+A112P+D142L;
D79L+S87P+D142L; and
A27K+D79L+Y82F+S87G+D104P+A112P+A126V+D142L.

In one embodiment, the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO2003/048353 or the mature part of SEQ ID NO: 1 in WO2010/008841.

The thermostable protease may also be derived from any bacterium as long as the protease has the thermostability properties.

In one embodiment, the thermostable protease is derived from a strain of the bacterium *Pyrococcus*, such as a strain of *Pyrococcus furiosus* (pfu protease).

In one embodiment, the protease is one shown as SEQ ID NO: 1 in U.S. Pat. No. 6,358,726-B1 (Takara Shuzo Company).

In one embodiment, the thermostable protease is a protease having a mature polypeptide sequence of at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1. The *Pyrococcus furiosus* protease can be purchased from Takara Bio, Japan.

The *Pyrococcus furiosus* protease may be a thermostable protease as described in SEQ ID NO: 13 of WO2018/098381. This protease (PfuS) was found to have a thermostability of 110% (80° C./70° C.) and 103% (90° C./70° C.) at pH 4.5 determined.

In one embodiment a thermostable protease used in a process described herein has a thermostability value of more than 20% determined as Relative Activity at 80° C./70° C. determined as described in Example 2 of WO2018/098381.

In one embodiment, the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In one embodiment, protease has a thermostability of between 20 and 50%, such as between 20 and 40%, such as 20 and 30% determined as Relative Activity at 80° C./70° C. In one embodiment, the protease has a thermostability between 50 and 115%, such as between 50 and 70%, such as between 50 and 60%, such as between 100 and 120%, such as between 105 and 115% determined as Relative Activity at 80° C./70° C.

In one embodiment, the protease has a thermostability value of more than 10% determined as Relative Activity at 85° C./70° C. determined as described in Example 2 of WO2018/098381.

In one embodiment, the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In one embodiment, the protease has a thermostability of between 10% and 50%, such as between 10% and 30%, such as between 10% and 25% determined as Relative Activity at 85° C./70° C.

In one embodiment, the protease has more than 20%, more than 30%, more than 40%, more than 50%, more than 60%, more than 70%, more than 80%, more than 90% determined as Remaining Activity at 80° C.; and/or the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2 of WO2018/098381.

In one embodiment, the protease may have a thermostability for above 90, such as above 100 at 85° C. as determined using the Zein-BCA assay as disclosed in Example 3 of WO2018/098381.

In one embodiment, the protease has a thermostability above 60%, such as above 90%, such as above 100%, such as above 110% at 85° C. as determined using the Zein-BCA assay of WO2018/098381.

In one embodiment, protease has a thermostability between 60-120, such as between 70-120%, such as between 80-120%, such as between 90-120%, such as between 100-120%, such as 110-120% at 85° C. as determined using the Zein-BCA assay of WO2018/098381.

In one embodiment, the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay of WO2018/098381, and described herein.

In one embodiment, the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay of WO2018/098381, and described herein.

Pullulanases

In some embodiments, a pullulanase is present and/or added in liquefaction step and/or saccharification step, or simultaneous saccharification and fermentation (SSF).

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

In some embodiments, the fermenting organism comprises a heterologous polynucleotide encoding a pullulanase. Any pullulanase described or referenced herein is contemplated for expression in the fermenting organism.

The pullulanase may be any pullulanase that is suitable for the host cells and/or the methods described herein, such as a naturally occurring pullulanase or a variant thereof that retains pullulanase activity.

In some embodiments, the fermenting organism comprising a heterologous polynucleotide encoding a pullulanase has an increased level of pullulanase activity compared to the host cells without the heterologous polynucleotide encoding the pullulanase, when cultivated under the same conditions. In some embodiments, the fermenting organism has an increased level of pullulanase activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the pullulanase, when cultivated under the same conditions.

Exemplary pullulanases that can be used with the host cells and/or the methods described herein include bacterial, yeast, or filamentous fungal pullulanases, e.g., obtained from any of the microorganisms described or referenced herein, as described supra under the sections related to alpha-amylases.

Contemplated pullulanases include the pullulanases from *Bacillus amyloderamificans* disclosed in U.S. Pat. No. 4,560,651 (hereby incorporated by reference), the pullulanase disclosed as SEQ ID NO: 2 in WO01/151620 (hereby incorporated by reference), the *Bacillus deramificans* disclosed as SEQ ID NO: 4 in WO01/151620 (hereby incorporated by reference), and the pullulanase from *Bacillus acidopullulyticus* disclosed as SEQ ID NO: 6 in WO01/151620 (hereby incorporated by reference) and also described in FEMS Mic. Let. (1994) 115, 97-106.

Additional pullulanases contemplated include the pullulanases from *Pyrococcus woesei*, specifically from *Pyrococcus woesei* DSM No. 3773 disclosed in WO92/02614.

In one embodiment, the pullulanase is a family GH57 pullulanase. In one embodiment, the pullulanase includes an X47 domain as disclosed in U.S. 61/289,040 published as WO2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase truncated at site X4 right after the X47 domain (i.e., amino acids 1-782). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in U.S. 61/289,040 published as WO2011/087836 (which is hereby incorporated by reference).

In another embodiment, the pullulanase is one comprising an X46 domain disclosed in WO2011/076123 (Novozymes).

The pullulanase may be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in WO2018/098381.

Suitable commercially available pullulanase products include PROMOZYME D, PROMOZYME™ D2 (Novozymes A/S, Denmark), OPTIMAX L-300 (DuPont-Danisco, USA), and AMANO 8 (Amano, Japan).

In one embodiment, the pullulanase is derived from the *Bacillus subtilis* pullulanase of SEQ ID NO: 114. In one embodiment, the pullulanase is derived from the *Bacillus licheniformis* pullulanase of SEQ ID NO: 115. In one embodiment, the pullulanase is derived from the *Oryza sativa* pullulanase of SEQ ID NO: 116. In one embodiment, the pullulanase is derived from the *Triticum aestivum* pullulanase of SEQ ID NO: 117. In one embodiment, the pullulanase is derived from the *Clostridium phytofermentans* pullulanase of SEQ ID NO: 118. In one embodiment, the pullulanase is derived from the *Streptomyces avermitilis* pullulanase of SEQ ID NO: 119. In one embodiment, the pullulanase is derived from the *Klebsiella pneumoniae* pullulanase of SEQ ID NO: 120.

Additional pullulanases contemplated for use with the present invention can be found in WO2011/153516 (the content of which is incorporated herein).

Additional polynucleotides encoding suitable pullulanases may be obtained from microorganisms of any genus, including those readily available within the UniProtKB database (www.uniprot.org).

The pullulanase coding sequences can also be used to design nucleic acid probes to identify and clone DNA encoding pullulanases from strains of different genera or species, as described supra.

The polynucleotides encoding pullulanases may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding pullulanases are described supra.

In one embodiment, the pullulanase has a mature polypeptide sequence that comprises or consists of the amino acid sequence of any one of the pullulanases described or referenced herein (e.g., any one of SEQ ID NOs: 114-120). In another embodiment, the pullulanase has a mature polypeptide sequence that is a fragment of the any one of the pullulanases described or referenced herein (e.g., any one of SEQ ID NOs: 114-120). In one embodiment, the number of amino acid residues in the fragment is at least 75%, e.g., at least 80%, 85%, 90%, or 95% of the number of amino acid residues in referenced full length pullulanase. In other embodiments, the pullulanase may comprise the catalytic domain of any pullulanase described or referenced herein (e.g., any one of SEQ ID NOs: 114-120).

The pullulanase may be a variant of any one of the pullulanases described supra (e.g., any one of SEQ ID NOs: 114-120). In one embodiment, the pullulanase has a mature polypeptide sequence of at least 60%, e.g., at least 65%, 70%, 75%, 80%, 85%, 90%, 95%, 97%, 98%, 99%, or 100% sequence identity to any one of the pullulanases described supra (e.g., any one of SEQ ID NOs: 114-120).

In one embodiment, the pullulanase has a mature polypeptide sequence that differs by no more than ten amino acids, e.g., by no more than five amino acids, by no more than four amino acids, by no more than three amino acids, by no more than two amino acids, or by one amino acid from the amino acid sequence of any one of the pullulanases described supra (e.g., any one of SEQ ID NOs: 114-120). In one embodiment, the pullulanase has an amino acid substitution, deletion, and/or insertion of one or more (e.g., two, several) of amino acid sequence of any one of the pullulanases described supra (e.g., any one of SEQ ID NOs: 114-120). In some embodiments, the total number of amino acid substitutions, deletions and/or insertions is not more than 10, e.g., not more than 9, 8, 7, 6, 5, 4, 3, 2, or 1.

In some embodiments, the pullulanase has at least 20%, e.g., at least 40%, at least 50%, at least 60%, at least 70%, at least 80%, at least 90%, at least 95%, at least 96%, at least 97%, at least 98%, at least 99%, or 100% of the pullulanase activity of any pullulanase described or referenced herein under the same conditions (e.g., any one of SEQ ID NOs: 114-120).

In one embodiment, the pullulanase coding sequence hybridizes under at least low stringency conditions, e.g., medium stringency conditions, medium-high stringency conditions, high stringency conditions, or very high stringency conditions with the full-length complementary strand of the coding sequence from any pullulanase described or referenced herein (e.g., any one of SEQ ID NOs: 114-120). In one embodiment, the pullulanase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any pullulanase described or referenced herein (e.g., any one of SEQ ID NOs: 114-120).

In one embodiment, the pullulanase comprises the coding sequence of any pullulanase described or referenced herein (e.g., any one of SEQ ID NOs: 114-120). In one embodiment, the pullulanase comprises a coding sequence that is a subsequence of the coding sequence from any pullulanase described or referenced herein, wherein the subsequence encodes a polypeptide having pullulanase activity. In one embodiment, the number of nucleotides residues in the subsequence is at least 75%, e.g., at least 80%, 85%, 90%, or 95% of the number of the referenced coding sequence.

The referenced coding sequence of any related aspect or embodiment described herein can be the native coding sequence or a degenerate sequence, such as a codon-optimized coding sequence designed for use in a particular host cell (e.g., optimized for expression in *Saccharomyces cerevisiae*).

The pullulanase can also include fused polypeptides or cleavable fusion polypeptides, as described supra.

Methods Using a Cellulosic-Containing Material

In some aspects, the methods described herein produce a fermentation product from a cellulosic-containing material. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic-containing material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one embodiment, the cellulosic-containing material is any biomass material. In another embodiment, the cellulosic-containing material is lignocellulose, which comprises cellulose, hemicelluloses, and lignin.

In one embodiment, the cellulosic-containing material is agricultural residue, herbaceous material (including energy crops), municipal solid waste, pulp and paper mill residue, waste paper, or wood (including forestry residue).

In another embodiment, the cellulosic-containing material is arundo, bagasse, bamboo, corn cob, corn fiber, corn stover, miscanthus, rice straw, switchgrass, or wheat straw.

In another embodiment, the cellulosic-containing material is aspen, eucalyptus, fir, pine, poplar, spruce, or willow.

In another embodiment, the cellulosic-containing material is algal cellulose, bacterial cellulose, cotton linter, filter paper, microcrystalline cellulose (e.g., AVICEL®), or phosphoric-acid treated cellulose.

In another embodiment, the cellulosic-containing material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic-containing material may be used as is or may be subjected to pretreatment, using conventional methods known in the art, as described herein. In a preferred embodiment, the cellulosic-containing material is pretreated.

The methods of using cellulosic-containing material can be accomplished using methods conventional in the art. Moreover, the methods of can be implemented using any conventional biomass processing apparatus configured to carry out the processes.

Cellulosic Pretreatment

In one embodiment the cellulosic-containing material is pretreated before saccharification.

In practicing the processes described herein, any pretreatment process known in the art can be used to disrupt plant cell wall components of the cellulosic-containing material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

In a one embodiment, the cellulosic-containing material is pretreated before saccharification (i.e., hydrolysis) and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

In one embodiment, the cellulosic-containing material is pretreated with steam. In steam pretreatment, the cellulosic-containing material is heated to disrupt the plant cell wall components, including lignin, hemicellulose, and cellulose to make the cellulose and other fractions, e.g., hemicellulose, accessible to enzymes. The cellulosic-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

In one embodiment, the cellulosic-containing material is subjected to a chemical pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115). In a specific embodiment the dilute acid pretreatment of cellulosic-containing material is carried out using 4% w/w sulfuric acid at 180° C. for 5 minutes.

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment. Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO2006/110891, WO2006/110899, WO2006/110900, and WO2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Tech-*

*nology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO2006/032282).

Ammonia fiber expansion (AFEX) involves treating the cellulosic-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one embodiment, the chemical pretreatment is carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic-containing material and held at a temperature in the range of preferably 140-200° C., e.g., 165-190° C., for periods ranging from 1 to 60 minutes.

In another embodiment, pretreatment takes place in an aqueous slurry. In preferred aspects, the cellulosic-containing material is present during pretreatment in amounts preferably between 10-80 wt. %, e.g., 20-70 wt. % or 30-60 wt. %, such as around 40 wt. %. The pretreated cellulosic-containing material can be unwashed or washed using any method known in the art, e.g., washed with water.

In one embodiment, the cellulosic-containing material is subjected to mechanical or physical pretreatment. The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in one embodiment, the cellulosic-containing material is subjected to physical (mechanical) or chemical pretreatment, or any combination thereof, to promote the separation and/or release of cellulose, hemicellulose, and/or lignin.

In one embodiment, the cellulosic-containing material is subjected to a biological pretreatment. The term "biological pretreatment" refers to any biological pretreatment that promotes the separation and/or release of cellulose, hemicellulose, and/or lignin from the cellulosic-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, DC, 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Enz. Microb. Tech. 18: 312-331; and Vallander and Eriksson, 1990, *Adv. Biochem. Eng./Biotechnol.* 42: 63-95).

Saccharification and Fermentation of Cellulosic-Containing Material

Saccharification (i.e., hydrolysis) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF).

SHF uses separate process steps to first enzymatically hydrolyze the cellulosic-containing material to fermentable sugars, e.g., glucose, cellobiose, and pentose monomers, and then ferment the fermentable sugars to ethanol. In SSF, the enzymatic hydrolysis of the cellulosic-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation organism can tolerate. It is understood herein that any method known in the art comprising pretreatment, enzymatic hydrolysis (saccharification), fermentation, or a combination thereof, can be used in the practicing the processes described herein.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

In the saccharification step (i.e., hydrolysis step), the cellulosic and/or starch-containing material, e.g., pretreated, is hydrolyzed to break down cellulose, hemicellulose, and/or starch to fermentable sugars, such as glucose, cellobiose, xylose, xylulose, arabinose, mannose, galactose, and/or soluble oligosaccharides. The hydrolysis is performed enzymatically e.g., by a cellulolytic enzyme composition. The enzymes of the compositions can be added simultaneously or sequentially.

Enzymatic hydrolysis may be carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic and/or starch-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

Saccharification in may be carried out using a cellulolytic enzyme composition. Such enzyme compositions are described below in the "Cellulolytic Enzyme Composition"-section below. The cellulolytic enzyme compositions can comprise any protein useful in degrading the cellulosic-containing material. In one aspect, the cellulolytic enzyme composition comprises or further comprises one or more (e.g., several) proteins selected from the group consisting of a cellulase, an AA9 (GH61) polypeptide, a hemicellulase, an esterase, an expansin, a ligninolytic enzyme, an oxidoreductase, a pectinase, a protease, and a swollenin.

In another embodiment, the cellulase is preferably one or more (e.g., several) enzymes selected from the group consisting of an endoglucanase, a cellobiohydrolase, and a beta-glucosidase.

In another embodiment, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another embodiment, the oxidoreductase is one or more (e.g., several) enzymes selected from the group consisting of a catalase, a laccase, and a peroxidase. The enzymes or enzyme compositions used in a processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

In one embodiment, an effective amount of cellulolytic or hemicellulolytic enzyme composition to the cellulosic-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic-containing material.

In one embodiment, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO2012/021401, and the soluble contents thereof. A liquor for cellulolytic enhancement of an AA9 polypeptide (GH61 polypeptide) can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one embodiment, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In the fermentation step, sugars, released from the cellulosic-containing material, e.g., as a result of the pretreatment and enzymatic hydrolysis steps, are fermented to ethanol, by a fermenting organism, such as yeast described herein. Hydrolysis (saccharification) and fermentation can be separate or simultaneous.

Any suitable hydrolyzed cellulosic-containing material can be used in the fermentation step in practicing the processes described herein. Such feedstocks include, but are not limited to carbohydrates (e.g., lignocellulose, xylans, cellulose, starch, etc.). The material is generally selected based on economics, i.e., costs per equivalent sugar potential, and recalcitrance to enzymatic conversion.

Production of ethanol by a fermenting organism using cellulosic-containing material results from the metabolism of sugars (monosaccharides). The sugar composition of the hydrolyzed cellulosic-containing material and the ability of the fermenting organism to utilize the different sugars has a direct impact in process yields. Prior to Applicant's disclosure herein, strains known in the art utilize glucose efficiently but do not (or very limitedly) metabolize pentoses like xylose, a monosaccharide commonly found in hydrolyzed material.

Compositions of the fermentation media and fermentation conditions depend on the fermenting organism and can easily be determined by one skilled in the art. Typically, the fermentation takes place under conditions known to be suitable for generating the fermentation product. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generate NAD+.

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

A fermentation stimulator can be used in a process described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Cellulolytic Enzymes and Compositions

A cellulolytic enzyme or cellulolytic enzyme composition may be present and/or added during saccharification. A cellulolytic enzyme composition is an enzyme preparation containing one or more (e.g., several) enzymes that hydrolyze cellulosic-containing material. Such enzymes include endoglucanase, cellobiohydrolase, beta-glucosidase, and/or combinations thereof.

In some embodiments, the fermenting organism comprises one or more (e.g., several) heterologous polynucleotides encoding enzymes that hydrolyze cellulosic-containing material (e.g., an endoglucanase, cellobiohydrolase, beta-glucosidase or combinations thereof). Any enzyme described or referenced herein that hydrolyzes cellulosic-containing material is contemplated for expression in the fermenting organism.

The cellulolytic enzyme may be any cellulolytic enzyme that is suitable for the host cells and/or the methods described herein (e.g., an endoglucanase, cellobiohydrolase, beta-glucosidase), such as a naturally occurring cellulolytic enzyme or a variant thereof that retains cellulolytic enzyme activity.

In some embodiments, the fermenting organism comprising a heterologous polynucleotide encoding a cellulolytic enzyme has an increased level of cellulolytic enzyme activity (e.g., increased endoglucanase, cellobiohydrolase, and/or beta-glucosidase) compared to the host cells without the heterologous polynucleotide encoding the cellulolytic enzyme, when cultivated under the same conditions. In some embodiments, the fermenting organism has an increased level of cellulolytic enzyme activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the cellulolytic enzyme, when cultivated under the same conditions.

Exemplary cellulolytic enzymes that can be used with the host cells and/or the methods described herein include bacterial, yeast, or filamentous fungal cellulolytic enzymes, e.g., obtained from any of the microorganisms described or referenced herein, as described supra under the sections related to proteases.

The cellulolytic enzyme may be of any origin. In an embodiment the cellulolytic enzyme is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme is derived from a strain of *Trichoderma reesei*.

The cellulolytic enzyme composition may further comprise one or more of the following polypeptides, such as enzymes: AA9 polypeptide (GH61 polypeptide) having cellulolytic enhancing activity, beta-glucosidase, xylanase, beta-xylosidase, CBH I, CBH II, or a mixture of two, three, four, five or six thereof.

The further polypeptide(s) (e.g., AA9 polypeptide) and/or enzyme(s) (e.g., beta-glucosidase, xylanase, beta-xylosidase, CBH I and/or CBH II may be foreign to the cellulolytic enzyme composition producing organism (e.g., *Trichoderma reesei*).

In an embodiment the cellulolytic enzyme composition comprises an AA9 polypeptide having cellulolytic enhancing activity and a beta-glucosidase.

In another embodiment the cellulolytic enzyme composition comprises an AA9 polypeptide having cellulolytic enhancing activity, a beta-glucosidase, and a CBH I.

In another embodiment the cellulolytic enzyme composition comprises an AA9 polypeptide having cellulolytic enhancing activity, a beta-glucosidase, a CBH I and a CBH II.

Other enzymes, such as endoglucanases, may also be comprised in the cellulolytic enzyme composition.

As mentioned above the cellulolytic enzyme composition may comprise a number of difference polypeptides, including enzymes.

In one embodiment, the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO2005/074656), and *Aspergillus oryzae* beta-glucosidase fusion protein (e.g., one disclosed in WO2008/057637, in particular shown as SEQ ID NOs: 59 and 60).

In another embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO2005/074656), and *Aspergillus fumigatus* beta-glucosidase (e.g., SEQ ID NO: 2 of WO2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, and *Aspergillus fumigatus* beta-glucosidase (e.g., SEQ ID NO: 2 of WO2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, and *Aspergillus fumigatus* beta-glucosidase (e.g., SEQ ID NO: 2 of WO2005/047499) or a variant disclosed in WO2012/044915 (hereby incorporated by reference), in particular one comprising one or more such as all of the following substitutions: F100D, S283G, N456E, F512Y.

In an embodiment the cellulolytic enzyme composition is a *Trichoderma reesei* cellulolytic composition, further comprising an AA9 (GH61A) polypeptide having cellulolytic enhancing activity, in particular the one derived from a strain of *Penicillium emersonii* (e.g., SEQ ID NO: 2 in WO2011/041397), *Aspergillus fumigatus* beta-glucosidase (e.g., SEQ ID NO: 2 in WO2005/047499) variant with one or more, in particular all of the following substitutions: F100D, S283G, N456E, F512Y and disclosed in WO2012/044915; *Aspergillus fumigatus* Cel7A CBH1, e.g., the one disclosed as SEQ ID NO: 6 in WO2011/057140 and *Aspergillus fumigatus* CBH II, e.g., the one disclosed as SEQ ID NO: 18 in WO2011/057140.

In a preferred embodiment the cellulolytic enzyme composition is a *Trichoderma reesei*, cellulolytic enzyme composition, further comprising a hemicellulase or hemicellulolytic enzyme composition, such as an *Aspergillus fumigatus* xylanase and *Aspergillus fumigatus* beta-xylosidase.

In an embodiment the cellulolytic enzyme composition also comprises a xylanase (e.g., derived from a strain of the genus *Aspergillus*, in particular *Aspergillus aculeatus* or *Aspergillus fumigatus*; or a strain of the genus *Talaromyces*, in particular *Talaromyces leycettanus*) and/or a beta-xylosidase (e.g., derived from *Aspergillus*, in particular *Aspergillus fumigatus*, or a strain of *Talaromyces*, in particular *Talaromyces emersonii*).

In an embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO2005/074656), *Aspergillus oryzae* beta-glucosidase fusion protein (e.g., one disclosed in WO2008/057637, in particular as SEQ ID NOs: 59 and 60), and *Aspergillus aculeatus* xylanase (e.g., Xyl II in WO94/21785).

In another embodiment the cellulolytic enzyme composition comprises a *Trichoderma reesei* cellulolytic preparation, further comprising *Thermoascus aurantiacus* GH61A polypeptide having cellulolytic enhancing activity (e.g., SEQ ID NO: 2 in WO2005/074656), *Aspergillus fumigatus* beta-glucosidase (e.g., SEQ ID NO: 2 of WO2005/047499) and *Aspergillus aculeatus* xylanase (Xyl II disclosed in WO94/21785).

In another embodiment the cellulolytic enzyme composition comprises a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO2005/074656), *Aspergillus fumigatus* beta-glucosidase (e.g., SEQ ID NO: 2 of WO2005/047499) and *Aspergillus aculeatus* xylanase (e.g., Xyl II disclosed in WO94/21785).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499) and *Aspergillus fumigatus* xylanase (e.g., Xyl III in WO2006/078256).

In another embodiment the cellulolytic enzyme composition comprises a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499), *Aspergillus fumigatus* xylanase (e.g., Xyl III in WO2006/078256), and CBH I from *Aspergillus fumigatus*, in particular Cel7A CBH1 disclosed as SEQ ID NO: 2 in WO2011/057140.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499), *Aspergillus fumigatus* xylanase (e.g., Xyl III in WO2006/078256), CBH I from *Aspergillus fumigatus*, in particular Cel7A CBH1 disclosed as SEQ ID NO: 2 in WO2011/057140, and CBH II derived from *Aspergillus fumigatus* in particular the one disclosed as SEQ ID NO: 4 in WO2013/028928.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499) or variant thereof with one or more, in particular all, of the following substitutions: F100D, S283G, N456E, F512Y; *Aspergillus fumigatus* xylanase (e.g., Xyl III in WO2006/078256), CBH I from *Aspergillus fumigatus*, in particular Cel7A CBH I disclosed as SEQ ID NO: 2 in WO2011/057140, and CBH II derived from *Aspergillus fumigatus*, in particular the one disclosed in WO2013/028928.

In another embodiment the cellulolytic enzyme composition is a *Trichoderma reesei* cellulolytic enzyme composition comprising the CBH I (GENSEQP Accession No. AZY49536 (WO2012/103293); a CBH II (GENSEQP Accession No. AZY49446 (WO2012/103288); a beta-glucosidase variant (GENSEQP Accession No. AZU67153 (WO2012/44915)), in particular with one or more, in particular all, of the following substitutions: F100D, S283G, N456E, F512Y; and AA9 (GH61 polypeptide) (GENSEQP Accession No. BAL61510 (WO2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288); a GH10 xylanase (GENSEQP Accession No. BAK46118 (WO2013/019827)); and a beta-xylosidase (GENSEQP Accession No. AZI04896 (WO2011/057140)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)); and an AA9 (GH61 polypeptide; GENSEQP Accession No. BAL61510 (WO2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)), an AA9 (GH61 polypeptide; GENSEQP Accession No. BAL61510 (WO2013/028912)), and a catalase (GENSEQP Accession No. BAC11005 (WO2012/130120)).

In an embodiment the cellulolytic enzyme composition is a *Trichoderma reesei* cellulolytic enzyme composition comprising a CBH I (GENSEQP Accession No. AZY49446 (WO2012/103288); a CBH II (GENSEQP Accession No. AZY49446 (WO2012/103288)), a beta-glucosidase variant (GENSEQP Accession No. AZU67153 (WO2012/44915)), with one or more, in particular all, of the following substitutions: F100D, S283G, N456E, F512Y; an AA9 (GH61 polypeptide; GENSEQP Accession No. BAL61510 (WO2013/028912)), a GH10 xylanase (GENSEQP Accession No. BAK46118 (WO2013/019827)), and a beta-xylosidase (GENSEQP Accession No. AZI04896 (WO2011/057140)).

In an embodiment the cellulolytic composition is a *Trichoderma reesei* cellulolytic enzyme preparation comprising an EG I (Swissprot Accession No. P07981), EG II (EMBL Accession No. M19373), CBH I (supra); CBH II (supra); beta-glucosidase variant (supra) with the following substitutions: F100D, S283G, N456E, F512Y; an AA9 (GH61 polypeptide; supra), GH10 xylanase (supra); and beta-xylosidase (supra).

All cellulolytic enzyme compositions disclosed in WO2013/028928 are also contemplated and hereby incorporated by reference.

The cellulolytic enzyme composition comprises or may further comprise one or more (several) proteins selected from the group consisting of a cellulase, a AA9 (i.e., GH61) polypeptide having cellulolytic enhancing activity, a hemicellulase, an expansin, an esterase, a laccase, a ligninolytic enzyme, a pectinase, a peroxidase, a protease, and a swollenin.

In one embodiment the cellulolytic enzyme composition is a commercial cellulolytic enzyme composition. Examples of commercial cellulolytic enzyme compositions suitable for use in a process of the invention include: CELLIC® CTec (Novozymes A/S), CELLIC® CTec2 (Novozymes A/S), CELLIC® CTec3 (Novozymes A/S), CELLUCLAST™ (Novozymes A/S), SPEZYME™ CP (Genencor Int.), ACCELLERASE™ 1000, ACCELLERASE 1500, ACCELLERASE™ TRIO (DuPont), FILTRASE® NL (DSM); METHAPLUS® S/L 100 (DSM), ROHAMENT™ 7069 W (Rohm GmbH), or ALTERNAFUEL® CMAX3™ (Dyadic International, Inc.). The cellulolytic enzyme composition may be added in an amount effective from about 0.001 to about 5.0 wt. % of solids, e.g., about 0.025 to about 4.0 wt. % of solids or about 0.005 to about 2.0 wt. % of solids.

Additional enzymes, and compositions thereof can be found in WO2011/153516 and WO2016/045569 (the contents of which are incorporated herein).

Additional polynucleotides encoding suitable cellulolytic enzymes may be obtained from microorganisms of any genus, including those readily available within the UniProtKB database (www.uniprot.org).

The cellulolytic enzyme coding sequences can also be used to design nucleic acid probes to identify and clone DNA encoding cellulolytic enzymes from strains of different genera or species, as described supra.

The polynucleotides encoding cellulolytic enzymes may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding cellulolytic enzymes are described supra.

In one embodiment, the cellulolytic enzyme has a mature polypeptide sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any cellulolytic enzyme described or referenced herein (e.g., any endoglucanase, cellobiohydrolase, or beta-glucosidase). In one aspect, the cellulolytic enzyme ha a mature polypeptide sequence that differs by no more than ten amino acids, e.g., by no more than five amino acids, by no more than four amino acids, by no more than three amino acids, by no more than two amino acids, or by one amino acid from any cellulolytic enzyme described or referenced herein. In one embodiment, the cellulolytic enzyme has a mature polypeptide sequence that comprises or consists of the amino acid sequence of any cellulolytic enzyme described or referenced herein, allelic variant, or a fragment thereof having cellulolytic enzyme activity. In one embodiment, the cellulolytic enzyme has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the cellulolytic enzyme has at least 20%, e.g., at least 40%, at least 50%, at least 60%, at least 70%, at least 80%, at least 90%, at least 95%, at least 96%, at least 97%, at least 98%, at least 99%, or 100% of the cellulolytic enzyme activity of any cellulolytic enzyme described or referenced herein (e.g., any endoglucanase, cellobiohydrolase, or beta-glucosidase) under the same conditions.

In one embodiment, the cellulolytic enzyme coding sequence hybridizes under at least low stringency conditions, e.g., medium stringency conditions, medium-high stringency conditions, high stringency conditions, or very high stringency conditions with the full-length complementary strand of the coding sequence from any cellulolytic enzyme described or referenced herein (e.g., any endoglucanase, cellobiohydrolase, or beta-glucosidase). In one embodiment, the cellulolytic enzyme coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any cellulolytic enzyme described or referenced herein.

In one embodiment, the polynucleotide encoding the cellulolytic enzyme comprises the coding sequence of any cellulolytic enzyme described or referenced herein (e.g., any endoglucanase, cellobiohydrolase, or beta-glucosidase). In one embodiment, the polynucleotide encoding the cellulolytic enzyme comprises a subsequence of the coding sequence from any cellulolytic enzyme described or referenced herein, wherein the subsequence encodes a polypeptide having cellulolytic enzyme activity. In one embodiment, the number of nucleotides residues in the subsequence is at least 75%, e.g., at least 80%, 85%, 90%, or 95% of the number of the referenced coding sequence.

The cellulolytic enzyme can also include fused polypeptides or cleavable fusion polypeptides, as described supra.

Xylose Metabolism

In one aspect, the fermenting organism (e.g., yeast cell) further comprises a heterologous polynucleotide encoding a xylose isomerase (XI). The xylose isomerase may be any xylose isomerase that is suitable for the host cells and the methods described herein, such as a naturally occurring xylose isomerase or a variant thereof that retains xylose isomerase activity. In one embodiment, the xylose isomerase is present in the cytosol of the host cells.

In some embodiments, the fermenting organism comprising a heterologous polynucleotide encoding a xylose isomerase has an increased level of xylose isomerase activity compared to the host cells without the heterologous polynucleotide encoding the xylose isomerase, when cultivated under the same conditions. In some embodiments, the fermenting organisms have an increased level of xylose isomerase activity of at least 5%, e.g., at least 10%, at least 15%, at least 20%, at least 25%, at least 50%, at least 100%, at least 150%, at least 200%, at least 300%, or at least 500% compared to the host cells without the heterologous polynucleotide encoding the xylose isomerase, when cultivated under the same conditions.

Exemplary xylose isomerases that can be used with the host cells and methods of use described herein include, but are not limited to, XIs from the fungus *Piromyces* sp. (WO2003/062430) or other sources (Madhavan et al., 2009, *Appl Microbiol Biotechnol.* 82(6), 1067-1078) have been expressed in *S. cerevisiae* host cells. Still other XIs suitable for expression in yeast have been described in US 2012/0184020 (an XI from Ruminococcus flavefaciens), WO2011/078262 (several XIs from *Reticulitermes speratus* and *Mastotermes darwiniensis*) and WO2012/009272 (constructs and fungal cells containing an XI from *Abiotrophia defectiva*). U.S. Pat. No. 8,586,336 describes a *S. cerevisiae* host cell expressing an XI obtained by bovine rumen fluid (shown herein as SEQ ID NO: 74).

Additional polynucleotides encoding suitable xylose isomerases may be obtained from microorganisms of any genus, including those readily available within the UniProtKB database (www.uniprot.org). In one embodiment, the xylose isomerases is a bacterial, a yeast, or a filamentous fungal xylose isomerase, e.g., obtained from any of the microorganisms described or referenced herein, as described supra.

The xylose isomerase coding sequences can also be used to design nucleic acid probes to identify and clone DNA encoding xylose isomerases from strains of different genera or species, as described supra.

The polynucleotides encoding xylose isomerases may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding xylose isomerases are described supra.

In one embodiment, the xylose isomerase has a mature polypeptide sequence of having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any xylose isomerase described or referenced herein (e.g., the xylose isomerase of SEQ ID NO: 74). In one aspect, the xylose isomerase has a mature polypeptide sequence that differs by no more than ten amino acids, e.g., by no more than five amino acids, by no more than four amino acids, by no more than three amino acids, by no more than two amino acids, or by one amino acid from any xylose isomerase described or referenced herein (e.g., the xylose isomerase of SEQ ID NO: 74). In one embodiment, the xylose isomerase has a mature polypeptide sequence that comprises or consists of the amino acid sequence of any xylose isomerase described or referenced herein (e.g., the xylose isomerase of SEQ ID NO: 74), allelic variant, or a fragment thereof having xylose isomerase activity. In one embodiment, the xylose isomerase has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the xylose isomerase has at least 20%, e.g., at least 40%, at least 50%, at least 60%, at least 70%, at least 80%, at least 90%, at least 95%, at least 96%, at least 97%, at least 98%, at least 99%, or 100% of the xylose isomerase activity of any xylose isomerase described or referenced herein (e.g., the xylose isomerase of SEQ ID NO: 74) under the same conditions.

In one embodiment, the xylose isomerase coding sequence hybridizes under at least low stringency conditions, e.g., medium stringency conditions, medium-high stringency conditions, high stringency conditions, or very high stringency conditions with the full-length complementary strand of the coding sequence from any xylose isomerase described or referenced herein (e.g., the xylose isomerase of SEQ ID NO: 74). In one embodiment, the xylose isomerase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any xylose isomerase described or referenced herein (e.g., the xylose isomerase of SEQ ID NO: 74).

In one embodiment, the heterologous polynucleotide encoding the xylose isomerase comprises the coding sequence of any xylose isomerase described or referenced herein (e.g., the xylose isomerase of SEQ ID NO: 74). In one embodiment, the heterologous polynucleotide encoding the xylose isomerase comprises a subsequence of the coding sequence from any xylose isomerase described or referenced herein, wherein the subsequence encodes a polypeptide having xylose isomerase activity. In one embodiment, the number of nucleotides residues in the subsequence is at least 75%, e.g., at least 80%, 85%, 90%, or 95% of the number of the referenced coding sequence.

The xylose isomerases can also include fused polypeptides or cleavable fusion polypeptides, as described supra.

In one aspect, the fermenting organism (e.g., yeast cell) further comprises a heterologous polynucleotide encoding a xylulokinase (XK). A xylulokinase, as used herein, provides enzymatic activity for converting D-xylulose to xylulose 5-phosphate. The xylulokinase may be any xylulokinase that is suitable for the host cells and the methods described herein, such as a naturally occurring xylulokinase or a variant thereof that retains xylulokinase activity. In one embodiment, the xylulokinase is present in the cytosol of the host cells.

In some embodiments, the fermenting organisms comprising a heterologous polynucleotide encoding a xylulokinase have an increased level of xylulokinase activity compared to the host cells without the heterologous polynucleotide encoding the xylulokinase, when cultivated under the same conditions. In some embodiments, the host cells have an increased level of xylose isomerase activity of at least 5%, e.g., at least 10%, at least 15%, at least 20%, at least 25%, at least 50%, at least 100%, at least 150%, at least 200%, at least 300%, or at least 500% compared to the host cells without the heterologous polynucleotide encoding the xylulokinase, when cultivated under the same conditions.

Exemplary xylulokinases that can be used with the fermenting organisms and methods of use described herein include, but are not limited to, the *Saccharomyces cerevisiae* xylulokinase of SEQ ID NO: 75. Additional polynucleotides encoding suitable xylulokinases may be obtained from microorganisms of any genus, including those readily available within the UniProtKB database (www.uniprot.org). In one embodiment, the xylulokinases is a bacterial, a yeast, or a filamentous fungal xylulokinase, e.g., obtained from any of the microorganisms described or referenced herein, as described supra.

The xylulokinase coding sequences can also be used to design nucleic acid probes to identify and clone DNA encoding xylulokinases from strains of different genera or species, as described supra.

The polynucleotides encoding xylulokinases may also be identified and obtained from other sources including microorganisms isolated from nature (e.g., soil, composts, water, etc.) or DNA samples obtained directly from natural materials (e.g., soil, composts, water, etc,) as described supra.

Techniques used to isolate or clone polynucleotides encoding xylulokinases are described supra.

In one embodiment, the xylulokinase has a mature polypeptide sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any xylulokinase described or referenced herein (e.g., the *Saccharomyces cerevisiae* xylulokinase of SEQ ID NO: 75). In one embodiment, the xylulokinase has a mature polypeptide sequence that differs by no more than ten amino acids, e.g., by no more than five amino acids, by no more than four amino acids, by no more than three amino acids, by no more than two amino acids, or by one amino acid from any xylulokinase described or referenced herein (e.g., the *Saccharomyces cerevisiae* xylulokinase of SEQ ID NO: 75). In one embodiment, the xylulokinase has a mature polypeptide sequence that comprises or consists of the amino acid sequence of any xylulokinase described or referenced herein (e.g., the *Saccharomyces cerevisiae* xylulokinase of SEQ ID NO: 75), allelic variant, or a fragment thereof having xylulokinase activity. In one embodiment, the xylulokinase has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the xylulokinase has at least 20%, e.g., at least 40%, at least 50%, at least 60%, at least 70%, at least 80%, at least 90%, at least 95%, at least 96%, at least 97%, at least 98%, at least 99%, or 100% of the xylulokinase activity of any xylulokinase described or referenced herein (e.g., the *Saccharomyces cerevisiae* xylulokinase of SEQ ID NO: 75) under the same conditions.

In one embodiment, the xylulokinase coding sequence hybridizes under at least low stringency conditions, e.g., medium stringency conditions, medium-high stringency conditions, high stringency conditions, or very high stringency conditions with the full-length complementary strand of the coding sequence from any xylulokinase described or referenced herein (e.g., the *Saccharomyces cerevisiae* xylulokinase of SEQ ID NO: 75). In one embodiment, the xylulokinase coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any xylulokinase described or referenced herein (e.g., the *Saccharomyces cerevisiae* xylulokinase of SEQ ID NO: 75).

In one embodiment, the heterologous polynucleotide encoding the xylulokinase comprises the coding sequence of any xylulokinase described or referenced herein (e.g., the *Saccharomyces cerevisiae* xylulokinase of SEQ ID NO: 75). In one embodiment, the heterologous polynucleotide encoding the xylulokinase comprises a subsequence of the coding sequence from any xylulokinase described or referenced herein, wherein the subsequence encodes a polypeptide having xylulokinase activity. In one embodiment, the number of nucleotides residues in the subsequence is at least 75%, e.g., at least 80%, 85%, 90%, or 95% of the number of the referenced coding sequence.

The xylulokinases can also include fused polypeptides or cleavable fusion polypeptides, as described supra.

In one aspect, the fermenting organism (e.g., yeast cell) further comprises a heterologous polynucleotide encoding a ribulose 5 phosphate 3-epimerase (RPE1). A ribulose 5 phosphate 3-epimerase, as used herein, provides enzymatic activity for converting L-ribulose 5-phosphate to L-xylulose 5-phosphate (EC 5.1.3.22). The RPE1 may be any RPE1 that is suitable for the host cells and the methods described herein, such as a naturally occurring RPE1 or a variant thereof that retains RPE1 activity. In one embodiment, the RPE1 is present in the cytosol of the host cells. In one embodiment, the recombinant cell comprises a heterologous polynucleotide encoding a ribulose 5 phosphate 3-epimerase (RPE1), wherein the RPE1 is *Saccharomyces cerevisiae* RPE1, or an RPE1 having at least 60%, e.g., at least 65%, 70%, 75%, 80%, 85%, 90%, 95%, 97%, 98%, 99%, or 100% sequence identity to a *Saccharomyces cerevisiae* RPE1.

In one aspect, the fermenting organism (e.g., yeast cell) further comprises a heterologous polynucleotide encoding a ribulose 5 phosphate isomerase (RKI1). A ribulose 5 phosphate isomerase, as used herein, provides enzymatic activity for converting ribose-5-phophate to ribulose 5-phosphate. The RKI1 may be any RKI1 that is suitable for the host cells and the methods described herein, such as a naturally occurring RKI1 or a variant thereof that retains RKI1 activity. In one embodiment, the RKI1 is present in the cytosol of the host cells.

In one embodiment, the fermenting organism comprises a heterologous polynucleotide encoding a ribulose 5 phosphate isomerase (RKI1), wherein the RKI1 is a *Saccharomyces cerevisiae* RKI1, or an RKI1 having a mature polypeptide sequence of at least 60%, e.g., at least 65%, 70%, 75%, 80%, 85%, 90%, 95%, 97%, 98%, 99%, or 100% sequence identity to a *Saccharomyces cerevisiae* RKI1.

In one aspect, the fermenting organism (e.g., yeast cell) further comprises a heterologous polynucleotide encoding a transketolase (TKL1). The TKL1 may be any TKL1 that is suitable for the host cells and the methods described herein, such as a naturally occurring TKL1 or a variant thereof that retains TKL1 activity. In one embodiment, the TKL1 is present in the cytosol of the host cells.

In one embodiment, the fermenting organism comprises a heterologous polynucleotide encoding a transketolase (TKL1), wherein the TKL1 is a *Saccharomyces cerevisiae* TKL1, or a TKL1 having a mature polypeptide sequence of at least 60%, e.g., at least 65%, 70%, 75%, 80%, 85%, 90%, 95%, 97%, 98%, 99%, or 100% sequence identity to a *Saccharomyces cerevisiae* TKL1.

In one aspect, the fermenting organism (e.g., yeast cell) further comprises a heterologous polynucleotide encoding a transaldolase (TAL1). The TAL1 may be any TAL1 that is suitable for the host cells and the methods described herein, such as a naturally occurring TAL1 or a variant thereof that retains TAL1 activity. In one embodiment, the TAL1 is present in the cytosol of the host cells.

In one embodiment, the fermenting organism comprises a heterologous polynucleotide encoding a transketolase (TAL1), wherein the TAL1 is a *Saccharomyces cerevisiae* TAL1, or a TAL1 having a mature polypeptide sequence of at least 60%, e.g., at least 65%, 70%, 75%, 80%, 85%, 90%, 95%, 97%, 98%, 99%, or 100% sequence identity to a *Saccharomyces cerevisiae* TAL1.

Fermentation Products

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one aspect, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603. In one embodiment, the fermentation product is ethanol.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene. In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. The term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery

The fermentation product, e.g., ethanol, can optionally be recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

In some aspects of the methods, the fermentation product after being recovered is substantially pure. With respect to the methods herein, "substantially pure" intends a recovered preparation that contains no more than 15% impurity, wherein impurity intends compounds other than the fermentation product (e.g., ethanol). In one variation, a substantially pure preparation is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of ethanol and contaminants, and sugar consumption can be performed using methods known in the art. For example, ethanol product, as well as other organic compounds, can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of ethanol in the fermentation broth can also be tested with the culture supernatant. Byproducts and residual sugar in the fermentation medium (e.g., glucose or xylose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

The invention may further be described in the following numbered paragraphs:

Paragraph [1]. A method of producing a fermentation product from a starch-containing or cellulosic-containing material comprising:
(a) saccharifying the starch-containing or cellulosic-containing material; and
(b) fermenting the saccharified material of step (a) with a fermenting organism;
wherein the fermenting organism comprises a heterologous polynucleotide encoding an alpha-amylase or a heterologous polynucleotide encoding a trehalase.

Paragraph [2]. The method of paragraph [1], wherein the alpha-amylase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 76-101, 121-174 and 231.

Paragraph [3]. The method of paragraph [1] or [2], wherein the heterologous polynucleotide encodes an alpha-amylase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 76-101, 121-174 and 231.

Paragraph [4]. The method of any one of paragraphs [1]-[3], wherein the heterologous polynucleotide encodes an alpha-amylase having a mature polypeptide sequence comprising or consisting of the amino acid sequence of any one of SEQ ID NOs: SEQ ID NOs: 76-101, 121-174 and 231.

Paragraph [5]. The method of any one of paragraphs [1]-[4], wherein the trehalase has mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 175-226.

Paragraph [6]. The method any one of paragraphs [1]-[5], wherein the heterologous polynucleotide encodes a trehalase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 175-226.

Paragraph [7]. The method of any one of paragraphs [1]-[6], wherein the heterologous polynucleotide encodes a trehalase having a mature polypeptide sequence comprising or consisting of the amino acid sequence of any one of SEQ ID NOs: SEQ ID NOs: 175-226.

Paragraph [8]. The method of any one of paragraphs [1]-[7], wherein saccharification of step (a) occurs on a starch-containing material, and wherein the starch-containing material is either gelatinized or ungelatinized starch.

Paragraph [9]. The method of paragraph [8], comprising liquefying the starch-containing material by contacting the material with an alpha-amylase prior to saccharification.

Paragraph [10]. The method of paragraph [9], wherein liquefying the starch-containing material and/or saccharifying the starch-containing material is conducted in presence of exogenously added protease.

Paragraph [11]. The method of any one of paragraphs [1]-[10], wherein fermentation is performed under reduced nitrogen conditions (e.g., less than 1000 ppm urea or ammonium hydroxide, such as less than 750 ppm, less than 500 ppm, less than 400 ppm, less than 300 ppm, less than 250 ppm, less than 200 ppm, less than 150 ppm, less than 100 ppm, less than 75 ppm, less than 50 ppm, less than 25 ppm, or less than 10 ppm).

Paragraph [12]. The method of any one of paragraphs [1]-[11], wherein fermentation and saccharification are performed simultaneously in a simultaneous saccharification and fermentation (SSF).

Paragraph [13]. The method of any one of paragraphs [1]-[11], wherein fermentation and saccharification are performed sequentially (SHF).

Paragraph [14]. The method of any one of paragraphs paragraph [1]-[13], comprising recovering the fermentation product from the from the fermentation.

Paragraph [15]. The method of paragraph [14], wherein recovering the fermentation product from the from the fermentation comprises distillation.

Paragraph [16]. The method of any one of paragraphs [1]-[15], wherein the fermentation product is ethanol.

Paragraph [17]. The method of any one of paragraphs [1]-[16], wherein the fermenting organism comprises a heterologous polynucleotide encoding a glucoamylase.

Paragraph [18]. The method of paragraph [17], wherein the glucoamylase has a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus glycoamylase* (e.g., a *Pycnoporus sanguineus* glucoamylase of SEQ ID NO: 229), a *Gloeophyllum* glucoamylase (e.g. a *Gloeophyllum sepiarium* of SEQ ID NO: 8), or a glucoamylase of any one of SEQ ID NOs: 102-113 (e.g., a *Saccharomycopsis fibuligera* glucoamylase of SEQ ID NO: 103 or 104, or a *Trichoderma reesei* glucoamylase of SEQ ID NO: 230).

Paragraph [19]. The method of any one of paragraphs [1]-[18], wherein the fermenting organism comprises a heterologous polynucleotide encoding a protease.

Paragraph [20]. The method of paragraph [19], wherein the protease has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69).

Paragraph [21]. The method of any one of paragraphs [1]-[20], wherein saccharification of step (a) occurs on a cellulosic-containing material, and wherein the cellulosic-containing material is pretreated.

Paragraph [22]. The method of paragraph [21], wherein the pretreatment is a dilute acid pretreatment.

Paragraph [23]. The method of any one of paragraphs [1]-[20], wherein saccharification occurs on a cellulosic-containing material, and wherein the enzyme composition comprises one or more enzymes selected from a cellulase, an AA9 polypeptide, a hemicellulase, a CIP, an esterase, an expansin, a ligninolytic enzyme, an oxidoreductase, a pectinase, a protease, and a swollenin.

Paragraph [24]. The method of paragraph [23], wherein the cellulase is one or more enzymes selected from an endoglucanase, a cellobiohydrolase, and a beta-glucosidase.

Paragraph [25]. The method of paragraph or [24], wherein the hemicellulase is one or more enzymes selected a xylanase, an acetylxylan esterase, a feruloyl esterase, an arabinofuranosidase, a xylosidase, and a glucuronidase.

Paragraph [26]. The method of any one of paragraphs [1]-[25], wherein the fermenting organism is a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell.

Paragraph [27]. The method of any one of paragraphs [1]-[26], wherein the fermenting organism is a *Saccharomyces cerevisiae* cell.

Paragraph [28]. A recombinant yeast cell comprising a heterologous polynucleotide encoding an alpha-amylase or a heterologous polynucleotide encoding a trehalase.

Paragraph [29]. The recombinant yeast cell of paragraph [28], wherein the alpha-amylase has a mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 76-101, 121-174 and 231.

Paragraph [30]. The recombinant yeast cell of paragraph or [29], wherein the heterologous polynucleotide encodes an alpha-amylase having a mature polypeptide sequence that differs by no more than ten amino acids, e.g., by no more than five amino acids, by no more than four amino acids, by no more than three amino acids, by no more than two amino acids, or by one amino acid from the amino acid sequence of any one of SEQ ID NOs: 76-101, 121-174 and 231.

Paragraph [31]. The recombinant yeast cell of any one of paragraphs [28]-[30], wherein the heterologous polynucleotide encodes an alpha-amylase having a mature polypeptide sequence comprising or consisting of the amino acid sequence of any one of SEQ ID NOs: SEQ ID NOs: 76-101, 121-174 and 231.

Paragraph [32]. The recombinant yeast cell of any one of paragraphs [28]-[31], wherein the trehalase has mature polypeptide sequence with 60%, e.g., at least 65%, 70%, 75%, 80%, 85%, 90%, 95%, 97%, 98%, 99%, or 100% sequence identity, to the amino acid sequence of any one of SEQ ID NOs: 175-226.

Paragraph [33]. The recombinant yeast cell of any one of paragraphs [28]-[32], wherein the heterologous polynucleotide encodes a trehalase having a mature polypeptide sequence that differs by no more than ten amino acids, e.g., by no more than five amino acids, by no more than four amino acids, by no more than three amino acids, by no more than two amino acids, or one amino acid from the amino acid sequence of any one of SEQ ID NOs: 175-226.

Paragraph [34]. The recombinant yeast cell of any one of paragraphs [28]-[33], wherein the heterologous polynucleotide encodes a trehalase having a mature polypeptide sequence comprising or consisting of the amino acid sequence of any one of SEQ ID NOs: SEQ ID NOs: 175-226

Paragraph [35]. The recombinant yeast cell of any one of paragraphs [28]-[34], wherein the fermenting organism comprises a heterologous polynucleotide encoding a glucoamylase.

Paragraph [36]. The recombinant yeast cell of paragraph [35], wherein the glucoamylase has a mature polypeptide sequence with 60%, e.g., at least 65%, 70%, 75%, 80%, 85%, 90%, 95%, 97%, 98%, 99%, or 100% sequence identity, to the amino acid sequence of a *Pycnoporus glycoamylase* (e.g., a *Pycnoporus sanguineus* glucoamylase of SEQ ID NO: 229), a *Gloeophyllum glucoamylase* (e.g. a *Gloeophyllum sepiarium* of SEQ ID NO: 8), or a *glucoamylase* of any one of SEQ ID NOs: 102-113 (e.g., a *Saccharomycopsis fibuligera glucoamylase* of SEQ ID NO: 103 or 104, or a *Trichoderma reesei glucoamylase* of SEQ ID NO: 230).

Paragraph [37]. The recombinant yeast cell of any one of paragraphs [28]-[36], wherein the fermenting organism comprises a heterologous polynucleotide encoding a protease.

Paragraph [38]. The recombinant yeast cell of paragraph [37], wherein the protease has a mature polypeptide sequence of at least 60%, e.g., at least 65%, 70%, 75%, 80%, 85%, 90%, 95%, 97%, 98%, 99%, or 100% sequence identity to the amino acid sequence of any one of SEQ ID NOs: 9-73 (e.g., any one of SEQ ID NOs: 9, 14, 16, 21, 22, 33, 41, 45, 61, 62, 66, 67, and 69; such as any one of SEQ NOs: 9, 14, 16, and 69).

Paragraph [39]. The recombinant yeast of any one of paragraphs [28]-[38], wherein the cell is a *Saccharomyces, Rhodotorula, Schizosaccharomyces, Kluyveromyces, Pichia, Hansenula, Rhodosporidium, Candida, Yarrowia, Lipomyces, Cryptococcus,* or *Dekkera* sp. cell.

Paragraph [40]. The recombinant yeast of paragraph [39], wherein the cell is a *Saccharomyces cerevisiae* cell.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. All references are specifically incorporated by reference for that which is described.

The following examples are offered to illustrate certain aspects of the present invention, but not in any way intended to limit the scope of the invention as claimed.

EXAMPLES

Materials and Methods

Chemicals used as buffers and substrates were commercial products of at least reagent grade.

ETHANOL RED® ("ER"): *Saccharomyces cerevisiae* yeast available from Fermentis/Lesaffre, USA.

YPD+clonNAT plates were composed of 10 g of yeast extract, 20 g of peptone, 20 g bacto agar, and deionized water to 960 ml, followed by autoclave treatment. 40 ml sterile 50% glucose and 1 ml clonNAT stock solution was added, followed by mixing and pouring.

clonNAT stock solution was composed of 2 g nourseothricin sulfate and deionized water to 20 ml.

Example 1: Construction of Yeast Strains Expressing a Heterologous Alpha-Amylase This example describes the construction of yeast cells containing a heterologous alpha-amylase under control of an S. cerevisiae TDH3 promoter (SEQ ID NO: 1) or ADH1 promoter (SEQ ID NO: 5). Three pieces of DNA containing the promoter, gene and terminator were designed to allow for homologous recombination between the 3 DNA fragments and into the X-3 locus of the yeast yMHCT484 (PCT/US2018/035596). The resulting strain has one promoter containing fragment (left), one gene containing fragment (middle) and one ENO2 terminator (SEQ ID NO: 228) fragment (right) integrated into the S. cerevisiae genome at the X-3 locus.

Construction of the Promoter Containing Fragments (Left Fragments)

Synthetic linear uncloned DNA containing 300 bp homology to the X-3 site, S. cerevisiae promoter ADH1 (SEQ ID NO: 5) or THD3 (SEQ ID NO: 1) and S. cerevisiae EXG1 signal sequence (SEQ ID NO: 227) were synthesized by Thermo Fisher Scientific. The 2 linear DNAs were designated 17ABCK4P and 17ABCK3P for each promoter listed above, respectively. To generate additional linear DNA for transformation into yeast, the DNA containing the left cassette was PCR amplified from 17ABCK4P and 17ABCK3P.

Construction of the Alpha-Amylase-Containing Fragments (Middle Fragments)

Synthetic linear uncloned DNA containing S. cerevisiae EXG1 signal peptide coding sequence (encoding the signal of SEQ ID NO: 227), a codon-optimized alpha-amylase gene and 50 bp of ENO2 terminator (SEQ ID NO: 228), were synthesized by Thermo Fisher Scientific.

To generate linear DNA for transformation into yeast, the DNA containing the alpha-amylase cassette was PCR amplified from the synthetic DNA with primers 1222985 (5'-ATGAT GAAAA AATAA GCAGA AAAGA CTAAT AATTC TTAGT TAAAA GC-3'; SEQ ID NO: 235) and 1222984 (5'-ATGCT TTCGC TTAAA ACGTT ACTGT G-3'; SEQ ID NO: 236). Fifty pmoles each of forward and reverse primer was used in a PCR reaction containing 5 ng of plasmid DNA as template, 0.1 mM each dATP, dGTP, dCTP, dTTP, 1× Phusion HF Buffer (Thermo Fisher Scientific), and 2 units Phusion Hot Start DNA polymerase in a final volume of 50 µL. The PCR was performed in a T100™ Thermal Cycler (Bio-Rad Laboratories, Inc.) programmed for one cycle at 98° C. for 1 minute followed by 32 cycles each at 98° C. for 10 seconds, 55° C. for 30 seconds, and 72° C. for 2 minutes with a final extension at 72° C. for 10 minutes. Following thermocycling, the PCR reaction products gel isolated and cleaned up using the NucleoSpin Gel and PCR clean-up kit (Machery-Nagel). The resulting linear DNAs were designated as indicated in Table 4.

TABLE 4

Alpha-amylase DNA product names and associated enzyme

| Product Number | DNA format | Signal peptide | Donor Organism (catalytic domain) | SEQ ID NO: (mature polypeptide) | Terminator Fragment |
|---|---|---|---|---|---|
| 17ABDQYP | linear | EXG1 | Rhizomucor pusillus | 121 | ENO2 |
| 17ABDQXP | linear | EXG1 | Bacillus licheniformis | 122 | ENO2 |
| 17ABDQWP | linear | EXG1 | Aspergillus niger | 123 | ENO2 |
| 17ABDQVP | linear | EXG1 | Aspergillus tamarii | 124 | ENO2 |
| 17ABDQUP | linear | EXG1 | Acidomyces richmondensis | 125 | ENO2 |
| 17ABDQTP | linear | EXG1 | Aspergillus bombycis | 126 | ENO2 |
| 17ABDQSP | linear | EXG1 | Alternaria sp | 127 | ENO2 |
| 17ABDQRP | linear | EXG1 | Rhizopus microsporus | 128 | ENO2 |
| 17ABDQQP | linear | EXG1 | Syncephalastrum racemosum | 129 | ENO2 |
| 17ABDQPP | linear | EXG1 | Rhizomucor pusillus | 130 | ENO2 |
| 17ABDQOP | linear | EXG1 | Dichotomocladium hesseltinei | 131 | ENO2 |
| 17ABDQNP | linear | EXG1 | Lichtheimia ramosa | 132 | ENO2 |
| 17ABDQMP | linear | EXG1 | Penicillium aethiopicum | 133 | ENO2 |
| 17ABDQLP | linear | EXG1 | Subulispora sp | 134 | ENO2 |
| 17ABDQKP | linear | EXG1 | Trichoderma paraviridescens | 135 | ENO2 |
| 17ABDQJP | linear | EXG1 | Byssoascus striatosporus | 136 | ENO2 |
| 17ABDQIP | linear | EXG1 | Aspergillus brasiliensis | 137 | ENO2 |
| 17ABDQHP | linear | EXG1 | Penicillium subspinulosum | 138 | ENO2 |
| 17ABDQGP | linear | EXG1 | Penicillium antarcticum | 139 | ENO2 |
| 17ABDQFP | linear | EXG1 | Penicillium coprophilum | 140 | ENO2 |
| 17ABDQEP | linear | EXG1 | Penicillium olsonii | 141 | ENO2 |
| 17ABDQDP | linear | EXG1 | Penicillium vasconiae | 142 | ENO2 |
| 17ABDQCP | linear | EXG1 | Penicillium sp | 143 | ENO2 |
| 17ABDQBP | linear | EXG1 | Heterocephalum aurantiacum | 144 | ENO2 |
| 17ABDQAP | linear | EXG1 | Neosartorya massa | 145 | ENO2 |
| 17ABDP7P | linear | EXG1 | Penicillium janthinellum | 146 | ENO2 |
| 17ABDP6P | linear | EXG1 | Aspergillus brasiliensis | 147 | ENO2 |
| 17ABDP5P | linear | EXG1 | Aspergillus westerdijkiae | 148 | ENO2 |
| 17ABDP4P | linear | EXG1 | Hamigera avellanea | 149 | ENO2 |
| 17ABDP3P | linear | EXG1 | Hamigera avellanea | 150 | ENO2 |
| 17ABDP2P | linear | EXG1 | Meripilus giganteus | 151 | ENO2 |

TABLE 4-continued

Alpha-amylase DNA product names and associated enzyme

| Product Number | DNA format | Signal peptide | Donor Organism (catalytic domain) | SEQ ID NO: (mature polypeptide) | Terminator Fragment |
|---|---|---|---|---|---|
| 17ABDPZP | linear | EXG1 | Cerrena unicolor | 152 | ENO2 |
| 17ABDPYP | linear | EXG1 | Physalacria cryptomeriae | 153 | ENO2 |
| 17ABDPXP | linear | EXG1 | Lenzites betulinus | 154 | ENO2 |
| 17ABDPWP | linear | EXG1 | Trametes ljubarskyi | 155 | ENO2 |
| 17ABDPVP | linear | EXG1 | Bacillus subtilis | 156 | ENO2 |
| 17ABDPUP | linear | EXG1 | Bacillus subtilis subsp. subtilis | 157 | ENO2 |
| 17ABDPTP | linear | EXG1 | Schwanniomyces occidentalis | 158 | ENO2 |
| 17ABDPSP | linear | EXG1 | Rhizomucor pusillus | 159 | ENO2 |
| 17ABDPRP | linear | EXG1 | Aspergillus niger | 160 | ENO2 |
| 17ABDPQP | linear | EXG1 | Bacillus stearothermophilus | 161 | ENO2 |
| 17ABDPPP | linear | EXG1 | Bacillus halmapalus | 162 | ENO2 |
| 17ABDPOP | linear | EXG1 | Aspergillus oryzae | 163 | ENO2 |
| 17ABDPNP | linear | EXG1 | Bacillus amyloliquefaciens | 164 | ENO2 |
| 17ABDPMP | linear | EXG1 | Rhizomucor pusillus | 165 | ENO2 |
| 17ABDPLP | linear | EXG1 | Kionochaeta ivoriensis | 166 | ENO2 |
| 17ABDPKP | linear | EXG1 | Aspergillus niger | 167 | ENO2 |
| 17ABDPJP | linear | EXG1 | Aspergillus oryzae | 168 | ENO2 |
| 17ABDPIP | linear | EXG1 | Penicillium canescens | 169 | ENO2 |
| 17ABDPHP | linear | EXG1 | Acidomyces acidothermus | 170 | ENO2 |
| 17ABDQ4P | linear | EXG1 | Kinochaeta ivoriensis | 171 | ENO2 |
| 17ABDQ3P | linear | EXG1 | Aspergillus terreus | 172 | ENO2 |
| 17ABDQ2P | linear | EXG1 | Thamnidium elegans | 173 | ENO2 |
| 17ABDQZP | linear | EXG1 | Meripilus giganteus | 174 | ENO2 |

Figure 3:
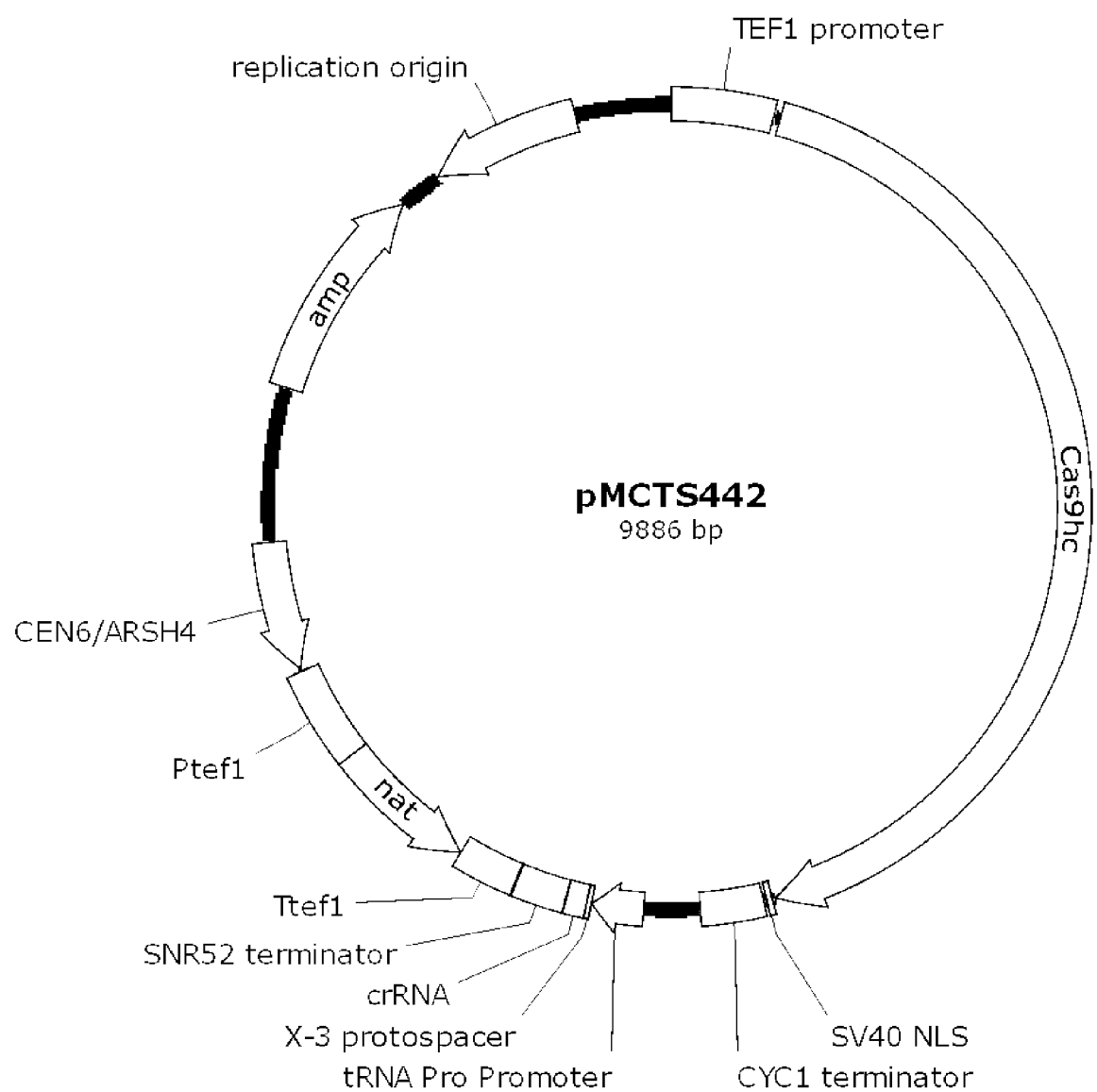
FIG. 3 shows a plasmid map for pMcTs442.

Integration of the Left, Middle and Right-Hand Fragments to Generate Yeast Strains with a Heterologous Alpha-Amylase The yeast yMHCT484 (PCT/US2018/035596) was transformed with the left, middle and right integration fragments described above. In each transformation pool a fixed left fragment and right fragment were used. The middle fragment consisted of a pool of 19-21 middle fragments containing the alpha-amylase gene with 100-600 ng of each fragment (1500 ng total). To aid homologous recombination of the left, middle and right fragments at the genomic X-3 sites a plasmid containing Cas9 and guide RNA specific to X-3 (pMcTs442) was also used in the transformation. These four components were transformed into the into S. cerevisiae strain yMHCT484 following a yeast electroporation protocol (See, Thompson et al. Yeast. 1998 Apr. 30; 14(6):565-71). Transformants were selected on YPD+cloNAT to select for transformants that contain the CRISPR/Cas9 plasmid pMcTs442 (FIG. 3). Transformants were picked using a Q-pix Colony Picking System (Molecular Devices) to inoculate 1 well of 96-well plate containing YPD+clonNAT media. The plates were grown for 2 days then glycerol was added to 20% final concentration and the plates were stored at −80° C. until needed. Integration of specific alpha-amylase construct was verified by PCR with locus specific primers and subsequent sequencing. The strains generated in this example are shown in Table 5.

TABLE 5

Alpha-amylase expressing S. cerevisiae strains.

| left piece | middle piece | Promoter | Signal peptide | Alpha-amylase gene donor (catalytic domain) | SEQ ID NO: (mature polypeptide) | strain ID |
|---|---|---|---|---|---|---|
| 17ABCK4P | 17ABDQJP | ADH1 | EXG1 | Byssoascus striatosporus | 136 | P110-A08 |
| 17ABCK4P | 17ABDQHP | ADH1 | EXG1 | Penicillium subspinulosum | 138 | P110-A09 |
| 17ABCK4P | 17ABDQUP | ADH1 | EXG1 | Acidomyces richmondensis | 125 | P110-B01 |
| 17ABCK4P | 17ABDQKP | ADH1 | EXG1 | Trichoderma paraviridescens | 135 | P110-B04 |
| 17ABCK4P | 17ABDQXP | ADH1 | EXG1 | Bacillus licheniformis | 122 | P110-B05 |
| 17ABCK4P | 17ABDQMP | ADH1 | EXG1 | Penicillium aethiopicum | 133 | P110-B08 |
| 17ABCK4P | 17ABDQSP | ADH1 | EXG1 | Alternaria sp | 127 | P110-C05 |
| 17ABCK4P | 17ABDQOP | ADH1 | EXG1 | Dichotomocladium hesseltinei | 131 | P110-D01 |
| 17ABCK4P | 17ABDQTP | ADH1 | EXG1 | Aspergillus bombycis | 126 | P110-D02 |
| 17ABCK4P | 17ABDQIP | ADH1 | EXG1 | Aspergillus brasiliensis | 137 | P110-D10 |
| 17ABCK4P | 17ABDQVP | ADH1 | EXG1 | Aspergillus tamarii | 124 | P110-F02 |
| 17ABCK4P | 17ABDQTP | ADH1 | EXG1 | Aspergillus bombycis | 126 | P110-F07 |
| 17ABCK4P | 17ABDQHP | ADH1 | EXG1 | Penicillium subspinulosum | 138 | P110-G03 |
| 17ABCK4P | 17ABDQUP | ADH1 | EXG1 | Acidomyces richmondensis | 125 | P110-G04 |
| 17ABCK4P | 17ABDQSP | ADH1 | EXG1 | Alternaria sp | 127 | P110-G06 |
| 17ABCK4P | 17ABDQLP | ADH1 | EXG1 | Subulispora sp | 134 | P110-H02 |

TABLE 5-continued

Alpha-amylase expressing *S. cerevisiae* strains.

| left piece | middle piece | Promoter | Signal peptide | Alpha-amylase gene donor (catalytic domain) | SEQ ID NO: (mature polypeptide) | strain ID |
|---|---|---|---|---|---|---|
| 17ABCK4P | 17ABDQHP | ADH1 | EXG1 | *Penicillium subspinulosum* | 138 | P110-H05 |
| 17ABCK4P | 17ABDQGP | ADH1 | EXG1 | *Penicillium antarcticum* | 139 | P110-H07 |
| 17ABCK4P | 17ABDPZP | ADH1 | EXG1 | *Cerrena unicolor* | 152 | P111-C03 |
| 17ABCK4P | 17ABDQAP | ADH1 | EXG1 | *Neosartorya massa* | 145 | P111-D10 |
| 17ABCK4P | 17ABDQDP | ADH1 | EXG1 | *Penicillium vasconiae* | 142 | P111-F01 |
| 17ABCK4P | 17ABDQCP | ADH1 | EXG1 | *Penicillium* sp | 143 | P111-H08 |
| 17ABCK4P | 17ABDPJP | ADH1 | EXG1 | *Aspergillus oryzae* | 168 | P112-A03 |
| 17ABCK4P | 17ABDQ3P | ADH1 | EXG1 | *Aspergillus terreus* | 172 | P112-A07 |
| 17ABCK4P | 17ABDQ3P | ADH1 | EXG1 | *Aspergillus terreus* | 172 | P112-B11 |
| 17ABCK4P | 17ABDQ2P | ADH1 | EXG1 | *Thamnidium elegans* | 173 | P112-C09 |
| 17ABCK4P | 17ABDPPP | ADH1 | EXG1 | *Bacillus halmapalus* | 162 | P112-D05 |
| 17ABCK4P | 17ABDPJP | ADH1 | EXG1 | *Aspergillus oryzae* | 168 | P112-D06 |
| 17ABCK4P | 17ABDPMP | ADH1 | EXG1 | *Rhizomucor pusillus* | 165 | P112-H03 |
| 17ABCK3P | 17ABDQIP | TDH3 | EXG1 | *Aspergillus brasiliensis* | 137 | P113-A03 |
| 17ABCK3P | 17ABDQYP | TDH3 | EXG1 | *Rhizomucor pusillus* | 121 | P113-B05 |
| 17ABCK3P | 17ABDQXP | TDH3 | EXG1 | *Bacillus licheniformis* | 122 | P113-B06 |
| 17ABCK3P | 17ABDQTP | TDH3 | EXG1 | *Aspergillus bombycis* | 126 | P113-C03 |
| 17ABCK3P | 17ABDQNP | TDH3 | EXG1 | *Lichtheimia ramosa* | 132 | P113-C06 |
| 17ABCK3P | 17ABDQVP | TDH3 | EXG1 | *Aspergillus tamarii* | 124 | P113-C09 |
| 17ABCK3P | 17ABDQYP | TDH3 | EXG1 | *Rhizomucor pusillus* | 121 | P113-C10 |
| 17ABCK3P | 17ABDQRP | TDH3 | EXG1 | *Rhizopus microsporus* | 128 | P113-D07 |
| 17ABCK3P | 17ABDQVP | TDH3 | EXG1 | *Aspergillus tamarii* | 124 | P113-D08 |
| 17ABCK3P | 17ABDQSP | TDH3 | EXG1 | *Alternaria* sp | 127 | P113-D10 |
| 17ABCK3P | 17ABDQNP | TDH3 | EXG1 | *Lichtheimia ramosa* | 132 | P113-F02 |
| 17ABCK3P | 17ABDQQP | TDH3 | EXG1 | *Syncephalastrum racemosum* | 129 | P113-F05 |
| 17ABCK3P | 17ABDQJP | TDH3 | EXG1 | *Byssoascus striatosporus* | 136 | P113-G04 |
| 17ABCK3P | 17ABDQTP | TDH3 | EXG1 | *Aspergillus bombycis* | 126 | P113-G09 |
| 17ABCK3P | 17ABDPSP | TDH3 | EXG1 | *Rhizomucor pusillus* | 159 | P114-A04 |
| 17ABCK3P | 17ABDP4P | TDH3 | EXG1 | *Hamigera avellanea* | 149 | P114-B02 |
| 17ABCK3P | 17ABDPUP | TDH3 | EXG1 | *Bacillus subtilis* subsp. *subtilis* | 157 | P114-B08 |
| 17ABCK3P | 17ABDPUP | TDH3 | EXG1 | *Bacillus subtilis* subsp. *subtilis* | 157 | P114-C01 |
| 17ABCK3P | 17ABDP2P | TDH3 | EXG1 | *Meripilus giganteus* | 151 | P114-C04 |
| 17ABCK3P | 17ABDPVP | TDH3 | EXG1 | *Bacillus subtilis* | 156 | P114-C05 |
| 17ABCK3P | 17ABDQAP | TDH3 | EXG1 | *Neosartorya massa* | 145 | P114-C06 |
| 17ABCK3P | 17ABDQEP | TDH3 | EXG1 | *Penicillium olsonii* | 141 | P114-C07 |
| 17ABCK3P | 17ABDPTP | TDH3 | EXG1 | *Schwanniomyces occidentalis* | 158 | P114-D02 |
| 17ABCK3P | 17ABDPRP | TDH3 | EXG1 | *Aspergillus niger* | 160 | P114-D07 |
| 17ABCK3P | 17ABDP3P | TDH3 | EXG1 | *Hamigera avellanea* | 150 | P114-F06 |
| 17ABCK3P | 17ABDP6P | TDH3 | EXG1 | *Aspergillus brasiliensis* | 147 | P114-F07 |
| 17ABCK3P | 17ABDPUP | TDH3 | EXG1 | *Bacillus subtilis* subsp. *subtilis* | 157 | P114-F08 |
| 17ABCK3P | 17ABDP2P | TDH3 | EXG1 | *Meripilus giganteus* | 151 | P114-H02 |
| 17ABCK3P | 17ABDQAP | TDH3 | EXG1 | *Neosartorya massa* | 145 | P114-H03 |
| 17ABCK3P | 17ABDPZP | TDH3 | EXG1 | *Cerrena unicolor* | 152 | P114-H07 |
| 17ABCK3P | 17ABDQAP | TDH3 | EXG1 | *Neosartorya massa* | 145 | P114-H08 |
| 17ABCK3P | 17ABDPKP | TDH3 | EXG1 | *Aspergillus niger* | 167 | P115-B03 |
| 17ABCK3P | 17ABDPMP | TDH3 | EXG1 | *Rhizomucor pusillus* | 165 | P115-C11 |
| 17ABCK3P | 17ABDPMP | TDH3 | EXG1 | *Rhizomucor pusillus* | 165 | P115-D09 |
| 17ABCK3P | 17ABDQ3P | TDH3 | EXG1 | *Aspergillus terreus* | 172 | P115-F06 |
| 17ABCK3P | 17ABDPJP | TDH3 | EXG1 | *Aspergillus oryzae* | 168 | P115-G04 |

Example 2: Activity Assay of Yeast Strains Expressing Alpha-Amylase

Yeast strains from Example 1 were cultivated overnight in standard YPD media containing 2% or 6% glucose. The cultured yeast medium was subjected to centrifugation at 3500 rpm for 10 min to harvest the supernatant. The culture supernatant is used for enzyme activity assays, as described below. Yeast may also be cultivated using other cultivation media such as minimal YNB media or clarified and filtered industrial liquefied corn mash.

Glucoamylase Activity Assay

Glucoamylase activity was measured using maltose as substrate. Enzyme-catalyzed hydrolysis of maltose yields glucose as the reaction product which can be detected and quantified using commercially available assay kits such as Wako Diagnostics AUTOKIT GLUCOSE C2. Reagents provided in the assay kits react with glucose resulted in a color change with maximal absorbance at 505 nm. The absorbance intensity measured spectrophotometrically is proportional to glucoamylase activity. The absorbance at 505 nm can be fit to standard curve generated using a purified glucoamylase enzyme to estimate enzyme activity. Reaction conditions and color development are described in Table 5 and Table 6, respectively. Glucoamylase units (AGU) for glucoamylase activity is defined as the amount of enzyme required to hydrolyze one micromole maltose per minute under the reaction conditions.

TABLE 5

| Glucoamylase reaction conditions | |
| --- | --- |
| Appropriate amount of yeast supernatant | 10-200 μl |
| Substrate | maltose, 10 mM |
| Buffer | acetate, 0.1M |
| pH | 5.0 ± 0.05 |
| Incubation temperature | 32° C. |
| Reaction time | 5-20 min |
| Glucoamylase assay range | 0.001-0.036 AGU/ml |

TABLE 6

| Color development | |
| --- | --- |
| Reaction mixture | 10 μl |
| AUTOKIT GLUCOSE C2 developing reagent | 200 μl |
| Incubation temperature | room temperature or 37° C. |
| Reaction time | 10-25 min |
| Wavelength | 505 nm |

Alpha Amylase Activity Assay

Alpha amylase activity was measured using blocked-p-nitrophenyl-maltoheptaoside (BPNPG7) as substrate, which is included as the amylase HR reagent from Megazymes. Enzyme hydrolysis of the alpha-bond of BPNPG7 releases a blocked maltosaccharide oligomer and a p-nitrophenyl maltosaccharide oligomer. The p-nitrophenyl maltosaccharide will react with a glucoamylase from Megayzmes yielding p-nitrophenol which may be detected using commercially available assay kits such as MEGAZYMES R-AMHR4. Reagents provided in the assay kits will specifically react with p-nitrophenol resulting in color formation. The color intensity measured using a spectrophotometer or microplate reader is proportional to alpha-amylase activity. Reaction conditions and color development are described in Table 7 and Table 8, respectively.

TABLE 7

| Alpha-amylase reaction conditions | |
| --- | --- |
| Appropriate amount of yeast supernatant | 10-200 μl |
| Substrate | blocked-p-nitrophenyl-maltoheptaoside (BPNPG7), 10 mM |
| Buffer | acetate, 0.1M |
| pH | 5.0 ± 0.05 |
| Incubation temperature | 32° C. |
| Reaction time | 20 min |
| Alpha amylase assay range | 5-200 ng/ml |

TABLE 8

| Color development | |
| --- | --- |
| Reaction mixture | 20 μl |
| blocked-p-nitrophenyl-maltoheptaoside (BPNPG7) | 80 μl |
| Stop solution (4% Tris) | 100 μl |
| Incubation temperature | Room temperature - 32° C. |
| Reaction time | 10-25 min |
| Wavelength | 400 nm |

Results

The absorbance at 505 nm increases as the amount of purified glucoamylase added to hydrolyze maltose to glucose increases. The absorbance at 400 nm increases as the amount of purified alpha-amylase added increases. Specifically, the alpha-amylase hydrolyzes blocked-p-nitrophenyl-maltoheptaoside (BPNPG7) releasing a blocked maltosaccharide oligomer and a p-nitrophenyl maltosaccharide oligomer. The p-nitrophenyl maltosaccharide reacts with a glucoamylase from Megazymes yielding p-nitrophenol which absorbs at 400 nm. A purified glucoamylase and alpha amylase standard curve was generated and used to estimate glucoamylase and alpha-amylase activity in yeast supernatants.

Results for alpha-amylase activity and glucoamylase activity are shown Table 9. A graphical representation of comparative alpha-amylase activity is shown in FIG. 1.

TABLE 9

| | | | | Alpha-amylase (AA) and glucoamylase (GA) activity and estimated secretion | | | |
| --- | --- | --- | --- | --- | --- | --- | --- |
| Yeast strain no. | Promoter for alpha-amylase expression | SEQ ID NO: (mature polypeptide) | AA gene donor (catalytic domain) | Glucoamylase activity | Conc. (ug/mL) | Alpha-amylase activity | Conc. (ug/mL) |
| 1 | Background strain with glucoamylase gene, without alpha amylase gene | | | 1.03 | 10.6 | N/A | N/A |
| 1 | Background strain with glucoamylase gene, without alpha amylase gene | | | 0.98 | 9.8 | N/A | N/A |
| 1 | Background strain with glucoamylase gene, without alpha amylase gene | | | 1.00 | 10.0 | N/A | N/A |
| 2 | PADH1 | 125 | Acidomyces richmondensis | 0.86 | 8.1 | 0.1753 | 0.04 |
| 3 | pADH1 | 125 | Acidomyces richmondensis | 1.03 | 10.6 | 0.5529 | 0.16 |
| 4 | PADH1 | 136 | Byssoascus striatosporus | 0.76 | 6.6 | 0.084 | 0.01 |
| 5 | pADH1 | 162 | Bacillus halmapalus | 1.58 | 18.5 | 0.4314 | 0.12 |
| 6 | pADH1 | 172 | Aspergillus terreus | 0.91 | 8.8 | 1.4154 | 0.44 |
| 7 | pTDH3 | 129 | Syncephalastrum racemosum | 0.87 | 8.2 | 1.3655 | 0.43 |
| 8 | pTDH3 | 151 | Meripilus | 0.60 | 4.3 | 1.6636 | 0.52 |
| 9 | pTDH3 | 141 | Penicillium olsonii | 0.99 | 10.0 | 0.0846 | 0.01 |
| 11 | pADH1 | 131 | Dichotomocladium hesseltinei | 0.75 | 6.5 | 0.084 | 0.01 |

TABLE 9-continued

Alpha-amylase (AA) and glucoamylase (GA) activity and estimated secretion

| Yeast strain no. | Promoter for alpha-amylase expression | SEQ ID NO: (mature polypeptide) | AA gene donor (catalytic domain) | Glucoamylase activity | Conc. (ug/mL) | Alpha-amylase activity | Conc. (ug/mL) |
|---|---|---|---|---|---|---|---|
| 12 | pADH1 | 122 | *Bacillus licheniformis* | 0.93 | 9.1 | 0.1147 | 0.02 |
| 13 | pADH1 | 133 | *Penicillium aethiopicum* | 1.03 | 10.5 | 0.0842 | 0.01 |
| 14 | pADH1 | 143 | *Penicillium* sp | 0.88 | 8.4 | 0.2047 | 0.05 |
| 15 | pADH1 | 168 | *Aspergillus oryzae* | 0.90 | 8.7 | 1.561 | 0.49 |
| 16 | pTDH3 | 122 | *Bacillus licheniformis* | 0.81 | 7.3 | 0.1219 | 0.02 |
| 17 | pTDH3 | 126 | *Aspergillus bombycis* | 0.98 | 9.8 | 0.1628 | 0.03 |
| 18 | pTDH3 | 145 | *Neosartorya massa* | 0.92 | 8.9 | 1.902 | 0.60 |
| 19 | pTDH3 | 160 | *Aspergillus niger* | 0.95 | 9.3 | 0.0899 | 0.01 |
| 20 | pTDH3 | 167 | *Aspergillus niger* | 0.98 | 9.8 | 1.2357 | 0.38 |
| 21 | pADH1 | 126 | *Aspergillus bombycis* | 0.95 | 9.3 | 0.3891 | 0.11 |
| 22 | pADH1 | 127 | *Alternaria* sp | 0.93 | 9.1 | 0.0866 | 0.01 |
| 23 | pADH1 | 138 | *Penicillium subspinulosum* | 0.97 | 9.7 | 0.0848 | 0.01 |
| 24 | pADH1 | 145 | *Neosartorya massa* | 0.93 | 9.1 | 0.8786 | 0.27 |
| 25 | pTDH3 | 132 | *Lichtheimia ramosa* | 0.89 | 8.5 | 1.1903 | 0.37 |
| 26 | pTDH3 | 132 | *Lichtheimia ramosa* | 0.88 | 8.3 | 1.7498 | 0.55 |
| 27 | pTDH3 | 121 | *Rhizomucor pusillus* | 0.78 | 7.0 | 1.334 | 0.42 |
| 28 | pTDH3 | 159 | *Aspergillus niger* | 0.90 | 8.7 | 1.9582 | 0.62 |
| 29 | pTDH3 | 147 | *Aspergillus brasiliensis* | 1.03 | 10.6 | 0.3469 | 0.09 |
| 30 | pTDH3 | 168 | *Aspergillus oryzae* | 0.92 | 9.0 | 1.5655 | 0.49 |
| 31 | pADH1 | 124 | *Aspergillus tamarii* | 0.87 | 8.3 | 1.1583 | 0.36 |
| 32 | pADH1 | 138 | *Penicillium subspinulosum* | 0.90 | 8.7 | 0.0848 | 0.01 |
| 34 | pADH1 | 172 | *Aspergillus terreus* | 0.88 | 8.4 | 1.3645 | 0.43 |
| 35 | pTDH3 | 137 | *Aspergillus brasiliensis* | 0.92 | 8.9 | 1.2183 | 0.38 |
| 36 | pTDH3 | 169 | *Penicillium canescens* | 0.83 | 7.7 | 1.8212 | 0.57 |
| 37 | pTDH3 | 127 | *Alternaria* sp | 0.95 | 9.4 | 0.0877 | 0.01 |
| 38 | pTDH3 | 151 | *Meripilus* | 0.56 | 3.8 | 1.3665 | 0.43 |
| 39 | pTDH3 | 152 | *Cerrena unicolor* | 0.98 | 9.8 | 0.0831 | 0.01 |
| 40 | pTDH3 | 172 | *Aspergillus terreus* | 0.98 | 9.9 | 0.8774 | 0.27 |
| 41 | pADH1 | 134 | *Subulispora* sp | 0.72 | 6.1 | 0.0916 | 0.01 |
| 42 | pADH1 | 127 | *Alternaria* sp | 0.80 | 7.3 | 0.0938 | 0.01 |
| 43 | pADH1 | 137 | *Aspergillus brasiliensis* | 0.94 | 9.2 | 1.1772 | 0.36 |
| 44 | pADH1 | 168 | *Aspergillus oryzae* | 0.92 | 9.0 | 1.5347 | 0.48 |
| 46 | pTDH3 | 126 | *Aspergillus bombycis* | 1.03 | 10.5 | 0.1955 | 0.05 |
| 47 | pTDH3 | 128 | *Rhizopus microsporus* | 0.65 | 5.1 | 0.9639 | 0.30 |
| 48 | pTDH3 | 157 | *Bacillus subtilis subsp. subtilis* | 0.94 | 9.2 | 1.2992 | 0.40 |
| 49 | pTDH3 | 156 | *Bacillus subtilis* | 0.93 | 9.1 | 1.1427 | 0.35 |
| 50 | pTDH3 | 157 | *Bacillus subtilis subsp. subtilis* | 0.95 | 9.4 | 1.3374 | 0.42 |
| 51 | pADH1 | 140 | *Penicillium coprophilum* | 0.90 | 8.6 | 0.7588 | 0.23 |
| 52 | pADH1 | 136 | *Byssoascus striatosporus* | 0.94 | 9.2 | 0.085 | 0.01 |
| 53 | pADH1 | 146 | *Penicillium janthinellum* | 0.79 | 7.0 | 0.3325 | 0.09 |
| 54 | pADH1 | 173 | *Thamnidium elegans* | 0.91 | 8.8 | 1.1844 | 0.37 |
| 55 | pADH1 | 163 | *Aspergillus oryzae* | 0.88 | 8.4 | 1.7175 | 0.54 |
| 56 | pTDH3 | 137 | *Aspergillus brasiliensis* | 0.93 | 9.0 | 0.9012 | 0.27 |
| 57 | pTDH3 | 123 | *Aspergillus niger* | 0.94 | 9.2 | 1.2994 | 0.40 |
| 58 | pTDH3 | 150 | *Hamigera avellanea* | 0.87 | 8.3 | 0.7698 | 0.23 |
| 59 | pTDH3 | 149 | *Hamigera avellanea* | 0.89 | 8.5 | 0.8048 | 0.24 |
| 60 | pTDH3 | 165 | *Rhizomucor pusillus* | 0.94 | 9.3 | 1.9117 | 0.60 |
| 61 | PADH1 | 138 | *Penicillium subspinulosum* | 0.76 | 6.7 | 0.1233 | 0.02 |
| 62 | PADH1 | 126 | *Aspergillus bombycis* | 0.94 | 9.3 | 0.3626 | 0.10 |
| 63 | pADH1 | 142 | *Penicillium vasconiae* | 0.74 | 6.4 | 0.1007 | 0.01 |
| 64 | pADH1 | 165 | *Rhizomucor pusillus* | 0.94 | 9.3 | 1.7183 | 0.54 |
| 66 | pTDH3 | 136 | *Byssoascus striatosporus* | 0.96 | 9.6 | 0.084 | 0.01 |
| 67 | pTDH3 | 124 | *Aspergillus tamarii* | 0.90 | 8.6 | 1.0263 | 0.32 |
| 68 | pTDH3 | 149 | *Hamigera avellanea* | 1.04 | 10.7 | 0.4173 | 0.12 |
| 69 | pTDH3 | 145 | *Neosartorya massa* | 0.96 | 9.5 | 0.2249 | 0.05 |

TABLE 9-continued

Alpha-amylase (AA) and glucoamylase (GA) activity and estimated secretion

| Yeast strain no. | Promoter for alpha-amylase expression | SEQ ID NO: (mature polypeptide) | AA gene donor (catalytic domain) | Glucoamylase activity | Glucoamylase Conc. (ug/mL) | Alpha-amylase activity | Alpha-amylase Conc. (ug/mL) |
|---|---|---|---|---|---|---|---|
| 70 | pTDH3 | 157 | Bacillus subtilis subsp. subtilis | 0.99 | 9.9 | 1.4 | 0.44 |
| 71 | pTDH3 | 165 | Rhizomucor pusillus | 0.89 | 8.4 | 2.2181 | 0.70 |
| 72 | pADH1 | 135 | Trichoderma paraviridescens | 0.92 | 9.0 | 0.0873 | 0.01 |
| 73 | pADH1 | 139 | Penicillium antarcticum | 0.78 | 6.9 | 0.0926 | 0.01 |
| 74 | pADH1 | 152 | Cerrena unicolor | 0.93 | 9.1 | 0.0858 | 0.01 |
| 76 | pADH1 | 173 | Thamnidium elegans | 0.89 | 8.6 | 1.2458 | 0.39 |
| 77 | pTDH3 | 121 | Rhizomucor pusillus | 0.80 | 7.2 | 1.6326 | 0.51 |
| 78 | pTDH3 | 124 | Aspergillus tamarii | 0.80 | 7.3 | 1.2964 | 0.40 |
| 79 | pTDH3 | 158 | Schwanniomyces occidentalis | 1.00 | 10.0 | 0.2679 | 0.07 |
| 80 | pTDH3 | 150 | | 0.83 | 7.7 | 0.7079 | 0.21 |
| 81 | pTDH3 | 145 | Neosartorya massa | 0.90 | 8.7 | 0.1957 | 0.05 |
| 82 | pTDH3 | 165 | Rhizomucor pusillus | 0.81 | 7.3 | 2.1273 | 0.67 |

Example 3: Simultaneous Saccharification and Fermentation (SSF) of Yeast Strains Expressing Alpha-Amylase Yeast strains were cultivated overnight in standard YPD media containing 2% glucose. The cultured yeast medium was centrifuged at 3000 rpm for 10 min to collect the supernatant. The supernatant was used for enzyme activity assay, as described below.

Alpha Amylase Activity Assay

Alpha-amylase activity was detected by measuring the amount of starch degraded through enzymatic hydrolysis of starch. Potassium iodide and iodine reagent was used to measure the residual starch based on the color development from application of the reagent. The color intensity measured on a spectrophotometer or microplate reader is inversely proportional to alpha-amylase activity. Reaction conditions and color development were described in Table 11 and Table 12, respectively.

TABLE 11

| Alpha-amylase reaction condition | |
|---|---|
| Amount of yeast supernatant | 20 μl |
| Amount of substrate | 130 μl |
| Substrate | 2 mM starch |
| Buffer | Sodium acetate, 0.1M, 0.01% Triton 100 |
| pH | 5.0 ± 0.05 |
| Incubation temperature | 20° C. |
| Reaction time | 2-3 hr |

TABLE 12

| Color development | |
|---|---|
| Reaction mixture | 150 μl |
| Amount of reagent | 50 μl |
| Reagent | 14.5 mM potassium iodide, 0.9 mM iodine |
| Incubation temperature | 20° C. |
| Reaction time | 10-15 min |
| Wavelength | 595 nm |

Simultaneous saccharification and fermentation (SSF) was performed via mini-scale fermentations using industrial corn mash (Avantec® Amp, Novozymes, A/S) using conditions shown in Table 13. Yeast strains were cultivated overnight in YPD media with 2% glucose for 24 hours at 30° C. and 300 rpm. The corn mash was supplemented with 250 ppm of urea. Approximately 0.6 mg of corn mash was dispensed per well to 96 well microtiter plates, followed by the addition of approximately 10^8 yeast cells/g of corn mash from the overnight culture. Plates were incubated at 32° C. without shaking. Duplicates of each strain were analyzed after 48 hour fermentations. Fermentation was stopped by the addition of 100 μL of 8% $H_2SO_4$, followed by centrifugation at 3000 rpm for 10 min. The supernatant was analyzed for ethanol using HPLC.

TABLE 13

| Microtiter plate fermentation reaction conditions | |
|---|---|
| Substrate | Avantec ® Amp corn mash |
| Yeast pitch | 10^8 cells/g corn mash |
| Supplementary urea | 250 ppm |
| pH | 5.0 ± 0.05 |
| Incubation temperature | 32° C. |
| Reaction time | 48 hours |

As shown in Table 14, higher ethanol was obtained from yeast expressing a heterologous alpha-amylase compared to yeast lacking heterologous alpha-amylase expression. "Mean (residual starch)" column shows the results from the YPD based alpha-amylase activity assay where the residual starch is inversely proportional to alpha-amylase activity, while "Mean (normalized ethanol)" columns shows the ethanol at the 48 hour timepoint from two different simultaneous and saccharification fermentation (SSF) experiments, normalized to that of the strain without heterologous alpha-amylase expression (yMHCT484).

TABLE 14

Strain IDs and normalized ethanol and alpha-amylase activity data.

| Promoter | Signal peptide | Alpha-amylase gene donor (catalytic domain) | SEQ ID NO: (mature polypeptide) | Mean (normalized ethanol) (exp 1) | Mean (normalized ethanol) (exp 2) | Mean (residual starch) |
|---|---|---|---|---|---|---|
| Background strain with glucoamylase gene, without alpha amylase gene | | | | 1.00 | 1.00 | 0.74 |
| ADH1 | EXG1 | Byssoascus striatosporus | 136 | 1.18 | 0.69 | 1.007 |
| ADH1 | EXG1 | Penicillium subspinulosum | 138 | 1.27 | 0.97 | 1.029 |
| ADH1 | EXG1 | Acidomyces richmondensis | 125 | 1.10 | 0.88 | 0.414 |
| ADH1 | EXG1 | Trichoderma paraviridescens | 135 | 1.14 | 0.78 | 0.564 |
| ADH1 | EXG1 | Bacillus licheniformis | 122 | 1.28 | 0.85 | 0.453 |
| ADH1 | EXG1 | Penicillium aethiopicum | 133 | 1.19 | 0.97 | 0.954 |
| ADH1 | EXG1 | Alternaria sp | 127 | 1.17 | 0.97 | 0.460 |
| ADH1 | EXG1 | Dichotomocladium hesseltinei | 131 | 1.15 | 0.74 | 0.980 |
| ADH1 | EXG1 | Aspergillus bombycis | 126 | 1.13 | 0.98 | 0.423 |
| ADH1 | EXG1 | Aspergillus brasiliensis | 137 | 1.16 | 1.06 | 0.507 |
| ADH1 | EXG1 | Aspergillus tamarii | 124 | 1.22 | 1.04 | 0.440 |
| ADH1 | EXG1 | Aspergillus bombycis | 126 | 1.14 | 0.97 | 0.479 |
| ADH1 | EXG1 | Acidomyces richmondensis | 125 | 1.11 | 1.00 | 0.464 |
| ADH1 | EXG1 | Alternaria sp | 127 | 1.13 | 0.77 | 0.411 |
| ADH1 | EXG1 | Subulispora sp | 134 | 1.03 | 0.64 | 0.452 |
| ADH1 | EXG1 | Penicillium subspinulosum | 138 | 1.11 | 0.82 | 0.607 |
| ADH1 | EXG1 | Penicillium antarcticum | 139 | 1.17 | 0.71 | 0.476 |
| ADH1 | EXG1 | Cerrena unicolor | 152 | 1.07 | 0.95 | 0.533 |
| ADH1 | EXG1 | Neosartorya massa | 145 | 1.05 | 1.13 | 0.422 |
| ADH1 | EXG1 | Penicillium vasconiae | 142 | 1.15 | 0.72 | 0.394 |
| ADH1 | EXG1 | Penicillium sp | 143 | 1.09 | 0.88 | 0.412 |
| ADH1 | EXG1 | Aspergillus oryzae | 168 | 1.21 | 1.16 | 0.038 |
| ADH1 | EXG1 | Aspergillus terreus | 172 | 1.15 | 1.22 | 0.038 |
| ADH1 | EXG1 | Aspergillus terreus | 172 | 1.17 | 1.22 | 0.037 |
| ADH1 | EXG1 | Thamnidium elegans | 173 | 1.25 | 1.13 | 0.037 |
| ADH1 | EXG1 | Aspergillus oryzae | 168 | 1.10 | 1.16 | 0.044 |
| ADH1 | EXG1 | Rhizomucor pusillus | 165 | 1.23 | 1.23 | 0.036 |
| TDH3 | EXG1 | Aspergillus brasiliensis | 137 | 1.16 | 1.07 | 0.042 |
| TDH3 | EXG1 | Rhizomucor pusillus | 121 | 1.27 | 1.20 | 0.040 |
| TDH3 | EXG1 | Bacillus licheniformis | 122 | 0.91 | 0.93 | 0.046 |
| TDH3 | EXG1 | Aspergillus bombycis | 126 | 1.20 | 0.97 | 0.039 |
| TDH3 | EXG1 | Lichtheimia ramosa | 132 | 1.19 | 1.12 | 0.051 |
| TDH3 | EXG1 | Aspergillus tamarii | 124 | 1.21 | 1.11 | 0.048 |
| TDH3 | EXG1 | Rhizopus microsporus | 128 | 1.02 | 1.01 | 0.041 |
| TDH3 | EXG1 | Aspergillus tamarii | 124 | 1.18 | 1.04 | 0.040 |
| TDH3 | EXG1 | Syncephalastrum racemosum | 129 | 1.17 | 1.24 | 0.042 |
| TDH3 | EXG1 | Byssoascus striatosporus | 136 | 1.04 | 0.96 | 0.541 |
| TDH3 | EXG1 | Aspergillus bombycis | 126 | 1.05 | 0.97 | 0.042 |
| TDH3 | EXG1 | Rhizomucor pusillus | 159 | | 1.25 | 0.141 |
| TDH3 | EXG1 | Hamigera avellanea | 149 | 1.11 | 1.03 | 0.055 |
| TDH3 | EXG1 | Bacillus subtilis subsp. subtilis | 157 | 1.19 | 1.08 | 0.043 |
| TDH3 | EXG1 | Bacillus subtilis subsp. subtilis | 157 | 1.25 | 1.11 | 0.044 |
| TDH3 | EXG1 | Meripilus giganteus | 151 | 1.20 | 1.14 | 0.045 |
| TDH3 | EXG1 | Bacillus subtilis | 156 | 1.35 | 1.27 | 0.048 |
| TDH3 | EXG1 | Neosartorya massa | 145 | 1.15 | 1.03 | 0.048 |
| TDH3 | EXG1 | Penicillium olsonii | 141 | 0.96 | 0.98 | 0.052 |
| TDH3 | EXG1 | Aspergillus niger | 160 | 1.06 | 0.98 | 0.053 |
| TDH3 | EXG1 | Hamigera avellanea | 150 | 1.11 | 1.04 | 0.046 |
| TDH3 | EXG1 | Bacillus subtilis subsp. subtilis | 157 | 1.16 | 1.13 | 0.045 |

TABLE 14-continued

Strain IDs and normalized ethanol and alpha-amylase activity data.

| Promoter | Signal peptide | Alpha-amylase gene donor (catalytic domain) | SEQ ID NO: (mature polypeptide) | Mean (normalized ethanol) (exp 1) | Mean (normalized ethanol) (exp 2) | Mean (residual starch) |
|---|---|---|---|---|---|---|
| TDH3 | EXG1 | *Meripilus giganteus* | 151 | 1.11 | 1.14 | 0.039 |
| TDH3 | EXG1 | *Cerrena unicolor* | 152 | 1.02 | 0.96 | 0.546 |
| TDH3 | EXG1 | *Neosartorya massa* | 145 | 1.25 | 1.04 | 0.053 |
| TDH3 | EXG1 | *Aspergillus niger* | 167 | 1.08 | 1.05 | 0.040 |
| TDH3 | EXG1 | *Rhizomucor pusillus* | 165 | 1.30 | 1.23 | 0.039 |
| TDH3 | EXG1 | *Aspergillus terreus* | 172 | 1.13 | 1.11 | 0.043 |
| TDH3 | EXG1 | *Aspergillus oryzae* | 168 | 1.13 | 1.17 | 0.037 |

Example 4: Construction of Yeast Strains Expressing a Heterologous Trehalase This example describes the construction of yeast cells containing a heterologous trehalase under control of an *S. cerevisiae* CCW12 promoter (SEQ ID NO: 232) or PGK1 promoter (SEQ ID NO: 4). Three pieces of DNA containing the promoter, gene and terminator were designed to allow for homologous recombination between the 3 DNA fragments and into the X-3 locus of the yeast yMHCT484 (PCT/US2018/035596). The resulting strain has one promoter containing fragment (left), one gene containing fragment (middle) and one TEF1 terminator (SEQ ID NO: 233) fragment (right) integrated into the *S. cerevisiae* genome at the X-3 locus.

Construction of the Promoter Containing Fragments (Left Fragments)

Synthetic linear uncloned DNA containing 300 bp homology to the X-3 site, *S. cerevisiae* promoter CCW12 (SEQ ID NO: 232) or PGK1 (SEQ ID NO: 4) and *S. cerevisiae* AGA2 signal sequence (SEQ ID NO: 234) were synthetized by Thermo Fisher Scientific. The 2 linear DNAs were designated 17ABCK6P and 17ABCK7P for each promoter listed above, respectively.

To generate additional linear DNA for transformation into yeast, the DNA containing the left cassette was PCR amplified from 17ABCK6P and 17ABCK7P. Fifty pmoles each of forward and reverse primer was used in a PCR reaction containing 12.5 ng of linear DNA as template, 0.1 mM each dATP, dGTP, dCTP, dTTP, 1× Phusion HF Buffer (Thermo Fisher Scientific), and 2 units Phusion Hot Start DNA polymerase in a final volume of 50 µL. The PCR was performed in a T100™ Thermal Cycler (Bio-Rad Laboratories, Inc.) programmed for one cycle at 98° C. for 1 minute followed by 32 cycles each at 98° C. for 10 seconds, 60° C. for 30 seconds, and 72° C. for 1 minute with a final extension at 72° C. for 10 minutes. Following thermocycling, the PCR reaction products gel isolated and cleaned up using the NucleoSpin Gel and PCR clean-up kit (Machery-Nagel).

Construction of the Trehalase Containing Fragments (Middle Fragments)

Synthetic linear uncloned DNA containing *S. cerevisiae* AGA2 signal peptide coding sequence (encoding the signal of SEQ ID NO: 234), a codon-optimized trehalase gene and 50 bp of TEF1 terminator (SEQ ID NO: 233), were synthetized by Thermo Fisher Scientific. The resulting linear DNAs were designated as indicated in Table 15.

A subset of the trehalase containing fragments were ordered as cloned synthetic plasmid DNA rather than linear uncloned DNA. Synthetic plasmid DNA containing *S. cerevisiae* AGA2 signal coding sequence, a codon-optimized trehalase gene and 50 bp of TEF1 terminator, were synthetized by Thermo Fisher Scientific. The resulting DNAs were designated as indicated in Table 15.

Construction of the Terminator Contain Fragment (Right Fragment)

Synthetic linear uncloned DNA containing *S. cerevisiae* TEF1 terminator and 300 bp homology to the X-3 site, were synthetized by Thermo Fisher Scientific.

TABLE 15

Trehalase DNA product names and associated enzyme

| Product number | DNA format | Signal Peptide | Donor Organism (catalytic domain) | SEQ ID NO: (mature polypeptide) | Terminator Fragment |
|---|---|---|---|---|---|
| 17ABFBKP | linear | AGA2 | *Chaetomium megalocarpum* | 175 | TEF1 |
| 17ABFBJP | linear | AGA2 | *Lecanicillium psalliotae* | 176 | TEF1 |
| 17ABFBIP | linear | AGA2 | *Doratomyces* sp | 177 | TEF1 |
| 17ABFBHP | linear | AGA2 | *Mucor moelleri* | 178 | TEF1 |
| 17ABFBGP | linear | AGA2 | *Phialophora cyclaminis* | 179 | TEF1 |
| 17ABFBFP | linear | AGA2 | *Thielavia arenaria* | 180 | TEF1 |
| 17ABFBEP | linear | AGA2 | *Thielavia antarctica* | 181 | TEF1 |
| 17ABFBDP | linear | AGA2 | *Chaetomium* sp | 182 | TEF1 |
| 17ABFBCP | linear | AGA2 | *Chaetomium nigricolor* | 183 | TEF1 |
| 17ABFBBP | linear | AGA2 | *Chaetomium jodhpurense* | 184 | TEF1 |
| 17ABFBAP | linear | AGA2 | *Chaetomium piluliferum* | 185 | TEF1 |
| 17ABFA7P | linear | AGA2 | *Myceliophthora hinnulea* | 186 | TEF1 |
| 17ABFA6P | linear | AGA2 | *Chloridium virescens* | 187 | TEF1 |
| 17ABFA5P | linear | AGA2 | *Gelasinospora cratophora* | 188 | TEF1 |
| 17ABFA4P | linear | AGA2 | *Acidobacteriaceae bacterium* | 189 | TEF1 |

TABLE 15-continued

Trehalase DNA product names and associated enzyme

| Product number | DNA format | Signal Peptide | Donor Organism (catalytic domain) | SEQ ID NO: (mature polypeptide) | Terminator Fragment |
|---|---|---|---|---|---|
| 17ABFA3P | linear | AGA2 | Acidobacterium capsulatum | 190 | TEF1 |
| 17ABFA2P | linear | AGA2 | Acidovorax wautersii | 191 | TEF1 |
| 17ABFAZP | linear | AGA2 | Xanthomonas arboricola | 192 | TEF1 |
| 17ABFAYP | linear | AGA2 | Kosakonia sacchari | 193 | TEF1 |
| 17ABFAXP | linear | AGA2 | Enterobacter sp | 194 | TEF1 |
| 17ABFAWP | linear | AGA2 | Saitozyma flava | 195 | TEF1 |
| 17ABFAVP | linear | AGA2 | Phaeotremella skinneri | 196 | TEF1 |
| 17ABFAUP | linear | AGA2 | Trichoderma asperellum | 197 | TEF1 |
| 17ABFATP | linear | AGA2 | Corynascus sepedonium | 198 | TEF1 |
| 17ABFASP | linear | AGA2 | Myceliophthora thermophila | 199 | TEF1 |
| 17ABFARP | linear | AGA2 | Trichoderma reesei GH37 | 200 | TEF1 |
| 17ABFAQP | linear | AGA2 | Chaetomium virescens | 201 | TEF1 |
| 17ABFAPP | linear | AGA2 | Rhodothermus marinus | 202 | TEF1 |
| 17ABFAOP | linear | AGA2 | Myceliophthora sepedonium | 203 | TEF1 |
| 17ABFANP | linear | AGA2 | Moelleriella libera | 204 | TEF1 |
| 17ABFAMP | linear | AGA2 | Acremonium dichromosporum | 205 | TEF1 |
| 17ABFALP | linear | AGA2 | Fusarium sambucinum | 206 | TEF1 |
| 17ABFAKP | linear | AGA2 | Phoma sp | 207 | TEF1 |
| 17ABFAJP | linear | AGA2 | Lentinus similis | 208 | TEF1 |
| 17ABFAIP | linear | AGA2 | Diaporthe nobilis | 209 | TEF1 |
| 17ABFAHP | linear | AGA2 | Solicoccozyma terricola | 210 | TEF1 |
| 17ABFAGP | linear | AGA2 | Dioszegia cryoxerica | 211 | TEF1 |
| 17ABFO6P | plasmid | AGA2 | Talaromyces funiculosus | 212 | TEF1 |
| 17ABFO5P | plasmid | AGA2 | Hamigera avellanea | 213 | TEF1 |
| 17ABFO4P | plasmid | AGA2 | Talaromyces ruber | 214 | TEF1 |
| 17ABFO3P | plasmid | AGA2 | Trichoderma lixii | 215 | TEF1 |
| 17ABFO2P | plasmid | AGA2 | Aspergillus cervinus | 216 | TEF1 |
| 17ABFOZP | plasmid | AGA2 | Rasamsonia brevistipitata | 217 | TEF1 |
| 17ABFOYP | plasmid | AGA2 | Acremonium curvulum | 218 | TEF1 |
| 17ABFOXP | plasmid | AGA2 | Talaromyces piceae | 219 | TEF1 |
| 17ABFOWP | plasmid | AGA2 | Penicillium sp | 220 | TEF1 |
| 17ABFOVP | plasmid | AGA2 | Talaromyces aurantiacus | 221 | TEF1 |
| 17ABFOUP | plasmid | AGA2 | Talaromyces pinophilus | 222 | TEF1 |
| 17ABFOTP | plasmid | AGA2 | Talaromyces leycettanus | 223 | TEF1 |
| 17ABFOSP | plasmid | AGA2 | Talaromyces variabilis | 224 | TEF1 |
| 17ABFORP | plasmid | AGA2 | Aspergillus niger | 225 | TEF1 |
| 17ABFOQP | plasmid | AGA2 | Trichoderma reesei GH65 | 226 | TEF1 |

Integration of the Left, Middle and Right-Hand Fragments to Generate Yeast Strains with a Heterologous Trehalase The yeast yMHCT484 (PCT/US2018/035596) was transformed with the left, middle and right integration fragments described above. In each transformation pool a fixed left fragment and right fragment were used. The middle fragment consisted of a pool of 13-21 middle fragments containing the trehalase gene with 100-600 ng of each fragment (1000 ng total). To aid homologous recombination of the left, middle and right fragments at the genomic X-3 sites a plasmid containing Cas9 and guide RNA specific to X-3 (pMcTs442) was also used in the transformation. These four components were transformed into the into S. cerevisiae strain yMHCT484 following a yeast electroporation protocol (See, Thompson et al. Yeast. 1998 Apr. 30; 14(6):565-71). Transformants were selected on YPD+cloNAT to select for transformants that contain the CRISPR/Cas9 plasmid pMcTs442. Transformants were picked using a Q-pix Colony Picking System (Molecular Devices) to inoculate 1 well of 96-well plate containing YPD+clonNAT media. The plates were grown for 2 days then glycerol was added to 20% final concentration and the plates were stored at −80° C. until needed. Integration of specific trehalase construct was verified by PCR with locus specific primers and subsequent sequencing.

Example 5: Activity Assay of Yeast Strain Expressing Trehalase

Yeast expressing a trehalase gene from Corynascus sepedonium driven by the promoter ADH1 (supra) was cultivated overnight in standard YPD media containing 2% glucose. The cultured yeast medium was centrifuged at 3000 rpm for 10 min to collect the supernatant. The supernatant was used for enzyme activity assay, as described below.

Trehalase activity was detected by measuring the amount of glucose released through enzymatic hydrolysis of trehalose. Glucose oxidase reagent was used to measure the glucose based on the color development from application of the reagent. The color intensity measured on a spectrophotometer or microplate reader is proportional to trehalase activity. Reaction conditions and color development are described in Table 16 and Table 17, respectively.

The Trehalase Novozymes Unit (TNU(A)) for trehalase assay standard is measured relative to an enzyme standard of declared activity.

TABLE 16

Trehalase reaction condition

| | |
|---|---|
| Amount of yeast supernatant | 20 µl |
| Amount of substrate | 100 µl |

TABLE 16-continued

| Trehalase reaction condition | |
|---|---|
| Substrate | Trehalose, 60 mM |
| Buffer | Sodium acetate, 0.1M, 0.01% Triton 100 |
| pH | 5.0 ± 0.05 |
| Incubation temperature | 20° C. |
| Reaction time | 2-3 hr |
| Trehalase assay range | 0.004-0.017 TNU(A)/ml |

TABLE 17

| Color development | |
|---|---|
| Reaction mixture | 20 µl |
| Glucose oxidase reagent | 200 µl |
| Incubation temperature | 20° C. |
| Reaction time | 10-15 min |
| Wavelength | 490 nm |

Assay results showed that trehalase expression proportionally increased the glucose released, measured as the optical density at 490 nm (0.10 for background strain lacking the trehalase gene compared to 0.88 for the trehalase-expressing strain).

Example 6: Activity Assay of Yeast Strains Expressing Trehalase

Yeast strains from Example 4 were cultivated overnight in standard YPD media containing 2% or 6% glucose. The cultured yeast medium was subjected to centrifugation at 3500 rpm for 10 min to harvest the supernatant. The culture supernatant is used for the described enzyme activity assays.

Yeast may also be cultivated using other cultivation media such as minimal YNB media or clarified and filtered industrial liquefied corn mash.

Glucoamylase activity was measured using maltose as substrate as described supra.

Trehalase activity was measured using trehalose as substrate. Enzyme hydrolysis of trehalose will release glucose as reaction product which may be detected using commercially available assay kits such as Wako Diagnostics AUTOKIT GLUCOSE C2. Reagents provided in the assay kits will specifically react with glucose resulted in color formation. The color intensity measured on spectrophotometer or microplate reader, is proportional to trehalase activity. Reaction conditions are described in Table 18. The Trehalase Unit (TNU) for standard trehalase is defined as the amount of enzyme, which hydrolyzes one micromole trehalose per minute under the standard conditions.

TABLE 18

| Trehalase reaction conditions | |
|---|---|
| Appropriate amount of yeast supernatant | 10-200 µl |
| Substrate | trehalose, 10 mM |
| Buffer | acetate, 0.1M |
| pH | 5.0 ± 0.05 |
| Incubation temperature | 32° C. |
| Reaction time | 5-20 min |
| Trehalase assay range | 0.002-0.036 TNU/ml |

The absorbance at 505 nm increases as the amount of purified glucoamylase or trehalase added to hydrolyze maltose or trehalose, respectively, to glucose increases. A purified glucoamylase and trehalase standard curve was generated and used to estimate glucoamylase and trehalase activity in yeast supernatants.

Figure 2:
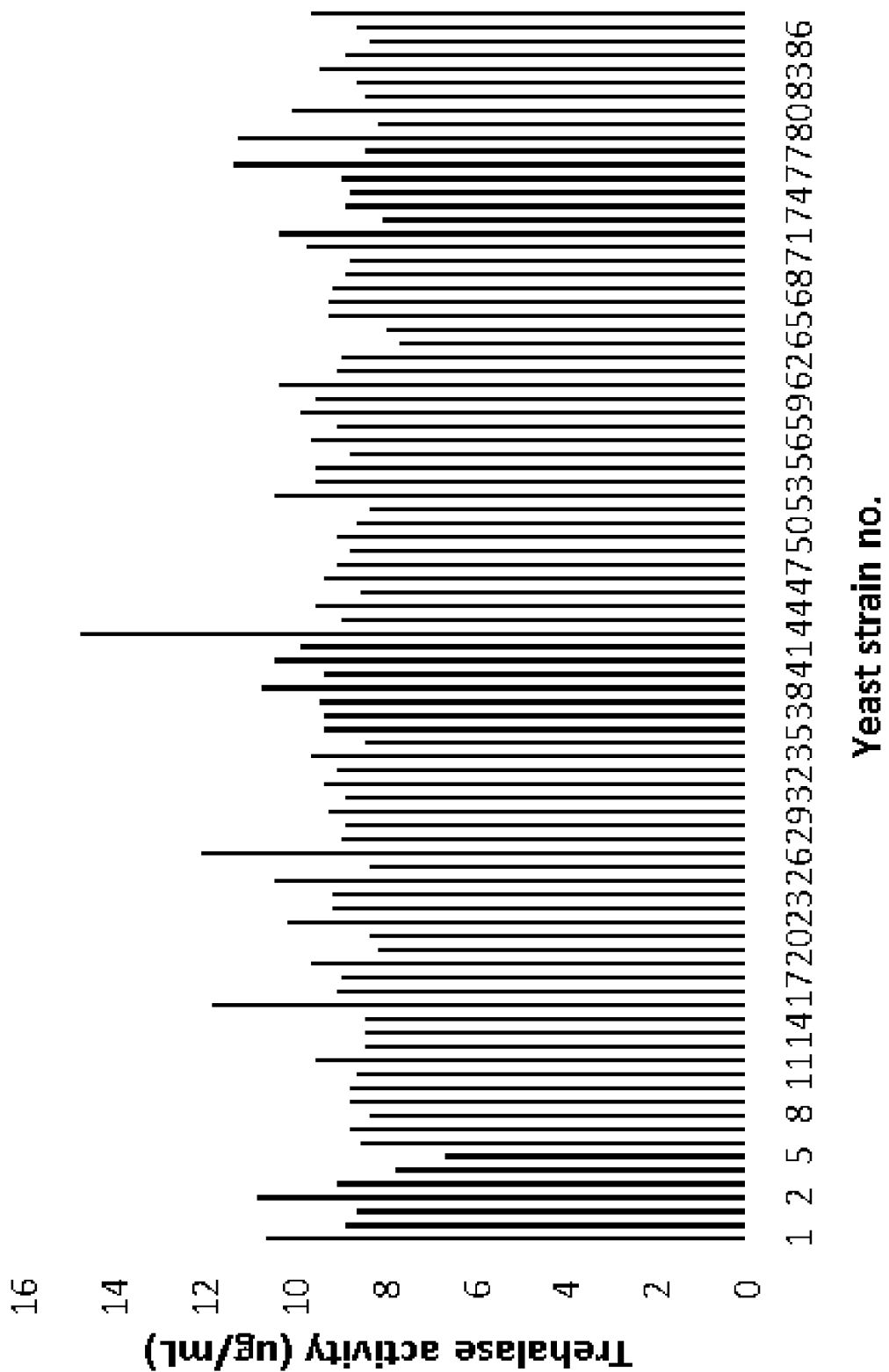
FIG. 2 shows trehalase activity for strains constructed in Example 4.

Results for trehalase activity and glucoamylase activity are shown Table 19. A graphical representation of comparative trehalase activity is shown in FIG. 2.

TABLE 19

Trehalase and glucoamylase (GA) activity, and estimated enzyme secretion.

| Yeast strain no. | Promoter for trehalase expression | SEQ ID NO: (mature polypeptide) | Donor Organism (catalytic domain) | Glucoamylase activity | Glucoamylase Conc. (ug/mL) | Trehalase activity | Trehalase Conc. (ug/mL) |
|---|---|---|---|---|---|---|---|
| 1 | Background strain with glucoamylase gene, without trehalase gene | | | 0.352 | 10.7 | N/A | N/A |
| 1 | Background strain with glucoamylase gene, without trehalase gene | | | 0.312 | 8.9 | N/A | N/A |
| 1 | Background strain with glucoamylase gene, without trehalase gene | | | 0.308 | 8.7 | N/A | N/A |
| 2 | pPGK1 | 189 | Acidobacteriaceae bacterium | 0.357 | 10.9 | 0.05 | 1.04 |
| 3 | pCCW12 | 191 | Acidovorax wautersii | 0.301 | 9.1 | 1.8 | 22.79 |
| 4 | pPGK1 | 218 | Acremonium curvulum | 0.287 | 7.8 | 0.07 | 1.08 |
| 5 | pCCW12 | 218 | Acremonium curvulum | 0.261 | 6.7 | 0.08 | 1.09 |
| 6 | pCCW12 | 205 | Acremonium dichromosporum | 0.304 | 8.6 | 0.78 | 3.78 |
| 7 | pCCW12 | 205 | Acremonium dichromosporum | 0.309 | 8.8 | 0.89 | 4.63 |
| 8 | pCCW12 | 216 | Aspergillus cervinus | 0.299 | 8.4 | 0.12 | 1.18 |
| 9 | pPGK1 | 216 | Aspergillus cervinus | 0.309 | 8.8 | 0.13 | 1.2 |
| 10 | pPGK1 | 225 | Aspergillus niger | 0.308 | 8.8 | 0.48 | 2.22 |
| 11 | pCCW12 | 225 | Aspergillus niger | 0.307 | 8.7 | 0.67 | 3.11 |
| 12 | pPGK1 | 184 | Chaetomium jodhpurense | 0.327 | 9.6 | 0.15 | 1.26 |

TABLE 19-continued

Trehalase and glucoamylase (GA) activity, and estimated enzyme secretion.

| Yeast strain no. | Promoter for trehalase expression | SEQ ID NO: (mature polypeptide) | Donor Organism (catalytic domain) | Glucoamylase activity | Conc. (ug/mL) | Trehalase activity | Conc. (ug/mL) |
|---|---|---|---|---|---|---|---|
| 13 | pCCW12 | 184 | *Chaetomium jodhpurense* | 0.302 | 8.5 | 1.77 | 21.85 |
| 14 | pCCW12 | 175 | *Chaetomium megalocarpum* | 0.302 | 8.5 | 1.77 | 21.85 |
| 15 | pCCW12 | 175 | *Chaetomium megalocarpum* | 0.303 | 8.5 | 0.4 | 1.95 |
| 16 | pPGK1 | 183 | *Chaetomium nigricolor* | 0.381 | 11.9 | 0.36 | 1.8 |
| 17 | pCCW12 | 183 | *Chaetomium nigricolor* | 0.315 | 9.1 | 0.66 | 3.05 |
| 18 | pCCW12 | 183 | *Chaetomium nigricolor* | 0.314 | 9 | 0.63 | 2.9 |
| 19 | pPGK1 | 182 | *Chaetomium* sp | 0.329 | 9.7 | 0.14 | 1.22 |
| 20 | pCCW12 | 182 | *Chaetomium* sp | 0.295 | 8.2 | 0.27 | 1.54 |
| 21 | pCCW12 | 182 | *Chaetomium* sp | 0.301 | 8.4 | 0.12 | 1.18 |
| 22 | pCCW12 | 201 | *Chaetomium virescens* | 0.341 | 10.2 | 0.53 | 2.43 |
| 23 | pPGK1 | 201 | *Chaetomium virescens* | 0.318 | 9.2 | 0.23 | 1.43 |
| 24 | pPGK1 | 187 | *Chloridium virescens* | 0.317 | 9.2 | 0.24 | 1.47 |
| 25 | pPGK1 | 187 | *Chloridium virescens* | 0.349 | 10.5 | 0.15 | 1.25 |
| 26 | pCCW12 | 211 | *Dioszegia cryoxerica* | 0.299 | 8.4 | 0.07 | 1.07 |
| 27 | pPGK1 | 211 | *Dioszegia cryoxerica* | 0.384 | 12.1 | 0.44 | 2.07 |
| 28 | pPGK1 | 177 | *Doratomyces* sp | 0.314 | 9 | 1.08 | 6.44 |
| 29 | pCCW12 | 177 | *Doratomyces* sp | 0.315 | 8.9 | 1.87 | 25.75 |
| 30 | pPGK1 | 194 | *Enterobacter* sp | 0.321 | 9.3 | 0.9 | 4.71 |
| 31 | pCCW12 | 194 | *Enterobacter* sp | 0.312 | 8.9 | 1.87 | 25.75 |
| 32 | pPGK1 | 206 | *Fusarium sambucinum* | 0.323 | 9.4 | 0.05 | 1.05 |
| 33 | pCCW12 | 188 | *Gelasinospora cratophora* | 0.315 | 9.1 | 0.66 | 3.05 |
| 34 | pCCW12 | 188 | *Gelasinospora cratophora* | 0.33 | 9.7 | 0.8 | 3.91 |
| 35 | pPGK1 | 213 | *Hamigera avellanea* | 0.302 | 8.5 | 0.63 | 2.89 |
| 36 | pCCW12 | 213 | *Hamigera avellanea* | 0.324 | 9.4 | 0.98 | 5.38 |
| 37 | pCCW12 | 213 | *Hamigera avellanea* | 0.322 | 9.4 | 1.13 | 6.97 |
| 38 | pPGK1 | 213 | *Hamigera avellanea* | 0.326 | 9.5 | 0.1 | 1.15 |
| 39 | pPGK1 | 193 | *Kosakonia sacchari* | 0.356 | 10.8 | 0.12 | 1.19 |
| 40 | pCCW12 | 193 | *Kosakonia sacchari* | 0.323 | 9.4 | 0.06 | 1.07 |
| 41 | pPGK1 | 176 | *Lecanicillium psalliotae* | 0.349 | 10.5 | 0.15 | 1.25 |
| 42 | pCCW12 | 176 | *Lecanicillium psalliotae* | 0.333 | 9.9 | 0.07 | 1.08 |
| 43 | pPGK1 | 176 | *Lecanicillium psalliotae* | 0.446 | 14.8 | 0.06 | 1.06 |
| 44 | pCCW12 | 208 | *Lentinus similis* | 0.314 | 9 | 0.05 | 1.05 |
| 45 | pPGK1 | 208 | *Lentinus similis* | 0.328 | 9.6 | 0.05 | 1.04 |
| 46 | pPGK1 | 204 | *Moelleriella libera* | 0.304 | 8.6 | 0.13 | 1.21 |
| 47 | pPGK1 | 198 | *Corynascus sepedonium* | 0.322 | 9.4 | 0.58 | 2.66 |
| 48 | pCCW12 | 198 | *Corynascus sepedonium* | 0.316 | 9.1 | 1.13 | 6.98 |
| 49 | pCCW12 | 198 | *Corynascus sepedonium* | 0.31 | 8.8 | 1.2 | 7.9 |
| 50 | pCCW12 | 178 | *Mucor moelleri* | 0.316 | 9.1 | 0.34 | 1.75 |
| 51 | pPGK1 | 178 | *Mucor moelleri* | 0.305 | 8.7 | 0.78 | 3.77 |
| 52 | pCCW12 | 186 | *Myceliophthora hinnulea* | 0.299 | 8.4 | 0.99 | 5.51 |
| 53 | pPGK1 | 186 | *Myceliophthora hinnulea* | 0.348 | 10.5 | 0.38 | 1.85 |
| 54 | pPGK1 | 203 | *Myceliophthora sepedonium* | 0.328 | 9.6 | 0.43 | 2.04 |

TABLE 19-continued

Trehalase and glucoamylase (GA) activity, and estimated enzyme secretion.

| Yeast strain no. | Promoter for trehalase expression | SEQ ID NO: (mature polypeptide) | Donor Organism (catalytic domain) | Glucoamylase activity | Conc. (ug/mL) | Trehalase activity | Conc. (ug/mL) |
|---|---|---|---|---|---|---|---|
| 55 | pPGK1 | 203 | Myceliophthora sepedonium | 0.328 | 9.6 | 0.41 | 1.97 |
| 56 | pCCW12 | 203 | Myceliophthora sepedonium | 0.31 | 8.8 | 1.2 | 7.9 |
| 57 | pPGK1 | 199 | Myceliophthora thermophila | 0.329 | 9.7 | 0.3 | 1.63 |
| 58 | pCCW12 | 199 | Myceliophthora thermophila | 0.315 | 9.1 | 0.74 | 3.54 |
| 59 | pPGK1 | 220 | Penicillium sp | 0.334 | 9.9 | 0.05 | 1.04 |
| 60 | pCCW12 | 220 | Penicillium sp | 0.326 | 9.6 | 0.05 | 1.04 |
| 61 | pPGK1 | 179 | Phialophora cyclaminis | 0.345 | 10.4 | 0.2 | 1.36 |
| 62 | pCCW12 | 179 | Phialophora cyclaminis | 0.315 | 9.1 | 0.66 | 3.05 |
| 63 | pPGK1 | 207 | Phoma sp | 0.312 | 9 | 0.07 | 1.09 |
| 64 | pCCW12 | 207 | Phoma sp | 0.283 | 7.7 | 0.09 | 1.12 |
| 65 | pCCW12 | 217 | Rasamsonia brevistipitata | 0.29 | 8 | 0.61 | 2.79 |
| 66 | pPGK1 | 217 | Rasamsonia brevistipitata | 0.321 | 9.3 | 0.54 | 2.46 |
| 67 | pCCW12 | 202 | Rhodothermus marinus | 0.319 | 9.3 | 0.3 | 1.61 |
| 68 | pPGK1 | 202 | Rhodothermus marinus | 0.318 | 9.2 | 0.12 | 1.18 |
| 69 | pPGK1 | 195 | Saitozyma flava | 0.312 | 8.9 | 0.25 | 1.48 |
| 70 | pCCW12 | 195 | Saitozyma flava | 0.309 | 8.8 | 0.39 | 1.9 |
| 71 | pCCW12 | 221 | Talaromyces aurantiacus | 0.332 | 9.8 | 0.6 | 2.77 |
| 72 | pPGK1 | 221 | Talaromyces aurantiacus | 0.345 | 10.4 | 0.57 | 2.63 |
| 73 | pCCW12 | 223 | Talaromyces leycettanus | 0.293 | 8.1 | 1.13 | 7.02 |
| 74 | pPGK1 | 223 | Talaromyces leycettanus | 0.311 | 8.9 | 0.71 | 3.35 |
| 75 | pPGK1 | 219 | Talaromyces piceae | 0.308 | 8.8 | 0.45 | 2.11 |
| 76 | pCCW12 | 219 | Talaromyces piceae | 0.313 | 9 | 0.73 | 3.48 |
| 77 | pCCW12 | 222 | Talaromyces pinophilus | 0.368 | 11.4 | 1.29 | 9.26 |
| 78 | pCCW12 | 222 | Talaromyces pinophilus | 0.302 | 8.5 | 0.95 | 5.13 |
| 79 | pPGK1 | 222 | Talaromyces pinophilus | 0.365 | 11.3 | 0.62 | 2.87 |
| 80 | pCCW12 | 224 | Talaromyces variabilis | 0.296 | 8.2 | 0.06 | 1.06 |
| 81 | pPGK1 | 181 | Thielavia antarctica | 0.338 | 10.1 | 0.08 | 1.1 |
| 82 | pCCW12 | 180 | Thielavia arenaria | 0.302 | 8.5 | 0.25 | 1.5 |
| 83 | pCCW12 | 215 | Trichoderma lixii | 0.306 | 8.7 | 0.06 | 1.06 |
| 84 | pPGK1 | 215 | Trichoderma lixii | 0.326 | 9.5 | 0.1 | 1.15 |
| 85 | pPGK1 | 200 | Trichoderma reesei GH37 | 0.312 | 8.9 | 0.05 | 1.04 |
| 86 | pCCW12 | 226 | Trichoderma reesei GH65 | 0.301 | 8.4 | 0.18 | 1.3 |
| 87 | pCCW12 | 192 | Xanthomonas arboricola | 0.306 | 8.7 | 0.46 | 2.17 |
| 88 | pPGK1 | 192 | Xanthomonas arboricola | 0.33 | 9.7 | 0.09 | 1.12 |

Example 7: Simultaneous Saccharification and Fermentation (SSF) of Yeast Strains Expressing Trehalase Simultaneous saccharification and fermentation (SSF) was performed via mini-scale fermentations for various trehalase-expressing strains described supra using industrial corn mash (Avantec® Amp, Novozymes, A/S). Yeast strains were cultivated overnight in YPD media with 2% glucose for 24 hours at 30° C. and 300 rpm. The corn mash was supplemented with 250 ppm of urea, dosed with 0.15 AGU/g-DS of an exogenous glucoamylase enzyme product (Spirizyme® Excel, Novozymes, A/S), and 30 mM trehalose. Approximately 0.6 mg of corn mash was dispensed per well to 96 well microtiter plates, followed by the addition of approximately $10^8$ yeast cells/g of corn mash from the overnight culture. Plates were incubated at 32° C. without shaking. Duplicates of each strain were analyzed after 48 hour fermentations. Fermentation was conducted using the conditions shown in Table 20, and then stopped by the addition of 100 µL of 8% H₂SO₄, followed by centrifugation at 3000 rpm for 10 min. The supernatant was analyzed for trehalose using HPLC.

TABLE 20

Microtiter plate fermentation reaction conditions

| Substrate | Avantec ® Amp corn mash |
|---|---|
| Yeast pitch | 10⁸ cells/g corn mash |
| Supplementary urea | 250 ppm |
| Supplementary trehalose | 30 mM |
| Exogenous glucoamylase product dose | 0.15 AGU/g-DS |
| PH | 5.0 ± 0.05 |
| Incubation temperature | 32° C. |
| Reaction time | 48 hours |

As shown in Table 21, higher reduction in trehalose was obtained from yeast expressing a heterologous trehalase compared to yeast lacking heterologous trehalase expression at 48 hours of simultaneous and saccharification fermentation (SSF).

TABLE 21

| Promoter | SEQ ID NO: (mature polypeptide) | Trehalase Donor Organism | Mean (trehalose % w/v) |
|---|---|---|---|
| | Background strain with glucoamylase gene, without trehalase gene | | 0.96 |
| pCCW12 | 191 | Acidovorax wautersii | 0.23 |
| pCCW12 | 218 | Acremonium curvulum | 0.29 |
| pCCW12 | 205 | Acremonium dichromosporum | 0.12 |
| pCCW12 | 216 | Aspergillus cervinus | 0.23 |
| pCCW12 | 225 | Aspergillus niger | 0.22 |
| pCCW12 | 184 | Chaetomium jodhpurense | 0.09 |
| pCCW12 | 175 | Chaetomium megalocarpum | 0.14 |
| pCCW12 | 183 | Chaetomium nigricolor | 0.12 |
| pCCW12 | 182 | Chaetomium sp | 0.19 |
| pCCW12 | 201 | Chaetomium virescens | 0.13 |
| pCCW12 | 21 | Dioszegia cryoxerica | 0.25 |
| pCCW12 | 177 | Doratomyces sp | 0.15 |
| pCCW12 | 194 | Enterobacter sp | 0.06 |
| pCCW12 | 188 | Gelasinospora cratophora | 0.12 |
| pCCW12 | 213 | Hamigera avellanea | 0.10 |
| pCCW12 | 193 | Kosakonia sacchari | 0.23 |
| pCCW12 | 176 | Lecanicillium psalliotae | 0.35 |
| pCCW12 | 208 | Lentinus similis | 0.43 |
| pCCW12 | 198 | Corynascus sepedonium | 0.13 |
| pCCW12 | 178 | Mucor moelleri | 0.13 |
| pCCW12 | 186 | Myceliophthora hinnulea | 0.14 |
| pCCW12 | 203 | Myceliophthora sepedonium | 0.13 |
| pCCW12 | 199 | Myceliophthora thermophila | 0.11 |

TABLE 21-continued

| Promoter | SEQ ID NO: (mature polypeptide) | Trehalase Donor Organism | Mean (trehalose % w/v) |
|---|---|---|---|
| pCCW12 | 220 | Penicillium sp | 0.95 |
| pCCW12 | 179 | Phialophora cyclaminis | 0.09 |
| pCCW12 | 207 | Phoma sp | 0.33 |
| pCCW12 | 217 | Rasamsonia brevistipitata | 0.16 |
| pCCW12 | 202 | Rhodothermus marinus | 0.42 |
| pCCW12 | 195 | Saitozyma flava | 0.19 |
| pCCW12 | 221 | Talaromyces aurantiacus | 0.15 |
| pCCW12 | 223 | Talaromyces leycettanus | 0.19 |
| pCCW12 | 219 | Talaromyces piceae | 0.19 |
| pCCW12 | 222 | Talaromyces pinophilus | 0.16 |
| pCCW12 | 224 | Talaromyces variabilis | 0.99 |
| pCCW12 | 180 | Thielavia arenaria | 0.11 |
| pCCW12 | 215 | Trichoderma lixii | 0.88 |
| pCCW12 | 226 | Trichoderma reesei GH65 | 0.27 |
| pCCW12 | 192 | Xanthomonas arboricola | 0.36 |
| pPGK1 | 189 | Acidobacteriaceae bacterium | 0.30 |
| pPGK1 | 218 | Acremonium curvulum | 0.40 |
| pPGK1 | 216 | Aspergillus cervinus | 0.29 |
| pPGK1 | 225 | Aspergillus niger | 0.11 |
| pPGK1 | 184 | Chaetomium jodhpurense | 0.17 |
| pPGK1 | 183 | Chaetomium nigricolor | 0.39 |
| pPGK1 | 182 | Chaetomium sp | 0.16 |
| pPGK1 | 201 | Chaetomium virescens | 0.17 |
| pPGK1 | 187 | Chloridium virescens | 0.20 |
| pPGK1 | 211 | Dioszegia cryoxerica | 0.15 |
| pPGK1 | 177 | Doratomyces sp | 0.19 |
| pPGK1 | 194 | Enterobacter sp | 0.18 |
| pPGK1 | 206 | Fusarium sambucinum | 0.26 |
| pPGK1 | 213 | Hamigera avellanea | 0.26 |
| pPGK1 | 193 | Kosakonia sacchari | 0.25 |
| pPGK1 | 176 | Lecanicillium psalliotae | 0.24 |
| pPGK1 | 208 | Lentinus similis | 0.15 |
| pPGK1 | 204 | Moelleriella libera | 0.18 |
| pPGK1 | 198 | Corynascus sepedonium | 0.18 |
| pPGK1 | 178 | Mucor moelleri | 0.20 |
| pPGK1 | 186 | Myceliophthora hinnulea | 0.17 |
| pPGK1 | 203 | Myceliophthora sepedonium | 0.16 |
| pPGK1 | 199 | Myceliophthora thermophila | 0.16 |
| pPGK1 | 220 | Penicillium sp | 1.19 |
| pPGK1 | 179 | Phialophora cyclaminis | 0.20 |
| pPGK1 | 207 | Phoma sp | 0.32 |
| pPGK1 | 217 | Rasamsonia brevistipitata | 0.11 |
| pPGK1 | 202 | Rhodothermus marinus | 0.44 |
| pPGK1 | 195 | Saitozyma flava | 0.19 |
| pPGK1 | 221 | Talaromyces aurantiacus | 0.16 |
| pPGK1 | 223 | Talaromyces leycettanus | 0.13 |
| pPGK1 | 219 | Talaromyces piceae | 0.20 |
| pPGK1 | 222 | Talaromyces pinophilus | 0.11 |
| pPGK1 | 181 | Thielavia antarctica | 0.25 |
| pPGK1 | 215 | Trichoderma lixii | 0.35 |
| pPGK1 | 200 | Trichoderma reesei GH37 | 0.42 |
| pPGK1 | 192 | Xanthomonas arboricola | 0.42 |

The invention claimed is:

1. A method of producing a fermentation product from a starch-containing or cellulosic-containing material comprising:
   (a) saccharifying the starch-containing or cellulosic-containing material; and
   (b) fermenting the saccharified material of step (a) with a recombinant yeast cell;
wherein the recombinant yeast cell comprises a heterologous polynucleotide encoding a trehalase having a mature polypeptide sequence with at least 95% sequence identity to the amino acid sequence of SEQ ID NO: 223.

2. The method of claim 1, wherein the trehalase has a mature polypeptide sequence comprising or consisting of the amino acid sequence of SEQ ID NO: 223.

3. The method of claim 1, wherein saccharification of step (a) occurs on a starch-containing material.

4. The method of claim 3, comprising liquefying the starch-containing material by contacting the material with an alpha-amylase prior to saccharification.

5. The method of claim 4, wherein liquefying the starch-containing material and/or saccharifying the starch-containing material is conducted in presence of exogenously added protease.

6. The method of claim 1, wherein fermentation and saccharification are performed simultaneously in a simultaneous saccharification and fermentation (SSF).

7. The method of claim 1, comprising recovering the fermentation product from the from the fermentation.

8. The method of claim 1, wherein the fermentation product is ethanol.

9. The method of claim 1, wherein the recombinant yeast cell comprises a heterologous polynucleotide encoding a glucoamylase or a protease.

10. The method of claim 1, wherein the recombinant yeast cell is a *Saccharomyces cerevisiae* cell.

11. The method of claim 1, wherein the trehalase has a mature polypeptide sequence with at least 97% sequence identity to the amino acid sequence of SEQ ID NO: 223.

12. The method of claim 1, wherein the trehalase has a mature polypeptide sequence with at least 98% sequence identity to the amino acid sequence of SEQ ID NO: 223.

13. The method of claim 1, wherein the trehalase has a mature polypeptide sequence with at least 99% sequence identity to the amino acid sequence of SEQ ID NO: 223.

* * * * *

SEQUENCE LISTING

```
Sequence total quantity: 236
SEQ ID NO: 1          moltype = DNA  length = 621
FEATURE               Location/Qualifiers
source                1..621
                      mol_type = genomic DNA
                      organism = Saccharomyces cerevisiae
SEQUENCE: 1
cagttcgagt ttatcattat caatactgcc atttcaaaga atacgtaaat aattaatagt   60
agtgattttc ctaactttat ttagtcaaaa aattagcctt ttaattctgc tgtaacccgt  120
acatgcccaa aataggtggc gggttacaca gaatatataa catcgtaggt gtctgggtga  180
acagtttatt cctggcatcc actaaatata atggagcccg cttttttaagc tggcatccag  240
aaaaaaaaag aatcccagca ccaaaatatt gttttcttca ccaaccatca gttcataggt  300
ccattctctt agcgcaacta cagagaacag gggcacaaac aggcaaaaaa cgggcacaac  360
ctcaatggag tgatgcaacc tgcctggagt aaatgatgac acaaggcaat tgacccacgc  420
atgtatctat ctcattttct tacaccttct attaccttct gctctctctg atttggaaaa  480
```

```
agctgaaaaa aaaggttgaa accagttccc tgaaattatt cccctacttg actaataagt   540
atataaagac ggtaggtatt gattgtaatt ctgtaaatct atttcttaaa cttcttaaat   600
tctactttta tagttagtct t                                             621

SEQ ID NO: 2              moltype = DNA   length = 644
FEATURE                   Location/Qualifiers
source                    1..644
                          mol_type = genomic DNA
                          organism = Saccharomyces cerevisiae
SEQUENCE: 2
agctacctat attccaccat aatatcaatc atgcggttgc tggtgtattt accaataatg    60
tttaatgtat atatattagg ggccgtatac ttacatatag tagatgtcaa gcgtaggcgc   120
ttcccctgcc ggctgtgacg gcgccataac caaggtatct atagaccgcc aatcagcaaa   180
ctacctccgt acattcatgt tgcacccaca catgtacaca cccagaccgc aacaaattac   240
ccataaggtt gtttgtgacg gcgtcgtaca agagaacgtg ggaactttt aggctcacca    300
aaaaagaaag gaaaaatacg agttgctgac agaagcctca agaaaaaaaa aattcttctt   360
cgactatgct ggaggcagag atgatcgagc cggtagttaa ctatatatag ctaaattggt   420
tccatcacct tcttttctgg tgtcgtcct tctagtgcta tttctggctt ttcctatttt    480
ttttttttcc attttctttt ctctcttcct aatatataaa ttctcttgca ttttctattt   540
ttctctctat ctattctact tgtttattcc cttcaaggtt ttttttttaag gagtacttgt   600
ttttagaata tacggtcaac gaactataat taagctagaa caaa                    644

SEQ ID NO: 3              moltype = DNA   length = 457
FEATURE                   Location/Qualifiers
source                    1..457
                          mol_type = genomic DNA
                          organism = Saccharomyces cerevisiae
SEQUENCE: 3
ctccagaaag gcaacgcaaa attttttttc cagggaataa actttctatg acccactact    60
tctcgtagga acaatttcgg gccctgcgt gttcttctga ggttcatctt ttacatttgt    120
ttctgctgga taattttcag aggcaacaag gaaaaattag atggcaaaaa gtcgtctttc   180
aaggaaaaat ccccaccatc cttcgagatc ccctgtaact tattggcaac tgaaagaatg    240
aaaaggagga aaatacaaaa tatactagaa ctgaaaaaaa aagtataaaa tagagacgat   300
atatgccaat acttcacaat gttcgaatcc attcttcatt tgcagctatt gtaaaataat   360
aaaacatcaa gaacaaacaa gctcaacttg tcttttctaa gaacaagaa taaacacaaa    420
aacaaaaagt ttttttaatt ttaatcgcta gaacaaa                            457

SEQ ID NO: 4              moltype = DNA   length = 700
FEATURE                   Location/Qualifiers
source                    1..700
                          mol_type = genomic DNA
                          organism = Saccharomyces cerevisiae
SEQUENCE: 4
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaa ctgaaaaaac ccagacacgc    240
tcgacttcct gtcatcctat tgattgcagc ttccaatttc gtcacacaac aaggtcctag   300
cgacggctca caggttttgt aacaagcaat cgaaggttct ggaatggcgg gaagggttt    360
agtaccacat gctatgatgc ccactgtgat ctccagagca aagttcgttc gatcgtactg   420
ttactctctc tcttttcaaac agaattgtcc gaatcgtgtg acaacaacag cctgttctca   480
cacactcttt tcttctaacc aaggggggtgg tttagtttag tagaaccctcg tgaaacttac  540
atttacatat atataaactt gcataaattg gtcaatgcaa gaaatacata tttggtcttt   600
tctaattcgt agttttccaa gttcttagat gctttctttt tctctttttt acagatcatc   660
aaggaagtaa ttatctactt tttacaacaa atataaaaca                         700

SEQ ID NO: 5              moltype = DNA   length = 705
FEATURE                   Location/Qualifiers
source                    1..705
                          mol_type = genomic DNA
                          organism = Sacharromyces cerevisiae
SEQUENCE: 5
atccttttgt tgtttccggg tgtacaatat ggacttcctc tttttctggca accaaaccca    60
tacatcggga ttcctataat accttcgttg gtctccctaa catgtggcta gcggaggga   120
gatatacaat agaacagata ccagacaaga cataatgggc taaacaagac tacaccaatt   180
acactgcctc attgatggtg gtacataacg aactaatact gtagccctag acttgatagc   240
catcatcata tcgaagtttc actacccttt ttccatttgc catctattga agtaataata   300
ggcgcatgca acttcttttc tttttttttc tttctctct cccccgttgt tgtctcacca    360
tatccgcaat gacaaaaaaa tgatggaaga cactaaagga aaaaattaac gacaaagaca   420
gcaccaacag atgtcgttgt tccagagctg atgaggggta tctcgaagca cacgaaactt   480
tttccttcct tcattcacgc acactactct ctaatgagca acggtatacg gccttccttc   540
cagttacttg aatttgaaat aaaaaaaaagt ttgctgtctt gctatcaagt ataaatagac   600
ctgcaattat taatctttg tttcctcgt attgttctcg ttccctttct tccttgtttc    660
tttttctgca caatatttca agctatacca agcatacaat caact                  705

SEQ ID NO: 6              moltype = DNA   length = 700
FEATURE                   Location/Qualifiers
source                    1..700
                          mol_type = genomic DNA
```

```
                        organism = Saccharomyces cerevisiae
SEQUENCE: 6
aagaggatgt ccaatatttt ttttaaggaa taaggatact tcaagactag attcccccct    60
gcattcccat cagaaccgta aaccttggcg ctttccttgg gaagtattca agaagtgcct   120
tgtccggttt ctgtggctca caaaccagcg cgcccgatat ggctttcttt tcacttatga   180
atgtaccagt acgggacaat tagaacgctc ctgtaacaat ctctttgcaa atgtgggggtt  240
acattctaac catgtcacac tgctgacgaa attcaaagta aaaaaaaatg ggaccacgtc   300
ttgagaacga tagattttct ttattttaca ttgaacagtc gttgtctcag cgcgctttat   360
gttttcattc atacttcata ttataaaata acaaaagaag aatttcatat tcacgcccaa   420
gaaatcaggc tgcttttccaa atgcaattga cacttcatta gccatcacac aaaactcttt   480
cttgctggag cttctttttaa aaagacctc agtacaccaa acacgttacc cgacctcgtt    540
attttacgac aactatgata aaattctgaa gaaaaaataa aaaaatttc atacttcttg    600
cttttattta aaccattgaa tgatttcttt tgaacaaaac tacctgtttc accaaaggaa    660
atagaaagaa aaaatcaatt agaagaaaac aaaaaacaaa                          700

SEQ ID NO: 7              moltype = AA  length = 19
FEATURE                   Location/Qualifiers
source                    1..19
                          mol_type = protein
                          organism = Saccharomyces cerevisiae
SEQUENCE: 7
MRFPSIFTTV LFAASSALA                                                  19

SEQ ID NO: 8              moltype = AA  length = 556
FEATURE                   Location/Qualifiers
source                    1..556
                          mol_type = protein
                          organism = Gloeophyllum sepiarium
SEQUENCE: 8
QSVDSYVSSE GPIAKAGVLA NIGPNGSKAS GASAGVVVAS PSTSDPDYWY TWTRDSSLVF     60
KSLIDQYTTG IDGTSSLRTL IDDFVTAEAN LQQVSNPSGT LTTGGLGEPK FNVDETAFTG    120
AWGRPQRDGP ALRSTALITY GNWLLSNGNT SYVTSNLWPI IQNDLGYVVS YWNQSTYDLW    180
EEVDSSSFFT TAVQHRALRE GAAFATAIGQ TSQVSSYTTQ ADNLLCFLQS YWNPSGGYIT    240
ANTGGGRSGK DANTLLASIH TYDPSAGCDA ATFQPCSDKA LSNLKVYVDS FRSVYSINSG    300
IASNAAVATG RYPEDSYQGG NPWYLTTFAV AEQLYDALNV WESQGSLEVT STSLAFFQQF    360
SSGVTAGTYS SSSSTYSTLT SAIKSFADGF VAVNAKYTPS NGGLAEQYSK SDGSPLSAVD    420
LTWSYASALT AFEARNNTQF AGWGAAGLTV PSSCSGNSGG PTVAVTFNVN AETVWGENIY    480
LTGSVDALEN WSADNALLLS SANYPTWSIT VNLPASTAIE YKYIRKNNGA VTWESDPNNS    540
ITTPASGSTT ENDTWR                                                   556

SEQ ID NO: 9              moltype = AA  length = 374
FEATURE                   Location/Qualifiers
source                    1..374
                          mol_type = protein
                          organism = Aspergillus niger
SEQUENCE: 9
APAPTRKGFT INQIARPANK TRTINLPGMY ARSLAKFGGT VPQSVKEAAS KGSAVTTPQN     60
NDEEYLTPVT VGKSTLHLDF DTGSADLWVF SDELPSSEQT GHDLYTPSSS ATKLSGYTWD    120
ISYGDGSSAS GDVYRDTVTV GGVTTNKQAV EAASKISSEF VQNTANDGLL GLAFSSINTV    180
QPKAQTTFFD TVKSQLDSPL FAVQLKHDAP GVYDFGYIDD SKYTGSITYT DADSSQGYWG    240
FSTDGYSIGD GSSSSSGFSA IADTGTTLIL LDDEIVSAYY EQVSGAQESE EAGGYVFSCS    300
TNPPDFTVVI GDYKAVVPGK YINYAPISTG SSTCFGGIQS NSGLGLSILG DVFLKSQYVV    360
FNSEGPKLGF AAQA                                                     374

SEQ ID NO: 10             moltype = AA  length = 590
FEATURE                   Location/Qualifiers
source                    1..590
                          mol_type = protein
                          organism = Trichoderma reesei
SEQUENCE: 10
SVHLLESLEK LPHGWKAAET PSPSSQIVLQ VALTQQNIDQ LESRLAAVST PTSSTYGKYL     60
DVDEINSIFA PSDASSSAVE SWLQSHGVTS YTKQGSSIWF QTNISTANAM LSTNFHTYSD    120
LTGAKKVRTL KYSIPESLIG HVDLISPTTY FGTTKAMRKL KSSGVSPAAD ALAARQEPSS    180
CKGTLVFEGE TFNVFQPDCL RTEYSVDGYT PSVKSGSRIG FGSFLNESAS FADQALFEKH    240
FNIPSQNFSV VLINGGTDLP QPPSDANDGE ANLDAQTILT IAHPLPITEF ITAGSPPYFP    300
DPVEPAGTPN ENEPYLQYYE FLLSKSNAEI PQVITNSYGD EEQTVPRSYA VRVCNLIGLL    360
GLRGISVLHS SGDEGVGASC VATNSTTPQF NPIFPATCPY VTSVGGTVSF NPEVAWAGSS    420
GGFSYYFSRP WYQQEAVGTY LEKYVSAETK KYYGPYVDFS GRGFPDVAAH SVSPDYPVFQ    480
GGELTPSGGT SAASPVVAAI VALLNDARLR EGKPTLGFLN PLIYLHASKG FTDITSGQSE    540
GCNGNNTQTG SPLPGAGFIA GAHWNATKGW DPTTGFGVPN LKKLLALVRF               590

SEQ ID NO: 11             moltype = AA  length = 511
FEATURE                   Location/Qualifiers
source                    1..511
                          mol_type = protein
                          organism = Thermoascus aurantiacus
SEQUENCE: 11
VPVEVAGSAQ GLDVTLSQVG NTRIKAVVKN TGSEDVTFVH LNFFKDAAPV QKVSLFRNAT     60
EVQFQGIKQR LITEGLSDDA LTTLAPGATI EDEFDIASTS DLSEGGTITI NSNGLVPITT    120
```

```
DNKVTGYIPF TSNELSIDVD AAEAASVTQA VKILERRTRI SSCSGSRQSA LTTALRNAAS   180
LANKAADAAQ SGSASKFSEY FKTTSSSTRQ TVAARLRAVA REASSSSSGA TTYYCLDPFG   240
YCSGNVLAYT LPSYNIIANC PIFYTYLPPL TSTCHAQDQA TTVLHEFTHA PGVYSPGTLD   300
LAYGYQAAMG LSSSQAVMNA DTYALYANAI YLGCTRISSC SGSRQSALTT ALRNAASLAN   360
AAADAAQSGS ASKFSEYFKT TSSSTRQTVA ARLRAVAREA SSSSSGATTY YCDDPYGYCS   420
SNVLAYTLPS YNIIANCDIF YTYLPALTST CHAQDQATTA LHEFTHAPGV YSPGTDDLAY   480
GYQAAMGLSS SQAVMNADTY ALYANAIYLG C                                 511

SEQ ID NO: 12           moltype = AA   length = 550
FEATURE                 Location/Qualifiers
source                  1..550
                        mol_type = protein
                        organism = Dichomitus squalens
SEQUENCE: 12
KPTARNLKLH ESRPSAPNGF SLVGSADSNR TLKLRLALAE SNFSELERKL YDVSTPKSAN    60
YGKHLSKAEV QQLVAPGQDS IDAVNAWLKE NDITAKTISS TGEWISFEVP VSKANDLFDA   120
DFSVFKHDDT GVEAIRTLSY SIPAELQGHL DLVHPTVTFP NPYSHLPVFQ SPVKKTAEIQ   180
NFTAGAIPSS CSSTITPACL QAIYNIPTTA ATESSNQLGV TGFIDQYANK KDLKTFLKKY   240
RTDISSSTTF TLQTLDGGSN SQTGSKAGVE ANLDIQYTVG VATGVPTTFI SVGDDFQDGD   300
LEGFLDVINA LLDEDAPPSV LTTSYGQDES TISRALAVKL CNAYAQLGAR GVSILFASGD   360
GGVSGSQSAS CSKFVPTFPS GCPYMTSVGA TQGVNPETAA DFSSGGFSNY WGVPDYQSDA   420
VSTYLSALGK TNSGKYNASG RGFPDVSTQG VSFEVVVDGS VEAVDGTSCA SPTFASIISL   480
VNDKLVAAGK SPLGFLNPFL YSDGVAALND ITSGSNPGCN TNGFPAKKGW DPVTGLGTPD   540
FKKLLTAVGL                                                        550

SEQ ID NO: 13           moltype = AA   length = 353
FEATURE                 Location/Qualifiers
source                  1..353
                        mol_type = protein
                        organism = Nocardiopsis prasina
SEQUENCE: 13
ATGALPQSPT PEADAVSMQE ALQRDLDLTS AEAEELLAAQ DTAFEVDEAA AEAAGDAYGG    60
SVFDTESLEL TVLVTDAAAV EAVEATGAGT ELVSYGIDGL DEIVQELNAA DAVPGVVGWY   120
PDVGDTVVL EVLEGSGADV SGLLADAGVD ASAVEVTTSD QPELYADIIG GLAYTMGGRC   180
SVGFAATNAA GQPGFVTAGH CGRVGTQVTI GNGRGVFEQS VFPGNDAAFV RGTSNFTLTN   240
LVSRYNTGGY ATVAGHNQAP IGSSVCRSGS TTGWHCGTIQ ARGQSVSYPE GTVTNMTRTT   300
VCAEPGDSGG SYISGTQAQG VTSGGSGNCR TGGTTFYQEV TPMVNSWGVR LRT          353

SEQ ID NO: 14           moltype = AA   length = 456
FEATURE                 Location/Qualifiers
source                  1..456
                        mol_type = protein
                        organism = Penicillium simplicissimum
SEQUENCE: 14
APASTAKDSV SSVVKNGVKY TVFEHAATGA KMEFVKNSGI CETTPGVNQY SGYLSVGSNM    60
NMWFWFFEAR NNPQQAPLAA WFNGGPGCSS MIGLFQENGP CHFVNGDSTP SLNEYSWNNY   120
ANMLYVDQPI GVGFSYGTDD VTSTVTAAPY VWKLLQAFYA QFPEYESRDF AIFTESYGGH   180
YGPEFASYIQ EQNSAIKTGS ISGENINLVA LGVNNGWIDS TIQEKAYIDF SYNNSYQQLI   240
DDSQRTSLLS AYNSQCLPAI QKCTKSGSNS DCQNADSVCY NKIEGPISSS GDWDVYDIRE   300
PSNDPYPPST YSTYLSNADV VKAIGAQSSY QECPNGPYNK FASTGDNPRS FLSTLSSVVK   360
SGINVLVWAG DADWICNWLG NYEVANAVDF SGHTEFSAKD LAPYTVNGTE KGMFKNVANF   420
SFLKVYGAGH EVPYYQPDTA LQVFEQVLQN KPIFST                            456

SEQ ID NO: 15           moltype = AA   length = 502
FEATURE                 Location/Qualifiers
source                  1..502
                        mol_type = protein
                        organism = Aspergillus niger
SEQUENCE: 15
LQNPHRRAVP PPLSHRSVAS RSVPVERRTT DFEYLTNKTA RFLVNGTSIP EVDFDVGESY    60
AGLLPNTPTG NSSLFFWFFP SQNPEASDEI TIWLNGGPGC SSLDGLLQEN GPFLWQPGTY   120
KPVPNPYSWT NLTNVVYIDQ PAGTGFSPGP STVNNEEDVA AQFNSWFKHF VDTFDLHGRK   180
VYITGESYAG MYVPYIADAM LNEEDTTYFN LKGIQINDPS INSDSVMMYS PAVRHLNHYN   240
NIFQLNSTFL SYINAKADKC GYNAFLDKAI TYPPPSPFPT APEITEDCQV WDEVVMAAYD   300
INPCFNYYHL IDFCPYLWDV LGFPSLASGP NNYFNRSDVQ KILHVPPTDY SVCSETVIFA   360
NGDGSDPSSW GPLPSVIERT NNTIIGHGWL DYLLFLNGSL ATIQNMTWNG KQGFQRPPVE   420
PLFVPYHYGL AELYWGDEPD PYNLDAGAGY LGTAHTERGL TFSSVYLSGH EIPQYVPGAA   480
YRQLEFLLGR ISSLSAKGNY TS                                          502

SEQ ID NO: 16           moltype = AA   length = 547
FEATURE                 Location/Qualifiers
source                  1..547
                        mol_type = protein
                        organism = Meriphilus giganteus
SEQUENCE: 16
TPTGRNLKLH EAREDLPAGF SLRGAASPDT TLKLRIALVQ NNPFAELEDKL YDVSTPSSAN   60
YGNHLSKEEV EQYIAPAPES VKAVNAWLTE NGLDAHTISP AGDWLAFEVP VSKANELFDA   120
DFSVFTHDES GLEAIRTLAY SIPAELQGHL DLVHPTVTFP NPNAHLPVVR STQPIRNLTG   180
RAIPASCAST ITPACLQAIY GIPTTKATQS SNKLAVSGFI DQFANKADLK SFLAQFRKDI   240
```

```
SSSTTFSLQT LDGGENDQSP SEAGIEANLD IQYTVGLATG VPTTFISVGD DFQDGNLEGF   300
LDIINFLLGE SNPPQVLTTS YGQNENTISA KLANQLCNAY AQLGARGTSI LFASGDGGVS   360
GSQSAHCSNF VPTFPSGCPF MTSVGATQGV SPETAAAFSS GGFSNVFGIP SYQASAVSGY   420
LSALGSTNSG KFNRSGRGFP DVSTQGVDFQ IVSGGQTIGV DGTSCASPTF ASVISLVNDR   480
LIAAGKSPLG FLNPFLYSSA GKAALNDVTS GSNPGCSTNG FPAKAGWDPV TGLGTPNFAK   540
LLTAVGL                                                             547

SEQ ID NO: 17          moltype = AA  length = 541
FEATURE                Location/Qualifiers
source                 1..541
                       mol_type = protein
                       organism = Lecanicillium sp.
SEQUENCE: 17
APAPHGPLVK FGEITKLPSK WIATGAADSD AVIKAQIGIK QNNIKGLQDK LADIADPNSP    60
NYGQWLSKEE VDKYSAPAAA DVAAVKAWLA SSGITDVTMP TNDWIEFSVP VSKMESLLGS   120
KYEWFVHLET GEKVPRTKQF SVPQNLHDLI DVVTPTTVLY HNMGPHAHAS PQAADASGLT   180
SPASIKSAYN VDYKGTGNTL VGTTGFLGVG ASHQDYANFA RQFSPGLTDF KDVSINGGSN   240
SGDGSALEGN LDTQYCGALA APNPSEYLAH APEGSDGSSF NDAMLAFGNY LNANSNPPSA   300
VSTSYGGEED GTDPNYMDRI CNEFMKAGSR GVSIFFSSGD NGVGGNGESS CYNGYYPLWP   360
ASCPYVTTVG GTEFDGSGRE VVANFEQYNK NVKSPGGGFS NHFPAPSYNK NVTTAYANSL   420
SAAQKQRLNP NGRGFPDIAL VSVKYQVNVN GQISQVLGTS ASSPSMAGLV GLLNDYRKTQ   480
GKPNLGFINP LLYSDKVKPA LRDVTSGANK GCDSSGLPAK TGWDAASGLG SFDFAKLRTL   540
V                                                                   541

SEQ ID NO: 18          moltype = AA  length = 633
FEATURE                Location/Qualifiers
source                 1..633
                       mol_type = protein
                       organism = Talaromyces proteolyticus
SEQUENCE: 18
VPAPSKRHVV HERRDALPHS WSEPRRVDGR TQLPVRIGLT QSNIDESHDM LMDIASPSSP    60
NYRKYMTVHE VNELFAPAGE AVSAVRDWLE SAGIAAERVT QSANKQWLQF DGDAAEVESL   120
LGAEYYIYTH DTNGRSHMGC EKYHVPEHIS HHIDYIIPGV KSLEVREPQP AELEKRTFGF   180
RKPQPPLFKA LPESLETIIN SILGGLLDLC STVITPSCIK TLYNITEGTT ATKGNELGIF   240
EDLGDYYSQT DLDLFFTLFY SQIPAGTGPT LKGIDGAQAP TQTLTQAGPE SDLDFQVSYP   300
IIWPQNSILF QTDDANYEAN YTFNGFLNNF LDAIDGSYCT YSAFGIDGNT ADDPPYPDPA   360
SNGYKGSLQC GVYEPTNVIS ISYGGDEAGL SVNYQKRQCN EYKKLGLQGV SVVVSSGDSG   420
VAGADGCLGG GKIFNPDFPA GCPYITTVGA TYLPSGASST SDSEVAVSRF PSGGGFSNIY   480
SQPSYQSDAV NTYLTQHTPP YPAYETSDNS SVGANGGIYN KAGRGYPDVA AVGDNIVIFN   540
AGAPTLIGGT SASAPIFASI LTRINEVLLA KKGTTVGFVN PTLYANPDAF HDITSGDNPG   600
CSTNGFSTAP GWDPVTGLGT PNYPALLKVF LGE                                633

SEQ ID NO: 19          moltype = AA  length = 371
FEATURE                Location/Qualifiers
source                 1..371
                       mol_type = protein
                       organism = Penicillium ranomafanaense
SEQUENCE: 19
VPTGGKKSFT VNQVAVSATK TQNFANNYAR ALAKYGAKVP THVQAAAQQS GSATTTPESD    60
DEEYLTPVNV GGTTLNLDFD TGSADLWVFS SELPASEQTG HSLYKPNNGT KLSGYTWSIS   120
YGDGSSASGD VYRDTVSGGG VKATGQAVEA ASTISQQFTQ DQNNDGLLGL AFSSINTVKP   180
KSQTTFFDTV KSTLASPLFA VSLKHNAPGS YDFGFIDKSK YTGSLTYTDV DSSQGFWGFT   240
ADSYKIGSTT GSSIKGIADT GTTLLLLDDE VVSAYYKQVS GAASDSSAGG YTFDCSSTLP   300
DFTVSISGYD AVVPGSLINY TPVSQGSSKC LGGIQSNSGL GFSIFGDIFL KSQYVVFDSN   360
GPRLGFAAQS S                                                        371

SEQ ID NO: 20          moltype = AA  length = 578
FEATURE                Location/Qualifiers
source                 1..578
                       mol_type = protein
                       organism = Aspergillus oryzae
SEQUENCE: 20
EAFEKLSAVP KGWHYSSTPK GNTEVCLKIA LAQKDAAGFE KTVLEMSDPD HPSYGQHFTT    60
HDEMKRMLLP RDDTVDAVRQ WLENGGVTDF TQDADWINFC TTVDTANKLL NAQFKWYVSD   120
VKHIRRLRTL QYDVPESVTP HINTIQPTTR FGKISPKKAV THSKPSQLDV TALAAAVVAK   180
NISHCDSIIT PTCLKELYNI GDYQADANSG SKIAFASYLE EYARYADLEN FENYLAPWAK   240
GQNFSVTTFN GGLNDQNSSS DSGEANLDLQ YILGVSAPLP VTEFSTGGRG PLVPDLTQPD   300
PNSNSNEPYL EFFQNVLKLD QKDLPQVIST SYGENEQEIP EKYARTVCNL IAQLGSRGVS   360
VLFSSGDSGV GEGCMTNDGT NRTHFPPQFP AACPWVTSVG ATFKTTPERG TYFSSGGFSD   420
YWPRPEWQDE AVSSYLETIG DTFKGLYNSS GRAFPDVAAQ GMNFAVYDKG TLGEFDGTSA   480
SAPAFSAVIA LLNDARLRAG KPTLGFLNPW LYKTGRQGLQ DITLGASIGC TGRARFGGAP   540
DGGPVVPYAS WNATQGWDPV TGLGTPDFAE LKKLALGN                           578

SEQ ID NO: 21          moltype = AA  length = 456
FEATURE                Location/Qualifiers
source                 1..456
                       mol_type = protein
                       organism = Talaromyces liani
SEQUENCE: 21
```

```
APASTTKDNV SSVVKNGVTY TVFEHAATGA KMEFVKNSGI CETTPGVNQY SGYLSVGNNM    60
NMWFWFFEAR NNPQTAPLAA WFNGGPGCSS MIGLFQENGP CHFVNGASTP SLNEYSWNNY   120
ANMLYVDQPI GVGFSYGTDD VTSTVTAAPY VWKLLQAFYA QFPEYQSRDF AIFTESYGGH   180
YGPEFAAYIQ EQNSGIAAGS VSGENINLIA LGVNNGWIDP AIQEKAYIDF SYNNSYQQLI   240
DDSQRTNLLS DYNDQCLPAI QQCAQTGRNS DCQNADNVCY DTIEGPISSS GNWDVYDIRE   300
PSNDPYPPST YSSYLSNSRV VKAIGAQTSY QECPNGPYNK FASTGDNPRS FLSTLSSVVQ   360
SGIHVLVWAG DADWICNWLG NYRVANAVDF PGHAEFSAKA LAPYTVNGTE KGMFKNVDNF   420
SFLKVYGAGH EVPYYQPATA LQVFEQILQN KSITST                            456

SEQ ID NO: 22          moltype = AA  length = 589
FEATURE                Location/Qualifiers
source                 1..589
                       mol_type = protein
                       organism = Thermoascus thermophilus
SEQUENCE: 22
EVFERLRAVP EGWRFSATPS DDQPIRLQIA LQQHDVEGFE RAVLDMSTPS SPNYGKHFQS    60
HDEMKRMLLP SDDAVDAVLD WLQSAGITDI EEDADWINFM TTVGVANELL DTQFQWFVSE   120
TSSHVRRLRA LEYSIPESVT PHIHMVQPTT RFGQIGRHHT TSREKPIVSG ADIHASIAGA   180
NNQTTGTDCN TEITPKCLQD LYKFGGYKAS ANSGSKVGFC SYLEEYARYD DLALFEEALA   240
PYAAGQNFSV ITYNGGLNDQ HSSSDSGEAN LDLQYIVGVS APLPVTEFST GGRGELVPDL   300
DQPNPADNSN EPYLDFLQNV LKLDQKDLPQ VISTSYGENE QSVPEKYARS VCNLFMQLGS   360
RGVVIFSSG DSGVGSACLT NDGKNQTRFM PQFPASCPWV TVGSTQHIA PEEATYFSSG    420
GFSDLWPMPD YQKSAVGEYL DRLGSKWAGL YNPQGRGFPD VAAQGVNFNV YDKGSLKRFD   480
GTSCSAPTFA GVIALLNDAR LRARQPPMGF LNPWLYGAGK GGLNDIVNGG STGCDGNARF   540
GGAPNGSPVV PFASWNATQG WDPVSGLGTP DFSRLLKLAV PSRVGGRLA              589

SEQ ID NO: 23          moltype = AA  length = 413
FEATURE                Location/Qualifiers
source                 1..413
                       mol_type = protein
                       organism = Pyrococcus furiosus
SEQUENCE: 23
AELEGLDESA AQVMATYVWN LGYDGSGITI GIIDTGIDAS HPDLQGKVIG WVDFVNGRSY    60
PYDDHGHGTH VASIAAGTGA ASNGKYKGMA PGAKLAGIKV LGADGSGSIS TIIKGVEWAV   120
DNKDKYGIKV INLSLGSSQS SDGTDALSQA VNAAWDAGLV VVVAAGNSGP NKYTIGSPAA   180
ASKVITVGAV DKYDVITSFS SRGPTADGRL KPEVVAPGNW IIAARASGTS MGQPINDYYT   240
AAPGTSMATP HVAGIAALLL QAHPSWTPDK VKTALIETAD IVKPDEIADI AYGAGRVNAY   300
KAINYDNYAK LVFTGYVANK GSQTHQFVIS GASFVTATLY WDNANSDLDL YLYDPNGNQV   360
DYSYTAYYDF EKVGYYNPTD GTWTIKVVSY SGSANYQVDV VSDGSLSQPG SSP          413

SEQ ID NO: 24          moltype = AA  length = 387
FEATURE                Location/Qualifiers
source                 1..387
                       mol_type = protein
                       organism = Trichoderma reesei
SEQUENCE: 24
LPTEGQKTAS VEVQYNKNYV PHGPTALFKA KRKYGAPISD NLKSLVAARQ AKQALAKRQT    60
GSAPNHPSDS ADSEYITSVS IGTPAQVLPL DFDTGSSDLW VFSSETPKSS ATGHAIYTPS   120
KSSTSKKVSG ASWSISYGDG SSSSGDVYTD KVTIGGFSVN TQGVESATRV STEFVQDTVI   180
SGLVGLAFDS GNQVRPHPQK TWFSNAASSL AEPLFTADLR HGQNGSYNFG YIDTSVAKGP   240
VAYTPVDLNSQ GFWEFTASGY SVGGGKLNRN SIDGIADTYT TLLLLDDNVV DAYYANVQSA   300
QYDNQQEGVV FDCDEDLPSF SFGVGSSTIT IPGDLLNLTP LEEGSSTCFG GLQSSSGIGI   360
NIFGDVALKA ALVVFDLGNE RLGWAQK                                      387

SEQ ID NO: 25          moltype = AA  length = 408
FEATURE                Location/Qualifiers
source                 1..408
                       mol_type = protein
                       organism = Rhizomucor miehei
SEQUENCE: 25
RPVSKQSESK DKLLALPLTS VSRKFSQTKF GQQQLAEKLA GLKPFSEAAA DGSVDTPGYY    60
DFDLEEYAIP VSIGTPGQDF LLLFDTGSSD TWVPHKGCTK SEGCVGSRFF DPSASSTFKA   120
TNYNLNITYG TGGANGLYFE DSIAIGDITV TKQILAYVDN VRGPTAEQSP NADIFLDGLF   180
GAAYPDNTAM EAEYGSTYNT VHVNLYKQGL ISSPLFSVYM NTNSGTGEVV FGGVNNTLLG   240
GDIAYTDVMS RYGGYYFWDA PVTGITVDGS AAVRFSRPQA FTIDTGTNFF IMPSSAASKI   300
VKAALPDATE TQQGWVVPCA SYQNSKSTIS IVMQKSGSSS DTIEISVPVS KMLLPVDQSN   360
ETCMFIILPD GGNQYIVGNL FLRFFVNVYD FGNNRIGFAP LASAYENE              408

SEQ ID NO: 26          moltype = AA  length = 548
FEATURE                Location/Qualifiers
source                 1..548
                       mol_type = protein
                       organism = Lenzites betulinus
SEQUENCE: 26
KPMGRNLKVH EAREEIPDGF SLQGSAAPDT TLKLRIALVQ SNFAELEQKL YDVSTPSSPN    60
YGAHLSKEEV EQLVAPSADS VDAVNAWLKE NDLSAQTISP AGDWLAFEVP VSKANELFDA   120
DFSVFTHDQT GLEAIRTMSY SIPAELQGHL DLVHPTVTFP NPYSHLPVVR SPIKASQNLT   180
SRATIPASCA STITPACLQD IYGIPTTKAT QSSNKLAVSG FIDQFANSAD LATFLKKFRT   240
DISSTTTFAL QTLDGGSNSQ SGSQAGVEAN LDIQYTVGLA SGVPVTFISV GDNFQDGDLE   300
```

```
GFLDIINFLL AESAPPQVLT TSYGQNENTI SVKLANQLCN AYAQLGARGT SILFASGDGG   360
VSGSQSSSCS KFVPTFPSGC PFMTSVGATQ GVNPETAADF SSGGFSNYFG IPSYQATAVK   420
TYLTALGTTN SGKFNTSGRA FPDVSTQGVD FEIVVDGRTE GVDGTSCASP TFAAIISLVN   480
DKLIAAGKSP LGFLNPFLYS TGASAFTDIT SGSNPGCNTK GFPAKAGWDP VTGLGTPNFA   540
KLLAAAGV                                                           548

SEQ ID NO: 27           moltype = AA  length = 547
FEATURE                 Location/Qualifiers
source                  1..547
                        mol_type = protein
                        organism = Neolentinus lepideus
SEQUENCE: 27
GPAPRNLVLH ESRDGVPEGF VKSSTASPDT TLKLRIALVQ GDMASLEKAL YDVSVPSSPL    60
YGQHLSKQEV EEYVKPTQES VDAVNQWLSS EGITANTISP AGDWLQFSVP VSKANEMFDA   120
DFSVFTHTES GQQAIRTLSY SIPKELVGHL DLVHPTITFP NPYSHLPVVS SPAPRNLTID   180
ASVPSSCGST ITPTCLQDLY GIPTTAATQS SNKLAVSGFI DQYANKADLK SFLTTYRKDI   240
SSSTTFTLET IDGGENPQDG SDAGVEANLD TQYTVGLATG VPTYFISVGD DYQDGDLEGF   300
LDIVNYLLSM DQPQQVLTTS YGQNENTMSR SLANNLCNAY MQLGARGTSI LFASGDGGVS   360
GSQSGSCGSK FVPTFPSGCP YLTSVGATTG INPEVAASFS SGGFSNYWGV PSYQQSVVSS   420
YISGLGSTNK GKYNSSGRGF PDVSAQGENV EIVVDGSTEG VDGTSCSSPI FASIVSLLND   480
ELIAAGKSPL GFLNPFLYSD GASAFNDITS GDNPGCNTNG FSAKSGWDPV TGLGTPNYAK   540
LRTAVGF                                                            547

SEQ ID NO: 28           moltype = AA  length = 399
FEATURE                 Location/Qualifiers
source                  1..399
                        mol_type = protein
                        organism = Thermococcus sp.
SEQUENCE: 28
VSAEKVRVII TIDKDFNENS VFALGGNVVA RGKVFPIVIA ELSPRAVERL KNAKGVVRVE    60
YDAEVQVLKG KSPGAGKPKP SQPAQTIPWG IERIKAPDVW SITDGSSSGV IEVAILDTGI   120
DYDHPDLAAN LAWGVSVLRG KVSTKPKDYK DQNGHGTHVA GTVAALNNDI GVVGAPAVE    180
IYAVRVLDAS GRGSYSDIIL GIEQALLGPD GVLDSDGDGI IVGDPDDDAA EVISMSLGGL   240
SDVQAFHDAI IEAYNYGVVI VAASGNEGAS SPSYPAAYPE VIAVGATDVN DQVPWWSNRG   300
VEVSAPGVDV LSTYPDDSYE TLSGTSMATP HVSGVVALIQ AAYYNKYGSV LPVGTFDDNT   360
MSTVRGILHI TADDLGSSGW DADYGYGIVR ADLAVQAVN                          399

SEQ ID NO: 29           moltype = AA  length = 396
FEATURE                 Location/Qualifiers
source                  1..396
                        mol_type = protein
                        organism = Thermococcus sp.
SEQUENCE: 29
EKVRVIITID KDFNENSVFA LGGNVVARGK VFPIVIAELS PRAVERLKNA KGVVRVEYDA    60
EVQVLKGKSP GAGKPKPSQP AQTIPWGIER IKAPDVWSIT DGSSSGVIEV AILDTGIDYD   120
HPDLAANLAW GVSVLRGKVS TKPKDYKDQN GHGTHVAGTV AALNNDIGVV GVAPAVEIYA   180
VRVLDASGRG SYSDIILGIE QALLGPDGVL DSDGDGIIVG DPDDDAAEVI SMSLGGLSDV   240
QAFHDAIIEA YNYGVVIVAA SGNEGASSPS YPAAYPEVIA VGATDVNDQV PWWSNRGVEV   300
SAPGVDVLST YPDDSYETLS GTSMATPHVS GVVALIQAAY YNKYGSVLPV GTFDDNTMST   360
VRGILHITAD DLGSSGWDAD YGYGIVRADL AVQAVN                             396

SEQ ID NO: 30           moltype = AA  length = 572
FEATURE                 Location/Qualifiers
source                  1..572
                        mol_type = protein
                        organism = Thermomyces lanuginosus
SEQUENCE: 30
APFQVVERLS APPDGWIKKE KAAPSAQIQF RLGLPQQNSE QLEQLALNIA TPGHELYRKH    60
LKRDEIKALV RPLASVSEKV LAWLRDEGVP EDRIHDDGAN IKFTVPVSTA EKLLNTEFFV   120
FHNERTGAEQ IRTLEYSVPQ DIHSLVKFIQ PTTHFSSLGP QVRRVVPLDV LPKLRITLED   180
CNKKITPDCL KQLYKIGDYV APEDPRNRIG ISGYLEQFAR YADFEEFLES YAPDRTDANF   240
TVVSINGGRN DQNSTLDSTE ASLDIDYAVT LSYKTQAVYY TTAGRGPLVP DESQPDPNEV   300
SNEPYMEQLQ FLLDLPDEEL PTVLTTSYGE NEQSLPGSYA DETCNMFRLL GMRGVSVIFS   360
SGDWGTGIVC KANDGSERIK FDPVYPASCP YVTSVGGTTG VNPERAVEFS SGGFSDRFPR   420
PKYQDEAVRS YLTKLGDHWK GLYNESGRAF PDVAAQADNF VVRDQGQWVS VGGTSASAPV   480
FAAIIANVNA ELLKAGKPPL GFLNPWLYGL KGRGFTDVVH GGSTGCPGTV PWTGLPAGHV   540
PYASWNATEG WDPVTGLGTP LYDELVKAAL GK                                 572

SEQ ID NO: 31           moltype = AA  length = 397
FEATURE                 Location/Qualifiers
source                  1..397
                        mol_type = protein
                        organism = Thermococcus thioreducens
SEQUENCE: 31
EKPELVRVIV HVDRGHFNTA DVATIGGHVV YQFKLIDAVV VEVPSTAVGR LKKLPGVKMV    60
EFDHKARILA GPPSWLGGGQ PSQQIPWGIS RVRAPDVWGI TDGSGGVIEV AVLDTGVDYD   120
HPDLAGNIAW CVSTLRGRVT TNPAQCKDQN GHGTHVIGTI AALNNDIGVV GVAPGVEIYS   180
IRVLDASGSG SYSDIAIGIE QALLGPDGIL DKDGDGIIVG DPDDDAAEVI SMSLGGPTDD   240
QYLHDMIITA YNYGVVIVAA SGNEGASSPS YPAAYPEVIA VGASDVNDQI ASWSNRQPEV   300
```

```
SAPGVDILST YPDDTYETLS GTSMATPHVS GVVALIQAAY YNKYGKVLPV GTFDDMGTNT    360
VRGILHVTAD DLGDAGWDIY YGYGIVRADL AVQAAIG                            397

SEQ ID NO: 32           moltype = AA  length = 549
FEATURE                 Location/Qualifiers
source                  1..549
                        mol_type = protein
                        organism = Polyporus arcularius
SEQUENCE: 32
KPMARSMKLH ESREGIPEGF SLRGAAQPEQ TIKLRLALVQ SNFAELERKL MDVSTPSSAN    60
YGKHLSKAEV QQLVAPTQDS VDAVKSWLKE NDISAKTISA TGDWLSFEVP VSKANELFDA    120
DFSIYTHDET GTEAVRTLSY SIPAELQGHL DLVHPTVTFP NPRGLPPVFT APIKAEAQNL    180
TSRATIPSSC ARTITPACLQ AIYNIPSTPA TESSNKLAVT GFIEQFANKA DLKTFLTRFR    240
TDISSSTSFT LQTLDGGSNP QSSSEAGVEA NLDIQYTVGV ATGVPTVFIS VGEDFQDGDL    300
EGFLDVVNSL LDEDTPPFVM TTSYGQNENT ISRNLANNLC NAYAQLGARG VSILFASGDG    360
GVAGSQSASC SKFVPTFPSG CPFMTSVGAT QGFSPETAAD FSSGGFSNYF AIPDYQTSAV    420
SGYIKALGNT NSGKYNATGR GFPDIATQGV NFEVVVGGQS GTVEGTSCSS PTLASIISLL    480
NDRLIAAGKS PLGFLNPFLY STGTSALNDI TSGSNPGCNT NGFPAKAGWD PVTGLGTPDF    540
NKLLSAVGL                                                           549

SEQ ID NO: 33           moltype = AA  length = 548
FEATURE                 Location/Qualifiers
source                  1..548
                        mol_type = protein
                        organism = Ganoderma lucidum
SEQUENCE: 33
KSTTRNLKLH ETRQGAPSGF SHTGSADPNQ TLKLRLALVQ GNTAELERKL YDVSTPSSAN    60
YGKHLSKEEV RQLVAPAQGS VDAVNAWLRE NGITAKSTSA AGDWLSFEVP VSKANELFDA    120
DFSVFKHDDT GVKAVRTLSY SIPAELQGHL DLVHPTVTFP NPNGHMPVFQ APVKDTDAVQ    180
NFSARAVPSS CSNTITPACL QALYNIPSDA ATQSSNKLAV TGFIEQYANQ VDLAVFLKQY    240
RADISSNTTF ALQTLDGGSN SQTNVPGVEA NLDIQYTVGI ATGVPTVFIS VGDQYQDGDL    300
EGFLDVINFL LDEDTPPYVV TTSYGQDEHT ISRKLAQNLC NAYAQLGARG VSILFASGDG    360
GVAGSRSNSC SKFVPTFPSG CPYMTSVGAT QGVPETAADF SSGGFSNYFG TPDYQASAVK    420
SYLSLTGSTN RGKFNASGRG FPDVATQGVN FEVIVDGEVE GVSGTSAASP MFAAIVALLN    480
DKLIAAGKSP LGFLNPFLYS KGVEALNDIT TGSNPGCGTI GFPAKEGWDP VTGLGTPDFQ    540
KLASAAGL                                                            548

SEQ ID NO: 34           moltype = AA  length = 548
FEATURE                 Location/Qualifiers
source                  1..548
                        mol_type = protein
                        organism = Ganoderma lucidum
SEQUENCE: 34
KTATRNLKLH ETSQGAPSGF SLTGSADPDQ TLKLRLALVQ GNVAELERRL YDVSTPSSPN    60
YGKHLSKSEV QQLVAPAQDS IDAINAWLKE NGISAKTTSA TGDWLSFEVP VSKANELFDA    120
DFSVYKHHDT GMEVVRTLSY SIPAELQAHL DLVHPTVTFP NPKGHPPVFQ APAMITNDVQ    180
NFSAGAVPSS CSSRITPACL QALYNIPSDP ATQPSNKLAV TGYIEQYANQ DDLAVFLKEY    240
RADMSSNTTF TLQTLDGGVN SQTDEAGIEA NLDVQYTVGI ATGVPTVFIS VGDQYQDGNL    300
EGFLDVVNFL LDEDTPPYVM TTSYGQDEHT MSRKLAQNLC NAYAQLGARG VSILFASGDG    360
GVAGSRSSSC SKFVPTFPSG CPYMTSVGAT QGVPETAADF SSGGFSNYFG IPDYQASAVS    420
GYLSALGHTN KGKYNASGRG FPDVSTQGVN FEVMVDGALE GVSGTSAASP TFAAVVALLN    480
DRLIAAGKSP LGFLNPFLYS KGVSALNDIT SGSNPGCRTN GFPAKEGWDP VTGLGTPDFQ    540
KLASAAGL                                                            548

SEQ ID NO: 35           moltype = AA  length = 541
FEATURE                 Location/Qualifiers
source                  1..541
                        mol_type = protein
                        organism = Ganoderma lucidum
SEQUENCE: 35
KPTARNLRLH ETRQGAPSGF SLTGSADPNQ TVRLRLALVQ GNTGELERKL YDVSTPSSAN    60
YGKHLSKAEV QQLVAPAQGS IDAVNAWLKE NDITAKTISA TGDWLSFEVP VNKANELFDA    120
DFSVFKHDDT GMEAVRTLSY SIPAELQGHL DLVHPTVTFP NPKGNLPLFQ TPIKSKRDVP    180
ADCSNNITPA CLQALYNIPS DAATQSSNTL AVTGYIEQYA NQQDLTSFLG QFRPDISSNT    240
TFALQTIDGG SNSQNGSDAG GEANLDIQYT VGLATGVPTV FISVGEQYQD GDLGGLLDVI    300
NFVLAEDAPP NVITTSYGQN ENTISLKLAQ NLCNAYAQLG ARGVSILFAS GDGGVAGSQS    360
DNCTQFVPTF PSGCPYMTSV GATQGVPETA ADFSTGGFSN LFSVPDYQAA AVQSYLSALG    420
GTYQGLFNAS GRAFPDVSTQ GVNFETVVDG SVSGASGTSA ASPTFAAIVA LLNDRLVAAG    480
KSPLGFLNPF LYSTGASALN DIATGSNPGC GTNGFSAQKG WDPVTGLGTP DFQKLAAAAG    540
L                                                                   541

SEQ ID NO: 36           moltype = AA  length = 547
FEATURE                 Location/Qualifiers
source                  1..547
                        mol_type = protein
                        organism = Trametes sp.
SEQUENCE: 36
TPTGRNLKLH EAREDIPTGY SLRGAASPDT TLKLRLALVQ NNFAELEDKL YDVSTPSSAN    60
YGNHLSKEEV EQYIAPAPES VKAVNAWLTE NGLDAHTISP AGDWLAFEVP VSKANELFDA    120
```

```
DFSVFTHDES GLEAIRTLAY SIPAELQGHL DLVHPTVTFP NPNAHLPVVR STKPIQNLTG    180
RAIPASCAST ITPACLQAIY GIPTTKATQS SNKLAVSGFI DQFANSADLK SFLSTFRKDI    240
SSSSTTFALQT LDGGQNNQSP SQAGIEANLD IQYTVGLATG VPVTFISVGD NFQDGDLEGF   300
LDIINFLLSE SNPPQVLTTS YGQNENTISA KLANQLCNAY AQLGARGTSI LFASGDGGVA    360
GSQSSSCRNF VPTFPSGCPF MTSVGATQGV SPETAADFSS GGFSNVFGIP SYQTSAVSGY    420
LSALGNTNSG KFNRSGRGFP DVATQGVNFQ IVSGGDTGGV DGTSCASPTF ASVISLINDR    480
LIAAGKSPLG FLNPFLYSAA GKAALNDVTS GSNPGCNTNG FPAKAGWDPV TGLGTPNFAK    540
LLTAVGL                                                             547

SEQ ID NO: 37             moltype = AA  length = 553
FEATURE                   Location/Qualifiers
source                    1..553
                          mol_type = protein
                          organism = Cinereomyces lindbladii
SEQUENCE: 37
KPTARNLLVH ESLDGVPTGF QLVGPASPDT VLSMRIALVQ SDPAGLEAAL YDVSTPSSAS    60
YGNHLSKAEV EKFVSPTSES VQAVNAWLTE NDLTATQLSP AGDWLGFEVP VSKAEDLFGT   120
QFSVFTHEAT GMQTVRTLSY SIPSELQGHL DLVFPTINFP DPNANLPVFR HASKKREVTT   180
LNANLTSDAV PSSCADTITP ACLQALYGIP TTPATSSTNQ LGVSGFIDQF ANQADLKTFL   240
QNFRTDISSS TTFSLETLDG GSNSQNRGDA GVEANLDTQY TVGLATDVPT VFISVGEDNQ   300
DGSLGGFLDI INFLLDQDSP PQVLTTSYGQ NENTVSRAVA NNLCNAYAQL GARGTSILFA   360
SGDGGVSGSQ SASCRTFVPT FPSGCPFMTS VGATTGINPE TAATFSAGF SNYFGTPSYQ    420
ASAVSSYLAA LGSTNSGKFN TSGRGYPDVS TQGENFEIVV SGEEEGVDGT SCASPTFASI   480
ISLVNDRLIA AGKPPLGFLN PFLYSTGASA FTDITTGDNP GCNTNGFPAK SGWDPVTGLG   540
TPNFSKLLTA VGL                                                     553

SEQ ID NO: 38             moltype = AA  length = 559
FEATURE                   Location/Qualifiers
source                    1..559
                          mol_type = protein
                          organism = Trametes versicolor
SEQUENCE: 38
AVASTLQLHE ARKGIPAGFS LHGAASPDTV LNLRMALVQS NFAGLEERLY DVSTPSSANY    60
GKHLSKAEVE QYVAPRQQSI TAVKAWLAAN GLSGTSISPA GDWIAAKVPV SKANKLLGAQ   120
FSVFNNDATG RQIIRTLAYS IPAELKGHLD LVHPTITFAD IKPLVPVVSA RRESRVLVDS   180
DLVANTIPAS CNAAITPACL QDLYGIPSTP ATQSSNQLGV SGFIDQFANQ ADLATFLTEF   240
RPDVSNSTTF TLQTLDGGQN PQDPSDAGVE ANLDTQYTVG VATNVPTTFF SVGDDTKDGI   300
FGFLDLISFL LAAAAPPQVL TTSYGADEGG LSANLVRNLC QAYAQLGARG TSILFSSGDG   360
GVSGSQAEGC VDFVPTFPSG CPFLTSVGAT QLTTASGLTV ETAAGFSSGG FSNYFPTPPY   420
QQAVVDAYIK KTLVNGTVNE GLFNASGRAF PDVSAVGVDY LIVVGGGTDI VSGTSASSPL   480
FASVIALIND RRLAAGKPPL GFLNPFLYSQ AGASALNDVT VGSNPGCASP GFPAAQGWDP   540
VTGLGTPNFA KLLAAALAL                                               559

SEQ ID NO: 39             moltype = AA  length = 541
FEATURE                   Location/Qualifiers
source                    1..541
                          mol_type = protein
                          organism = Paecilomyces hepialid
SEQUENCE: 39
APAPHGPLVK FGEIRKLPSK WVATGAADAN AVIKGQIGIK QNNIQGLQAK LADIADPNSP    60
NYGQWLSKEE VDKYSAPAAA DVAAVKAWLA SSGITDVTMP TNDWIEFSVP VSKMESLLGS   120
KYEWFVHLET GEKVPRTKEF SVPQNLHDLI DVVTPTTVLY HNINPHTHSS PQAAGAAGLT   180
SPASIKSAYN VDYKGTGNTL VGTTGFLGVG ASHTDYANFG QQFSPGLKDF QDVSVNGGSN   240
SGDGSALEGN LDTQYCGALA APNPSEYLAH APEGSDNNSF NDAMLAFGNY LNSARNPPSA   300
VSTSYGGEED GVDASYLDRI CNEFMKAGSR GVSIFFSSGD NGVGGNGESS CQNGYYPLWP   360
ATCPYVTTVG GTEFDNSGRE VVANFEQYNK NIKSPGGGYS NHFAAPSYNK AVTTSYANGL   420
AAPQKQRLNP NGRGYPDISL VSVKYQVNVN NQISQVLGTS ASSPSIAGLV GLLNDYRKTQ   480
GKPNLGFINP LLYSDKVKPA LRDVTSGSNK GCDSVGLPAK TGWDAASGLG SFDFGKLRTL   540
V                                                                  541

SEQ ID NO: 40             moltype = AA  length = 541
FEATURE                   Location/Qualifiers
source                    1..541
                          mol_type = protein
                          organism = Isaria tenuipes
SEQUENCE: 40
APAPHGPLVK FGELKKLPSQ WVATGAANGD AVIKAQIGIK QNNIKGLQDK LAEISDPNSP    60
SYGQWLSKEE VAKYTAPADA DVAAVKAWLS SAGITEVTMP TNDWLEFSVP VSKMESLLGS   120
KYEWFVHLET GEKAPRTKEF SVPQNLHGII DVVTPTTVLY HNINPNSHGN ELSASASGLT   180
SPASIKSAYN VDYKGTGNTL VATTGFLGVG ASHNDYLAFG HQFSPGLKDF QDVSVNGGSN   240
SGDGSALEGN LDTQYCGALA SPNPSQYLAN SPEGSDNNSF NDAMTAFGNY LNSASNPPSA   300
VSTSYGGEED GVDAGYLDRI CNEFMKAGSR GISVFFSSGD NGVGGNGEPS CQNGYYPLWP   360
ATCPYVTTVG GTEFDDSGRE VVANFEQYNK NVKSPGGGYS NHFPAPDYNK NVTTAYANSL   420
SAAQQQRLNP NGRGFPDISL VSVKYQVSLN GQTKQVLGTS ASSPSVAGLV GLLNDYRKTQ   480
GKSNLGFLNP LLYSGKVNAA LRDVTSGSNK GCDSVGLPAK SGWDAASGLG SFDFAKLRSL   540
I                                                                  541

SEQ ID NO: 41             moltype = AA  length = 578
FEATURE                   Location/Qualifiers
```

```
source                  1..578
                        mol_type = protein
                        organism = Aspergillus tamarii
SEQUENCE: 41
EAFEKLSAVP KGWHYSSTPE GSTSVCLKIA LAQKDAAGFE KRVYEMSDPD HPNYGQHFTT    60
HEEMKRMLLP RDDTVDAVRQ WLENGGVTDV RQDSDWINFC TTVDTANKLL NAQFKWYVSD   120
VKHIRRLRTL QYDVPGSVAS HVNTIQPTTR FGKITPKKAV THSKPSQLDV TALAAAVVAK   180
NISHCDSIIT PTCLKELYNI GDYQADANSG SKIAFASYLE EYARYADLEN FENYLAPWAK   240
GQNFSVITYN GGLNDQNSSS DSGEANLDLQ YILGVSAPLP VTEFSTGGRG PLVPDLTQPD   300
PNANSNEPYL EFFQNVLKLD QEQLPQVIST SYGENEQEIP EKYARTVCNL IAQLGSRGVS   360
VLFSSGDSGV GEGCMTNDGT NRTHFPPQFP AACPWVTSVG ATYKTTPERA TYFSSGGFSD   420
YWARPEWQEE AVSSYLETIG DAFKGLYNAS GRAFPDVAAQ GMNFAVYDKG TLGEFDGTSA   480
SAPAFSAIIA LLNDARLRAG KPTLGFLNPW LYKTGRQGLQ DITLGASTGC TGRARFGGAP   540
DGGPVVPFAS WNATQGWDPV TGLGTPDFAE LKKLALAN                           578

SEQ ID NO: 42           moltype = AA  length = 587
FEATURE                 Location/Qualifiers
source                  1..587
                        mol_type = protein
                        organism = Aspergillus brasiliensis
SEQUENCE: 42
EIFEKLSGVP NGWRYANNPQ GNEVIRLQIA LQQHDVTGFE QAVMDMSTPG HADYGKHFRT    60
HEEMKRMLLP SDTAVDSVRD WLESAGVHNI QVDADWIKFH TTVTKANALL DADFKWYVSE   120
ARHIRRLRTL QYSIPDALVS HINMIQPTTR FGQIQPNRAT MRSKPKHADE TFLTAATLAQ   180
NTSHCDSIIT PSCLKQLYNI GDYQADPKSG SKIGFASYLE EYARYADLEK FEQHLAPNAI   240
GQNFTVVQFN GGLNDQLSTK DSGEANLDLQ YILGVSAPLF VTEYSTGGRG ELVPDLSSPD   300
PNDNSNEPYL DFLQNILKLN NSDLPQVIST SYGEDEQTIP VPYARAVCNL YAQLGSRGVS   360
VIFSSGDSGV GAACLTNDGT NRTHFPPQFP ASCPWVTSVG ATSKTPEQA VSFSSGGFSD    420
LWPRPSYQHA AVQTYLTEHL GNKFSGLFNA SGRAFPDVSA QGVNYAVYDK GILGQFDGTS   480
CSAPTFSGVI ALLNDARLRA GLPVMGFLNP FLYGAGSKLG GLNDIVTGGS VGCDGRNRFG   540
GTPNGSPVVP FASWNATTGW DPVSGLGTPD FAKLKVVALG ESEGDEN                 587

SEQ ID NO: 43           moltype = AA  length = 582
FEATURE                 Location/Qualifiers
source                  1..582
                        mol_type = protein
                        organism = Aspergillus iizukae
SEQUENCE: 43
EVFDTLAAVP KGWHYSHTPR ADQPISLKIA LKQHNVEGFE QAVLDMSTPG HEHYGKHFRE    60
HDEMKRMLLP SDATVDAVKD WLLAADVTDY EVDADWINLH TTVQQANELL DTEFAWYVSD   120
VRAVRRLRTL RYSVPDAVAP HINMVQPTTR FGQIHPDRAT FRAGSTHFGA HILSAMSAVG   180
DVSSANVTCD DVITPLCLKE LYKVDGYRAE AEHGSKIAFA SYLEEYARYD DMVRFQEKLA   240
PYAKGENFSV ILYNGGVDDQ QSTSDSGEAN LDLQTIMGLS APLPITEYIT GGRGKLIPDL   300
SQPDPNDNSN EPYLEWIQNV LKHSPEELPQ VISTSYGEDE QTIPRGYAES VCNLLAQLGS   360
RGVSVIFSSG DSGVGSACQT NDGTNTTHFP PQFPASCPWV TSVGATSKTH PEEAVYFSSG   420
GFSDLWARPA WQDDAVSTYI ESIGGKFAGL YNASGRAFPD VSAQGQNYAI FDKGRLGKMD   480
GTSCSAPAFA GIVSLLNDAR LRANRPVLGF LNPWLYGTAR EGLNDIVHGG SKGCDGRDRF   540
GGKPNGSPVV PYASWNATPG WDPVSGLGTP NFATLVQVAL HD                      582

SEQ ID NO: 44           moltype = AA  length = 456
FEATURE                 Location/Qualifiers
source                  1..456
                        mol_type = protein
                        organism = Penicillium sp.
SEQUENCE: 44
APASTAKDSV SSVVKNGVKY TVFEHAATGA KMEFVKNSGI CETTPGVNQY SGYLSVGSNM    60
NMWFWFFEAR NNPQQAPLAA WFNGGPGCSS MIGLFQENGP CHFVNGDSTP SLNEYSWNNY   120
ANMLYVDQPI GVGFSYGTDD VTSTVTAAPY VWKLLQAFYA QFPEYESRDF AIFTESYGGH   180
YGPEFASYIQ DQNAAIKAGS VSGENINLVA LGVNNGWIDS TIQEKAYIDF SYNNSYKQLI   240
DDSQRTSLLS AYNDQCLPAI QKCTSSGSNS DCKNADSVCY NQIEGPISSS GDWDVYDIRE   300
PSNDPYPPST YSTYLSNADV VKAIGAQSSY QECPNGPYNK FTSTGDNPRS FLSTLSSVVK   360
SGINVLVWAG DADWICNWLG NYEVANAVDF SGHTDFSAKD LAPYTVNGTE KGLFKNVDNF   420
SFLRVYGAGH EVPYYQPDTA LQVFEQILQK KPIFST                             456

SEQ ID NO: 45           moltype = AA  length = 456
FEATURE                 Location/Qualifiers
source                  1..456
                        mol_type = protein
                        organism = Aspergillus denticulatus
SEQUENCE: 45
STASAAKDSV SSIVKNGVKY TVFEHAATGA KMEFVKNSGI CETTPGVNQY SGYLSVGDNM    60
NMWFWFFEAR NNPQQAPLAA WFNGGPGCSS MIGLFQEHGP CHFVNGEDTP SLNEYSWNNY   120
ANMLYVDQPI GVGFSYGTDD VTSTVTAAPY VWKLLQAFYA QFPEYESRDF AVFTESYGGH   180
YGPEFASYIQ QQNAAIKAGT VSGENINLIA LGVNNGWIDS AIQEKAYIDF SYNNTYKQLI   240
SSSDRTRLLS VYNSQCLPAI QKCTSTGTTA ACRNADSVCY NNIEGPISSS GDWDVYDIRE   300
PANDPYPPAT YSTYLADPDV VKAIGAQTSY QECPNGPYNK FASTGDNPRS FLSTLSNVVK   360
SGINVLVWAG DADWICNWLG NYEVANAVDY PGQSEFEAKD LAPYTVNGAE KGMFKNVDNF   420
SFLRVYGAGH EVPYYQPETA LQVFQQTLQK KPIFST                             456
```

```
SEQ ID NO: 46             moltype = AA  length = 456
FEATURE                   Location/Qualifiers
source                    1..456
                          mol_type = protein
                          organism = Hamigera sp.
SEQUENCE: 46
APASTAKDTL SSIVKNGVTY NVFEHADSGA KIEFVKNSGI CETTPGVNQY SGYLSVGDNM   60
NMWFWFFEAR NNPQKAPLAA WFNGGPGCSS MIGLFQENGP CHFVNGENTP SLNEYSWNNY  120
ANMLYVDQPI GVGFSYGTDD VDSTVTAAPY VWKLLQAFYA QFPEYESRDF AIFTESYGGH  180
YGPEFAHYIQ QQNAAIKSGS VKGENINLIG LGVNNGWIDS AIQEKAYIDF SYNNSYKQLI  240
DFSQRTSLMR AYKNQCLPAI QKCYQTGTNA DCTDASSVCY NNIEGPISSS GDWDVYDIRE  300
PSNDPYPPKT YSSYLSDPKV VKAIGARTNY KECPNGPYNK FSTTGDNPRS FLSTLSDVVK  360
SGINVILWAG DADWICNWLG GYGVANAVDY PGHAQFRAKA LAPYTVNGTE KGQFKTVDNF  420
QFLKVYGAGH EVPYYQPETA LQVFEQILQK KPIHST                            456

SEQ ID NO: 47             moltype = AA  length = 456
FEATURE                   Location/Qualifiers
source                    1..456
                          mol_type = protein
                          organism = Penicillium janthinellum
SEQUENCE: 47
APASTAKDTV SSVVKDGVTY TVFEHAATGA KMEFVKNSGI CETTPGVNQY SGYLSVGSNM   60
NMWFWFFEAR NNPQQAPLAA WFNGGPGCSS MIGLFQENGP CHFVNGESTP SLNENSWNNY  120
ANMIYIDQPI GVGFSYGTDR VTSTVTAAPY VWKLLQAFYA QFPEYESRDF AIFTESYGGH  180
YGPEFASYIE QQNAAIKAGS VTGQNVNIVA LGVNNGWIDA TIQEKAYIDF SYNNSYQQII  240
DSSTRDSLLD AYNNQCLPAL QQCAQSGSNS DCTNADSVCY QNIEGPISSS GDFDVYDIRE  300
PSNDPYPPKT YSTYLSDPTV VKAIGARTNY QECPNGPYNK FASTGDNPRS FLSTLSSVVQ  360
SGINVLVWAG DADWICNWLG NYAVANAVDF PGNAQFSAMD LAPYTVNGVE KGQFKTVDNF  420
SFLKVYGAGH EVPYYQPDTA LQVFKQILQK KPISST                            456

SEQ ID NO: 48             moltype = AA  length = 456
FEATURE                   Location/Qualifiers
source                    1..456
                          mol_type = protein
                          organism = Penicillium vasconiae
SEQUENCE: 48
APASTAKDSV SSVVKNGVKY TVFEHAATGA KMEFVKNSGI CETTPGVNQY SGYLSVGSNM   60
NMWFWFFEAR NNPQQAPLAA WFNGGPGCSS MIGLFQENGP CHFVNGDSTP SLNEYSWNNY  120
ANMLYVDQPI GVGFSYGTDD VTSTVTAAPY VWKLLQAFYA QFPEYESRDF AIFTESYGGH  180
YGPEFASYIQ EQNAAITAGS VSGQKINLIA LGVNNGWIDS TIQEKAYIDF SYNNSYQQLI  240
DDSQRTSLLS AYNKQCLPAI QKCTQTGSNS ACQNAANVCY NNIEGPISSS GDWDVYDIRE  300
PSNDPYPPST YSTYLANSDV VKAIGAQSSY QECPNGPYNK FASTGDNPRS FLSTLSSVVK  360
SGINVLVWAG DADWICNWLG NYEVANAVDF SGHAEFSAKD LAPYTVNGAE KGMFKNVDNF  420
SFLKVYGAGH EVPYYQPETA LQVFEQILQK KPISST                            456

SEQ ID NO: 49             moltype = AA  length = 454
FEATURE                   Location/Qualifiers
source                    1..454
                          mol_type = protein
                          organism = Hamigera paravellanea
SEQUENCE: 49
APSLRDKRSF VERDGVTYTV FEHAATGAKM EFVQNSGICE TTPGVNQYSG YLSVGDNMNM   60
WFWFFEARNN PTAAPLAAWF NGGPCSSMI GLFQENGPCH FVNGESTPSL NEYSFNNYAN   120
VLYVDQPIGT GFSYGTDDVT STVTAAPYVW KLLQAFYAQF PEYESRDFGI FTESYGGHYG  180
PEFASYIQEQ NAAIKAGSVS GDNINLVALG INNGWFDAGI QEKAYIDFSY NNSYRQIISS  240
SQRSSYLDAY NHDCLPAIES CASSGTNSAC KNAESVCYNG IEGPISSAAD FDVYDVRQPS  300
NDPYPPATYS TYLQSASVRK AIGARTKYQE CPNGPYNKFE TTGDNSRSFL STLSDVVNTG  360
ITVLVWAGDA DWICNWVGGH AVADAVTFAR QKTFQAKPLE PYTVNGTEKG RFKTVDNFTF  420
LRVYEAGHEV PYYQPETALQ VFVQTMQKKA IFST                              454

SEQ ID NO: 50             moltype = AA  length = 453
FEATURE                   Location/Qualifiers
source                    1..453
                          mol_type = protein
                          organism = Talaromyces variabilis
SEQUENCE: 50
AAVPQDKRSI VKRDGVTYNV FEHAATGAKM EFVKNSGICE TTPGVNQYSG YLSVGDNMNM   60
WFWFFESRNN ASGAPLAAWF NGGPCSSMI GLFQENGPCH FVNGEKKPSL NKYSFNEYAN   120
VLYVDQPIGV GFSYGTDDVT STESAAPYVW KLLQAFYAQF PQYESRDFGI FTESYGGHYG  180
PEFAHYLQQQ NEGVKNGSVD GENINLVALG INNGWFDTQL QEGAYIDYAY SNNYKKIIDS  240
SQRSSLEDSL KSDCLPAVKQ CLSSGSDSDC ENASDTCGQI ESSIQQAADF DVYDVREPSN  300
DPYPPSTYSD YLADSSVVKA IGAKSTYKEC PNGPYYKFSS TGDNTRSFLS ELSSVVQSGI  360
QVLVWAGDAD WICNYMGVQR VADAVEFDGS SQFSNATLKP YTVNGTKKGE YKNVDNFSYL  420
RVYGAGHEVP YYQPAVALQV FKQTMQQQAI KST                               453

SEQ ID NO: 51             moltype = AA  length = 456
FEATURE                   Location/Qualifiers
source                    1..456
                          mol_type = protein
```

```
                        organism = Penicillium arenicola
SEQUENCE: 51
APATHLQDKR SIVERDGVNY TVFEHAATGA KLEFVTNSGI CETTSGVNQY SGYLSVGTNM    60
NMWFWFFESR NSPSTAPLAA WFNGGPGCSS MIGLFQENGP CQFYDGASTP SLNPYSFNEY   120
ANMIYIDQPI GVGFSYGTDD VTSTVTAAPY VWKLIQAFYA SPPAYESREF GLFTESYGGH   180
YGPEFAYYIQ QQNAAIASGT VTGDTIDIVA LGINNGWIDS ALQEKAYIEY SYNNSYKQII   240
TSSQRTSYLS TYTNDCLPAI NKCTTGGSNS ACSNAADVCY NDIESPIMSD ADFDVYDIRQ   300
PSNDAYPPET YVTYLQTSSV VKAIGASSTY QECPDAPYNK FATTGDNDRS FLATLSTVVQ   360
SGITVLLWAG DADWICNWVG NQYVADAVTW SGQSSFAAQT LTPYTVNGSE VGTFKTLDNL   420
SFLRVYEAGH EVPYYQPATA LQAFIQTMQK KALSST                            456

SEQ ID NO: 52           moltype = AA  length = 354
FEATURE                 Location/Qualifiers
source                  1..354
                        mol_type = protein
                        organism = Nocardiopsis kunsanensis
SEQUENCE: 52
APAPQNPTEP AEATTMAEAL ERDLGLNEAE ATDLIDAQES ALDVDAEATE AAGEHYGGSL    60
FDTETHDLTV LVTDSAAVPG VEAAGAEAAV VEHGVEGLDD LISDLDSAGA QEGVVGWYPE   120
VENDTVVIET LEGADADVDA LLSSAGVDPA DVRVETTDEA PEVYANIVGG DAYTIGGSSR   180
CSVGFPASDS YGQPGFVTAG HCGTTGSSVS IGNGSGVFSQ SVFPGNDAAF VRGTSNFSLT   240
NLVNRYNSGS DVAVSGSTQA PIGSQVCRSG STTGWHCGTI QARGQTVSYP QGTVRDLTRT   300
SVCAEPGDSG GSFISGSQAQ GVTSGGSGNC SWGGTTYYQE VNPMLNSWNL NLST         354

SEQ ID NO: 53           moltype = AA  length = 425
FEATURE                 Location/Qualifiers
source                  1..425
                        mol_type = protein
                        organism = Streptomyces parvulus
SEQUENCE: 53
GTAPSPAAPT AAESLRADAA PPALLRAMER DLGLGREQAE RRLGNEAEAG AVAGRLRADL    60
GGDFAGAWVR GAESGTLTVA TTDAADVPAI EARGAVAEVV RHSLADLGAA KSRLDRAAAH   120
RDTAEAPVRY VDVRTNTVTV QAVRPSAARA LLAAAGVDAG LARVETSAER PRPLYDLRGG   180
EAYYINNSGR CSVGFPVTKG TQQGFATAGH CGRAGASTSG ANRVAQGTFQ GSVFPGRDMA   240
WVAANSQWTA TPYVSGAGGQ NVQVAGSTQA PVGASVCRSG STTGWHCGTI QQHDTSVTYP   300
EGTITGVTRT TVCAEPGDSG GSYISGSQAQ GVTSGGSGNC GSGGTTFFQP INPLLQNYGL   360
TLKTTGGGGE DPGEPGEPGG TWAAGTVYRP GDTVTYGGAT YRCLQGHQAQ RGWEPANVPA   420
LWQRV                                                               425

SEQ ID NO: 54           moltype = AA  length = 350
FEATURE                 Location/Qualifiers
source                  1..350
                        mol_type = protein
                        organism = Saccharopolyspora endophytica
SEQUENCE: 54
LTATIADPAG PPVSPELVTA MQRDLGLTAD QAVARLGQEA VAARADSALR DALAGSYGGS    60
YFDANLGKLV VGTTDAAKSD EVRAAGAEPR QVDASERQLG GIVEALNGRG AQVPAAVTGA   120
YADVRENAVV VTTQPGTAEQ ATGFVRDAQV PQESVRVWES PAQPETYADV VGGYAYYTAS   180
GARCSMGFAV QGGFVTAGHC GAPGESTTQP TGYFAGSSFP GNDYAFVNTG TDDTGYPLVY   240
NYSSGYVRVS GSAEAPLGSS ICRSGSTTGW HCGTVLAKNQ SVRYQEGTVS GLTRTNVCAE   300
PGDSGGSFIS GNQAQGMTSG GWDCRTGGE TYYQPVREAL SAYGLTLLTQ               350

SEQ ID NO: 55           moltype = AA  length = 355
FEATURE                 Location/Qualifiers
source                  1..355
                        mol_type = protein
                        organism = Luteus cellwall
SEQUENCE: 55
ASGPLPQSPS PDSDVATTMA EALERDLNLT STEAQELLTA QEAAFEADEA AAQAAGDAYG    60
GSVFDTETLD LTVMVTDAAA VQAVEATGAK ADVVSYGIDG LDTIIDDLNE ADAPEGVVGW   120
YPDIDSDTVV LEVLEGSGAD VDALLAEAGV DASAVKVEST TEQPELYADI IGGLAYYMGG   180
RCSVGFAATN ASGQPGFVTA GHCGRVGTQV TIGNGRGVFE RSVFPGNDAA FVRGTSNFTL   240
TNLVSRYNSG GYATVSGSSV APIGSSVCRS GSTTGWRCGT IQARGQTVTY PQGTIYNMTR   300
TSACAEPGDS GGSFISGTQA QGVTSGGSGN CSWGGTTFYQ EVNPMLNSWN LRLRT        355

SEQ ID NO: 56           moltype = AA  length = 406
FEATURE                 Location/Qualifiers
source                  1..406
                        mol_type = protein
                        organism = Saccharothrix australiensis
SEQUENCE: 56
GPPTTHQEES GLIAAMARDF KITPDQARAR LVREAKAATT EQSLKSRLGG HYAGAWLNEG    60
ATELVVAVTD AAQAKVVEDA GATPKVVQRS QIQLDELKAK LDANKNAPKD VPAWYVDVKT   120
NSVVVLARNT ASAKAFARAS GLSEADVRIE QSTEDPRPLI DVIGGNAYYM GSGGRCSVGF   180
SVNGGFVTAG HCGRVGTTTT QPSGTFAGST FPGRDYAWVR VSSGNTMRGL VNRYPGTVPV   240
KGSNESSVGA SVCRSGSTTG WHCGTIQQKN TSVTYPEGTI SGVTRTNACA EPGDSGGSWL   300
TGDQAQGVTS GGSGNCSSGG TTYFQPVNPI LQAYGLQLVI EGGPTGTTGP TTTSSNPGGT   360
TWQPGVAYTA GTTVTYEGVG YECLQGHTSQ IGWEPSAVPA LWERVG                  406
```

```
SEQ ID NO: 57             moltype = AA  length = 346
FEATURE                   Location/Qualifiers
source                    1..346
                          mol_type = protein
                          organism = Nocardiopsis baichengensis
SEQUENCE: 57
DAFPEGTEPL AEAIERDLGV ASGQADELLT AEESARSLEK EAEKAAGEAF AGAVFDTETH   60
ELTVSVADPS AVEAVEATGA ETRVVEASQD ELDAAMADLD AASEDGVSEE VTGWHVDLES  120
NTVVVEALEG SEDAAEDLIA DAGLDSAPVV VEKADAQPET FGAIVGGDAY YPGNSRCSIG  180
FSVRGGFVTA GHCGSTGTSV SGSAGESGRV AGSVFPGRDM GYVRANSGWT PSPYVNNYRG  240
GRVAVRGSNE ASVGASVCRS GSTTGWHCGT IQAKNQTVNY PQGTVRGLTR TTACAEPGDS  300
GGSWLSGNQA QGVTSGGSGN CSWGGTTFFQ PVNPILSQWG LSLTTT              346

SEQ ID NO: 58             moltype = AA  length = 353
FEATURE                   Location/Qualifiers
source                    1..353
                          mol_type = protein
                          organism = Streptomyces sp.
SEQUENCE: 58
NDTLTERADA AVAELPAGVL DAMERDLGLS EQEAGLQLVA QYDASLLGET LSADLDAYAG   60
SWLADGTDLV VATTDRAEAA QITEAGAKVE IVDHTLTELE SVKAALDEAA ESYDTTDAPV  120
WYVDITTNDV VLLTSDTAEA KGFVEAAGVD AGAVSIQTSD EQPQAFYDLV GGDAYYMGGS  180
RCSVGFSVTQ GSTPGFATAG HCGTVGTSTT GFNQAAQGTF EESSFPGDDM AWVSVNSNWN  240
TTPTVNDGAV TVSGSTQGAV GASICRSGST TGWHCGTIEQ HNTSVTYPEG TITGVTRTSV  300
CAEPGDSGGS YISGSQAQGV TSGGSGNCTS GGTTYHQPIN PLLSAYGLDL VTG         353

SEQ ID NO: 59             moltype = AA  length = 353
FEATURE                   Location/Qualifiers
source                    1..353
                          mol_type = protein
                          organism = Actinoalloteichus spitiensis
SEQUENCE: 59
DTPSPDGADA TVASPEMLSA MQRDLGLTEQ EALTRVAVEA TAVETEDELR ASLGPAFGGA   60
HFDGDTNTLV VGVTSAAKAD EVRAAGATPE VVAFSADTLD GVVSTLNETS EVPDGVTGWY  120
VDTADNTVVV TTALGSGEAA ADFVAESGVN ADAVTVVEST EQPRTLYDII GGDAYYFGGS  180
RCSVGFSVSV GYVTAGHCGG VGTATQGYNR VSSGQVAGSV FPGSDMGYVR TNANWTPRPL  240
VNRYSGGATV TVSGSNEAAV GASICRSGST TGWRCGTVQA KNQTVFYAQG AVSGLTRTNA  300
CAEGGDSGGS WLSGSQAQGV TSGGSGNCTW GGTTYFQPLN PILSRWGLSL TRG         353

SEQ ID NO: 60             moltype = AA  length = 338
FEATURE                   Location/Qualifiers
source                    1..338
                          mol_type = protein
                          organism = Byssochlamys verrucosa
SEQUENCE: 60
FPAAVDVKRA PSSLGITLSQ VSNTLIKAVV QNTGRGEVSF IHLNFFKDDA PVKKVAVYRN   60
GSEVQFEGIQ RRYKSTGLTR DAFTTLAPGK TAEDVFDIAS TCDLISGGPV TIRSEGVVPY  120
ATANGIDIAG YIPYSSNELT IDVDGAIAST VSKAIAPLNR RTNISSCSGS EQSTLTMALK  180
NAASLAHAAA DAAESGSASK FSEYFKTTAS STRKTVAARL RAVAQEASSS SSGSTTYYCN  240
DAYGYCTTNV LAYTLPSHNT IATCDLYYTN LSALTRTCHA QDQATTSLHE FTHAPGVYSP  300
GTDDLAYGYA SSTSLSSSQA VMNADSYALY ANAIYVGC                         338

SEQ ID NO: 61             moltype = AA  length = 339
FEATURE                   Location/Qualifiers
source                    1..339
                          mol_type = protein
                          organism = Hamigera terricola
SEQUENCE: 61
SPVNVNVGRE ELPALDVTLS QIGNTQIKAV VKNTGSEDVT FMHLNFFTDS APVKKVSVFQ   60
NNTEVEFQGI LRRVKYTDVS TDSVTTLAPG ASIEDVFDIA TTTDLASGGA VTVKTDGFVP  120
ILASAENKVT GYARYTSNEL HLDVGPSAA TVSKAIAPLD RRTRLSSCSG SRSSALQTAL  180
RNTVSLANAA ANAARSGSAS KFSEYFKTTS SSVRSTVAAR LSAVASEASS TSSGSTTYYC  240
NDPYGYCSTD VLAYTLPSYN IIANCDIYYS YLPALTGSCH AQDQATTTLH EFTHAPGVYS  300
PGTEDYGYGY NAATSLSSSQ AVLNADSYAL YANAIYLGC                         339

SEQ ID NO: 62             moltype = AA  length = 334
FEATURE                   Location/Qualifiers
source                    1..334
                          mol_type = protein
                          organism = Aspergillus tamarii
SEQUENCE: 62
IPVEVPASAP GLDVTLSQVG NTRIKAVVKN TGSEEVTFVH LNFFKDAAPV QKVSLFRNAT   60
EVQFQGIKQR LITEGLSDEA LTTLAPGATI EDEFDIASTS DLSEGGTITI NSNGLVPITT  120
ENKVTGYIPF ASNELSIDVD AAEAATVSQA VKILDRRTKV TSCSGSRSSA LQTALRNTVS  180
LARAAASAAQ SGSSSRFQEY FKTTSSSTRS TVAARLNAVA NEAASTASGS TTYYCSDVYG  240
YCSSNVLAYT LPAYNIIANC DLYYSYLPAL TSTCHAQDQA TTTLHEFTHA PGVYSPGTDD  300
LGYGYSAATA LSASQALLNA DTYALFANAV NLNC                              334

SEQ ID NO: 63             moltype = AA  length = 334
```

```
FEATURE                 Location/Qualifiers
source                  1..334
                        mol_type = protein
                        organism = Aspergillus niveus
SEQUENCE: 63
LPAKTGEQLQ  KLDVALSQVD  NTLIKAVVKN  TGSEDITFVH  LNFFRDTAPV  KKVSLFRNTT   60
EVPFHGIKQR  LRSDGLSADA  LTVLAPGESI  EDEFDIAATS  DLSEGGSITI  SADGFVPIAS  120
GNKITGYVPF  SSNELSVEVD  AAQAASVASA  VKPLDRRTKV  ASCSGSRSSA  LTQALRNTVS  180
LANAAASAAQ  SGSSTRFQEY  FKTTSSSVRS  SVAARFRAVA  SEASSTSAGS  TTYYCTDVYG  240
YCSSNVLAYT  LPAYNIIANC  DIYYTYLPAL  TSTCHAQDQA  TTTLHEFTHA  PGVYSPGTDD  300
LGYGYDAATA  LSSSQALNNA  DSYALFANAV  NLNC                                334

SEQ ID NO: 64           moltype = AA  length = 372
FEATURE                 Location/Qualifiers
source                  1..372
                        mol_type = protein
                        organism = Penicillium sclerotiorum
SEQUENCE: 64
IPTGGKKSSF  SVDQVAIPAT  KTKNFADTYA  RAISKFGGNV  PSHVRAAAQQ  SGAATTTPEA   60
NDEEYLTPVN  VGGTTLNLDF  DTGSADLWVF  SEQLPSSEQS  GHSVYKPNNG  TKLSGATWSI  120
SYGDGSSASG  DVYKDTVSVG  PVKATGQAVE  AASKISAQFT  RDSNNDGLLG  LAFSSINTVK  180
PKAQTTFFDT  VKSSLASPLF  AVTLKHNAPG  TYDFGFVDSS  KYTGSLAYTD  VDNSQGFWEF  240
TADSYKVGSQ  SGSSIKGIAD  TGTTLLLLDD  EVVSAYYKQV  SGASDSQSAG  GYTFDCSADL  300
PDFTVTISGY  DAVVPGSLIN  YAPVSDGSST  CLGGIQSNSG  IGFSIFGDIF  LKSQYVVFDS  360
NGPRLGFAAQ  SS                                                          372

SEQ ID NO: 65           moltype = AA  length = 371
FEATURE                 Location/Qualifiers
source                  1..371
                        mol_type = protein
                        organism = Penicillium bilaiae
SEQUENCE: 65
VPTGGKKSFS  INQVAIPATK  TKNFAGNYAH  AIAKYGGNVP  SHVEAAAQQS  GAATTTPESN   60
DEEYLTPVNV  GGTTLNLDFD  TGSADLWVFS  AELPSAEQSG  HALYKPSNGT  KLSGASWSIS  120
YGDGSSASGD  VYKDTVSVGS  VKATGQAVEA  ASKISAQFTK  DKNNDGLLGL  AFSSINTVKP  180
KAQTTFFDTV  KSSLASPLFA  VTLKHNAPGT  YDFGFIDKSK  YTGSLAYADV  DNSQGFWEFT  240
ADSYVGSSK   GSSIKGIADT  GTTLLLLDDE  VVSAYYKQVQ  GAQQDSSAGG  YTFDCSSKLP  300
DFTVTISGYD  AVVPGDLINF  APASEGSSTC  LGGIQSNSGI  GFSIFGDIFL  KSQYVVFDSN  360
GPRLGFAAQS  S                                                           371

SEQ ID NO: 66           moltype = AA  length = 373
FEATURE                 Location/Qualifiers
source                  1..373
                        mol_type = protein
                        organism = Penicillium antarticum
SEQUENCE: 66
SPLVTPRKGF  TINQETRAVT  KSKTVNLPGV  YAQALSKYGA  TVPQHVHAAA  VSGSAVTTPE   60
ESDVEYLTPV  NVGGTTLNLD  FDTGSADLWV  FSSELTSSQQ  SGHSIYKPSS  SATKLSGSSW  120
SISYGDGSSA  SGDVYKDTVT  VGGVKATGQA  VEAASKISSA  FLQDVNNDGL  LGLAFSSINT  180
VSPRAQTTFF  DTVKSQLDSP  LFAVTLKHNA  PGSYDFGYID  KSKYTGSLTY  ANVDDSQGFW  240
SFTASSYKIG  TTTGGSITGI  ADTGTTLLLL  PDSVVSAYYK  KVSGSQNSNY  YGGYVFPCSA  300
TLPDFTVTIN  GYNAVVPGNL  INFAQATTGS  STCYGGIQSN  SGIGFSIFGD  IFLKSQYVVF  360
DSEGPRLGFA  AQA                                                         373

SEQ ID NO: 67           moltype = AA  length = 370
FEATURE                 Location/Qualifiers
source                  1..370
                        mol_type = protein
                        organism = Penicillium sumatrense
SEQUENCE: 67
VPTNNVASKF  SVNQVSRPAT  KTTNFAANYG  RALSKYGAGV  PSHVEAAAAA  SGSAVTTPES   60
NDVEYLTPVS  IGGTTLNLDF  DTGSADLWVF  STELSSSEQS  GHSVYNPSKS  GKKISGASWD  120
ISYGDGSGAS  GDVYTDTVTV  GGVTASKQAV  EAAKQISSQF  QQDTNDNGLL  GLAFSSINTV  180
SPTPQKTFFD  NVKSSLSQPL  FAVALKHNAP  GVYDFGFISS  SKHTGSIAYT  SVDSSQGFWS  240
FTVDGYKVGS  KSGAGFDGIA  DTGTTLLLLD  DSVVSAYYSQ  VSGAKNDNNA  GGYVFDCSAD  300
LPDFSVTIGS  YTATVPGSLI  NYGDSGDNSC  IGGIQSNSGI  GFSIFGDIFL  KSQYVVFNAN  360
GPKLGFAPQA                                                              370

SEQ ID NO: 68           moltype = AA  length = 384
FEATURE                 Location/Qualifiers
source                  1..384
                        mol_type = protein
                        organism = Trichoderma lixii
SEQUENCE: 68
LPTEGQKTAS  IEVTYNKNYV  AHGPTALFKA  KRKYGAPISD  NLRAAVAAKH  SLTKRQTGSA   60
NTNPSDSADD  EYITSVSIGT  PAQVLPLDFD  TGSSDLWVFS  SETPKSSASG  HVTYSPSKSS  120
TAKKLSGSTW  SITYGDHSSS  SGDVYTDVVS  IGGFSVKTQA  IESATKVSTQ  FVQDTVISGL  180
VGLGFDVGNT  VKPRAQKTWF  SNAASSLAEP  LFTADLRHQE  TGSYNFGFID  NSLAKGTIGY  240
TPADGSEGYW  GFTATGYSVG  GAKLGRSSIT  GIADTGTTLL  LLPDNVVDAY  YNNVESAQYD  300
```

```
DSQEGVVFDC SEDLPSFSFG VGGQTITISG DLLNLTPIEE GSSTCFGGLQ SSADIGINIF    360
GDVALKAALV VFDLGNERLG FAQK                                          384

SEQ ID NO: 69            moltype = AA  length = 384
FEATURE                  Location/Qualifiers
source                   1..384
                         mol_type = protein
                         organism = Trichoderma brevicompactum
SEQUENCE: 69
LPTEGQKTAS VEVTYNQNYA AHGPTQLYKA KRKYGAPISD NLKAIVANRK ALIKRQTGSA    60
PNHPSDSADD EYITNVSIGT PAQVLPLDFD TGSSDLWVFS SETPKSSASG HTIYTPSKSS    120
TSKKLSGATW SIEYGDKSTS SGDVYTDKVT VGGFSVSTQA VESATKVSAQ FVQDTANSGL    180
LGLAFDSINT VSPRQKTWF SNAANSLAQP LFTANLNHQA TGSYNFGPID TSLASGPINY     240
VPVDNSQGFW GFTASGYSVG GGKLNRSSLS GIADTGTTLL LLPDAVVNAY YANVESAEYD    300
DEQEGVVFDC SEDLPTFSFG VGSGTITIPG DLLNLTPIDS SGQTCYGGLQ SSSDIGINIF    360
GDVALKAALV VFDLGNERLG WAQK                                          384

SEQ ID NO: 70            moltype = AA  length = 379
FEATURE                  Location/Qualifiers
source                   1..379
                         mol_type = protein
                         organism = Penicillium cinnamopurpureum
SEQUENCE: 70
IPTGVPNRKG FTVNQQVRPV TNGTKSKTLN LPAIYANALS KYGVAVPANI KAAAESGTAT    60
TTPEDNDIEY LTPVDVGGTT LNLDFDTGSA DLWVFSSELP SSESSGHSIY KPSQSGKKLD    120
GYSWKISYGD SSSASGDVYT DTVTVGGVTA DGQAVEAAKK ISQQFVQDKN NDGLLGLAFS    180
SINTVQPKAQ TTFFDTVKDQ LDSPLFAVTL KHNAPGSYDF GFIDKSKYTG SLTYADVDKS    240
DGFWAFTADG YSVGSGSSSS SRIKGIADTG TTLLLIDDEI VSAYYKQVDG AQESYSVGGY    300
TFDCSTKLPD FNIKIGDYTA VIPGDVINYA PVQQGSSTCF GGIQSNSGLP FSIFGDIFLK    360
SQYVVFDANG PRLGFAAQA                                                379

SEQ ID NO: 71            moltype = AA  length = 350
FEATURE                  Location/Qualifiers
source                   1..350
                         mol_type = protein
                         organism = Bacillus lichenformis
SEQUENCE: 71
AQPAKNVEKD YIVGFKSGVK TASVKKDIIK ESGGKVDKQF RIINAAKAKL DKEALKEVKN    60
DPDVAYVEED HVAHALAQTV PYGIPLIKAD KVQAQGFKGA NVKVAVLDTG IQASHPDLNV    120
VGGASFVAGE AYNTDGNGHG THVAGTVAAL DNTTGVLGVA PSVSLYAVKV LNSSGSGSYS    180
GIVSGIEWAT TNGMDVINMS LGGASGSTAM KQAVDNAYAR GVVVVAAAGN SGSSGNTNTI    240
GYPAKYDSVI AVGAVDSNSN RASFSSVGAE LEVMAPGAGV YSTYPTNTYA TLNGTSMASP    300
HVAGAAAILS KHPNLSASQ VRNRLSSTAT YLGSSFYYGK GLINVEAAAQ                350

SEQ ID NO: 72            moltype = AA  length = 360
FEATURE                  Location/Qualifiers
source                   1..360
                         mol_type = protein
                         organism = Bacillus subtilis
SEQUENCE: 72
FSNMSAQAAG KSSTEKKYIV GFKQTMSAMS SAKKKDVISE KGGKVQKQFK YVNAAAATLD    60
EKAVKELKKD PSVAYVEEDH IAHEYAQSVP YGISQIKAPA LHSQGYTGSN VKVAVIDSGI    120
DSSHPDLNVR GGASFVPSET NPYQDGSSHG THVAGTIAAL NNSIGVLGVA PSASLYAVKV    180
LDSTGSGQYS WIINGIEWAI SNNMDVINMS LGGPTGSTAL KTVVDKAVSS GIVVAAAAGN    240
EGSSGSTSTV GYPAKYPSTI AVGAVNSSNQ RASFSSAGSE LDVMAPGVSI QSTLPGGTYG    300
AYNGTSMATP HVAGAAAILS KHPTWTNAQ VRDRLESTAT YLGSSFYYGK GLINVQAAAQ     360

SEQ ID NO: 73            moltype = AA  length = 548
FEATURE                  Location/Qualifiers
source                   1..548
                         mol_type = protein
                         organism = Trametes cf versicol
SEQUENCE: 73
TPTARNLKLH ESREEIPAGF SLSGAASPDT TLKLRLALVQ SNFAELEDKL YDVSTPSSAN    60
YGQHLSKEEV EQLVAPSAES VNAVNAWLTE NGLTAQTISP AGDWLAFEVP VSKANELFDA    120
DFSVFTHDES GLKAVRTLAY SIPAELQGHL DLVHPTITFP NPNSHLPVVR SPVKPVQNLT    180
SRAVPASCAS TITPACLQAL YGIPTTKATQ SSNKLAVSGF IDQAFANSADL KTFLGKFRTD    240
ISSSTTFTLQ TLDGGSNSQS SSQAGVEANL DIQYTVGLAS AVPTIFISVG DDFQDGDLEG    300
FLDIINFLLN ESAPPQVLTT SYGQNENTIS AKLANQLCNA YAQLGARGTS ILFASGDGGV    360
SGSQSSSCSK FVPTFPSGCP FMTSVGATQG INPETAADFS SGGFSNVFAR PSYQSTAVSS    420
YLTALGSTNS GKFNTSGRAF PDIATQGVDF EIVVSGRTEG VDGTSCASPT LAAIISLLND    480
RLIAAGKSPL GFLNPPFLYSA AGTAALTDIT SGSNPGCNTN GFPAKAGWDP VTGLGTPNFA    540
KLLTAVGL                                                            548

SEQ ID NO: 74            moltype = AA  length = 439
FEATURE                  Location/Qualifiers
source                   1..439
                         mol_type = protein
                         organism = Bos taurus
```

```
SEQUENCE: 74
MAKEYFPFTG KIPFEGKDSK NVMAFHYYEP EKVVMGKKMK DWLKFAMAWW HTLGGASADQ    60
FGGQTRSYEW DKAECPVQRA KDKMDAGFEI MDKLGIEYFC FHDVDLVEEA PTIAEYEERM   120
KAITDYAQEK MKQFPNIKLL WGTANVFGNK RYANGASTNP DFDVVARAIV QIKNSIDATI   180
KLGGTNYVFW GGREGYMSLL NTDQKREKEH MATMLGMARD YARAKGFKGT FLIEPKPMEP   240
SKHQYDVDTE TVIGFLKAHG LDKDFKVNIE VNHATLAGHT FEHELACAVD AGMLGSIDAN   300
RGDAQNGWDT DQFPIDNFEL TQAMLEIIRN GGLGNGGTNF DAKIRRNSTD LEDLFIAHIS   360
GMDAMARALM NAADILENSE LPAMKKARYA SFDSGIGKDF EDGKLTFEQV YEYGKKVEEP   420
KQTSGKQEKY ETIVALHCK                                               439

SEQ ID NO: 75          moltype = AA   length = 591
FEATURE                Location/Qualifiers
source                 1..591
                       mol_type = protein
                       organism = Saccharomyces cerevisiae
SEQUENCE: 75
MLCSVIQRQT REVSNTMSLD SYYLGFDLST QQLKCLAINQ DLKIVHSETV EFEKDLPHYH    60
TKKGVYIHGD TIECPVAMWL GALDLVLSKY REAKFPLNKV MAVSGSCQQH GSVYWSSQAE   120
SLLEQLNKKP EKDLLHYVSS VAFARQTAPN WQDHSTAKQC QEFEECIGGP EKMAQLTGSR   180
AHFRFTGPQI LKIAQLEPEA YEKTKTISLV SNFLTSILVG HLVELEEADA CGMNLYDIRE   240
RKFMYELLHL IDSSSKDKTI RQKLMRAPMK NLIAGTICKY FIEKYGFNTN CKVSPMTGDN   300
LATICSLPLR KNDVLVSLGT STTVLLVTDK YHPSPNYHLF IHPTLPNHYM GMICYCNGSL   360
ARERIRDELN KERENNYEKT NDWTLFNQAV LDDSESSENE LGVYFPLGEI VPSVKAINRK   420
VIFNPKTGMI EREVAKFKDK RHDAKNIVES QALSCRVRIS PLLSDSNASS QQRLNEDTIV   480
KFDYDESPLR DYLNKRPERT FFVGGASKND AIVKKFAQVI GATKGNFRLE TPNSCALGGC   540
YKAMWSLLYD SNKIAVPFDK FLNDNFPWHV MESISDVDNE NWIAIIPRLS P           591

SEQ ID NO: 76          moltype = AA   length = 444
FEATURE                Location/Qualifiers
source                 1..444
                       mol_type = protein
                       organism = Bacillus subtilis
SEQUENCE: 76
ETANKSNELT APSIKSGTIL HAWNWSFNTL KHNMKDIHDA GYTAIQTSPI NQVKEGNQGD    60
KSMSNWYWLY QPTSYQIGNR YLGTEQEFKE MCAAAEEYGI KVIVDAVINH TTFDYAAISN   120
EVKSIPNWTH GNTQIKNWSD RWDVTQNSLL GLYDWNTQNT QVQSYLKRFL ERALNDGADG   180
FRFDAAKHIE LPDDGSYGSQ FWPNITNTSA EFQYGEILQD SASRDAAYAN YMDVTASNYG   240
HSIRSALKNR NLGVSNISHY AYDVSADKLV TWVESHDTYA NDDEESTWMS DDDIRLGWAV   300
IASRSGSTPL FFSRPEGGGN GVRFPGKSQI GDRGSALFED QSITAVNRFH NVMAGQPEEL   360
SNPNGNNQIF MNQRGSHGVV LANAGSSSVS INTPTKLPDG RYDNKAGAGS FQVNDGKLTG   420
TINARSVAVL YPDDIEIRCN TFFQ                                         444

SEQ ID NO: 77          moltype = AA   length = 476
FEATURE                Location/Qualifiers
source                 1..476
                       mol_type = protein
                       organism = Saccharomycopsis fibuligera
SEQUENCE: 77
QPVTLFKRET NADKWRSQSI YQIVTDRFAR TDGDTSASCN TEDRLYCGGS FQGIIKKLDY    60
IKDMGFTAIW ISPVVENIPD NTAYGYAYHG YWMKNIYKIN ENFGTADDLK SLAQELHDRD   120
MLLMVDIVTN HYGSDGSGDS IDYSEYTPFN DQKYFHNYCL ISNYDDQAQV QSCWEGDSSV   180
ALPDLRTEDS DVASVFNSWV KDFVGNYSID GLRIDSAKHV DQGFFPDFVS ASGVYSVGEV   240
FQGDPAYTCP YQNYIPGVSN YPLYYPTTRF FKTTDSSSSE LTQMISSVAS SCSDPTLLTN   300
FVENHDNERF ASMTSDQSLI SNAIAFVLLG DGIPVIYYGQ EQGLSGKSDP NNREALWLSG   360
YNKESDYYKL IAKANAARNA AVYQDSSYAT SQLSVIFSND HVIATKRGSV VSVFNNLGSS   420
GSSDVTISNT GYSSGEDLVE VLTCSTVSGS SDLQVSIQGG QPQIFVPAKY ASDICS       476

SEQ ID NO: 78          moltype = AA   length = 487
FEATURE                Location/Qualifiers
source                 1..487
                       mol_type = protein
                       organism = Debaryomyces occidentalis
SEQUENCE: 78
QPIIFDKRDV GSSADKWKDQ SIYQIVTDRF ARSDGSTTAD CLVSDRKYCG GSYKGIIDKL    60
DYIQGMGFTA IWISPVVEQI PDNTAYGYAY HGYWMKNIDE LNTNFGTADE LKQLASELHS   120
RSMLLMVDVV YNHYAWNGDG SSVDYSSFTP FNQQSYFHDY CLITNYNDQT NVEDCWEGDT   180
EVSLPDLSTE DNEVIGVFQT WVSDFVQNYS IDGLRIDSAK HVDTASLTKF EDASGVYNLG   240
EVYQGDPTYT CPYQSYMKGV TNYPLYYPVY RFFSDTSATS SELTSMISTL QSSCSDVSLL   300
GNFIENHDQV RFPSVTSDTS LIKNAMAFII LGDGIPIIYY GQEQGLNGGS DPANREALWL   360
SGYNTDSEYY ELISKLNQIR NQAIKKDSAY STYKSSVVSS SDHYIATRKG SDANQLISIF   420
NNLGSNGSQD ITVSNTGYSS GDKVIDIISC NSVSAGDFGS LSVSISGGMP QVYAPSSVLS   480
GSGICNQ                                                            487

SEQ ID NO: 79          moltype = AA   length = 487
FEATURE                Location/Qualifiers
source                 1..487
                       mol_type = protein
                       organism = Debaryomyces occidentalis
SEQUENCE: 79
```

```
KPIFLSKRDA GSSAAAAWRS ESIYQLVTDR FARTDGSTSA TCNTGDRVYC GGTFQGIIDK    60
LDYIQGMGFT AIWISPVVEQ IPDDTGYGYA YHGYWMKDIY AINSNFGTAD DLKNLSNELH   120
KRNMKLMVDI VTNHYAWNGA GSSVAYSNYN PFNQQSYFHD YCLITNYDDQ TNVEDCWEGD   180
NTVSLPDLRT EDSDVSSIFN LWVAELVSNY SIDGLRIDSA KHVDESFYPS FQSAAGVYLL   240
GEVYDGDPAY TCPYQNYMSG VTNYPLYYPM LRFFQGTSNS VDELNAMISS LESDCKDITL   300
LGNFIENHDQ PRLPSYTSDS ALIKNAIAFN LMSDGIPIIY YGQEQGYSGS SDPNNREALW   360
LSGYSTSNGY YKLISSVNQI RNQAIYKDSK YTTYWSDVLY ASGHVIALQR GADDQRIVSV   420
FNNLGSSGSQ TVTFSTKYSG GEKVVDVLTC QTSYANSDST LTVSISGGAP RIYAPASLIA   480
NSGICNF                                                            487

SEQ ID NO: 80           moltype = AA  length = 570
FEATURE                 Location/Qualifiers
source                  1..570
                        mol_type = protein
                        organism = Lipomyces kononenkoae
SEQUENCE: 80
MCGSTLSASL YVYNDDYDKI VTLYYLTSSG TTGSTLALIL PVWSNNWELW TLSAIAAGAV    60
EITGASYVDS DTSVTYTTSL DLPLTTTSAS VPTGTAANWR GRSIYQVVTD RFARTDGSIT   120
YSCDVTDRVY CGGSYRGIIN MLDYIQGMGF TAIWISPIVE NIPDDTGYGY AYHGYWMKDI   180
FALNTNFGGA DDLIALATEL HNRGMYLMVD IVVNHFAFSG NHADVDYSEY FPYSSQDYFH   240
SFCWITDYSN QTNVEECWLG DDSVPLVDVN TQLDTVKSEY QSWVKQLIAN YSIDGLRIDT   300
VKHVQMDFWA PFQEAAGIYT VGEVFDGDPS YTCPYQENLD GVLNYPVYYP VVSAFQRVGG   360
SISSLVDMID TLKSECIDTT LLGSFLENQD NPRFPSYTSD ESLIKNAIAF TILSDGIPII   420
YYGQEQGLNG GNDPYNREAL WPTGYSTTST FYEYIASLNQ IRNHAIYIDD TYLTYQNWVI   480
YSDSTTIAMR KGFTGNQIIT VLSNLGSSGS SYTLTLSNTG YTASSVVYEI LTCTAVTVDL   540
SGNLAVPMSG GLPRVFYPES QLVGSGICSM                                   570

SEQ ID NO: 81           moltype = AA  length = 476
FEATURE                 Location/Qualifiers
source                  1..476
                        mol_type = protein
                        organism = Lipomyces kononenkoae
SEQUENCE: 81
KTAAEWKELS IYQVITDRFA TTNLTAPDCW IRAYCGGTWK GLERKLDYIQ NMGFDAVWIS    60
PVIHNIEVNT TWGFAFHGYW GDDPYRLNEH FGTAADLKSL SDSLHARGMS LMVDVVINHL   120
ASYTLPQDVD YSLYPAPFNT SSAFHQPCPI DFSNQSSIED CWLVTEPAPA LVDLKNEDQV   180
ILDALINSVV DLVETYDIDG IRLDTARHVP KPSLAKFQEK VGVFVTGEAL NQSVPYVAQY   240
QGPLNSAINY PLWYALVDSF MGRTTFDYLE SVVKSEQATF SDAHALTNFL DNQDQPRFAS   300
YLGDGNGDDV LRDENAATFL FFVSGIPVIY YGFEQRFDGG FDPVNREPMW TSGYNTSTPL   360
YNYLARLNAI RKYAASITGT QVFYSDDTVF LGSGVSHMAM QRGPLVIVLT NVGQHIIDNT   420
GYTVTGSQFS AGDSLTDLVS CTKVKVVGAN GTFTSPSNGG KARIWIKSKY AGKFCS       476

SEQ ID NO: 82           moltype = AA  length = 626
FEATURE                 Location/Qualifiers
source                  1..626
                        mol_type = protein
                        organism = Bacillus subtilis
SEQUENCE: 82
ETANKSNELT APSIKSGTIL HAWNWSFNTL KHNMKDIHDA GYTAIQTSPI NQVKEGNQGD    60
KSMSNWYWLY QPTSYQIGNR YLGTEQEFKE MCAAAEEYGI KVIVDAVINH TTSDYAAISN   120
EVKSIPNWTH GNTQIKNWSD RWDVTQNSLL GLYDWNTQNT QVQSYLKRFL DRALNDGADG   180
FRFDAAKHIE LPDDGSYGSQ FWPNITNTSA EFQYGEILQD SASRDAAYAN YMDVTASNYG   240
HSIRSALKNR NLGVSNISHY ASDVSADKLV TWVEESHDTYA NDDEESTWMS DDDIRLGWAV   300
IASRSGSTPL FFSRPEGGGN GVRFPGKSQI GDRGSALFED QAITAVNRFH NVMAGQPEEL   360
SNPNGNNQIF MNQRGSHGVV LANAGSSSVS INTATKLPDG RYDNKAGAGS FQVNDGKLTG   420
TINARSVAVL YPDDIAKAPH VFLENYKTGV THSFNDQLTI TLRADANTTK AVYQINNGPE   480
TAFKDGDQFT IGKGDPFGKT YTIMLKGTNS DGVTRTEKYS FVKRDPASAK TIGYQNPNHW   540
SQVNAYIYKH DGSRVIELTG SWPGKPMTKN ADGIYTLTLP ADTDTTNAKV IFNNGSAQVP   600
GQNQPGFDYV LNGLYNDSGL SGSLPH                                       626

SEQ ID NO: 83           moltype = AA  length = 483
FEATURE                 Location/Qualifiers
source                  1..483
                        mol_type = protein
                        organism = Bacillus subtilis
SEQUENCE: 83
VNGTLMQYFE WYTPNDGQHW KRLQNDAEHL SDIGITAVWI PPAYKGLSQS DNGYGPYDLY    60
DLGEFQQKGT VRTKYGTKSE LQDAIGSLHS RNVQVYGDVV LNHKAGADAT EDVTAVEVNP   120
ANRNQETSEE YQIKAWTDPF FPGRGNTYSD FKWHWYHFDG ADWDESRKIS RIFKFRGEGK   180
AWDWEVSSEN GNYDYLMYAD VDYDNPDVVA ETKKWGNWYA NELSLDGFRI DAAKHIKFSF   240
LRDWVQAVRQ ATGKEMFTVA EYWQNNAGKL ENYLNKTSFN QSVFDVPLHF NLQAASSQGG   300
GYDMRRLLDG TVVSRHPEKA VTFVENHDTQ PGQSLESTVQ TWFKPLAYAF ILTRESGYPQ   360
VFYGDMYGTK GTSPKEIPSL KDNIEPILKA RKEYAYGPQH DYIDHPDVIG WTREGDSSAA   420
KSGLAALITD GPGGSKRMYA GLKNAGETWY DITGNRSDTV KIGSDGWGEF HVNDGSVSIY   480
VQK                                                                483

SEQ ID NO: 84           moltype = AA  length = 589
FEATURE                 Location/Qualifiers
source                  1..589
```

```
                              mol_type = protein
                              organism = Bacillus subtilis
SEQUENCE: 84
MMEYAAIHHQ  PFSTDAYSYD  GRTVHIKIRT  KKGDADHIRF  IWGDPYEYND  GKWSANEQPM   60
RKIAATEMHD  YWFAEVVPPF  RRLQYAFVVT  DDHEDIFFGS  SGVCPYNEKT  LETIHYYFKF  120
PFVHEADTFQ  APEWVKSTVW  YQIFPERFAN  GREDLSPKNA  LPWGSKDPGV  NDFFGGDLQG  180
IVDKLDYLED  LGVNGIYLTP  IFSAPSNHKY  DTLDYFSIDP  HFGDPEIFRT  LVSQLHQRGM  240
RIMLDAVFNH  IGSASPQWQD  VVKNGDQSRY  KDWFHIHSFP  VTDDNYDRFA  FTADMPKLNT  300
ANPEVQKYLL  DIALYWIREF  DIDGWRLDVA  NEVDHVFWKT  FRQAVSTEKP  DVYILGEIWH  360
SAEPWLRGDE  FHAAMNYPFT  EPMIEYFADQ  TISASRMAHR  VNAHLMNGMK  QANEVMFNLL  420
DSHDTKRLLT  RCRNDEKKAR  ALLAFMFAQT  GSPCIYYGTE  IGLDGENDPL  CRKCMVWEKE  480
KQNQDMLQFM  KRLIALRKQE  NTLLTEGHLE  WNLLDDKNDF  ISFSRTLDEK  ILIYFFNQGN  540
VVQHISLREL  NIDRNNKICD  AWTEQPLHYH  DVIAVQPGEF  LILSAAAPV               589

SEQ ID NO: 85             moltype = AA  length = 483
FEATURE                   Location/Qualifiers
source                    1..483
                          mol_type = protein
                          organism = Bacillus lichenformis
SEQUENCE: 85
ANLNGTLMQY  FEWYMPNDGQ  HWKRLQNDSA  YLAEHGITAV  WIPPAYKGTS  QADVGYGAYD   60
LYDLGEFHQK  GTVRTKYGTK  GELQSAIKSL  HSRDINVYGD  VVINHKGGAD  ATEDVTAVEC  120
DPADRNVIS   GEHLIKAWTH  FHFPGRGSTY  SDFKWHWYHF  DGTDWDESRK  LNRIYKFQGK  180
AWDWEVSNEN  GNYDYLMYAD  IDYDHPDVAA  EIKRWGTWYA  NELQLDGGRL  DAVKHIKFSF  240
LRDWVNHVRE  KTGKEMFTVA  EYWQNDLGAL  ENYLNKTNFN  HSVFDVPLHY  QFHAASTQGG  300
GYDMRKLLNG  TVVSKHPLKS  VTFVDNHDTQ  PGQSLESTVQ  TWFKPLAYAF  ILTRESGYPQ  360
VFYGDMYGTK  GDSQREIPAL  KHKIEPILKA  RKQYAYGAQH  DYFDHHDIVG  WTREGDSSVA  420
NSGLAALITD  GPGGAKRMYV  GRQNAGETWH  DITGNRSEPV  VINSEGWGEF  HVNGGSVSIY  480
VQR                                                                     483

SEQ ID NO: 86             moltype = AA  length = 478
FEATURE                   Location/Qualifiers
source                    1..478
                          mol_type = protein
                          organism = Aspergillus niger
SEQUENCE: 86
ATPADWRSQS  IYFLLTDRFA  RTDGSTTATC  NTADQKYCGG  TWQGIIDKLD  YIQGMGFTAI   60
WITPVTAQLP  QTTAYGDAYH  GYWQQDIYSL  NENYGTADDL  KALSSSALHER GMYLMVDVVA  120
NHMGYDGAGS  SVDYSVFKPF  SSQDYFHPFC  FIQNYEDQTQ  VEDCWLGDNT  VSLPDLDTTK  180
DVVKNEWYDW  VGSLVSNYSI  DGLRIDTVKH  VQKDFWPGYN  KAAGVYCIGE  VLDGDPAYTC  240
PYQNVMDGVL  NYPIYYPLLN  AFKSTSGSMD  DLYNMINTVK  SDCPDSTLLG  TFVENHDNPR  300
FASYTNDIAL  AKNVAAFIIL  NDGIPIIYAG  QEQHYAGGND  PANREATWLS  GYPTDSELYK  360
LIASRNAIRN  YAISKDTGFV  TYKNWPIYKD  DTTIPMRKGT  DGSQIVTILS  NKGASGDSYT  420
LSLSGAGYTA  GQQLTEVIGC  TTVTVGSDGN  VPVPMAGGLP  RVLYPTEKLA  GSKICSSS    478

SEQ ID NO: 87             moltype = AA  length = 477
FEATURE                   Location/Qualifiers
source                    1..477
                          mol_type = protein
                          organism = Aspergillus niger
SEQUENCE: 87
ATPADWRSQS  IYFLLTDRFA  RTDGSTTATC  NTADQKYCGG  TWQGIIDKLD  YIQGMGFTAI   60
WITPVTAQLP  QTTAYGDAYH  GYWQQDIYSL  NENYGTADDL  KALSSSALHER GMYLMVDVVA  120
NHMGYDGAGS  SVDYSVFKPF  SSQDYFHPFC  FIQNYEDQTQ  VEDCWLGDNT  VSLPDLDTTK  180
DVVKNEWYDW  VGSLVSNYSI  DGLRIDTVKH  VQKDFWPGYN  KAAGVYCIGE  VLDGDPAYTC  240
PYQNVMDGVL  NYPIYYPLLN  AFKSTSGSMD  DLYNMINTVK  SDCPDSTLLG  TFVENHDNPR  300
FASYTNDIAL  AKNVAAFIIL  NDGIPIIYAG  QEQHYAGGND  PANREATWLS  GYPTDSELYK  360
LIASRNAIRN  YAISKDTGFV  TYKNWPIYKD  DTTIPMRKGT  DGSQIVTILS  NKGASGDSYT  420
LSLSGAGYTA  GQQLTEVIGC  TTVTVGSDGN  VPVPMAGGLP  RVLYPTEKLA  GSKICYG     477

SEQ ID NO: 88             moltype = AA  length = 431
FEATURE                   Location/Qualifiers
source                    1..431
                          mol_type = protein
                          organism = Streptomyces avermitilis
SEQUENCE: 88
SPPGTKDVTA  VLFEWKFDSV  ARECTNTLGP  AGYGYVQVSP  PAEHIQGSQW  WTSYQPVSYK   60
IAGRLGDATA  FQNMINTCHT  AGVKVVVDTV  VNHMSAGSGT  GTGGSAYTKY  NYPGLYSSYD  120
MDDCTATITD  YTNRANVQNC  ELVGLADLDT  GEEYVRKTIA  GYMNTLLGYG  ADGFRVDAVK  180
HIPAADLANI  KSRLTNPSVY  WKQEVIYASG  EAAVQPTEYTG NGDVQEFRYA  YDLKRVFNNE  240
NLAYLKNYGE  GWGYLNSSVA  GVFVDNHDTE  RNGSTLNYKD  GANYTLANVF  MLAYPYGAPD  300
INSGYEWSDA  DAGPPGGGTV  NACWQDGWKC  QHAWPEIKAM  VAFRNATRGE  SVTNWWDNGG  360
DAIAFGRGAK  GYVAINHESG  SLTRTYQTSL  TAGTYCNVQN  NTGVTVDSSG  RFTATLGANT  420
ALALYSGKST  C                                                           431

SEQ ID NO: 89             moltype = AA  length = 643
FEATURE                   Location/Qualifiers
source                    1..643
                          mol_type = protein
```

```
                              organism = Clostridium phytofermentans
SEQUENCE: 89
MYTLKSKLRD LYRHPVGYDV INKILLQAGL SKGLIENPVI GALPLSFLNR IAGKKLGNGF    60
FDALLALLNQ SNDRLDPYSS KDKKITPTWW KEAVFYQIYP RSFMDGNGDG VGDLPGIISK   120
LDYLKELGVD ALWLSPIYDS PGDDNGYDIR DYQKIDSQFG TMEDFDLLLT ELHARNMRLV   180
MDLVVNHTSD EHHWFKEALK SSESTYRDYY FLRKEPNNWT SFFSGSAWNH YPEEDLWGLH   240
LFSKKQMDLN WENPKLRQDI YQMIRWWLEK GVDGFRLDVI NYISKETGLP DGDSFIGNLM   300
GFTGIEHYFY GPKLHNHLQE IQKEAFTPYQ AFSVGETPGI GMKMGKLLTD DSRGELNMMF   360
SFDHLETSGH ARFDQYEYDL NYYKSYIMDW MENFADTSWM SLFYDNHDNP RMLSKVDHTH   420
THRQELAKML AMIQMTLKGT PFLYQGQELG MINKDFHEIS NFRDVESINK YKELCEKMPK   480
EEAFLQILAG SRDHARTPMQ WSAKPGCGFS NAVPWIDSDG DELVCNAEIQ MQDSESVLSF   540
YRDLIALRRK TPALIYGDIE FTHKKRKDIL IYTRYLEGET YLIICNLSND EQKLPGNVPV   600
SESLEGLESL SASADERKGL VLCNYPAKVM KSLRAYEGRV YRI                    643

SEQ ID NO: 90             moltype = AA  length = 1016
FEATURE                   Location/Qualifiers
source                    1..1016
                          mol_type = protein
                          organism = Clostridium phytofermentans
SEQUENCE: 90
ATDTITIHYH RDDGDYEKWN LWLWAEGKDG AAYYFDGEDA FGPYVSVSLD KSADRIGFIV    60
RTDSWEKDVS EDRFIDTSLG DEIWISSGES TFSYEAPEGY EKEVSIESFQ LKLNYLRYDE   120
EYTDISFRLT FEDGTTDFLT KEHMRIENGI LKAEKEVKYG KKITLDVLKN GLEEDYQGVS   180
FSTAKIDEES KLEMYWMQGT GTISPKADFI KRSKEIESAL ITSMKEITVK LSVPCRVDDI   240
KQDGFKLSPK LAVSKVEATS TRDSEYKTIK EGYADTFIIT MEEPLDMSKK YALSKTDYGS   300
RNLTLDSGLY TSEEFEAAYT YEGNDLGATY SKEKTVFKVW SPSAESISVL FYPHGEAKDG   360
EKPEITYPMK QTGAGVWQAE IEGDLKNKYY VYQVTVDGKT KLVVDPYAKA AGVNGERGMV   420
IDLSETDPDG FREHSSPEFK NPVDAVIYEI HVRDLSMNEN SGIENKGKFL GFTETGTTNS   480
AGLSTGLDHM KELGVTHVHL LPSFDYKTID ESKLGENKFN WGYDPQNYNL PEGSYTTDPY   540
QGEVRVREYK EMVQALHENG LHVVMDVVYN HTYTAGDSNF TSLVPGYYYR TDINGNFTNG   600
SGCGNETASE RAMVRKFIVD SVVYWATEYK VDGFRFDLMG LHDIETMNMV REALDKIDPS   660
ILLYGEGWTG GSTPLPDSKQ AIKNNAVELN ERIACFSDDI RDAIKGSVFD ASDTGFINSG   720
KRNVSNRDES IKFGIVASVS HPQVNLSGVP YSSRFWANEP SQTINYASAH DNLTLWDKLL   780
ETNKMASKEE LVQMNKLSAA IVLTSQGIPF FQAGEEMART KKGNDNSYQS PDSINMLNWD   840
NKTEYKDLFE YYKGLIALRK TYDAFRMQTA EEIQQKLEFV DSDSSVIAYR IHDAVKDGRE   900
IALIFNGTLE EKEVVLSANA WDVLVNQDTA GTDVIETITG GTIKVPAKST LVLLENKDAV   960
IKGDKDAVKG DEIQELPTNM QEVAEKESGN AWLWVGIATV CVLAGGVLFW ILKRKR      1016

SEQ ID NO: 91             moltype = AA  length = 554
FEATURE                   Location/Qualifiers
source                    1..554
                          mol_type = protein
                          organism = Clostridium phytofermentans
SEQUENCE: 91
MKNTNTLHPW WESAAAYQIY PRSFMDSNGD GVGDLQGIIS RLPYLSELGF DLIWICPIYP    60
SPNDDNGYDI SDYQNIQKEY GTMEDFEELL HKAHERGIRV IMDLVVNHTS SSHPWFIESR   120
SSKDNPKRDW YIWKDGKDNV EPNNWESIFG GSTWEYDEKS GQYFLHVFGK TMPDINWENT   180
QVKKAIFDMI CWWLDKGIDG FRVDAISHIK KPDFNDMPNP KNERYVSSFD KHMNQSGILD   240
LLNELKENAF SKYDIFTVAE ANGVRIEEIE EWVSSEKGIF NSLFQFDHLN LWNVGSEEGK   300
ISIKKLKNAL TKWQKAAPMD GNVALVMENH DLVRSISRFG SEDKYWKESA KCLALMYYMQ   360
KGVPFIYQGQ EIGMLNADYE SHLDFRDDPT LFAYQDRINN GMSPAESLQV LKKSSRDNSR   420
TPMQWDASPH AGFTTGTPWM KVNQNYHWLN AEVQKEDEDS ILNFYKKLIK IKKETTGLIY   480
GDYKLLMEES ESIYAYTREY EEKNYLVVCN LSEELSELQI DLDITKGEIL ISNYEDRNSK   540
EMLLKPYECR LYSL                                                    554

SEQ ID NO: 92             moltype = AA  length = 538
FEATURE                   Location/Qualifiers
source                    1..538
                          mol_type = protein
                          organism = Clostridium phytofermentans
SEQUENCE: 92
MVKKWWHSSV VYQIYPRSFN DSNGDGIGDL KGIIEKLDYL KNLGIDVIWL SPVFKSPNDD    60
NGYDISDYED IMDEFGTLED MELLLKEANN RGIKILMDLV ANHTSDEHKW FIESRKSKDN   120
AYRDYYIWRD PVDGHEPNDL GSTFSGSAWE WDEATGQYYL HLFSKKQPDL NWENPIVREE   180
VWKSMNFWID KGIGGFRMDV IELLGKIPDE KIISNGPMLH EYIREMNRNS FGDKDLLTVG   240
ECWGATPEIA KMYSNPDGSE LSMVFQFEHI GLDQIPKGDK WDLQPLNLID LKNVFHKWQT   300
CFHDDGWNSL FWNNHDTPRI VSRWGNDKVY KIESAKMLAT LLHGLKGTPY IYQGEELGMA   360
NIKFKDINQY KDIETLNMYK DRLNKGYKHE DIMESIYAKG RDNARTPMQW SDEIDGGFTT   420
GTPWIEVNPN FTEINAKEQV SNPNSIYNYY KKLIEIRKNN EVIVYGDFEM LLPEDKNIFA   480
YVRTLKDSKI VVVCNFYENE VEYNIPKEYE EKKEVLISNY GLSLTGRLRP FEAIMYRV    538

SEQ ID NO: 93             moltype = AA  length = 555
FEATURE                   Location/Qualifiers
source                    1..555
                          mol_type = protein
                          organism = Clostridium phytofermentans
SEQUENCE: 93
CKKADVNQNP SELNQDESQK EKEENDDEGT PEVSQDETKA VIPYDYVQNL NIIDDNYRNF    60
YEIFVYSFYD SNGDGIGDIN GVISKLDYIN DGNDATDSDL GFNGIWLMPI MPSTTYHKYD   120
```

```
VTDYYNIDPQ YGTLEDFKNL VSECHKRGIH LIIDFVFNHT SAKHPWFLEA VSYLESLKEG    180
EEPDLEKCPY VGYYHFTKDY NGSKTYYKAG TSNWYYEGVF WDQMPDLALE NENVRKEIED    240
IAKYWLDLGV DGFRLDAAKE YFSGEKERNI EVLKWFSDYV KSVKEDADIV AEVWDEEGTI    300
AAYYESGIPS LFNFPLSQHN GLITNTARKL GTSSGKNFAK TLLRLDEKYK EGNPKYIDAP    360
FISNHDTTRI SAQCVNDEDQ MKMSAGMLLT MNGSPYVYYG EEIGMNSKGT KDENKRLPMQ    420
WSATDTTGIT TPPANADSVE QKFPPVDEQM KDPLSLYNYY KRAVRIRNEN PEIARGDMSV    480
IEELCTKDIS AIKKVYQGSE IVILYNINTE SANILLKDAG LTELNIRGYL SVDGNAVTMS    540
DGVVSMPKYS IVILK                                                    555

SEQ ID NO: 94          moltype = AA   length = 583
FEATURE                Location/Qualifiers
source                 1..583
                       mol_type = protein
                       organism = Clostridium phytofermentans
SEQUENCE: 94
MKFEAIYHRT SDNYCYPLNE EDLIINIKTG HDIERVFIYY GDPFEGGILG GNWTWNGVEE     60
ELIYKKNLTH HIWWTTTVKP KFKRCKYYFK LVANDTSYYY FEDGFYTEAE MNHQDKNLVY    120
FTFPWMNSID INKTPDWVND TVWYQIFPER FNNGDKENDP KNVKAWGFHT VSNDEFYGGD    180
LQGIINRLDY LADIGISGIY LTPIFEANTS HKYDTKDYMK IDPHFGDEKV FKNLVDTAHE    240
KGIRIMLDGV FNHCGNQFAP WLDVLKNGPD SKYFNWFMIN KWPFNKEDHN TNDGSFYSFA    300
FTSRMPKLNT NNPEVIKYLL DVVEYWVKNF DIDGIRLDVA NEISHRFCKD LRKLTKELKP    360
DFYILGELWH DAITWLHGDE FDGVMNYPLA TSLADYWVYP EKTNYDFECA INHNFTMYMQ    420
QTNDVLFNLL DSHDTNRLID KVKDIDIFYQ QLAVLFTMPG SPCIYYGTEI AMEGSYDPDC    480
RRCMPWEDID AGLFKDRIEI IKALIHLRKT NNAFKSRHYH FIEDKNNRV IHYIKTDEDH     540
KQVEVILNCS KDSIVVQRKG NELFSLLNED TILKPKGVFI QQI                      583

SEQ ID NO: 95          moltype = AA   length = 575
FEATURE                Location/Qualifiers
source                 1..575
                       mol_type = protein
                       organism = Clostridium thermocellum
SEQUENCE: 95
MKLEAIYHKP YSEFAFPVAP DTLVIRLRTA KNDVNTCILI YHEKYDTSQR GKVKMDKVAS     60
DGMFDYYEVE LNVGIKRIKY MFYLEDNYSI KWYSSDGFPD YMPQWGHFTY SYICKDDIFH    120
EVEWFRNSTI YQIFPDRFAK FPPDTENSGK RTIHGGNIKG IIDRFDHLVK LGVDVVYLNP    180
IFKSESYHRY DVVDYYEIDP MFGSKEELRE LMDLCHKNGI KVIFDGVFNH SGDKFFAFRD    240
VVEKGEKSKY ANWYFINSFP VQGYPRPNYE CFSFYGGMPK LNTGNPETAK YFLDVVKYWT    300
VEFGVDGWRL DAADEVDRKF WRKLRDMLKD LNKDVVLIGE IFDEASSWLW GDQFDSVINY    360
PLKAMINDLF AYRSIDVETF RNRISGYIMK FNKKVLSSLV NIISTHDTPR FLTLCNGDEK    420
RFEMAVVFQF TFPGVPLIYY GDEIGMEGEG DPDCRRPMIW DEAKWNKKTL ELYKFLIGLR    480
KRFDALRTGE YGELPVTGCN GILAYRRGRG ENGIIVAMNT LDRKENVVVE TGDSFDTVKA    540
FESLKDEERL NVDKKRINIC LNPFEWRIYK ACGEL                               575

SEQ ID NO: 96          moltype = AA   length = 655
FEATURE                Location/Qualifiers
source                 1..655
                       mol_type = protein
                       organism = Thermobifida fusca
SEQUENCE: 96
MIGRFPILDV SPVVDIGTAK AVVGETFPVR ATVFREGHEA LGAGVVLYTP EGQRQPLVPL     60
REIAPGTDRY EAEVTVTSEG LWHFAIEAWS DPYATWCHDA RIKIPAGQDV ELMLEEGARL    120
LERAARRVPR RPALAEIAAA MRDGSRSAHE RLDLALSDLV RDELAERPLR ELVTRSQRFP    180
VMVSRRRALF GSWYEFFPRS EGAVLDTEDG EPRSGTFATA ARRLPAIADM GFDVVYIPPI    240
HPVGYSFRKG RNNSTVAQPG DPGSWAIGS HEGGHDAIHP DLGTIDDFDA FVARARELGL     300
EIAMDLALQA SPDHPWVKEH PEWFTVRADG SIAYAENPPK KYQDIYPINF DKDPEGIFTE    360
VRRIVRYWMS HGVRIFRVDN PHTKPVAFWE RLLADIAATD PDVIFLSEAF TRPAMMHTLA    420
KIGFHQSYTY FTWRNTKQEL EEYLTELTGE AAAYMRPNFF VNTPDILHAY LQHGGRPAFE    480
VRAILAATLS PTWGMYSGYE LCENRALKPG SEEYLDSEKY QYKPRDWEAA EAAGITITPL    540
IRKLNSLRRS HPALQELRNL RFHYADQPEI ICYSKRLAGA NHGADDTILV VANLDPHHTR    600
EATVWLDMPA LGFAPGDHIT VTDQLSGHSY HWVEANYVRL DPHVQTAHIF TVAPA         655

SEQ ID NO: 97          moltype = AA   length = 572
FEATURE                Location/Qualifiers
source                 1..572
                       mol_type = protein
                       organism = Thermobifida fusca
SEQUENCE: 97
APSGNRDVIV HLFQWRWKSI ADECRTTLGP HGFGAVQVSP PQEHVVLPAE DYPWWQDYQP     60
VSYKLDQTRR GSRADFIDMV NTCREAGVKI YVDAVINHMT GTGSAGAGPG SAGSSYSKYD    120
YPGIYQSQDF NDCRRDITNW NDKWEVQHCE LVGLADLKTS SPYVQDRIAA YLNELIDLGV    180
AGFRIDAAKH IPEGDLQAIL SRLKNVHPAW GGGKPYIFQE VIADSTISTG SYTHLGSVTE    240
FQYHRDISHA FANGNIAHLT GLGSGLTPSD KAVVFVVNHD TQRYEPILTH TDGARYDLAQ    300
KFMLAHPYGT PKVMSSYTWS GDDKAGPPMH SDGTTRPTDC SADRWLCEHR AVAGMVGFHN    360
AVAGQGIGSA VTDGNGRLAF ARGSAGYAAF NATNTAWTRT FTTSLPDGVY CDVANGTFVD    420
GVCDGPSYQV SGGKFTATVP ANGAVALHVE APGSCGPDGC GTPPGGGDDC TTVTARFHAT    480
VTTWYGQEVA VVGSIPELGS WQPAQGVRLR TDSGTYPVWS GAVDLPAGVG FEYKYVKLNP    540
DGTVEWEQGG NRIATVDDSG GGCSQNFYDS WR                                  572

SEQ ID NO: 98          moltype = AA   length = 825
```

```
FEATURE                 Location/Qualifiers
source                  1..825
                        mol_type = protein
                        organism = Anaerocellum thermophilum
SEQUENCE: 98
MLVRAYIDDF NEIVVVLSQM VHSVKKEDFK VFLNEEEIDI EKIDKIIPHS DNPAEAETRG    60
YEICEQKGKI RFVLKEGHFD YHRKPYKKPV FVIGEMNDWQ ISPEWEMTYS KLRGRYELIK   120
DLKEIKIGQK FKFAEGASQK LWYPPGFGND IVITEYFDRE TAFTNMIRII PSNRLLPNLK   180
YKVVYKSEHI WARPREILTR PEFFYPGELG IKYEPYGTYF KLWAPTAYKV KVKVFDESEN   240
FRFEKEMARS ENGTWNIYLT GDLKNHYYLY EVWHYNYDED EGFIVYEVPD PYSKASSSNS   300
QKSFIFDPAD TLIEGWQQDE FVKTIEKQQD AIIYEMHVRD FTIDKNSGVD EKFRGKFLGL   360
CQKSFYKEKF STGLLHLKEL GITHIHLLPI SDFGSVDDKN PDKKYNWGYD PVLYQCPEYW   420
YSTKSGGIEA LKELKTMIKT LHQNGIGVVM DVVFNHTYHT KGGKFSIFDK IVPGYFYRID   480
DYGDYSNATG CGNEIATEKP MVRKFILDTI IYWTEDFHID GFRFDLMGLI DTLTMRMIAK   540
EVRKRNPYAL IYGEGWVMGD SMCLLEERAT IESTAHHGYS IGLFNDRIRD SIRGDLDGFK   600
TGYMHGNLSD IERLKQGIRA AIDDFAKEPD ECVNYVSCHD NLTLFDKAQK TMVGEDIFWI   660
DRVCRLANAI ILTSQGIPFL HGGVEFNRSK GGHPNTYNAG DNINKIDWSL KEKFYDTFKF   720
YCDLIKLRKE HVAFRMRSSG EIRKYLKFLP APDGIVAFLI SYPYDAWKKI IVAYNPFKEK   780
KVITLPEGVW KIKANDGIIF SEENELEAIG SFEISPVSLF IAYQK                   825

SEQ ID NO: 99           moltype = AA  length = 1104
FEATURE                 Location/Qualifiers
source                  1..1104
                        mol_type = protein
                        organism = Anaerocellum thermophilum
SEQUENCE: 99
DEKTTLIIHY YRYNEDYQGW NLWIWPVEPV GAEGKAYEFT SKDDFGVKAV VELPGKVTKV    60
GIIVRKGNWE AKDVAVDRFI SGISGSKEVW LIEGEEQIYT SQPQKTPKMT APIDGLNTIV   120
VKLAKKADIL SNNRTQGFKV TAFYEEVPIK KVEPVLPKIN KNFKPEEAGY ELIDGGTKVK   180
FILKPGAGDF KFTDTSGKLD VYVSGTMNDW GGTASSEGKY KPLPAWKMTW NAEKGYYELV   240
KELGKDGVVI GAKFKFTSWD GTSAKWYPDG MGNDKVIEEL YTGNEKITKV DTFKITTEDE   300
LEPQVPYVVS KDSFKPTVAQ ARNILDNPKY YYKGNDLGCT YTKAYSAFRL WAPTAIGVIL   360
RLYDDYKTTK YKEYEMQQSF NGTWYLKING DLKGKYYQYE VWHASNSITD DTIRKYVVPD   420
PYSRATSANS ERTLIFDPKD TNPVGWEKDT FVTLKNQEDA IIYETHVRDF TIDASSGVRP   480
EFRGKYLGFT QTGAKGPNGV KTGIDHLKEL GITHVHLLPT YDFGSIDETN PDKGYNWGYD   540
PVLYQNVEGS YATNPNTIVR IKEYKQMVMA LHKAGIGIIQ DVVFNHTFQI GDAKFSIFDK   600
IVPGYFYRKD KDGNYSNASG CGNEIATEKP MVRKFIIDTL TYLTKEYHID GFRFDLMAAI   660
DRVTMAKAQE EVRKINPSAV IYGEGWLAGS TPLDSSLRME IGSFNQAGLH IGLFNDRIRE   720
AIRGNLDNES KGFMQGNYSF RLEDLKRGIQ GGLGDFAADP DECINYVSAH DNLTLWDKLQ   780
KSVPNEPDYI KDKMGRLANA IVLTAQGVPF LHGGVEFNRT KYMNHNSYNA GDKINKYNWN   840
LKVKWYNTFK YYQGLIALRK AHPAFRMTTA EDIQKYLTFI QTPKGTLGFR LTYPKDTWND   900
IIVVYNSTKK VQEVTLPEGN WVVVANGDEV GTTPIKNLTN FVAGKALVAP ISMFVAYKSN   960
EFPQGFTKVT GKDPVSLESS STVTVPKVYG NGNIEVTFKV KVPHGTDDDV IYLAGSFGKA  1020
GLSDWNPGDK DGAIELVRLQ DGTYTVTVKL NAGETFEYKY TRGSWTTVEK GANKEEIENR  1080
KLTVKDEGGG KMIVSDTVLN WADK                                         1104

SEQ ID NO: 100          moltype = AA  length = 611
FEATURE                 Location/Qualifiers
source                  1..611
                        mol_type = protein
                        organism = Anaerocellum thermophilum
SEQUENCE: 100
MRKPHIIEAI IGNTKVLGQL DSNGILQRFY WPAVDYYQQL KLFLAAVFLD GLVFFEDENF    60
KIKSGFVDDF VYFFEYKIAD KTIFQLDFVD FETDSLVRLW ETGFEDFYVF LEPMINSSSL   120
FNAAKVDKEN EIVYAYFKGT YIGLAFENKI KSFTVKNGID DANDNQLEGW NEATNPQIAV   180
KLKNTGKVVC FLAFGNSKDE IYQKLSYLKQ KGYDEVYRQN KAFWEKKFSK VKLICTQDPK   240
DMQLQKRSAY VFYVLQNSKT GGILAASEVD EKFPHCGGYG FVWGRDAAFI VSAMDELGLS   300
REVEKFFGFK FSCQEKEGFW DQRYYTDGSL APSWGIQIDE TASVVWGFLE HCEKQNSLHL   360
IDLHKEQLKK ALLFLIAAVD SEKGVIFRSF DLWEEREGIH LYSNASIYAA LKKAKKYFPE   420
LESEIEKKLK AIKNQMATRF YSPKLSRYVR STDVRIPHEE FLKLPEENRY MQKDERYEIT   480
YYFKKQDEVV DISMLGIYYP FEMVDSSDKA FKATILAIER ECQNSIVGGY KRYSDDRYIG   540
GNPWILTTLW LAIYYKKTGQ IDRAEKLFEW AKAHSLPNGL FPEQVDRITG KPAWVVPLAW   600
SHAMYVLYLY E                                                       611

SEQ ID NO: 101          moltype = AA  length = 529
FEATURE                 Location/Qualifiers
source                  1..529
                        mol_type = protein
                        organism = Streptomyces avermitilis
SEQUENCE: 101
MTSFRPAPAW LADAVFYQIY PQSFADSDGD GIGDFNGIVQ RLDHLVWLGV TAVWLNPCFV    60
SPFRDAGYDV SDYLNVAPRY GSADDLAELV DEAGRRGIRV LLDLVAGHTS DEHPWFTASA   120
NDPDDHRYIW APEGRPDGFV TSPGTRPGAY LPNFFDTQPA LNFGYGRKNP AEPWRQPVDA   180
AGPRANREAL RTIMDHWLGL GLAGFRVDMA ASLVKDDPGR TETARIWTEL RHWLDTAHPD   240
AVLLSEWGEP EVSVPAGFHT DFFLQFGGAT DGLPLRSLWS NGDGTVNEAW DPLDCFFDAS   300
GKGSPRPFVE AWRKASDAVG ATGFVSLPTA NHDFSRLNCG PRTAEQLPAA FAFQLTWPTL   360
PAIYYGDEIG MRYVGGLPDK EGSVLGPRYN RAGSRTPMQW DDGPGAGFST APADRLYLPL   420
DPSPDRPTVA AQRADDGSLL HLVRRLVALR ASTPALGSGG SVEVLHTGYP FVYVRGGRYL   480
VVVNPQRNEV RCPYDATREA RALEASGVRV GNGTIEAEGF SYGVFDLGR               529
```

```
SEQ ID NO: 102            moltype = AA  length = 431
FEATURE                   Location/Qualifiers
source                    1..431
                          mol_type = protein
                          organism = Streptomyces avermitilis
SEQUENCE: 102
SPPGTKDVTA VLFEWKFDSV ARECTNTLGP AGYGYVQVSP PAEHIQSGSQW WTSYQPVSYK   60
IAGRLGDATA FQNMINTCHT AGVKVVVDTV VNHMSAGSGT GTGGSAYTKY NYPGLYSSYD   120
MDDCTATITD YTNRANVQNC ELVGLADLDT GEEYVRKTIA GYMNTLLGYG ADGFRVDAVK   180
HIPAADLANI KSRLTNPSVY WKQEVIYASG EAVQPTEYTG NGDVQEFRYA YDLKRVFNNE   240
NLAYLKNYGE GWGYLNSSVA GVFVDNHDTE RNGSTLNYKD GANYTLANVF MLAYPYGAPD   300
INSGYEWSDA DAGPPGGGTV NACWQDGWKC QHAWPEIKAM VAFRNATRGE SVTNWWDNGG   360
DAIAFGRGAK GYVAINHESG SLTRTYQTSL TAGTYCNVQN NTGVTVDSSG RFTATLGANT   420
ALALYSGKST C                                                        431

SEQ ID NO: 103            moltype = AA  length = 503
FEATURE                   Location/Qualifiers
source                    1..503
                          mol_type = protein
                          organism = Saccharomycopsis fibuligera
SEQUENCE: 103
LPLQEGPLNK RAYPSFEAYS NYKVDRTDLE TFLDKQKDVS LYYLLQNIAY PEGQFNDGVP    60
GTVIASPSTS NPDYYYQWTR DSAITFLTVL SELEDNNFNT TLAKAVEYYI NTSYNLQRTS   120
NPSGSFDDEN HKGLGEPKFN TDGSAYTGAW GRPQNDGPAL RAYAISRYLN DVNSLNKGKL   180
VLTDSGDINF SSTEDIYKNI IKPDLEYVIG YWDSTGFDLW EENQGRHFFT SLVQQKALAY   240
AVDIAKSFDD GDFANTLSST ASTLESYLSG SDDGGFVNTDV NHIVENPDLL QQNSRQGLDS   300
ATYIGPLLTH DIGESSSTPF DVDNEYVLQS YYLLLEDNKD RYSVNSAYSA GAAIGRYPED   360
VYNGDGSSEG NPWFLATAYA AQVPYKLVYD AKSASNDITI NKINYDFFNK YIVDLSTINS   420
GYQSSDSVTI KSGSDEFNTV ADNLVTFGDS FLQVILDHIN DDGSLNEQLN RNTGYSTSAY   480
SLTWSSGALL EAIRLRNKVK ALA                                           503

SEQ ID NO: 104            moltype = AA  length = 497
FEATURE                   Location/Qualifiers
source                    1..497
                          mol_type = protein
                          organism = Saccharomycopsis fibuligera
SEQUENCE: 104
VPVELDKRNT GHFQAYSGYT VARSNFTQWI HEQPAVSWYY LLQNIDYPEG QFKSAKPGVV    60
VASPSTSEPD YFYQWTRDTA ITFLSLIAEV EDHSFSNTTL AKVVEYYISN TYTLQRVSNP   120
SGNFDSPNHD GLGEPKFNVD DTAYTASWGR PQNDGPALRA YAISRYLNAV AKHNNGKLLL   180
AGQNGIPYSS ASDIYWKIIK PDLQHVSTHW STSGFDLWEE NQGTHFFTAL VQLKALSYGI   240
PLSKTYNDPG FTSWLEKQKD ALNSYINSSG FVNSGKKHIV ESPQLSSRGG LDSATYIAAL   300
ITHDIGDDDT YTPFNVDNSY VLNSLYYLLV DNKNRYKING NYKAGAAVGR YPEDVYNGVG   360
TSEGNPWQLA TAYAGQTFYT LAYNSLKNKK NLVIEKLNYD LYNSFIADLS KIDSSYASKD   420
SLTLTYGSDN YKNVIKSLLQ FGDSFLKVLL DHIDDNGQLT EEINRYTGFQ AGAVSLTWSS   480
GSLLSANRAR NKLIELL                                                  497

SEQ ID NO: 105            moltype = AA  length = 747
FEATURE                   Location/Qualifiers
source                    1..747
                          mol_type = protein
                          organism = Saccharomyces cerevisiae
SEQUENCE: 105
FPTALVPRGS SSSNITSSGP SSTPFSSATE SFSTGTTVTP SSSKYPGSKT ETSVSSTTET    60
TIVPTTTTTS VITPSTTTIT TTVCSTGTNS AGETTSGCSP KTITTTVPCS TSPSETASES   120
TTTSPTTPVT TVVSTTVVTT EYASTSTKQG GEITTTFVTK NIPTTYLTTI APTSSVTTVT   180
NFTPTTITTT VCSTGTNSAG ETTSGCSPKT VTTTVPCSTG TGEYTTEATA PVTTAVTTTV   240
VTTESSTGTN SAGKTTTSYT TKSVPTTYVF DFGKGILDGS CGVFSNNGS SQVQLRDVVL   300
MNGTVVYDSN GAWDSSPLEE WLQRQKKVSI ERIFENIGPS AVYPSILPGV VIASPSQTHP   360
DYFYQWIRDS ALTINSIVSH SADPAIETLL QYLNVSFHLQ RTNNTLGAGI GYTNDTVALG   420
DPKWNVDNTA FTEPWGRPQN DGPALRSIAI LKIIDYIKQS GTDLGAKYPF QSTADIFDDI   480
VRWDLRFIID HWNSSGFDLW EEVNGMHFFT LLVQLSAVDR SLSYFNASER SSPFVEELRQ   540
TRRDISKFLV DPANGFINGK YNYIVETPMI ADTLRSGLDI STLLAANTVH DAPSASHLPF   600
DIDDDPAVLNT LHHHLMHMRS IYPINDSSKN ATGIALGRYP EDVYDGYGVG EGNPWVLATC   660
AASTTLYQLI YRHISEQHDL VVPMNNDCSN AFWSELVFSN LTTLGNDEGY LILEFNTPAF   720
NQTIQKIFQL ADSFLVKLKA TWEQTGN                                       747

SEQ ID NO: 106            moltype = AA  length = 621
FEATURE                   Location/Qualifiers
source                    1..621
                          mol_type = protein
                          organism = Aspergillus niger
SEQUENCE: 106
NVISKRATWD SWLSNEATVA RTAILNNIGA DGAWVSGADS GIVVASPSTD NPDYFYTWTR    60
DSGLVLKTLV DLFRNGDTSL LSTIENYISA QAIVQGISNP SGDLSSGAGL GEPKFNVDET   120
AYTGSWGRPQ RDGPALRATA MIGFGQWLLD NGYTSTATDI VWPLVRNDLS YVAQYWNQTG   180
YDLWEVNGSS FFTIAVQHRA LVEGSAFATA VGSSCSWCDS QAPEILCLYQ SFWTGSFILA   240
NFDSSRSAKD ANTLLLGSIH TFDPEAACDD STFQPCSPRA LANHKEVVDS FRSIYTLNDG   300
```

```
LSDSEAVAVG RYPEDTYYNG NPWFLCTLAA AEQLYDALYQ WDKQGSLEVT DVSLDFFKAL    360
YSDATGTYSS SSSTYSSIVD AVKTFADGFV SIVETHAASN GSMSEQYDKS DGEQLSARDL    420
TWSYAALLTA NNRRNVVPSA SWGETSASSV PGTCAATSAI GTYSSVTVTS WPSIVATGGT    480
TTTATPTGSG SVTSTSKTTA TASKTSTSTS STSCTTPTAV AVTFDLTATT TYGENIYLVG    540
SISQLGDWET SDGIALSADK YTSSDPLWYV TVTLPAGESF EYKFIRIESD DSVEWESDPN    600
REYTVPQACG TSTATVTDTW R                                             621

SEQ ID NO: 107          moltype = AA  length = 593
FEATURE                 Location/Qualifiers
source                  1..593
                        mol_type = protein
                        organism = Aspergillus oryzae
SEQUENCE: 107
VQPVLRQATG LDTWLSTEAN FSRQAILNNI GADGQSAQGA SPGVVIASPS KSDPDYFYTW     60
TRDSGLVMKT LVDLFRGGDA DLLPIIEEFI SSQARIQGIS NPSGALSSGG LGEPKFNVDE    120
TAFTGAWGRP QRDGPALRAT AMISFGEWLV ENSHTSIATD LVWPVVRNDL SYVAQYWSQS    180
GFDLWEEVQG TSFFTVAVSH RALVEGSSFA KTVGSSCPYC DSQAPQVRCY LQSFWTGSYI    240
QANFGGGRSG KDINTVLGSI HTFDPQATCD DATFQPCSAR ALANHKVVTD SFRSIYAINS    300
GRAENQAVAV GRYPEDSYYN GNPWFLTTLA AAEQLYDALY QWDKIGSLAI TDVSLPFFKA    360
LYSSAATGTY ASSTTVYKDI VSAVKAYADG YVQIVQTYAA STGSMAEQYT KTDGSQTSAR    420
DLTWSYAALL TANNRRNAVV PAPWGETAAT SIPSACSTTS ASGTYSSVVI TSWPTISGYP    480
GAPDSPCQVP TTVSVTFAVK ATTVYGESIK IVGSISQLGS WNPSSATALN ADSYTTDNPL    540
WTGTINLPAG QSFEYKFIRV QNGAVTWESD PNRKYTVPST CGVKSAVQSD VWR           593

SEQ ID NO: 108          moltype = AA  length = 579
FEATURE                 Location/Qualifiers
source                  1..579
                        mol_type = protein
                        organism = Rhizopus oryzae
SEQUENCE: 108
ASIPSSASVQ LDSYNYDGST FSGKIYVKNI AYSKKVTVIY ADGSDNWNNN GNTIAASYSA     60
PISGSNYEYW TFSASINGIK EFYIKYEVSG KTYYDNNNSA NYQVSTSKPT TTTATATTTT    120
APSTSTTTPP SRSEPATFPT GNSTISSWIK KQEGISRFAM LRNINPPGSA TGFIAASLST    180
AGPDYYYAWT RDAALTSNVI VYEYNTTLSG NKTILNVLKD YVTFSVKTQS TSTVCNCLGE    240
PKFNPDASGY TGAWGRPQND GPAERATTFI LFADSYLTQT KDASYVTGTL KPAIFKDLDY    300
VVNVWSNGCF DLWEEVNGVH FYTLMVMRKG LLLGADFAKR NGDSTRASTY SSTASTIANK    360
ISSFWVSSNN WIQVSQSVTG GVSKKGLDVS TLLAANLGSV DDGFFTPGSE KILATAVAVE    420
DSFASLYPIN KNLPSYLGNS IGRYPEDTYN GNGNSQGNSW FLAVTGYAEL YYRAIKEWIG    480
NGGVTVSSIS LPFFKKFDSS ATSGKKYTVG TSDFNNLAQN IALAADRFLS TVQLHAHNNG    540
SLAEEFDRTT GLSTGARDLT WSHASLITAS YAKAGAPAA                           579

SEQ ID NO: 109          moltype = AA  length = 644
FEATURE                 Location/Qualifiers
source                  1..644
                        mol_type = protein
                        organism = Clostridium thermocellum
SEQUENCE: 109
MANTYFNDAI IGNSGMLVCL TRNGELTRLF WPNIDYPQHF EKMATGIFYT GQKNSTSWFY     60
EDNWHHTQYY VEDTNILKTI CEDGGRGLRV EQTDFVLKDR DVMVRRYVIE NIGPNEVDLG    120
FVQYSSTVST TPELRSTLFD FNVDALIHYR HNYYISISSD SEVVQFQLGN NAFDCARYTE    180
LYGYDSIGMM KDGAMSFNIG KIEPGGKKTF NLFICASHTL KGVKELVRWC RKMNVDEEYE    240
KTRKYWLDFL KNARLIVTGD KNIDNLYKRS ILVFKLMSDE RTGGLLASAE IDEGFTRCGR    300
YAYCWGRDAA FITGALDTAG LTEAVDKFYQ WAVMTQDDDG SWQQRYHMDG NLAPSWGLQI    360
DETGTLIWGM LKHYEVTKNI DFLKSMWESI KKGVEFLTRF IDSDTGLPAP SYDLWEERVG    420
EHTYSSAAVY AGIKAGAEAA RILGASEELI EKWEKAASDM KASIEKNFWR DEAGRFIRSV    480
RTKLNPWGSE HSPYTTVIKV NEKGYFRDVT LEDWTIDVSL LGVSIPFGVF DVHDERVKKT    540
VEAIERALTS HPVGGIKRYE NDNYIGGNPW VLATLWVALY YIEIKEYEKA KDYLRWATKS    600
CTALGLLPEQ VSKDNGEPCW VIPLTWSHAM YVLVLAGLKE AGVL                     644

SEQ ID NO: 110          moltype = AA  length = 644
FEATURE                 Location/Qualifiers
source                  1..644
                        mol_type = protein
                        organism = Clostridium thermocellum
SEQUENCE: 110
MQKSYYNNAI TGNSSMLACF SERAELLRLF WPDIDYIQNL DKMFLGLFEK NKTGSTVWLN     60
DIRCEHHQEY LPDSNIIKNM VTNFFDGYKV VLYDFVHPEM DVLVRRFEIE NLRGESRELG    120
LMSFSAATSS DSEVACSLFD FMNEALVHYK PDSYIAVTSD IPVYQFQIGN NANDAAVNTY    180
LYGKDDIGMM KDAAISWDLG VFQPHAVKTT NVYLCAADTL KSCKALVRRV KTVGGLTAFR    240
ETGRYWKDYL EKTTKLKSGN TLLDDLYKRS LLVFRLMYSK KSGGLMAAPE VDEYFTKCGK    300
YAYCWGRDAA FITGALDIGG LCESVDHFYK WAVNVQDEDG SWQQRYHMNG NLGPCWGLQV    360
DETGTIIWGM LNHYNYTKNT DFLKSVWDSV KAAADFLVRF IDSETGLPRP SFDLWEERYG    420
EHAYSSASVC AGLKSASEMA RILGKPSQEY IQWETTADSI KKAIVKYPWK EDYRRFIRSI    480
RVKLNGFGQE PSSDTMLIKV NPKGYVRDVT KEDWIVDVSL VGLGIPFEIF ELNDPMLRDT    540
VSLIEQVLTA QGVGGIKRYE NDTYIGGNPW ILTTLWIALY HAKSGNYKKA KEYLIWAASG    600
KTELGLLPEQ INRDTGKPEW IIPLTWSHAM YVHVYSELIN AGVL                     644

SEQ ID NO: 111          moltype = AA  length = 608
FEATURE                 Location/Qualifiers
```

```
source                      1..608
                            mol_type = protein
                            organism = Arxula adeninivorans
SEQUENCE: 111
DSCHTFTLAN SPPDDKAVAL SSYSYCGGYL SASAFVKNLS YDKLVTLYWT NADNKSTPLN      60
AGSLDYVKAA SDDQSWELWS LNVTTVPDGV DALLNITYVA ASIGKTNSQQ LNVQVEATGD     120
PIPTPQIPTI YKPYASPSDF SDDITNWLKP SNDSQTGIAK SFLFNNINIP GAAPGTVIAA     180
QSYSEPDYAY TWVRDASLVM DVVNRLYSSA KSEEKRQLYE KILFQYAKAG AQEQNDPTAI     240
SGMGEPKFYL NNTAFTGSWG RPQNDGPATR AITLIEFANR YLANGGSQDT VREQLYDSDK     300
YPQVAPIKKD LQFVASNWSS PSFDLWEEEE SAHFYTRLVQ RKALLLGADF ANDMGDHELS     360
DKLKTQASKL SDTLPEFWDS ARQLILYEYG PVLRGKYSYK DISVVLGVMH GYANDNVFSY     420
TNDQILATAY QVSTSFLDVY KVANTTSDES GKPLGIPVGR YPEDVYDGVG TSQGNPWYLT     480
TMAMAEFLYR SVQEFEDAGS IIIISDTSLPF WKYFASSVDH KAGAKYNKND QSFKTSLKSL    540
TGWGDAFMRR AKYHTPSSGH MSEEFNRTTG EPRGAKDLTW SYASLLSAAF AREELRNQKN     600
YLTNVADL                                                              608

SEQ ID NO: 112              moltype = AA  length = 595
FEATURE                     Location/Qualifiers
source                      1..595
                            mol_type = protein
                            organism = Hormoconis resinae
SEQUENCE: 112
APTELKARDL SSFIASERAI ALQGALNNIG PDGSAVPGAG AGFVVASPSK ANPDYFYTWS      60
RDSALTKMI IDEFILGNTT LQTIIEQYIH AQAVLQTVSN PSGTFLPDGV GLGEPKFMVD      120
GTRFNGPWGR PQRDGPALRA IALMTYSNWL IKNGQFAEAK TKIWPIIAND LSYVGQYWNQ     180
SGFDLWEETY ASSFFTIQNQ HRALVEGAQL AHDLGVTCTG CDQAPEVLCF LQSFWNGKYI     240
VSNINVNNGR TGLDGNSILG AISTFDIDAY CDSPTLQPCH SQSLANFKVL TDTFRNLYTI     300
NAGIPEGQGV AVGRYAEDVY MGGNPWYLIT TAAAEFLYDA VAQWKARHVL TVDETSLAFF     360
KDIYPEVTVR EYKSGNANSP FAQIMDAVTA YADSYVAIAE KYIPSNGSLS EQFNRDTGTP     420
LSAIDLTWSY AAFITMSQRR AGQYPSSWGS RNALPPPTTC SASSTPGIYT PATAAGAPNV     480
TSSCQVSITF NINATTYYGE NLYVIGNSSD LGAWNIADAY PLSASAYTQD RPLWSAAIPL     540
NAGEVISYQY VRQEDCDQPY IYETVNRTLT VPACGGAAVT TDDAWMGPVG SSGNC          595

SEQ ID NO: 113              moltype = AA  length = 601
FEATURE                     Location/Qualifiers
source                      1..601
                            mol_type = protein
                            organism = Aureobasidium pullulans
SEQUENCE: 113
LPSPESIQER ATGSLSSWLS SENTVALQGV LNNIGASGSK ASGASAGVVV ASPSKSNPDY      60
FYTWTRDSAL VFKALVDQLI AGNKSLEPLI QQYISAQAKL QTVNNPSGGL CSGGLAEPKF     120
EVDLTPFTGA WGRPQRDGPA LRATAMIAYS RYLIANGNTT TVNNIIWPIV QNDLSYVTQY     180
WNQTTFDLWE EINSSSFFTT AVQYRALVEG NNLATQLGKS CPNCVSQAPL VLCFLQSYWT     240
GSYALSNTGG GRSGKDANSI LTSIHIFDPA ASCDSTTFQP CSDKALANHK VVTDSFRSIY     300
SINQGIAQGS GVAVGRYPED SYYNGNPWYL NTFAAAEQLY DAVYQWKKIG SISITSISLP     360
FFKDVYSSAA VGTYSSSTVT FTSIVNAVQT YADSYMSIAQ KYTPSNGALS EQYNRADGTP     420
LSAVDLTWSY AAFLTAYNAR ANVLPASWGA SSAKLPNSCS SGSATGPCAA ATNTNWGNPG     480
SPSTGTPTTT TGGSCTTPTS IAVTFNEQKT TSYGENIYIV GSIPALGNWN TANAVALSAS     540
KYTSSNPLWT VTINFATGTS FNYKYIKKAQ DGSVTWESDP NRSYTVTGNC AGTATENDSW     600
R                                                                     601

SEQ ID NO: 114              moltype = AA  length = 718
FEATURE                     Location/Qualifiers
source                      1..718
                            mol_type = protein
                            organism = Bacillus subtilis
SEQUENCE: 114
MVSIRRSFEA YVDDMNIITV LIPAEQKEIM TPPFRLETEI TDFPLAVREE YSLEAKYKYV      60
CVSDHVPTFG KIHCVRASSG HKTDLQIGAV IRTAAFDDEF YDGELGAVY TADHTVFKVW      120
APAATSAAVK LSHPNKSGRT FQMTRLEKGV YAVTVTGDLH GYEYLFCICN NSEWMETVDQ     180
YAKAVTVNGE KGVVLRPDQM KWTAPLKPFS HPVDAVIYET HLRDFSIHEN SGMINKGKYL     240
ALTETDTQTA NGSSSGLAYV KELGVTHVEL LPVNDFAGVD EEKPLDAYNW GYNPLHFFAP     300
EGSYASNPHD PQTRKTELKQ MINTLHQHGL RVILDVVFHN VYKRENSPFE KTVPGYFFRH     360
DECGMPSNGT GVGNDIASER RMARKFIADC VVYWLEEYNV DGFRFDLLGI LDIDTVLYMK     420
EKATKAKPGI LLFGEGWDLA TPLPHEQKAA LANAPRMPGI GFFNDMFRDA VKGNTFHLKA     480
TGFALGNGES AQAVMHGIAG SSGWKALAPI VPEPSQSINY VESHDNHTFW DKMSFALPQE     540
NDSRKRSRQR LAAAIILLAQ GVPFIHSGQE FFRTKQGVEN SYQSSDSINQ LDWDRRETFK     600
EDVHYIRRLI SLRKAHPAFR LRSAADIQRH LECLTLKEHL IAYRLYDLDE VDEWKDIIVI     660
HHASPDSVEW RLPNDIPYRL LCDPSGFQED PTEIKKTVAV NGIGTVILYL ASDLKSFA      718

SEQ ID NO: 115              moltype = AA  length = 710
FEATURE                     Location/Qualifiers
source                      1..710
                            mol_type = protein
                            organism = Bacillus licheniformis
SEQUENCE: 115
MPGISRPFEA YLDEMRTITV LVPKSRASSC SPPFLLEDDQ GERIELSVKA QVELEEQFKY      60
VLESSCTVPF GRVHKVCCEE SVWTDLQIGS VTRSAAFDKA FFYDGRLGAF YSKGSTLFKV     120
WAPTASAAAI KLEDPDSLQT NTFQMMRRKK GVFEVTVEGD LNGWSYLYEL YVNGKPLLTV     180
```

```
DPYAKAVTAN GEKGVVLDPE EVKVEKHRAP RLHSPCDAVI YEVHIRDFSI HEDSGMRHKG    240
KYVAFTEDGT ETSGGFSTGI AYLKELGVTH IEVLPFHDFA GVDELSPDQS YNWGYNPLHF    300
NAPEGSYSLD PQNPKCRITE LKTMIQSLHK HGFSVIMDAV YNHVYKRETS PFEKTVPGYF    360
FRHNEYGFPS DGTGVGNDIA SERLMVRKYI LDSVRYWLEE YDVDGIRFDL MGILDIETVR    420
QISTLAENVK PGVPLFGEGW DLNTPLDSGQ KATLQNAGKV PAVGFFNDRF RNAVKGSTFE    480
LSDRGYALGD TGKKAALQHG IAGSPGFLQP AQSINYVECH DNHTFWDKMA LCFEEDADTK    540
RLRQRLAVSI VLLSQGVPFL HAGQEFCRTK NGDSNSYRSG DDINKLDWEK RAELCEDVEY    600
VRQLIRLRRS HPAFRLQKEE EVKEHLSFMD GTGEVTAYKL KNIAAIDPWN EIIVVHCPFA    660
KKETLKLPDQ KQYLLHCDPF TFFNGKVQAE KRLRLNGIGT YVLYEPKGIF              710

SEQ ID NO: 116          moltype = AA  length = 918
FEATURE                 Location/Qualifiers
source                  1..918
                        mol_type = protein
                        organism = Oryza sativa
SEQUENCE: 116
MAVGEECAAA VASQGFVSDA RAYWVTRSLI AWNVNDQDTS LFLYASRDAT MHVSDGAIHG    60
YDSKIELEPE HASLPDNVAE KFPFIRSYRT FRVPSSVDVT SLVKCQLAVA SYDAHGRHQD   120
VTGLQLPGVL DDMFAYTGPL GAVFSDKDVD LYLWAPTAQD VRVCFYDGPA GPLLQTVQLK   180
ELNGVWSVTV PRYRENQYYL YEVKVYHPST SQVEKCLADD PYARGLSANG TRTWLVDINS   240
ETLKPASWDE LSDEKPNLES FSDISIYELH IRDFSAHDST VDCNSRGGFR AFTFQDSAGI   300
RHLRKLSAAG LTHVHLLPSF HFASVDDNKS NWKFVDEAQL AKLPPGSDEQ QAAIVSIQQE   360
DPYNWGYDPV LWGVPKGSYA SNPDGPSRII EYRQMVQALN RIGLRVVMDV VYNHLDSSGP   420
FGVSSVLDKI VPGYYLRRNV NGQIENSAAM NNTASEHFMV DRLIVDDLLN WAINYKVDGF   480
RFDLMGHIMK STMFTVMSIC TISTIIKIKD VFADTLIRAK SAIRSLTRDV HGVDGSKIYL   540
YGEGWDFGEV AQNKRGINAS QINMSGTGIG SFNDRIRDSV NGGNPFGNPL QQGFSTGLFL   600
EPNGYYQGNE ADTRRELATY ADHIQIGLAG NLKDYVLRTH TGEAKKGSDI YTFDGSPVGY   660
TSSPVETINY VSAHDNETLF DIVSIKTPIG LSIDEKCRIN HLASSMIALS QGIPFFHAGD   720
EILRSKSLDR DSYNSGDWFN KLDFTYETNN WGVGLPPRDK NEENWHLIKP RLENPSFRPL   780
KNHILSVFDN FVDILKIRYS SPLFRLSTAS DIEQRVRFHN TGPSMVPGVI VMSIKDAQNE   840
KCKMAQLDKN FSYVVTIFNV CPHEVSIEIH DLASLGLELH PIQVNSSDAL VRQSAYEASK   900
GRFTVPRRTT AVFVQPRC                                                918

SEQ ID NO: 117          moltype = AA  length = 963
FEATURE                 Location/Qualifiers
source                  1..963
                        mol_type = protein
                        organism = Triticum aestivum
SEQUENCE: 117
MPMPMRTMLL RHLSPAPALP NPRRSSASSP QRRPARARPP PLHSARATAL RARRTPMAAG    60
ETGASVSVSA AEAEAEATQA FMPDARAYWV TSDLIAWNVS EQEAASVYLY ASRTAAMGLS   120
PSNGGIQGYD SKVELQPESA GLPETVTQKF PFISSYRAFR VPSSVDASL VKCQLVIASF    180
GADGKHVDVT GLQLPGVLDD IFAYTGPLGA VFREDSVSLH LWAPTAQDVS VCFFDGPAGP   240
VLETVQLKES NGVWSVTGPR EWENRYYLYE VDVYHPTKAQ VLKCLAGDPY ARGLSANGAR   300
TWLVDINNET LKPASWDELA DEKPLDSFS DITIYELHIR DFSAHDGTVD SDSCGGFRAF    360
AYQASAGMQH LRKLSDAGLT HVHLLPSFHF AGVDDIKSNW KFVDECKLAT FPPGSDMQQE   420
AVVAIQEEDP YNWGYNPVLW GVPKGSYASD PDGPSRIIEY RQMVQALNRI GLRVVMDVVY   480
NHLDSSGPCG ISSVLDKIVP GYYVRRDTNG QIENSAAMNN TASEHFMVDR LIVDDLLNWA   540
VNYKIDGFRF DLMGHIMKHT MMRAKAALQS LTRDAHGVDG SKIYLYGEGW DFAEVARNQR   600
GINGSQLNMS GTGIGSFNDR IRDAVNGGNP FGNPLQQGFN TGLFLEPNGF YQGNEADTRR   660
SLATYADQIQ IGLAGNLRDY VLITHGTETK KGSEIHTFDG LPVGYTSSPI EIINYVSAHD   720
NETLFDVISV KTPMNLSVDE RCRINHLASS MMALSQGIPF FHAGDEILRS KSIDRDSYNS   780
GDWFNKLDFT YETNNWGVGL PPSEKNEDNW PLMKPRLENP SFKPAKGHIL AALDSFVDIL   840
KIRYSSPLFR LSTASDIKQR VHFHNTGPSS VPGVIVMGIE DARDEKPEMA QLDANFSYVV   900
TVFNVCPHEV SMDIPALASM RLELHPVQVN SSDALVGKSV YEAATGRFTV PRRTVSVFVE   960
PRC                                                                963

SEQ ID NO: 118          moltype = AA  length = 647
FEATURE                 Location/Qualifiers
source                  1..647
                        mol_type = protein
                        organism = Clostridium phytofermentans
SEQUENCE: 118
MDEFWNSIDG EKQYYYDGND LGCTYTNRST KLKVWAPTAS MVVVNLYQNG NAGKPYITEI    60
MKKEESGIWS VCLLGDLEGV YYTYLVTVDG QTKEAVDPYA RTTGLNGKRA MILDLEKTNP   120
TGFLEDTKPK FDSFLDAVIY ELHIRDLSME SDSGIKEKGK LLGLTELNTR NSDGLTTGLS   180
HILDLGVTHI HLLPCFDYAS VDEENSSIFN WGYDPENYNV VEGSYSTNPY DGAVRVKEFK   240
TLVQSLHENG LRVIMDVVYN HTMKTEESNF NKIVPDVYYR KVGDKFSDAS ACGNETASER   300
LMVRKFIVDS IIYWAKEYHI DGFRFDLMGI HDIETMNEVR KVLDQIDPSI ILYGEGWVGG   360
DSPLPAGQRA MKANMSMLPG IAAFSDDFRD GLKGSVFLAE EKGFATGDSD KKESVKFGVV   420
ASTLHPQIDY KKVNYSDSPW ALEPAQCINY VSAHDNYTLW DKIACSCKED TYEIRVKKNK   480
LCAAIVFTSQ GIPFLQAGEE MLRNKPSSEI AGEFVENSYN SSDSVNCIKW SNKANVIDVV   540
SYYEGLIRFR KEHKALRMQS AKEISKRLTF LPEEREDVIS YLIQGDLVDK TLCVIYNSSE   600
EKVTIRLPES DWTVYIDGNN SGVEPLYEVK GTTVEVEPIS CMVLVKD                647

SEQ ID NO: 119          moltype = AA  length = 1764
FEATURE                 Location/Qualifiers
source                  1..1764
                        mol_type = protein
```

```
                        organism = Streptomyces avermitilis
SEQUENCE: 119
ATPPAPPSDA KLAAEPARHD ATREQFYFVM PDRFANGDTS NDKGGLTGSR LSTGYDPTDK    60
GFYQGGDLKG LTRKLDYIKG LGTTSIWLAP IFKNQPVQGT GKDASAGYHG YWITDFTKVD   120
PHFGTNKDLE TLISKAHAKG MKVFFDVITN HTADVVDYEE KSYGYLSKGA FPYLTKDGRP   180
FDDAGYTDGP RKFPAVDGDS FPRTPAVAAR KKNAKVPSWL NDPTMYHNRG DSTFAGESST   240
HGDFSGLDDL WTERPEVVRG MEKIYEKWVR DFGIDGFRID TVKHVNTEFW TQWATALDAY   300
AKKRGKDDFF MFGEVYSADT SVTSPYVTQG RLDSTLDFPF QDAARSYASQ GGSAKKLASV   360
FGDDYKYTTD KANAYEQVTF LGNHDMGRIG YFLNQDNPKA TDAELLRKDR LANELMFLSR   420
GNPVVYYGDE QGFTGSGGDK DARQTMFASK VADYLDDDEI GTDRGHASDA YDTSAPLYKE   480
IAALSKLRKD NPALADGIQT ERYAADGAGV YAFSRTDART GTEYVVAVNN ADKASAATFA   540
TGSADTAFKG IHGTDDVLKS DADKKITVTV PAGAAVVLKA AGRPGTPAAK PSLTLKAPDA   600
GATGTVELSA DVDGGRLNRV VFAAQVGNAK WRTLGSADHA PYRVTQTIGK DVPAGTALRY   660
KAVVIDAAGR TASATAASTT GTPPAAETPT ASSRDYAIVH YKRPDGDYTD WRLYAWGDLA   720
DGESTTWPAG HDFVGRDAYG AFAYVKLKPG ASTVNFLVID KDGDKDVSAD RTIDVTKAGE   780
VWWEQGKETV RTERPDYPAQ DKTKAVIHYH RADGDLTGWG LHVWTGAATP TDWSKPLEPV   840
RTDAYGAVFE VPLTDGATSL SYIIHKGDEK DLSADRSLDL TADGHEVWLL NGQENHLLPQ   900
PAGSAAALDL TTSKAVWIDR NTVAWNGSDA AASTQLLSSR DGSIAVKDGS LTSDDERWLR   960
LSKTSLTDAQ KAAFPHLKSY TAWSVDPRDR DRVREALAGQ VVASQRAANG AVLAATGVQL  1020
AGVLDDLYDA TKADLGPTFR GGHPTLAVWA PTAQSVSLEL DGAHVRMKRN NATGVWSVTG  1080
PASWKGKPYR YVVKVWAPTV RKVVTNKVTD PYSVALTTDS ERSLVVDLDD RSLAPSGWSS  1140
LKKPKAVPLR DAEIQEHLIR DFSVADRTVP AKDRGTYLAF TDKNSDGSRH LRQLAESGTS  1200
YVHLLPAFDI ATIAEKKSGQ QATDCDLASY AADSEKQQEC LTAVAAKDAY NWGYDPYHYT  1260
VPEGSYATDA NGTRRTVEFR RMVKSLNQDG LRVVMDVVYN HTAAAGQAGT SVLDRIVPGY  1320
YQRLLADGSV ATSTCCANTA TENAMMGKLV VDSLVTWAKE YKVDGFRPDL MGHQPKANIL  1380
AVRKALDALT VAKDGVDGKK IILYGEGWNF GEVADDARFV QATQKNMAGT GIATFSDRAR  1440
DAVRGGGPFD ADPGVQGFGS GLYTDPNSSD ANGTPAEQKA RLLHYQDLIK VGLSGNLAKY  1500
RPFTDSSGKEV TGSEVDYNGT GAGYADAPGD ALAYADAHDN ESLYDALTYK LPKGTPAGDR  1560
ARMQVLAMAT AALAQGPSLS QAGSDLLRSK SLDRNSYDSG DWFNAIHWNC QDGNGFGRGL  1620
PMAADNKSKW PYATPLLTSV KVGCDQIEGT SAGYQDLLRI RTTEPDFSLS TAGQVQSKLT  1680
FPLSGKDETP GVITMKLGDL VVVFNATPDQ QEQTVAALAG KDYALHPVQA AGADPIVKSA  1740
SYTAKSGMFA VPGRTVAIFS QVAR                                        1764

SEQ ID NO: 120          moltype = AA  length = 1079
FEATURE                 Location/Qualifiers
source                  1..1079
                        mol_type = protein
                        organism = Klebsiella pneumoniae
SEQUENCE: 120
SSSSPSGSPG SPGNPGNPGT PGTPDPQDVV VRLPDVAVPG EAAQASANQA VIHLVDIAGI    60
TSSTPADYAT KNLYLWNNET CDALSAPVAD WNDVSTTPTG SDKYGPYWVI PLTKESGCIN   120
VIVRDGTNKL IDSDLRVSFG DFTDRTVSVI AGNSAVYDSV ADAFRAAFGV ALADAHWVDK   180
TTLLWPGGEN KPIVRLYYSH SSKVAADSNG EFTDKYVKLT PTTVSQQVSM RFPHLASYPA   240
FKLPDDVNVD ELLQGETVAI SAESDGILSS ATQVQTAGVL DDTYAAAAEA LSYGAQLTDS   300
GVTFRVWAPT AQQVELVVYS ADKKVVASHP MTRDSASGAW SWQGGSDLKG AFYRYAMTVY   360
HPQSRKVEQY EVTDPYAHSL STNSEYSQVV DLNDSALKPE GWDGLTMPHA QKTKADLAKM   420
TIHESHIRDL SAWDQTVPAE LRGKYLALTA QESNMVQHLK QLSASGVTHI ELLPVFDLAT   480
VNEFSDKVAD IQQPFSRLCE INSAVKSSEF AGYCDSGSTV EEVLTQLKQN DSKDNPQVQA   540
LNTLVAQTDS YNWGYDPFHY TVPEGSYATD PEGTARIKEF RTMIQAIKQD LGMNVIMDVV   600
YNHTNAAGPT DRTSVLDKIV PWYYQRLNET TGSVESATCC SDSAPEHRMF AKLIADSLAV   660
WTTDYKIDGF RFDLMGYHPK AQILSAWERI KALNPDIYFT GEGWDSNQSD RFEIASQINL   720
KGTGIGTFSD RLRDAVRGGG PFDSGDALRQ NQGVGSGAGV LPNELTSMTD DQARHLADLT   780
RLGMAGNLAD FVLIDKDGAV KKGSEIDYNG APGGYAADPT EVVNYVSKHD NQTLWDMISY   840
KAAQEADLDT RVRMQAVSLA TVMLGQGIAF DQQGSELLRS KSFTRDSYDS GDWFNRVDYS   900
LQDNNYNVGM PRSSDDGSNY DIIARVKDAV ATPGETELKQ MTAFYQELTA LRKSSPLFTL   960
GDGATVMQRV DFRNTGADQQ TGLLVMTIDD GMQAGASLDS RVDGIVVAIN AAPESRTLQD  1020
FAGTSLQLSA IQQAAGDRSL ASGVQVAADG SVTLPAWSVA VLELPQGESQ GAGLPVSSK   1079

SEQ ID NO: 121          moltype = AA  length = 546
FEATURE                 Location/Qualifiers
source                  1..546
                        mol_type = protein
                        organism = Rhizomucor pusillus
SEQUENCE: 121
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFDDA SLYHPKCTID YNNQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSAGA TSPGGSSGSV EVTFDVYATT VYGQNIYITG DVSELGNWTP   480
ANGVVALSSAN YPTWSATIAL PADTTIQYKY VNIDGSTVIW EDAISNREIT TPASGTYTEK   540
DTWDES                                                             546

SEQ ID NO: 122          moltype = AA  length = 481
FEATURE                 Location/Qualifiers
source                  1..481
                        mol_type = protein
```

```
                        organism = Bacillus licheniformis
SEQUENCE: 122
VNGTLMQYFE WYTPNDGQHW KRLQNDAEHL SDIGITAVWI PPAYKGTSQA DVGYGAYDLY    60
DLGEFHQKGT VRTKYGTKGE LQSAIKSLHS RDINVYGDVV INHKGGADAT EDVTAVEVDP   120
ADRNRVISGE HLIKAWTHPH FPGRGSTYSD FKWYWYHFDG TDWDESRKLN RIYKFQGKTW   180
DWEVSNEFGN YDYLMYADID YDHPDVVAEI KRWGTWYANE LQLDGFRLDA VKHIKFSFLR   240
DWVNHVREKT GKEMFTVAEY WSNDLGALEN YLNKTNFNHS VFDVPLHYQF HAASTQGGGY   300
DMRKLLNGTV VSKHPLKSVT FVDNHDTQPG QSLESTVQTW FKPLAYAFIL TRESGYPQVF   360
YGDMYGTKGD SQREIPALKH KIEPILKARK QYAYGAQHDY FDHHDIVGWT REGDSSVANS   420
GLAALITDGP GGAKRMYVGR QNAGETWHDI TGNRSEPVVI NSEGWGEFHV NGGSVSIYVQ   480
R                                                                  481

SEQ ID NO: 123           moltype = AA  length = 484
FEATURE                  Location/Qualifiers
source                   1..484
                         mol_type = protein
                         organism = Aspergillus niger
SEQUENCE: 123
LSAAEWRTQS IYFLLTDRFG RTDNSTTATC DTGDQIYCGG SWQGIINHLD YIQGMGFTAI    60
WISPITEQLP QDTADGEAYH GYWQQKIYDV NSNFGTADDL KSLSDALHAR GMYLMVDVVP   120
NHMGYAGNGN DVDYSVFDPF DSSSYFHPYC LITDWDNLTM VQDCWEGDTI VSLPDLNTTE   180
TAVRTIWYDW VADLVSNYSV DGLRIDSVLE VEPDFFPGYQ AEAGVYCVGE VDNGNPALDC   240
PYQKVLDGVL NYPIYWQLLY AFESSSGSIS NLYNMIKSVA SDCSDPTLLG NFIENHDNPR   300
FASYTSDYSQ AKNVLSYIFL SDGIPIVYAG EEQHYSGGKV PYNREATWLS GYDTSAELYT   360
WIATTNAIRK LAISADSAYI TYANDAFYTD SNTIAMRKGT SGSQVITVLS NKGSSGSSYT   420
LTLSGSGYTS GTKLIEAYTC TSVTVDSSGD IPVPMASGLP RVLLPASVVD SSSLCGGSGR   480
LYVE                                                               484

SEQ ID NO: 124           moltype = AA  length = 586
FEATURE                  Location/Qualifiers
source                   1..586
                         mol_type = protein
                         organism = Aspergillus tamarii
SEQUENCE: 124
ATPADWRSQS IYFLLTDRFA RTDGSTTAAC NTEDRKYCGG TWQGIIDKLD YIQGMGFTAI    60
WITPVTGQLP QHTAYGDAYH GYWQQDIYSL NENYGTADDL KALSSALHER GMYLMVDVVA   120
NHMGYDGAGA SVDYSVFKPF NSQEYFHSFC LIQNYEDQTQ VENCWLGDNT VSLPDLDTTK   180
DEVKNEWYDW VGTLVSNYSI DGLRVDTVKH VQKDFWPGYN KAAGVYCIGE VLDGDPAYTC   240
PYQDVMDGVL NYPIYYPLLN AFKSTSGSMN DLYNMINTVK SDCPDSTLLG TFVENHDNPR   300
FASYTNDIAL AKNVAAFIIL NDGIPIIYAG QEQHYAGGND PANREATWLS GYATDSELYK   360
LIASANAIRS HAISKDTGFV TYKNWPIYKD DTTIAMRKGT DGSQVVTILS NKGASGDSYT   420
LSLGDTGYKA GQQLTEVIGC TTVTVGSDGK VPVPMAGGLP RVLYPTEKLA DSKICSSSGA   480
TSPGGSSGSV EVTFDVYATT VYGQNIYITG DVSELGNWTP ANGVALSSAN YPTWSATIAL   540
PADTTIQYKY VNIDGSTVIW EDAISNREIT TPASGTYTEK DTWDES                 586

SEQ ID NO: 125           moltype = AA  length = 603
FEATURE                  Location/Qualifiers
source                   1..603
                         mol_type = protein
                         organism = Acidomyces richmondensis
SEQUENCE: 125
LTPAEWRAQS IYQVLTDRFA LTNGSTTAPC NLNEYCGGTW QGIINKLDYI QGMGFTAIWI    60
SPVVENIPAS DNTADGESYH GYWAQRIYEV NPNFGSAADL EALSEAIHAR GMYLMVDIVT   120
NHMGYDGCGT CVDYSVFDPF DNQSYFHPFC LINYNNATSI QVCWEGDNIV SLPDLRTEDS   180
DVLGMWETWI TQLVANYSID GLRVDSMQQV DQAFWQPFMS AAGDLYAVGE VFNGDPTYTC   240
PYQQYLPGVL NYPAYYWITQ AFESTSGSIG NLVNGINEMK NDCLDTTLLG SFLENHDNPR   300
FPSYTSDYSL DKNAIAFAML QDGIPIVYEG QEQHYSGGSV PNNREDIWSS GYSTTSELYT   360
FIKIIINAIRT QALTKDSSYL TYKAYPVYSD SQTIAMRKGE TYPIISVFTN SGASGSAYSI   420
TLSSSDTGFS ENQSITELLT CTVSTTDSGG NLVVNISSGL PRVYYPTSAI SGSTVCAEST   480
STLTISSPIS TSTSDCTTAS SVAVTFDETV TTTYGETIKL SGSISQLGDW NTQDAILLSA   540
ADYKSTDNVW FVTINLPAGI VFQYKYINVD SDGDVTWEAD PNHTYTVSAT CATAATIHDT   600
WQN                                                                603

SEQ ID NO: 126           moltype = AA  length = 588
FEATURE                  Location/Qualifiers
source                   1..588
                         mol_type = protein
                         organism = Aspergillus bombycis
SEQUENCE: 126
ATPADWRSQS IYFLLTDRFA RTDGSTTATC NTEDRKYCGG TWQGIIDKLD YIQGMGFTAI    60
WITPVTGQLP QDTAYGEAYH GYWQQDIYAL NENHGTADDL KALSSALHER GMYLMVDVVA   120
NHMGYDGAGA SVDYSVFNPF SSQDYFHSFC LIENYDDQTQ SENCWLGDNS VSLPDLDTTK   180
DEVKNEWYEW VGNLVSNYSI DGLRVDTVKH VQKDFWPGYN EAAGVYCIGE VLNGDPAYTC   240
PYQDVMDGVL NYPIYYPLLN AFKSTSGSMN DLYNMINTVK SDCPDSTLLG TFVENHDNPR   300
FASYTNDIAL AKNVAAFIIL NDGIPIIYAG QEQHYAGGND PANREATWLS GYSTDSEIYK   360
LIASANAIRN HAVSTDTGFV TYKNWPIYKD DTTIAMRKGT DGSQIVTILS NKGASGDAYT   420
LSLGNTGYTA GQQLTEVIGC TTLTVGSDGN VPVPMAGGLP RVLYPTEKLG DSKICSSSGR   480
GATSPGGSSG SVEVTFDVYA TTVYGQNIYI TGDVSELGNW TPANGVALSS ANYPTWSATI   540
ALPADTTIQY KYVNIDGSTV IWEDAISNRE ITTPASGTYT EKDTWDES               588
```

```
SEQ ID NO: 127          moltype = AA  length = 570
FEATURE                 Location/Qualifiers
source                  1..570
                        mol_type = protein
                        organism = Alternaria sp.
SEQUENCE: 127
ADTSAWKSRS IYFVLTDRIA RSSSDTGGGS CSNLGNYCGG TFKGLESKLD YIKNLGFDAI    60
WITPVVANSA GGYHGYWAQD LYAVNSNYGT AADLKSLVNT AHSKGIYVMV DVVANHMGQG   120
AISGNRPEPL NQDSSYHSAC DINYSSQTSI EQCRIANLPD LNTQSSQIRS LLNTWISWLV   180
NEYSFDGVRI DTVKHVEKDF WPGFASAAGV YSIGEVWDGN PTYLAEYARL MPGLLNYATY   240
YPMNNFYQQK GSSQALVDMM NTVRDTFPDP SALGTFLDNH DNNRWLNQKN DVTLLKNALA   300
FVILSRGIPI VYYGTEQGYA GGADPANRED LWRSSFNTNA DLYQAIKKLN AARTSAGGLA   360
GNDHTHLYVS SNAYAWSRAN GNLVVLTTNA GSGSNAQHCF NTQKANGRWT NVYGNGATVT   420
ADGSGNICVN VANGEPVVLL VSTATPTSAT PTSNPSPTTL LTTSTACPTS VSVSFTHRVT   480
TVFGDTIKIT GNTAQLGNWN PSNGVALSAA SYTSSNPIWT LTLPLPAGSA IQYKFVKVSS   540
GGTVTWESDP NRSYSVPGCQ ASASVSSQWQ                                   570

SEQ ID NO: 128          moltype = AA  length = 551
FEATURE                 Location/Qualifiers
source                  1..551
                        mol_type = protein
                        organism = Rhizopus microsporus
SEQUENCE: 128
SPITIRSQNS NDWSSRVIYQ LLTDRFAKTV DDQSPCSDLG NYCGGSFQGI INHLDYIAGM    60
GFDAIWISPI PQNAQGGYHG YWATNFSAIN SNFGSSNDLK KLVQAAHAKN MYVMLDVVAN   120
HVGTPSTPNN YNGYTFNQGS YYHSYCDINY NDQTSVEQCW LSGLPDLNTE NDYVVNTLYS   180
TVSNWISEYG FDGIRIDTVK HVRKDFWDGY VKAAGVFATG EVLHGSVSYV APYQSHVPSL   240
INYPLYYPIY DVFTKAATMT RLKSGYNDIQ SGGFSNLNLL LNFIDNHDNP RLLSKADQSL   300
VKNALTYSML IQGIPVVYYG TEQSYKGGND PNNREPLWTS GYSSSSEMYQ FIKQVIQIRK   360
GSNATVTMDI DQADNVYVFQ RGNYLAVVNN YGQGSTNSVT VKSGSFADGT VLKDVFSGAT   420
ATVKNKSITF QLQNGNPAVF SPQGATSPGG SSGSVEVTFD VYATTVYGQN IYITGDVSEL   480
GNWTPANGVA LSSANYPTWS ATIALPADTT IQYKYVNIDG STVIWEDAIS NREITTPASG   540
TYTEKDTWDE S                                                       551

SEQ ID NO: 129          moltype = AA  length = 565
FEATURE                 Location/Qualifiers
source                  1..565
                        mol_type = protein
                        organism = Syncephalastrum racemosum
SEQUENCE: 129
VPLSIIDKRA GVTTLSKRAA ADDWKSRSIY QIVTDRFARS DGSTSGCGDL SNYCGGDYKG    60
IQNQLDYIAG MGFDAIWISP IPENTDGGYH GYWAKNFEAL NTNFGSADDL KALVTAAHGK   120
GMYVMLDVVA NHAGPTSGGD YSGFTFDSAS NYHAQCDIDY ENQTSIEQCW VADNLPDINT   180
EDDTIVSKLH SIVSDWVTTY DFDGIRIDTV KHIRKDFWSG YEEAAGVFAT GEVFDGAAY    240
VGPYQDQLSS LINYPLYYAI RDVFTAGSGF SRISDMLSSI NSNFKDPSVL TTFVDNQDNA   300
RFLSVKSDTS LYKNALAFTI LTEGIPVVYY GTEQGFRSGN DPNNREVLWT SNYDTSSDLY   360
KFIKIVNDQV RQKSNKTVKL NVDVGTNTYA FTHGKNLIVV NNYGSGSTAS VTVKVGDSIA   420
DGTKLVDAVS NITATVSGGS ITFSLNNGLP ALFVPSSGAT SPGGSSGSVE VTFDVYATTV   480
YGQNIYITGD VSELGNWTPA NGVALSSANY PTWSATIALP ADTTIQYKYV NIDGSTVIWE   540
DAISNREITT PASGTYTEKD TWDES                                        565

SEQ ID NO: 130          moltype = AA  length = 583
FEATURE                 Location/Qualifiers
source                  1..583
                        mol_type = protein
                        organism = Rhizomucor pusillus
SEQUENCE: 130
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFDDA SLYHPKCTID YNNQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                    583

SEQ ID NO: 131          moltype = AA  length = 553
FEATURE                 Location/Qualifiers
source                  1..553
                        mol_type = protein
                        organism = Dichotomocladium hesseltinei
SEQUENCE: 131
QPVNITKRAS AADWRSRAIY QVLTDRFART DGSTSGCSNL SNYCGGTFKG ITNKLDYIAN    60
LGFDAIWISP IPTNSPGGYH GYWATDFYGI NSNFGSSNDL KELVNAAHAK GMYVMLDVVA   120
NHAGPTSNGD YSGYTFGSSG LYHNRCSINY NDQRSIEQCW VADDLPDINT ENNDNVKPN    180
NIVSTWVKTY GFDAIRIDTV KHVRKDFWPG YTSAAGVFAT GEVFDGNPSY VADYQNYMES   240
```

```
LINYPLYYAL NDVFASGYSF SRSLNQRVAN YHAFKDVSVL PIFIDNHDNP RFLNKKNDIA    300
QFKNALTYVL LGEGIPVVYY GSEQAYAGGA DPANREALWS SGFSTNSDMY QFIAKLNRVR    360
QKSNKSVYMD LDVQNNVYAF MHGKSLVVLN NFGNGASRQV TVNVGAQVAS NTRLTDVVSG    420
TSVTVSGSSV TFTINNGLPA VFTVSGATSP GGSSGSVEVT FDVYATTVYG QNIYITGDVS    480
ELGNWTPANG VALSSANYPT WSATIALPAD TTIQYKYVNI DGSTVIWEDA ISNREITTPA    540
SGTYTEKDTW DES                                                      553

SEQ ID NO: 132          moltype = AA  length = 552
FEATURE                 Location/Qualifiers
source                  1..552
                        mol_type = protein
                        organism = Lichtheimia ramosa
SEQUENCE: 132
RPFVKRATAD DWRDRAIYQI LTDRFARSDG STDNCSDLSN YCGGNYQGII QQLDYIEGMG    60
FDAIWISPIP ANADGGYHGY WATDFESLND HFGSQDDLKA LVDAAHERGM YVMLDVVANH    120
AGPTNNGDYS GYTFGSSDLY HPQCSIDYSN QNSIEQCWVA DNLPDIDTEN DSNVNKLHDI    180
VSTWVSTYGF DGIRIDTVKH VRKDFWPGYA SAAGVFATGE VYDGDQTYVG AYQDYLDSLL    240
NYPLYYALND VFASGQGFQR LSNQRNAIMS AFKDVSVLTS FVDNHDVARF LSTKNDQALF    300
KNALAFVLLG ETIPVVYYGS EQGFAGGADP ANREALWSSG YDTSSDLYQF IATINNNVRQ    360
KSGKKVYMDL DVQDNVYAFM HGDALVVLNN YGSGASNQVS VNVGAQVAES TSFTDAISGT    420
SITVSSGSVT FTLDNGNPAI FVPAGATSPG GSSGSVEVTF DVYATTVYGQ NIYITGDVSE    480
LGNWTPANGV ALSSANYPTW SATIALPADT TIQYKYVNID GSTVIWEDAI SNREITTPAS    540
GTYTEKDTWD ES                                                       552

SEQ ID NO: 133          moltype = AA  length = 587
FEATURE                 Location/Qualifiers
source                  1..587
                        mol_type = protein
                        organism = Penicillium aethiopicum
SEQUENCE: 133
ARTADWKPRS IYQTMTDRFA RTDGSTTSPC NTKAGLYCGG TWRGTIDHLD YIQGMGFDAV    60
MISPIIENIE GRVDYGEAYH GYWPLNLDNL NSHFGTHQDL LDLSDALHSR GMYFMMDTVI    120
NNMAYITNGS DPATDIDYSV FTPFNNADYF HPYCTMNWSV PAIAQRCNTG DDTVALPDLF    180
TEHEDVQQLL IKWANKAIKT YSIDGLRIDA AKHVNPDFLR KFSDGVDIFM TGEVLEGSVS    240
IMEDYQSNYI NSLPNYPIYF EILSAFTNGN TSQLAIAVEN MRVAIPDVNA MASFSENHDK    300
PRIASYNDDM SIAKNVLVFT MLFDGIPMIY QGQEQHLKGD GVPHNREAIW LSKYDTEAEL    360
YKLIAKLNRI RNHAGYLGSD YFEDATHPIY QGSSELAFTK GVQGRQVVMV LSNQPSTSGR    420
YALDLAVSYN AGTELMDVLN CNNYTVDNQG VLRVDMDKGE PRVFFPRKYM EGSGLCGYSG    480
ATSPGGSSGS VEVTFDVYAT TVYGQNIYIT GDVSELGNWT PANGVALSSA NYPTWSATIA    540
LPADTTIQYK YVNIDGSTVI WEDAISNREI TTPASGTYTE KDTWDES                 587

SEQ ID NO: 134          moltype = AA  length = 597
FEATURE                 Location/Qualifiers
source                  1..597
                        mol_type = protein
                        organism = Subulispora sp.
SEQUENCE: 134
LTPAEWGSQS IYQVLTDRFA LTDGSTTASC DLNTYCGGTW LGIQNHLDYI QGMGFTAIWI    60
SPIVTNIAGD SVDGDSYHGY WAQDITTVNS AFGTEQDLIN LSAALHERGM YLMVDVVNNH    120
MGYLGCGTCV DYSEYTPFNE ESYYHPYCPT DYSNLTSIQV CWEGDNIVSL PDLRTEDSDV    180
RSMWYDWITP LVAKYSIDGL RMDSAEHVEK SFWPGWVSAS GVYNVGEVDE GDPTIFPDWL    240
NYIDGTLNYP AYYWITQAFQ STSGSISNLV TGVNQLKASM KTSTFGSFLE NHDQPRFPSL    300
TSDTDLAKNA IAFAMLADGV PIVYYGQEQG YSGGGVPNDR EPLWTSGYST TSAGYTFIKT    360
INAVRHLAVT QDTAYVAYQA YPIYSDSRVI AMKKSSVLAV FSNIGSSGSG YSITLPAGAF    420
AASQALTDAV SCQTYTADAS GGLTFTFGQA PSVFYATASL AGSGLCGTTG TGGSTGTTTA    480
SETGGSSPTS TACASVPVTF NEKVTTVVGE TIKISGSVAA LGDWATGSAV ALSAASYTSS    540
NPQWDVTISF APGTVIEYKY INVASSGAVT WEADPNHTYT VPASCATAAV VSDTWQT      597

SEQ ID NO: 135          moltype = AA  length = 601
FEATURE                 Location/Qualifiers
source                  1..601
                        mol_type = protein
                        organism = Trichoderma paraviridescens
SEQUENCE: 135
LTAAQWRSQS IYQVLTDRFS QTNGATNSAC NAGNQVYCGG TWQGIIKNLD YIKSMGFTAI    60
WISPVVENLA GNSADGEAYH GYWAQDIYQV TNTNFGSAADL RALSEALHNA GMYLMVDIVT    120
NHMGYLGCGT CVQYNTFNPF NSQSYYHPFC LINFNSSNMT QIQNCWEGDN TVSLPDLATE    180
NANVLSMWQT WITQLVANYT IDGLRMDSCF ELNYGYFEPF QSSANVYIVG EVDNGDPAIV    240
CPYQKNYGLN TLNYPAYYWI TQAFQSTSGS ISNLVNGLNT MKSECSDTTL LGSFMENHDN    300
PRFPSLTSDI SLAKNAIAFT MLADGIPIIY EGQEQHLNGG GVPNREAIW LSGYSTSAVL     360
YTHIKALNQI RSQAIKQNSA YVTTQAAVTY SDSSTIVTRK GSTGSQIVGV FSNKGANGNS    420
YTLTLPSADT GFTSNEQVVE ILSCTAYTTD SSGNLAVAMA GGLPRVFYAR SSLSGSGICP    480
NLGSGGGTPT STPPTSCTAI PVTFDEKVTT TFGQTIKIAG DISALGNWNT ANAVTLSAAN    540
YTSSNPLWAI TLNLAPGQVV EYKYINVAQN GGVTWEADPN HTYTVPSACT AQPTVANTWQ   600
G                                                                  601

SEQ ID NO: 136          moltype = AA  length = 598
FEATURE                 Location/Qualifiers
source                  1..598
```

```
                         mol_type = protein
                         organism = Byssoascus striatosporus
SEQUENCE: 136
LSADDWRAQS IYQLLTDRFA LTNGSTTAPC DTEEQIYCGG SWQGIIDKLD YIQGMGFTAI   60
WISPVVENLS GDSADGEAYH GYWAQNVYEV NPNFGATSDL VALSQVVHDK GMYLMLDVVT  120
NHMGYLGCGT CVDYSVFNPF NEESYYHPFC LIDYDNTTSI EVCWEGDNIV SLPDLRTEDS  180
DVLSTWESWV TELVSNYTVD GIRLDSTEEL DQAFLPPFES AAGVYIVGEV DNGDPAVVCP  240
YQEYVSGVLN YPAYYWITQA FESTSGSIGN LVNGINTMKS DCSDTSLLGS FLENHDQPRF  300
ASLTSDISLA KNAIAFSMLQ DGIPIVYAGE EQHYSGGAVP NDREALWLSG YPTSSTLYTW  360
ITSLNQIRSH AIATNSSYLT YNAYPVYSDD STIVMRKGFA DNQIVSVYTN QGADATAYTL  420
DLPSTDTGFT ASQSLVEIGG CTTTATDDSG NLAVAMASGL PRIYYPAAGL SGSGVCGQLG  480
SGGGTPTSTP PTSCTAIPVT FDEKVTTTFG QTIKIAGDIS ALGNWNTANA VTLSAANYTS  540
SNPLWAITLN LAPGQVVEYK YINVAQNGGV TWEADPNHTY TVPSACTAQP TVANTWQG    598

SEQ ID NO: 137          moltype = AA  length = 615
FEATURE                 Location/Qualifiers
source                  1..615
                        mol_type = protein
                        organism = Aspergillus brasiliensis
SEQUENCE: 137
LSAAEWRTQS IYFLLTDRFG RTDNSTTATC NTGDQIYCGG SWQGIINHLD YIQGMGFTAI   60
WISPITEQLP QDTSDGEAYH GYWQQKIYDV NSNFGTADDL KSLSDALHAR GMYLMIDVVP  120
NHMGYAGSGN DVDYSVFDPF DSSSYFHPYC LITDWDNLTM VQDCWEGDTI VSLPDLNTTE  180
TVVRTIWYDW VADLVSNYSV DGLRIDSVLE VEPDFFPGYQ EAAGVYCVGE VDNGNPALDC  240
PYQDYLDGVL NYPIYWQLLY AFESSSGSIS DLYNMIKSVA SDCSDPTLLG NFIENHDNPR  300
FAYYTSDYSQ AKNVLSYIFL SDGIPIVYAG EEQHYSGGDV PYNREATWLS GYDTSAELYT  360
WIATTNAIRK LAIAADSSYI TYANDPIYTD SNTIAMRKGT SGSQVITVLS NKGSSGSSYT  420
LTLSGSGYTS GTKLIEAYTC TSVTVDSNGD IPVPMASGLP RVLLPASVVD DSSLCGGSGS  480
STSTTTSTAT ATTTSKTSTT SSSSSSSSCT ASATAIPITF EELVTTTYGE EIYLSGSISQ  540
LGDWDTSDAV KLSADDYTSS NPEWSVTVTL PVGTTFEYKF IKVESGGSVT WESDPNREYT  600
VPECGSGETV VDTWR                                                  615

SEQ ID NO: 138          moltype = AA  length = 604
FEATURE                 Location/Qualifiers
source                  1..604
                        mol_type = protein
                        organism = Penicillium subspinulosum
SEQUENCE: 138
ALSAEWRTQS IYFLLTDRFG RTDNSTTATC DTGDQIYCGG SWQGVINHLD YIQGMGFTAI   60
WISPITEQLS GDTSDGEAYH GYWQQKIYNV NSNFGTADDL VALSDALHAR DMYLMLDVVP  120
NHMGYDGDGD DVDYSVFDPF DSSSYFHPYC LITDYDDIEM VQDCWEGDTI VSLPDLNTTE  180
TVVQDIWYAW VADLVANYSV DGLRIDSVLE VQPAFFPAYQ SAAGVYCVGE VDNGDPTLDC  240
PYQDYLDGIL NYPIYYQLLY AFESSSGSIS DLYDMINSVA SDCSDPTLLG NFIENHDNPR  300
FAYYTSDYSQ AKNVASFIFL SDGIPIVYAG QEQHYSGGDV PYDREATWLS GYSTTAELYT  360
WIATTNSIRK LAISLDDDYI TYVNDPFYTD ENTIAMRKGT SGLQVITVLS NLGADGSAYT  420
LTLSGSGYDS GTDLIEVYTC TSVTVDSSGD IAVPMESGLP RVFLPESSIK DSDLCSGTTT  480
TTTSTAATAT ATSTSTCTAA TEVSIIFEEL VTTTYGEEIY LSGSISELGS WDTSDALELS  540
AANYTSSNPE WYLEVTLPVG TSFEYKFIMI ESDGTVVWES DPNRSYTVPS ACSGAVETVV  600
DTWR                                                              604

SEQ ID NO: 139          moltype = AA  length = 606
FEATURE                 Location/Qualifiers
source                  1..606
                        mol_type = protein
                        organism = Penicillium antarcticum
SEQUENCE: 139
LTPAEWRSQS IYFMLTDRFG RSDNSTTAAC NVSDRTYCGG TWQGIINHLD YIQGMGFTAI   60
WITPVTEQLP QDTGDGEAYH GYWQQNIYEV DSNLGTAADL LALSEALHAR GMYLMVDVVA  120
NHMGYAGAGS SVEYSVFHPF SSSSYFHSYC LISNYDDQSN VEDCWLGDTI VSLPDVDTTQ  180
TAVQTLWYDW IGDLVSNYSI DGLRIDTVKH VQKSFWPGYN DAAGVYCVGE IFDGDPAYTC  240
DYQNYMDGVL NYPIYYQLLY AFQSSSGSIS DLYDMINSVK SDCADPTLLG NFIENHDNPR  300
FASYTSDYSQ AKNVISFLFL SDGIPIIYSG QEQHYSGGAD PANREATWLS GYSTTAELYK  360
YIATTNRIRK AAVSADSSYI TTKNVPFYQD SHTLAMKKGS SASPVITVLS NYGSSGSSYT  420
LSLSGSGYSS GTNLMEMYTC TSVTVDSSGN IAVPMASGLP RVLMLASSAS SICASSTTTS  480
TATVATQTTT LTTTGTSCTQ ATVLPVLFKE LVTTTYGQNV YISGSISQLG SWDTSSAIAL  540
SASSYNSSNP LWQVAITLPV GTSFQYKFLE KTTGSTTIQW ESDPNRSYTV PTGCVGTTAT  600
AIATWR                                                            606

SEQ ID NO: 140          moltype = AA  length = 609
FEATURE                 Location/Qualifiers
source                  1..609
                        mol_type = protein
                        organism = Penicillium coprophilum
SEQUENCE: 140
LTPAEWRSQS IYFLLTDRFG RTDNSVTANC NVNDRVYCGG TWQGIINQLD YIQGMGFTAI   60
WITPVTKQLS QNTGDGTSYH GYWQQDIYNV NPNHGTSDDL LALSKALHAR GMYLMVDVVA  120
NHMGYAGAGN NVDYSVFTPF NSASYFHSYC LISNYNDQSN VENCWLGDTT VSLPDLDTTQ  180
SSVQTLWNNW ISDLVSKYSI DGLRVDTVKH VQKSFWPAFN RAAGVYSVGE VFDGSPSYTC  240
DYQKYMDGVL NYPMYYPLLR AFQSTSGSIS DLYNMIGTLS STCADSTLLG NFIENHDNPR  300
```

```
FPSYTSDYSQ AKNVLSFLFL SDGIPIVYSG QEQHYSGGSD PANREALWLS KYSTTAELYK    360
YIATTNKIRK AAVAADSSYI TSKNVAFYQD SHTLAMKKGS GSSPVITVLS NAGSSGSSYT    420
LYLSGSGYSS GTQLMELYTC TSVTVDSSNK IAVPMASGLP RVFVLASSVS NSGLCGSSTP    480
TTTATTATTA TQTTTATTTA GGCTQATALP VLFKELVTTS YGQDIYISGS ISQLGTWDTS    540
KAVALSADSY TSSNPLWQAT ITLPVGTTFQ YKFIKKANGA ITWESDPNRS YTVPTGCSGS    600
TATVTASWK                                                            609

SEQ ID NO: 141         moltype = AA  length = 602
FEATURE                Location/Qualifiers
source                 1..602
                       mol_type = protein
                       organism = Penicillium olsonii
SEQUENCE: 141
LTPAEWRSQS IYFLLTDRFG RDDNSTTATC NTGDRTYCGG TWQGIINQLD YIQGMGFTAI     60
WITPVTEQLS ANTGYGTAYH GYWQQDIYEV NPNHGSSADL KALSAALHAR GMYLMVDVVA    120
NHMGYNGIGS SVDYSVFNPF SSSSYFHSYC LISNYNDQSN VENCWLGDTT VSLPDLDTTQ    180
TAVQTIWNEW ITDLVSNYSI DGLRIDTVKH VQKSFWPGFN DAAGVYSVGE IFDGNPSYTC    240
DYQNYLDGVL NYPIYYPLLY AFQSTSGSIS DLYNMINTVA SDCADSTLLG NFIENHDNPR    300
FPSYTGDYSQ AKNVISYLFL SDGIPIIYSG QEQHYSGASD PANREALWLS GYSTTAELYK    360
WIATTNKIRK LAVSADSSYI TSKNSPFYQD SHTLGMKKGS VITILSNNGA SGSSYTLSLS    420
GSGYSSGTKL MELYTCTSIT VDSSGNIPVP MVSGLPRALI PASSIGSNGL CGSTTSPTTT    480
AATQTTTATT TGTCTQATAL PVLFKELVTT SYGQNVYISG SISQLGNWDA SSAIALSASS    540
YTSSNPLWQV TITLPVGTKF EYKFIEKSSG SATATWESDP NRSYTVPTGC AGTTATVTAT    600
WR                                                                   602

SEQ ID NO: 142         moltype = AA  length = 621
FEATURE                Location/Qualifiers
source                 1..621
                       mol_type = protein
                       organism = Penicillium vasconiae
SEQUENCE: 142
LTAAEWRTQS IYFLLTDRFG RTDNSTTATC SVSDRIYCGG SWQGIINHLD YIQGMGFTAI     60
WITPVTEQLS QDTGDGEAYH GYWQQEIYNV NTNYGTAADL LALSKALHSR GMYLMVDVVA    120
NHMGYDGAGN TVDYSVFNPF DSSSYFHSYC EISDYSNQTN VEDCWLGDTT VSLPDLDTTL    180
SSVQTIWYNW VTELVSNYSI DGLRIDTVKH VQKSFWPGYN SAAGVYCVGE VFDGDPAYTC    240
PYQSYLDGVL NYPIYYQLLY AFESTSGSIS SLYNMINSVA SDCSDPTLLG NFIENHDNPR    300
FASYTSDYSQ AKNVISFIFF SDGIPIVYAG QEQHYSGGSD PANREATWLS GYDTTATLYK    360
YITSTNKIRS LAISKDTAYI TSKNNAFYTD SNTIAMKKGS SGSQVITVLS NRGSSGSSYT    420
LTLSGSGYSS GTQLMEMYTC TAVTVDSSGN IAVPMASGLP RIYMLASSAC SICSSSCSTT    480
TTTSTTSTST TTASTLKTTT STTSATSTTS TSCTQATALP VLFKEIVTTS YGQNIYISGS    540
ISQLGSWDTS NAVALSADQY TSSNNLWYVV VTIPVGTSFE YKFIEETSGS STITWESDPN    600
RSYTVPTGCA GSTATVTATW R                                              621

SEQ ID NO: 143         moltype = AA  length = 615
FEATURE                Location/Qualifiers
source                 1..615
                       mol_type = protein
                       organism = Penicillium sp.
SEQUENCE: 143
LTAAEWRSQS IYFLLTDRFG RTDNSTTATC NVSDRIYCGG SWQGIINHLD YIQGMGFTAI     60
WITPVTEQLS QDTGDGEAYH GYWQQEIYNV NTNYGTAADL LALSKALHSR GMYLMVDVVA    120
NHMGYDGAGN TVDYSVFNPF DSSSYFHSYC EITDYSNQTN VEDCWLGDTT VSLPDLNTTL    180
SSVQTIWYDW VAALVSNYSI DGLRIDTVKH VQESFWPEYN SAAGVYCVGE VFDGDPAYTC    240
PYQNYLDGVL NYPIYYQLLY AFESTSGSIS DLYNMINSVA SDCSDPTLLG NFIENHDNPR    300
FASYTSDYSQ AKNVLSFIFF SDGIPIVYAG QEQHYSGGSD PANREATWLS GYDTSAELYT    360
WITSTNKIRS LAVSKDTAYI TSKNDAFYTD SNTIAMKKGS GGSQVVTVLS NRGSSGSSYT    420
LTLSGSGYSS GTKLMEMYTC TAVTVDSSGN IAVPMASGLP RVYMLASSAC SICSSACSTT    480
TTSSTTSTAT TTSTTLKTTT TTTSTSCTQA TALPVLFKEI VTTSYGQNIY ISGSISELGD    540
WDTSNAVALS ADQYTSSNNL WYVVVTIPVG TSFEYKFIEE TSGSSSITWE SDPNRSYTVP    600
TGCAGSTATV TATWR                                                     615

SEQ ID NO: 144         moltype = AA  length = 606
FEATURE                Location/Qualifiers
source                 1..606
                       mol_type = protein
                       organism = Heterocephalum aurantiacum
SEQUENCE: 144
LTAAEWRQQS IYFLLTDRFA RTDGSTTAAC NLSQRAYCGG SWQGIINHLD YIQGMGFTAI     60
WITPVTKQIE ASTSDGTAYH GYWQQDIYNI NSHYGTADDL RALSSALHSR GMYLMIDVVA    120
NHMGYPGAGT SVDYSIFTPF GSSSYFHSYC QITDYDNQSN VENCWLGDNV VSLPDLNTQN    180
SNVRNLWYDW VEELVANYSV DGLRVDTVKH VEKDFWPSYN AAAGVYCVGE VFHGDPAYTC    240
PYQNYMDGVL NYPIYYQLLY AFQSSSGSIT DLYNMINSVA SDCKDPTTLG NFIENHDNPR    300
FPSYTSDMSQ AKSVIAFLFL SDGIPIIYAG QEQHYSGGAD PNNREAIWLS GYSTSSTLYQ    360
FISSTNSIRK LAISKDSSYL TSRNNPFYTD SNTIAMRKGS SGSQVITVLS NKGSGSNSYT    420
LTLTNHGYSS GAQLTELYTC SSIQVASSGG LAVPMASGLP RVLVPSSWIQ GSGLCGGGST    480
TTTTTATTTT TTTTSTSSCA AATSLAVVFN ELVTTYYGEN IFIAGSISQL GSWDTGKSVA    540
LSASQYTSSN PLWTATVSLP VGTSFQYKFI KKEPDGQVVW ESDPNRSYTV PAGCAGTTQT    600
VNTSWR                                                               606
```

```
SEQ ID NO: 145           moltype = AA  length = 602
FEATURE                  Location/Qualifiers
source                   1..602
                         mol_type = protein
                         organism = Neosartorya massa
SEQUENCE: 145
LTPAEWRSQS IYFLLTDRFG REDNSTTAAC DVTQRLYCGG SWQGIINHLD YIQGMGFTAI   60
WITPVTEQFY EDTGDTSYH  GYWQQNIYEV NYNYGTAQDL KNLADALHAR GMYLMVDVVA  120
NHMGYDGAGN TVDYSVFTPF DSSSYFHPYC LISDYSNQTN VEDCWLGDTT VSLPDLDTTD  180
TTVRTIWYDW VKGLVANYSI DGLRIDTVKH VEKDFWPGYN DAAGVYCVGE VFSGDPTYTC  240
PYQNYLDGVL NYPIYYQLLY AFESTSGSIS NLYDMINSVA SDCADPTLLG NFIENHDNPR  300
FASYTSDYSQ AKNVISFIFF SDGIPIVYAG QEQHYSGGAD PANREAVWLS GYSTSATLYS  360
WIASTNRIRK LAISKDAAYI TSKNNPFYYD SNTLAMRKGS IAGAQVITVL SNKGSSGSSY  420
TLSLSGTGYS AGASLVEMYT CTTLTVDSSG NLPVPMASGL PRVLVPSSWV SGSGLCGSGS  480
TTTTTTTATA TTTACTSATA LPIVFEEVVT TTYGENVYLT GSISQLGNWD TSSAIALSAS  540
KYTSSNPEWY VTVTLPVGTS FQYKFFKKES DGSIVWESDP NRSYTVPTGC AGTTVTVSDT  600
WR                                                                602

SEQ ID NO: 146           moltype = AA  length = 588
FEATURE                  Location/Qualifiers
source                   1..588
                         mol_type = protein
                         organism = Penicillium janthinellum
SEQUENCE: 146
ATPAQWRSQS IYFMLTDRFA RTDGSTTAPC DTSQRAYCGG TWQGIIDKLD YIQGMGFTAI   60
WITPVTGQLD GDTGDGTAYH GYWQQDIYSL NSNYGTASDL KALASALHAR GMYLMVDVVA  120
NHMGYNGAGN TVDYSVFDAF NSNQYFHSYC EVTNYSNQTN VEDCWLGDTT VSLPDLNTEL  180
SSVQSIWYNW VGSLVSNYSI DGLRVDTVKH VQKDFWPGYN KAAGVYCVGE VFDGDASYTC  240
PYQEVMDGVL NYPMYYPLLR AFQSTSGSMS DLYNMINTVK STCSDSTLLG TFVENHDNPR  300
FASYTNDMSL AKNVAAFTIM ADGIPIIYAG QEQHYSGGSD PANREAVWLG GYNTDSALYK  360
LIAKVNAIRS YAISQSASYV TYKNYPIYQD ASTLAMRKGS SGTQTITVLS NRGASGSQYT  420
LSLGNTGYST GTTLTEIITC AKITVDSSGN VPVPMASGEP RILYPSSSIK GSAICASSGR  480
GATSPGGSSV SVEVTFDVYA TTVYGQNIYI TGDVSELGNW TPANGVALSS ANYPTWSATI  540
ALPADTTIQY KYVNIDGSTV IWEDAISNRE ITTPASGTYT EKDTWDES              588

SEQ ID NO: 147           moltype = AA  length = 589
FEATURE                  Location/Qualifiers
source                   1..589
                         mol_type = protein
                         organism = Aspergillus brasiliensis
SEQUENCE: 147
ATPAEWRSQS IYFLLTDRFA RTDNSTTASC DLSARQYCGG SWQGIINQLD YIQGMGFTAI   60
WTPVTAQIP  QDTGYGQAYH GYWQQDAYAL NSHYGTADDL KALATALHSR GMYLMVDVVA  120
NHMGHNGTGS SVEYSVYNPF NAKKYFHNLC WISNYDNQTN VEDCWLGDNT VALPDLDTTR  180
TDVKNMWYDW VKSLVSNYSV DGLRVDTVKN VQKNFWPGYN NASGVYCIGE VFDGDASYTC  240
PYQDDLDGVL NYPMYYPLLR AFKSTTGSIS DLYNMINTVK STCKDSTLLG TFIENHDNPR  300
FANYTSDMSL AKNVATFTIL ADGIPIIYAG QEQHYSGGND PYNREATWLS GYKTTSELYT  360
HIAASNKIRT HAIKQDSGYL TYKNYPIYQD TSTLAMRKGY NGTQTITVLS NLGASGSSYT  420
LSLPGTGYTA GQKITEIYTC TNLTVNSNGS VPVPMKSGLP RILYPTDKLV NGSSFCSSSG  480
RGATSPGGSS GSVEVTFDVY ATTVYGQNIY ITGDVSELGN WTPANGVALS SANYPTWSAT  540
IALPADTTIQ YKYVNIDGST VIWEDAISNR EITTPASGTY TEKDTWDES              589

SEQ ID NO: 148           moltype = AA  length = 588
FEATURE                  Location/Qualifiers
source                   1..588
                         mol_type = protein
                         organism = Aspergillus westerdijkiae
SEQUENCE: 148
ATPAQWRSQS IYFLLTDRFA RDDGSTTATC NTEDRKYCGG TWQGIIDQLD YIQGMGFTAI   60
WITPVTAQLT EDTKYGDAYH GYWQQDIYSL NENYGTADDL KALADALHER DMYLMVDVVA  120
NHMGYAGAGD SVDYSVFNPF NSQDYFHSFC LIQDYNDQTQ SEDCWLGDNS VSLPDLDTTK  180
SEVQDIWYDW VGGLVSNYSI DGLRIDTVKH VQKEFWPGYN DAAGVYCIGE ILDGDASYTC  240
PYQEVLDGVL NYPIYYPLLN AFKSTSGSIS DLYNMINTVK SDCPDSTLMG TFIENHDNPR  300
FASYTDDIAL AKNVAAFTIL ADGIPIYAG  QEQHYAGGED PANREATWLG KYNTDSELYK  360
LIAASNAIRN HAISTDKEYV NYKNYPIYKD DSTIAMRKGF DGAQIITVLS NQGSSGSSYT  420
LSLGDTGFSS GDKLTEIYTC TAVTVDSDGK VPVPMDGGAP RALFPTEKLS GSSLCSGSGR  480
GATSPGGSSV SVEVTFDVYA TTVYGQNIYI TGDVSELGNW TPANGVALSS ANYPTWSATI  540
ALPADTTIQY KYVNIDGSTV IWEDAISNRE ITTPASGTYT EKDTWDES              588

SEQ ID NO: 149           moltype = AA  length = 476
FEATURE                  Location/Qualifiers
source                   1..476
                         mol_type = protein
                         organism = Hamigera avellanea
SEQUENCE: 149
ATPADWRSRS IYFILTDRFA RTDGSTTAEC DTSARAYCGG TWRGIINKLD YIQNMGFTAI   60
WITPVTAQLP GSTGHGSAYH GYWQQDIYSL EPNYGTADDL RALASALHER NMYLMVDVVA  120
NHMGWAGSGD SVDYSVFNPF DSADYFHPYC LISNYEDQTE VENCWLGDTN VALVDLDTTR  180
SDVQNIWYEW VDSLVGNYSI DGLRIDTVRH VQKDFWPGFN DAAGVYSVGE VFSGDTAYTC  240
```

```
PYQEVLDGVL NYPIYYPLLR AFQSTSGSIN DLYNMINTVK SDCADSTLMG TFLENHDNPR    300
FASYTSDVAL AKNAIAFTIL SDGIPIIYAG QEQHYSGGND PANREAVWLS GYSTDSELYS    360
FVAVTNQIRN YAISQDQGYV TWKNVPIYQD TSTLAMRKGT DGSQVITVLS NLGASGSSYT    420
LTLGGSGYSS GQQLTEIFSC ATVTVDSSGN IPVPMGSGQP KVFYPTAGLG GSGICQ       476

SEQ ID NO: 150          moltype = AA   length = 586
FEATURE                 Location/Qualifiers
source                  1..586
                        mol_type = protein
                        organism = Hamigera avellanea
SEQUENCE: 150
ATPADWRSRS IYFILTDRFA RTDGSTTAEC DTSARAYCGG TWRGIINKLD YIQNMGFTAI    60
WITPVTAQLP GSTGHGSAYH GYWQQDIYSL EPNYGTADDL RALASALHER NMYLMVDVVA    120
NHMGWAGSGD SVDYSVFNPF DSADYFHPYC LISNYEDQTE VENCWLGDTN VALVDLTTR     180
SDVQNIWYEW VDSLVGNYSI DGLRIDTVRH VQKDFWPGFN DAAGVYSVGE VFSGDTAYTC    240
PYQEVLDGVL NYPIYYPLLR AFQSTSGSIN DLYNMINTVK SDCADSTLMG TFLENHDNPR    300
FASYTSDVAL AKNAIAFTIL SDGIPIIYAG QEQHYSGGND PANREAVWLS GYSTDSELYS    360
FVAVTNQIRN YAISQDQGYV TWKNVPIYQD TSTLAMRKGT DGSQVITVLS NLGASGSSYT    420
LTLGGSGYSS GQQLTEIFSC ATVTVDSSGN IPVPMGSGQP KVFYPTAGLG GSGICQSSGA    480
TSPGGSSGSV EVTFDVYATT VYGQNIYITG DVSELGNWTP ANGVALSSAN YPTWSATIAL    540
PADTTIQYKY VNIDGSTVIW EDAISNREIT TPASGTYTEK DTWDES                   586

SEQ ID NO: 151          moltype = AA   length = 576
FEATURE                 Location/Qualifiers
source                  1..576
                        mol_type = protein
                        organism = Meripilus giganteus
SEQUENCE: 151
RPTVFDAGAD AHSLHARAPS GSKDVIIQMF EWNWDSVAAE CTNFIGPAGY GFVQVSPPQE    60
TIQGAQWWTD YQPVSYTLTG KRGDRSQFAN MITTCHAAGV GVIVDTIWNH MAGVDSGTGT    120
AGSSFTHYNY PGIYQNQDFH HCGLEPGDDI VNYDNAVEVQ TCELVNLADL ATDTEYVRGR    180
LAQYGNDLLS LGADGLRLDA SKHIPVGDIA NILSRLSRSV YITQEVIFGA GEPITPNQYT    240
GNGDVQEFRY TSALKDAFLS SGISNLQDFE NRGWVPGSGA NVFVVNHDTE RNGASLNNNS    300
PSNTYVTATI FSLAHPYGTP TILSSYDGFT NTDAGAPNNN VGTCSTSGGA NGWLCQHRWT    360
AIAGMVGFRN NVGSAALNNW QAPQSQQIAF GRGALGFVAI NNADSAWSTT FTTSLPDGSY    420
CDVISGKASG SSCTGSSFTV SGGKLTATVP ARSAIAVHTG QKGSGGATPT SAPSTTPTSG    480
TVSMTFAEQA TTTFGENIFL VGSISQLGNW NPASAIALSS AAYPTWSVSV NIPAGTTFQY    540
KFIRKETDGS VVWESDPNRQ ATAPASGTTT LTSSWR                              576

SEQ ID NO: 152          moltype = AA   length = 575
FEATURE                 Location/Qualifiers
source                  1..575
                        mol_type = protein
                        organism = Cerrena unicolor
SEQUENCE: 152
RPLNASNALD ARAPSGAKSV IIQMFEWTWD SVAAECTNFI GPAGYGFVQV SPPQETIQGD    60
QWWTDYQPVS YILTSKRGTR DQFAAMIDTC HDAGVKIVTD TIWNHMAGVE SGTGVAGSSF    120
THYNYPGIYQ NQDFHHCGLE SGDDIVNYDN AQEVQTCELV NLADLATETD YVRGRLAEYG    180
NDLLSLGADG LRLDAAKHIA VGDLANIIGR LNSTPYITQE VIFGSGEPIT PNQYTGNGDV    240
QKFRYTSALK DAFLNGDISS LQDFENRGWV AGSGANVFVT NHDTERNGNS LNNNSPNNAY    300
TLAMIFSLAH PYGTPSILSS YSGFTDTDAG APNGGAGTCS SGGGSNGWLC QHRWTAVAGM    360
VGFRNTVGSA ALNNWVSPQS SQIAFGRGAL GFVAINNGDS TWSTTFTTSL PDGTYCDVIT    420
GTSSSGSCTG SSFTVSGGTF TANVAARDAV AIHTGATGTG SGSGNTSTGS GGTTSDTVSV    480
SFAETATTTF GENIFLVGSI SQLGAWDPAS AIALSSASYP TWTVTVTLPA GTTFEYKFIR    540
KETDGSVVWE SDPNRQATTP SSSDAATTTL STSWR                               575

SEQ ID NO: 153          moltype = AA   length = 562
FEATURE                 Location/Qualifiers
source                  1..562
                        mol_type = protein
                        organism = Physalacria cryptomeriae
SEQUENCE: 153
APFLELQVRA PSSTKQVIIQ MFEWTWDSVA AECTDFIGPA GYGYVQVSPP AEHITGDQWW    60
TDYQPVSYIL TSKRGNRSQF ANMVTTCHTA GVLVIADALF NHMAGIESGT GTAGSSFTHY    120
DYPGIYQTQD FHHCGLTSGD DISDYSSQAQ VQTCELVNLA DLATDTEYVR AKLASYANDL    180
ISLGVNGLRL DAAKHIATDD IKNILSRLSS TVYITQEVIF GSGEPVTPSM YTQNGDVQEF    240
RYTSTLQSAF SGGDISQLQN LDSKGWIAGT SANVFVANHD TERGGSSLNY KSSSNTYVTA    300
TIFSLAHPYG TPTILSSYEF SDTDAGSPNG GAGTCSTGAG ANGWLCQHRW VAFSGMVGFH    360
NNVGTASLTN WVSPQSNQIA FERSGKGFVA INNADSAWTA TFTTSLAAGS YCDVITGTSN    420
GSACSGTSYT VSGGSFSATV AARSAVAIHT GATGSGSGGG GGSTGSVAIT FQETATTTLG    480
ENIFLVGSIS QLRTWAPASA IALSSASYPT WSVTVSIPAG TTFEYKFIRK ESDGSVVWES    540
DPNRSATASS SASTQTILTS WR                                             562

SEQ ID NO: 154          moltype = AA   length = 578
FEATURE                 Location/Qualifiers
source                  1..578
                        mol_type = protein
                        organism = Lenzites betulinus
SEQUENCE: 154
```

```
RPASTVFHGA ETRSLDARAP SGSKDVIIQM FEWTWDSVAA ECTNFIGPAG YGFVQGSPPQ    60
EHIQGAQWWT DYQPVSYTLT SKRGDRTSFA NMIQTCHTAG VGVIVDTLFN HMAGVDSGTG   120
VAGSSFTHYN YPGIYQNQDF HHCGLEPGDD IVNYDNAVEV QTCELDNLAD LATETEYVRG   180
RLAQYGNDLL SLGADGMRLD AAKHIAVGDI ANILSRLNRT VYITQEVIFG AGEPITPNQY   240
TGNGDVQEFR YTSALQDAFL NSGIANLQVL ENRGWVPGSG ANVFVTNHDT ERNGASLNNN   300
SPSNTYVTAM IFSLAHPFGT PSILSSYSGF TDTDAGAPNG GVGTCSGSGG TNGWLCQHRW   360
TAVAGMVGFR NQVGSAALGN WQSPQSQQIA FGRGALGFVA INNADSAWSA TFTTSLPDGS   420
YCDVISGQTS GSTCTGSSFT VSGGGSLSATV PARSAIAVHT GQKGTGSGSG TGTGGGGSTG   480
SGNVAVNFAE TATTTFGENI FVVGSISQLG TWNTANAIAL SSPSYPTWTV SISIPAGTTF   540
QYKFIRKETD GSVVWESDPN RQATAPASGS TTLSTSWR                           578

SEQ ID NO: 155          moltype = AA  length = 571
FEATURE                 Location/Qualifiers
source                  1..571
                        mol_type = protein
                        organism = Trametes ljubarskyi
SEQUENCE: 155
RPATFDAADA RSVQPRAPSG SKDVIIQMFE WTWDSVAAEC TNFIGPAGYG FVQGNPPQEH    60
IQGDQWWTDY QPVSYILTSK RGDRTAFANM ISTCHAAGVG VIVDTIFNHM SGVDSGTGVA   120
GSSFTHYNYP GIYQNQDFHH CGLEPGDDIV NYDNAVEVQT CELENLADLA TDTEYVRGRL   180
AQYANDLLSL GADGLRLDAA KHIPTGDIAN ILSRLNRSVY ITQEVIYGDG EPITPNQYTG   240
NGDVQEFRYT TALKNAFLGG GISSLQSFDN LGWVPGTGAN VFVTNHDTER NGNSLNNNSP   300
SNTYVTAMIF SLAHPYGTPT ILSSYSGFTN TDAGAPNGGT GTCSGSGGAN GWLCQHRWTA   360
VAGMVGFRNN VGSAALTNWQ SPQSQQIAFG RGALGFVAIN NADSAWSTTF TTSLPDGSYC   420
DVVSGTSSNG GCTGSSFSVS GGSLTATVPA RSAIAIHTGE TGSGSNSGGG SGGSGTVTIN   480
FAETATTTFG ENIFVVGSIP QLGSWNPANA IALSSASYPT WTVSVSVPAG TTFEYKFIRK   540
ETDGSVVWES DPNRSDTAPA SGTQTITTSW R                                  571

SEQ ID NO: 156          moltype = AA  length = 451
FEATURE                 Location/Qualifiers
source                  1..451
                        mol_type = protein
                        organism = Bacillus subtilis
SEQUENCE: 156
GPAAASAETA NKSNELTAPS IKSGTILHAW NWSFNTLKHN MKDIHDAGYT AIQTSPINQV    60
KEGNQGDKSM SNWYWLYQPT SYQIGNRYLG TEQEFKEMCA AAEEYGIKVI VDAVINHTTS   120
DYAAISNEVK SIPNWTHGNT QIKNWSDRWD VTQNSLLGLY DWNTQNTQVQ SYLKRFLERA   180
LNDGADGFRF DAAKHIELPD DGSYGSQFWP NITNTSAEFQ YGEILQDSAS RDAAYANYMD   240
VTASNYGHSI RSALKNRNLG VSNISHYAYD VSADKLVTWV ESHDTYANDD EESTWMSDDD   300
IRLGWAVIAS RSGSTPLFFS RPEGGGNGVR FPGKSQIGDR GSALFEDQSI TAVNRFHNVM   360
AGQPEELSNP NGNNQIFMNQ RGSHGVVLAN AGSSSVSINT PTKLPDGRYD NKAGAGSFQV   420
NDGKLTGTIN ARSVAVLYPD DIEIRCNTFF Q                                  451

SEQ ID NO: 157          moltype = AA  length = 633
FEATURE                 Location/Qualifiers
source                  1..633
                        mol_type = protein
                        organism = Bacillus subtilis
SEQUENCE: 157
GPAAASAETA NKSNELTAPS IKSGTILHAW NWSFNTLKHN MKDIHDAGYT AIQTSPINQV    60
KEGNQGDKSM SNWYWLYQPT SYQIGNRYLG TEQEFKEMCA AAEEYGIKVI VDAVINHTTS   120
DYAAISNEVK SIPNWTHGNT QIKNWSDRWD VTQNSLLGLY DWNTQNTQVQ SYLKRFLDRA   180
LNDGADGFRF DAAKHIELPD DGSYGSQFWP NITNTSAEFQ YGEILQDSAS RDAAYANYMD   240
VTASNYGHSI RSALKNRNLG VSNISHYASD VSADKLVTWV ESHDTYANDD EESTWMSDDD   300
IRLGWAVIAS RSGSTPLFFS RPEGGGNGVR FPGKSQIGDR GSALFEDQAI TAVNRFHNVM   360
AGQPEELSNP NGNNQIFMNQ RGSHGVVLAN AGSSSVSINT ATKLPDGRYD NKAGAGSFQV   420
NDGKLTGTIN ARSVAVLYPD DIAKAPHVPL ENYKTGVTHS FNDQLTITLR ADANTTKAVY   480
QINNGPETAF KDGDQFTIGK GDPFGKTYTI MLKGTNSDGV TRTEKYSFVK RDPASAKTIG   540
YQNPNHWSQV NAYIYKHDGS RVIELTGSWP GKPMTKNADG IYTLTLPADT DTTNAKVIFN   600
NGSAQVPGQN QPGFDYVLNG LYNDSGLSGS LPH                                633

SEQ ID NO: 158          moltype = AA  length = 487
FEATURE                 Location/Qualifiers
source                  1..487
                        mol_type = protein
                        organism = Schwanniomyces occidentalis
SEQUENCE: 158
KPIFLSKRDA GSSAAAAWRS ESIYQLVTDR FARTDGSTSA TCNTGDRVYC GGTFQGIIDK    60
LDYIQGMGFT AIWISPVVEQ IPDDTGYGYA YHGYWMKDIY AINSNFGTAD DLKNLSNELH   120
KRNMKLMVDI VTNHYAWNGA GSSVAYSNYN PFNQQSYFHD YCLITNYDDQ TNVEDCWEGD   180
NTVSLPDLRT EDSDVSSIFN LWVAELVSNY SIDGLRIDSA KHVDESFYPS FQSAAGVYLL   240
GEVYDGDPAY TCPYQNYMSG VTNYPLYYPM LRFFQGTSNS VDELNAMISS LESDCKDITL   300
GNFIENHDQ PRLPSYTSDS ALIKNAIAFN LMSDGIPIIY YGQEQGYSGS SDPNNREALW   360
LSGYSTSNGY YKLISSVNQI RNQAIYKDSK YTTYWSDVLY ASGHVIALQR GADDQRIVSV   420
FNNLGSSGSQ TVTFSTKYSG GEKVVDVLTC QTSYANSDST LTVSISGGAP RIYAPASLIA   480
NSGICNF                                                             487

SEQ ID NO: 159          moltype = AA  length = 583
FEATURE                 Location/Qualifiers
```

```
source                  1..583
                        mol_type = protein
                        organism = Rhizomucor pusillus
SEQUENCE: 159
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFGDA SLYHPKCTID YNDQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                    583

SEQ ID NO: 160          moltype = AA  length = 616
FEATURE                 Location/Qualifiers
source                  1..616
                        mol_type = protein
                        organism = Aspergillus niger
SEQUENCE: 160
AEWRTQSIYF LLTDRFGRTD NSTTATCDTG DQIYCGGSWQ GIINHLDYIQ GMGFTAIWIS    60
PITEQLPQDT ADGEAYHGYW QQKIYDVNSN FGTADDLKSL SDALHARGMY LMVDVVPNHM   120
GYAGNGNDVD YSVFDPFDSS SYFHPYCLIT DWDNLTMVQD CWEGDTIVSL PDLNTTETAV   180
RTIWYDWVAD LVSNYSVDGL RIDSVLEVEP DFFPGYQEAA GVYCVGEVDN GNPALDCPYQ   240
KVLDGVLNYP IYWQLLYAFE SSSGSISNLY NMIKSVASDC SDPTLLGNFI ENHDNPRFAS   300
YTSDYSQAKN VLSYIFLSDG IPIVYAGEEQ HYSGGKVPYN REATWLSGYD TSAELYTWIA   360
TTNAIRKLAI SADSAYITYA NDAFYTDSNT IAMRKGTSGS QVITVLSNKG SSGSSYTLTL   420
SGSGYTSGTK LIEAYTCTSV TVDSSGDIPV PMASGLPRVL LPASVVDSSS LCGGSGRTTT   480
TTTAATSTSK ATTSSSSSSA AATTSSSCTA TSTTLPITFE ELVTTTYGEE VYLSGSISQL   540
GEWDTSDAVK LSADDYTSSN PEWSVTVSLP VGTTFEYKFI KVDEGGSVTW ESDPNREYTV   600
PECGNGSGET VVDTWR                                                  616

SEQ ID NO: 161          moltype = AA  length = 512
FEATURE                 Location/Qualifiers
source                  1..512
                        mol_type = protein
                        organism = Bacillus stearothermophilus
SEQUENCE: 161
APFNGTMMQY FEWYLPDDGT LWTKVANEAN NLSSLGITAL WLPPAYKGTS RSDVGYGVYD    60
LYDLGEFNQK GTVRTKYGTK AQYLQAIQAA HAAGMQVYAD VVFDHKGGAD GTEWVDAVEV   120
NPSDRNQEIS GTYQIQAWTK FDFPGRGNTY SSFKWRWYHF DGVDWDESRK LSRIYKFRGK   180
AWDWEVDTEF GNYDYLMYAD LDMDHPEVVT ELKNWGKWYV NTTNIDGFRL DAVKHIKFSF   240
FPDWLSYVRS QTGKPLFTVG EYWSYDINKL HNYITKTDGT MSLFDAPLHN KFYTASKSGG   300
AFDMRTLMTN TLMKDQPTLA VTFVDNHDTE PGQALQSWVD PWFKPLAYAF ILTRQEGYPC   360
VFYGDYYGIP QYNIPSLKSK IDPLLIARRD YAYGTQHDYL DHSDIIGWTR EGGTEKPGSG   420
LAALITDGPG GSKWMYVGKQ HAGKVFYDLT GNRSDTVTIN SDGWGEFKVN GGSVSVWVPR   480
KTTVSTIARP ITTRPWTGEF VRWTEPRLVA WP                                512

SEQ ID NO: 162          moltype = AA  length = 483
FEATURE                 Location/Qualifiers
source                  1..483
                        mol_type = protein
                        organism = Bacillus halmapalus
SEQUENCE: 162
HHNGTNGTMM QYFEWHLPND GNHWNRLRDD ASNLRNRGIT AIWIPPAWKG TSQNDVGYGA    60
YDLYDLGEFN QKGTVRTKYG TRSQLESAIH ALKNNGVQVY GDVVMNHKGG ADATENVLAV   120
EVNPNNRNQE ISGDYTIEAW TKFDFPGRGN TYSDFKWRWY HFDGVDWDQS RQFQNRIYKF   180
RGKAWDWEVD SENGNYDYLM YADVDMDHPE VVNELRRWGE WYTNTLNLDG FRIDAVKHIK   240
YSFTRDWLTH VRNATGKEMF AVAEFWKNDL GALENYLNKT NWNHSVFDVP LHYNLYNASN   300
SGGNYDMAKL LNGTVVQKHP MHAVTFVDNH DSQPGESLES FVQEWFKPLA YALILTREQG   360
YPSVFYGDYY GIPTHSVPAM KAKIDPILEA RQNFAYGTQH DYFDHHNIIG WTREGNTTHP   420
NSGLATIMSD GPGGEKWMYV GQNKAGVWH  DITGNKPGTV TINADGWANF SVNGGSVSIW   480
VKR                                                                483

SEQ ID NO: 163          moltype = AA  length = 478
FEATURE                 Location/Qualifiers
source                  1..478
                        mol_type = protein
                        organism = Aspergillus oryzae
SEQUENCE: 163
ATPADWRSQS IYFLLTDRFA RTDGSTTATC NTADQKYCGG TWQGIIDKLD YIQGMGFTAI    60
WITPVTAQLP QTTAYGDAYH GYWQQDIYSL NENYGTADDL KALSSSALHER GMYLMVDVVA   120
NHMGYDGAGS SVDYSVFKPF SSQDYFHPFC FIQNYEDQTQ VEDCWLGDNT VSLPDLDTTK   180
DVVKNEWYDW VGSLVSNYSI DGLRIDTVKH VQKDFWPGYN KAAGVYCIGE VLDGDPAYTC   240
PYQNVMDGVL NYPIYYPLLN AFKSTSGSMD DLYNMINTVK SDCPDSTLLG TFVENHDNPR   300
FASYTNDIAL AKNVAAFIIL NDGIPIIYAG QEQHYAGGND PANREATWLS GYPTDSELYK   360
LIASANAIRN YAISKDTGFV TYKNWPIYKD DTTIAMRKGT DGSQIVTILS NKGASGDSYT   420
LSLSGAGYTA GQQLTEVIGC TTVTVGSDGN VPVPMAGGLP RVLYPTEKLA GSKICSSS     478
```

```
SEQ ID NO: 164          moltype = AA  length = 483
FEATURE                 Location/Qualifiers
source                  1..483
                        mol_type = protein
                        organism = Bacillus amyloliquefaciens
SEQUENCE: 164
VNGTLMQYFE WYTPNDGQHW KRLQNDAEHL SDIGITAVWI PPAYKGLSQS DNGYGPYDLY    60
DLGEFQQKGT VRTKYGTKSE LQDAIGSLHS RNVQVYGDVV LNHKAGADAT EDVTAVEVNP   120
ANRNQETSEE YQIKAWTDFR FPGRGNTYSD FKWHWYHFDG ADWDESRKIS RIFKFRGEGK   180
AWDWEVSSEN GNYDYLMYAD VDYDHPDVVA ETKKWGIWYA NELSLDGFRI DAAKHIKFSF   240
LRDWVQAVRQ ATGKEMFTVA EYWQNNAGKL ENYLNKTSFN QSVFDVPLHF NLQAASSQGG   300
GYDMRRLLDG TVVSRHPEKA VTFVENHDTQ PGQSLESTVQ TWFKPLAYAF ILTRESGYPQ   360
VFYGDMYGTK GTSPKEIPSL KDNIEPILKA RKEYAYGPQH DYIDHPDVIG WTREGDSSAA   420
KSGLAALITD GPGGSKRMYA GLKNAGETWY DITGNRSDTV KIGSDGWGEF HVNDGSVSIY   480
VQK                                                                483

SEQ ID NO: 165          moltype = AA  length = 583
FEATURE                 Location/Qualifiers
source                  1..583
                        mol_type = protein
                        organism = Rhizomucor pusillus
SEQUENCE: 165
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFDDA SLYHPKCTID YNNQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                    583

SEQ ID NO: 166          moltype = AA  length = 623
FEATURE                 Location/Qualifiers
source                  1..623
                        mol_type = protein
                        organism = Kionochaeta ivoriensis
SEQUENCE: 166
LSPAGWRQQS IYQVMTDRFA RTDGSTIASC DTSQQAYCGG TWQGLINKLD YIQGMGFTAV    60
WISPMVHQMA GATSDGESYH GYWAQDINTV NSAFGTAADL KALSAALHAR GMYLMLDVVT   120
NHFAYDGCGT CVDYSIFNPF NSESYFHPFC LIDYSNTTSI QVCWEGDNTV SLPDLRTEDS   180
DVRSIWNSWI SSVISTYGVD GLRVDSAQQV ETSFWAGFEA AAGVYMVGEV FNGDPTYVTP   240
FQDYMDGVLN YPAYYWITQA FESTSGSISN LANGMNTMKS LAKNTSLLGS FLENHDNPRF   300
PSLTSDMSLA QNAIAFTMLM DGIPIIYQGQ EQHFSGGGVP SDREAVWLSG YPNDTTLYAW   360
ITKLNAVRSW AIAKDSSYLA YMAYPVYTDT HTIAMRKGKT GYQVISVYTN VGASGSSYSV   420
TLTSADTGFT ASQSVVDLVG CKTYTADSTG SLSLSLTGGI PIILYPAASL TGNTICTSTG   480
GTTTTATPTG SGSVTSTSKT TATASKTSTS TSSTSCTTPT AVAVTFDLTA TTTYGENIYL   540
VGSISQLGDW ETSDGIALSA DKYTSSDPLW YVTVTLPAGE SFEYKFIRIE SDDSVEWESD   600
PNREYTVPQA CGTSTATVTD TWR                                          623

SEQ ID NO: 167          moltype = AA  length = 588
FEATURE                 Location/Qualifiers
source                  1..588
                        mol_type = protein
                        organism = Aspergillus niger
SEQUENCE: 167
LSAAEWRTQS IYFLLTDRFG RTDNSTTATC DTGDQIYCGG SWQGIINHLD YIQGMGFTAI    60
WISPITEQLP QDTADGEAYH GYWQQKIYDV NSNFGTADDL KSLSDALHAR GMYLMVDVVP   120
NHMGYAGNGN DVDYSVFDPF DSSSYFHPYC LITDWDNLTM VQDCWEGDTI VSLPDLNTTE   180
TAVRTIWYDW VADLVSNYSV DGLRIDSVLE VEPDFFPGYQ EAAGVYCVGE VDNGNPALDC   240
PYQKVLDGVL NYPIYWQLLY AFESSSGSIS NLYNMIKSVA DCSDPTLLG NPIENHDNPR   300
FASYTDYSQ AKNVLSYIFL SDGIPIVYAG EEQHYSGGKV PYNREATWLS GYDTSAELYT   360
WIATTNAIRK LAISADSSAYI TYANDAFYTG SNTIAMRKGT SGSQVITVLS NKGSSGSSYT   420
LTLSGSGYTS GTKLIEAYTC TSVTVDSSGD IPVPMASGLP RVLLPASVVD SSSLCGGSGR   480
GATSPGGSSG SVEVTFDVYA TTVYGQNIYI TGDVSELGNW TPANGVALSS ANYPTWSATI   540
ALPADTTIQY KYVNIDGSTV IWEDAISNRE ITTPASGTYT EKDTWDES              588

SEQ ID NO: 168          moltype = AA  length = 588
FEATURE                 Location/Qualifiers
source                  1..588
                        mol_type = protein
                        organism = Aspergillus oryzae
SEQUENCE: 168
ATPADWRSQS IYFLLTDRFA RTDGSTTATC NTADQKYCGG TWQGIIDKLD YIQGMGFTAI    60
WITPVTAQLP QTTAYGDAYH GYWQQDIYSL NENYGTADDL KALSSALHER GMYLMVDVVA   120
NHMGYDGPGS SVDYSVFVPF NSASYFHPFC FIQNWDNQTQ VEDCWLGDNT VSLPDLDTTK   180
DVVKNEWYDW VGSLVSNYSI DGLRIDTVKH VQKDFWPGYN KAAGVYCIGE VLDGDPAYTC   240
```

```
PYQEVLDGVL NYPIYYPLLN AFKSTSGSMD DLYNMINTVK SDCPDSTLLG TFVENHDNPR    300
FASYTNDIAL AKNVAAFIIL NDGIPIIYAG QEQHYAGGND PANREATWLS GYPTDSELYK    360
LIASANAIRN YAISKDTGFV TYKNWPIYKD DTTIAMRKGT DGSQIVTILS NKGASGDSYT    420
LSLSGAGYTA GQQLTEVIGC TTVTVDSSGD VPVPMAGGLP RVLYPTEKLA GSKICSSSGR    480
GATSPGGSSG SVEVTFDVYA TTVYGQNIYI TGDVSELGNW TPANGVALSS ANYPTWSATI    540
ALPADTTIQY KYVNIDGSTV IWEDAISNRE ITTPASGTYT EKDTWDES                588

SEQ ID NO: 169          moltype = AA   length = 583
FEATURE                 Location/Qualifiers
source                  1..583
                        mol_type = protein
                        organism = Penicillium canescens
SEQUENCE: 169
LTPAEWRSQS IYFMLTDRFG RSDNSTTAAC NVSDRTYCGG TWQGIINHLD YIQGMGFTAI     60
WITPVTEQLP QDTGDGEAYH GYWQQNIYEI DSKLGTAADL LALSKALHAR GMYLMVDVVA    120
NHMGYAGSGN SVDYSVFNPF SSSSYFHSYC LISNYDDQSN VENCWLGDTI VSLPDLDTTQ    180
TAVQTIWYDW IADLVSNYSI DGLRIDTVKH VQKSFWPGYN DAAGVYCVGE IFDGDPAYTC    240
DYQNYMDGVL NYPIYYQLLY AFQSSSGSIS DLYNMINSVK SDCADSTLLG NFIENHDNPR    300
FASYTSDYSQ AKNVISFLFL SDGIPIIYSG QEQHYSGGAD PANREATWLS GYSTTAELYK    360
YIATTNKIRK LAVSDSSYLT TKNVPFYQDS HTLAMKKGSS ASPVITVLSN YGSSGSSYTL    420
SLSGSGYSSG TKLMEMYTCT SVTVDSSGNI AVPMASGLPR VLMLASSANS LCGSSGATSP    480
GGSSGSVEVT FDVYATTVYG QNIYITGDVS ELGNWTPANG VALSSANYPT WSATIALPAD    540
TTIQYKYVNI DGSTVIWEDA ISNREITTPA SGTYTEKDTW DES                     583

SEQ ID NO: 170          moltype = AA   length = 583
FEATURE                 Location/Qualifiers
source                  1..583
                        mol_type = protein
                        organism = Acidomyces acidothermus
SEQUENCE: 170
LTPAQWRGQS IYQVLTDRFG RTDDSTTAAC DVNDYCGGSW QGIINHLDYI QDMGFSAIWI     60
SPVVENLVGD TQDGSAYHGY WAQNIYALNP NFGTVSDLVA LSAALHQRGM YLMVDVVTNH    120
MGYDGCGDCV DYSVFTPFNS QSYFHPFCLI DYNNSTSIKV CWEGDNIVSL PDMRTEDSDV    180
ATEWNTWISE LVSNYSIDGL RIDSAQQVDN AFFPPFQAAA GGIHVLGEVF NGDPNYVCPY    240
QDFMSGVLNY PAYYYITQAF QSTSGSISNL VNGINQMKST CTDTTLLGSF LENHDNPRFP    300
SYTSDLSLSDK NAITFTILQD GIPIIYEGQE QHYSGGTVPN NREAIWLSGY DKSAPLYTWI    360
ASVNQIRNQA IFKDSNYLTY MAWPIYSDAS TIAMRKGFDG LQIISVYSNK GASAASYTIS    420
LESSTTGFTA NEALVEVMSC TTYTTDGSGN LAVTISGGLP AVFYPKAQLA GSGICGATSP    480
GGSSGSVEVT FDVYATTVYG QNIYITGDVS ELGNWTPANG VALSSANYPT WSATIALPAD    540
TTIQYKYVNI DGSTVIWEDA ISNREITTPA SGTYTEKDTW DES                     583

SEQ ID NO: 171          moltype = AA   length = 586
FEATURE                 Location/Qualifiers
source                  1..586
                        mol_type = protein
                        organism = Kinochaeta ivoriensis
SEQUENCE: 171
LSPAGWRQQS IYQVMTDRFA RTDGSTIASC DTSQQAYCGG TWQGLINKLD YIQGMGFTAV     60
WISPMVHQMA GATSDGESYH GYWAQDINTV NSAFGTAADL KALSAALHAR GMYLMLDVVT    120
NHFAYDGCGT CVDYSIFNPF NSESYFHPFC LIDYSNTTSI QVCWEGDNTV SLPDLRTEDS    180
DVRSIWNSWI SSVISTYGVD GLRVDSAQQV ETSFWAGFEA AAGVYMVGEV FNGDPTYVTP    240
FQDYMDGVLN YPAYYWITQA FESTSGSISN LANGMNTMKS LAKNTSLLGS FLENHDNPRF    300
PSLTSDMSLA QNAIAFTMLM DGIPIIYQGQ EQHFSGGGVP SDREAVWLSG YPNDTTLYAW    360
ITKLNAVRSW AIAKDSSYLA YMAYPVYTDT HTIAMRKGDT GYQVISVYTN VGASGSSYSV    420
TLTSADTGFT ASQSVVDLVG CKTYTADSTG SLSLSLTGGI PIILYPAASL TGNTICTSGA    480
TSPGGSSGSV EVTFDVYATT VYGQNIYITG DVSELGNWTP ANGVALSSAN YPTWSATIAL    540
PADTTIQYKY VNIDGSTVIW EDAISNREIT TPASGTYTEK DTWDES                  586

SEQ ID NO: 172          moltype = AA   length = 585
FEATURE                 Location/Qualifiers
source                  1..585
                        mol_type = protein
                        organism = Aspergillus terreus
SEQUENCE: 172
LTPAEWRSQS IYFLLTDRFG RTDNSTTAAC DTSDRVYCGG SWQGIINQLD YIQGMGFTAI     60
WITPVTGQFY ENTGDGTSYH GYWQQDIYDL NYNYGTAQDL KNLANALHER GMYLMVDVVA    120
NHMGYDGAGN TVDYSVFNPF SSSSYFHPYC LISNYDNQTN VEDCWLGDTT VSLPDLDTTS    180
TAVRNIWYDW VADLVANYSI DGLRVDTVKH VEKDFWPGYN SAAGVYCVGE VYSGDPAYTC    240
PYQNYMDGVL NYPIYYQLLY AFESSSGSIS DLYNMISSVA SSCKDPTLLG NFIENHDNPR    300
FASYTSDYSQ AKNVITFIFL SDGIPIVYAG QEQHYSGGSD PANREATWLS GYSTSATLYT    360
WIATTNQIRS LAISKDAGYV QAKNNPFYSD SNTIAMRKGT TAGAQVITVL SNKGASGSSY    420
TLSLSGTGYS AGVTLVETYT CTTVTVDSSG NLPVPMTSGL PRVFVPSSWV NGSALCNGAT    480
SPGGSSGSVE VTFDVYATTV YGQNIYITGD VSELGNWTPA NGVALSSANY PTWSATIALP    540
ADTTIQYKYV NIDGSTVIWE DAISNREITT PASGTYTEKD TWDES                   585

SEQ ID NO: 173          moltype = AA   length = 565
FEATURE                 Location/Qualifiers
source                  1..565
                        mol_type = protein
```

```
                        organism = Thamnidium elegans
SEQUENCE: 173
VPLSVLDKRN GVTTLSKRAA AADWKSRSIY QLVTDRFGRS DGSTSACGDL SNYCGGDYKG      60
IQNQLDYIAG MGFDAIWISP IPENTDGGYH GYWAKDFEKL NTNFGSADDL KALVTAAHGK     120
GMYVMLDVVA NHAGPASGGD YSGFTFSSAS NYHPQCTIDY DNQTSVEQCW VADDLPDINT     180
EDDTIVSKLH SIVSDWVTTY DFDGIRIDTV KHIRKDFWSG YEEAAGVFAT GEVFDGDAAY     240
VGPYQDQLSS LINYPLYYAI RDVFSAGSGF SRISDMLSTI KSNFKDPSVL TTFVDNQDNA     300
RFLSVKSDMS LYKNALAFTI LTEGIPVVYY GTEQGFKGGD DPKNREVLWT SNYDTSSDLY     360
KPIKIVNNDV RQKSDKTVTL DVDVGTNTYA FTHGKNLIVV NNYGSGSTES VTVKVGDSVA     420
DGTKLVDAVS NITATVSGGS ITFSLKDGLP ALFVPSSGAT SPGGSSGSVE VTFDVYATTV     480
YGQNIYITGD VSELGNWTPA NGVALSSSANY PTWSATIALP ADTTIQYKYV NIDGSTVIWE    540
DAISNREITT PASGTYTEKD TWDES                                          565

SEQ ID NO: 174          moltype = AA  length = 574
FEATURE                 Location/Qualifiers
source                  1..574
                        mol_type = protein
                        organism = Meripilus giganteus
SEQUENCE: 174
RPTVFDAGAD AHSLHARAPS GSKDVIIQMF EWNWDSVAAE CTNFIGPAGY GFVQVSPPQE      60
TIQGAQWWTD YQPVSYTLTG KRGDRSQFAN MITTCHAAGV GVIVDTIWNH MAGVDSGTGT     120
AGSSFTHYNY PGIYQNQDFH HCGLEPGDDI VNYDNAVEVQ TCELVNLADL ATDTEYVRGR     180
LAQYGNDLLS LGADGLRLDA SKHIPVGDIA NILSRLSRSV YITQEVIFGA GEPITPNQYT     240
GNGDVQEFRY TSALKDAFLS SGISNLQDFE NRGWVPGSGA NVFVVNHDTE RNGASLNNNS     300
PSNTYVTATI FSLAHPYGTP TILSSYDGFT NTDAGAPNNN VGTCSTSGGA NGWLCQHRWT     360
AIAGMVGFRN NVGSAALNNW QAPQSQQIAF GRGALGFVAI NNADSAWSTT FTTSLPDGSY     420
CDVISGKASG SSCTGSSFTV SGGKLTATVP ARSAIAVHTG QKGSGGGATS PGGSSGSVEV     480
TFDVYATTVY GQNIYITGDV SELGNWTPAN GVALSSSANYP TWSATIALPA DTTIQYKYVN   540
IDGSTVIWED AISNREITTP ASGTYTEKDT WDES                                574

SEQ ID NO: 175          moltype = AA  length = 671
FEATURE                 Location/Qualifiers
source                  1..671
                        mol_type = protein
                        organism = Chaetomium megalocarpum
SEQUENCE: 175
LYINGSVTAP CDSPIYCQGE ILKAIELARP FSDSKTFVDM PTIKPVDEVI AAFSRLSQPL      60
SNNSELTAFL AENFAPAGGE LEEVPISELE TDPSFLNKLE DVDIKEFVGK VIDIWPDLTR     120
RYAGPGNCSQ CANSFIPVNR TFVVAGGRFR EPYYWDSYWI LEGLLRTGGA FTQISKNMIE     180
NFLDFVETIG FVPNGARIYY LNRSQPPLLT LMVKTYVDYT NDTSILERAL PLLVKEYEFW     240
TNNRTVSITA TDGKEYTLNR YSVNNNQPRP ESYREDYVTA NNASYYAQSG IIYPVKTPLN     300
ETEKAELYSN LASGAESGWD YTARWLKTPD DAARDVYFPL RSLNVRSIVS VDLNSILYQN     360
EVIISEYLEQ AGNSSEAKRF ADAAEQRSEA MYALMWNATH WSYFDYNLTD NSQRVFYEAD     420
ADTAPSDQTA APPGQQVLFD IAQLYPFWTG AAPASLKANP LAVQNAYARV ARMLDTKAGA     480
IAATNLRTGQ QWDQPNVWPP LQHILMKGLL NTPATFGTED PAYAHTQDLA LRLAQRYLDS     540
TFCTWYATGG STSATPQLQG AAPGATGTMF EKYADDATNV AGGGGEYEVV EGFGWTNGVL     600
IWAADVFGDR LVRPDCGNIT AAHTSSEKR TVAGASRPDA GASGVRRERR AVELDPWDAA      660
WTKMFGRSKL R                                                         671

SEQ ID NO: 176          moltype = AA  length = 662
FEATURE                 Location/Qualifiers
source                  1..662
                        mol_type = protein
                        organism = Lecanicillium psalliotae
SEQUENCE: 176
LYQNGSVIAP CDSPIYCHGD ILKEVELARP FTDSKTFVDM PAKKPLAEIQ AAFDKLEKPL      60
SNNTALNEFL STYFEDAGGE LKAVSKDKLK TDAKFVDKLN DTVIKEFVNK VIDIWPDLTR     120
EYAGSATNCT NCPNSFIPVN RTFVVAGGRF REPYYWDSYW IVEGLLRTGG AFVDITKNTI     180
ENFLDLIEQF GFIPNGARLY YLNRSQPPLL SQMVKNYISY TNDTDILKRA LPILVKEHEF     240
FMNNRSVEIT VENKTYTLNR YAVSNTQPRP ESFREDYNTV NNNSYYAASG IIYPVKTPLN     300
ESEQATLYAN LASGAESGLD YTTAKWSTNP RDSMEDIYFP LRSLNIMNIV PVDLNSILYG     360
NEKAISEFYN ITGNSSEADS WSKKAAERQE AIQAVFWNET LYSYFDYNRT SSSQHIYIPS     420
DDDTQSFENA TAPAGMQEVF TVTQFYPFWM GAAPDYIRNN PHAVKTAYSR IAKYLELKPG     480
GIPSSNLRSG QQWDQPSVWP PLMHVLMKGL VNTPATFGKE DPAYKDVHKL ALTLGQRYLD     540
STFCTWYATG GSTSETPQLS GLSDSDVGIM FEKYDDTSIN HAGGGGEYEV VEGFGWSNGV     600
LMWVADTFGN ELKRPDCGNI TAANVHPGKR SVSAVELSSR DAQRVKKFGR RAEGRMKVPG     660
VL                                                                   662

SEQ ID NO: 177          moltype = AA  length = 637
FEATURE                 Location/Qualifiers
source                  1..637
                        mol_type = protein
                        organism = Doratomyces sp.
SEQUENCE: 177
LYTNGSIIAP CDSPIYCHGD ILHQVQLAHP FPDSKTFVDM PAIKSVDEIQ AAFDKLDKPL      60
KNDTALQNFL AENFAEAGHE LAEVDPSELS TDPRFLDKVS DTVIHEFTQK VIDIWPDLTR     120
SYSPSGAGSD CPDCPNSFLP VNRTFVVAGG RFREPYYWDS YWIVEGLLRT GGDFLGVSRN     180
IIENFLDFVD DFGFVPNGAR RYYLNRSQPP LLSLMVKSYV EQTNDTEILD RAVPLLIKEY     240
EFWTKNRTVE VPFGNETITL NQYNVDNTQP RPESYREDYI TATNASYYSA SGEVYEEVEK     300
```

```
                                         -continued

LNETQRATVY RNLATGAESG WDYTSRWMAR PRDAVEDVYF PLRSLNIIEI VPVDLNSILY   360
ANELAIAEFV RLAGADDCEE EAAAWEALAE KRSADMHRLM WNDTLHSYFD YNLTSSSQNV   420
YVPADNDTAP FERPGGTPEG SQVFFSAAQF YPFWTGAAPS SLRDDPAAVQ LAYSRVASYL   480
DLRAGGIPAT NLRTGQQWDQ PSVWPPLMHI LTSGLLNTSP ASASDDDDPS YAPTRDLALS   540
LAQRYLDSTF CTWYATGGST SETPQLDGFT DEDKGAMFEK YDDSATNVAG GGGEYEVVEG   600
FGWTNGVLIW MVDTFGDELS RPDCGDIEAA NAHPARK                           637

SEQ ID NO: 178          moltype = AA  length = 601
FEATURE                 Location/Qualifiers
source                  1..601
                        mol_type = protein
                        organism = Mucor moelleri
SEQUENCE: 178
IQNHTSFSCD SPIYCEGDIL HTVQLAKIFS DSKTFVDMPT SKSESQVIEA FKAIGGRNAT    60
IAQVQQFLNE NFLTAGTEVK RLTNITIPEL NWIDNITDPD YRGWISKLNQ AWSNLTFTFD   120
TSVLCQDCAT STLPVSRPFV VPGGRFREFY YWDSFFVIKG LLLSDQVELA KNMILNFFDF   180
IDTYGFIPNG ARIYYLNRSQ PPFLTQMVEA FWEKTSDKEF MTNALPFLDK EYNFWMTNNS   240
ISVPDDPKNPS KKYKMNHYVT LNTSPRPESY VEDYNTVNNG TDYSQAVKLQ LYADIAAGAE  300
TGWDYSSRWT RQKHPAPNQT EGYEMLRSIN TANIVPIDLN SLLWNTETML AEWHDRFGEK   360
SKSKKKSAYY QTQAKKRLDA MEKLMWNPTD YTYYDYNLTS SSQNLEFTPA NLFPIWLGAL   420
PNKVMKNKTE LARVFDETEN ALRKYPGILT TSYYNTTMQW DWPNGWPPLS YVAMEGMNKV   480
EESLNGKKGS KQDGKTYTTS RGTSLARLSF TLAERYAASA YCGWYKTGGS IPGILNKIDG   540
VADDGHMFEK FDVNTIGISG SQGEYVSQTG FGWTNGIALW IFDTYANLTA PDCNQTITLN   600
I                                                                  601

SEQ ID NO: 179          moltype = AA  length = 650
FEATURE                 Location/Qualifiers
source                  1..650
                        mol_type = protein
                        organism = Phialophora cyclaminis
SEQUENCE: 179
LYINGSVIAP CDSPIYCHGE LLKAIELARP FSDSKTFVDM PTRKPVDEVV AAFEKLSKPV    60
VNDTKLGEFL QANFLPAGGD LSDFPPGSLE TDPKFLDNIN DTVIREFTEA VIDIWPDLTR   120
RYVGASNCTG CANSFIPVNR TFVVAGGRFR EPYYWDSYWI IEGLLRTGGN FVQISKNIIE   180
NFLDFVETIG FVPNGARIYY LNRSQPPLLT AMVKAYLEHT NDTKILDRAV PLLIKEYNFW   240
ITNRSVTLTG PDGNEYTLQR YSVNNNQPRP ESYREDYNTA NNKSYYSTSG IIYPENVSLN   300
DSEKKELYAN LATGAESGWD YGTRWLSRPA DALRDVYFPL RYVKTRDLVP VDLNAILYQN   360
EASISSFLYI QGNDTGAAHF AKLAAARQKA MTAVLWNATL FSYFDYNMTS SSHFSFIPVD   420
DDATSIETAT APRGFQQIFH VAQLYPFWTG AAPASLRENP LAVQRAFSRV SQMLEEKAGS   480
IPATNFYTGQ QWDEPNVWPP LQHIIMEGLR NTPATFGEDD PIYQGVQDLA LRVAQRYLDS   540
TFCTWYATGG STSLTPKLAG LTDNAKGIMF EKYGDNSTNV AGGGGEYEVV EGFGWTNGVL   600
IWAVDTFGNK LKRPDCGDIQ PAHVEARGLQ RRAVELDKWD AQWVKRFGAK              650

SEQ ID NO: 180          moltype = AA  length = 654
FEATURE                 Location/Qualifiers
source                  1..654
                        mol_type = protein
                        organism = Thielavia arenaria
SEQUENCE: 180
LYINGSVIAP CDSPLYCHGD ILKAIELARP FQDSKTFVDM PTIRPVEEVI AAFNRLSQPL    60
SNNSELNAFL QANFPAPAGGE LEEVPESELS TNPVFLDKLN DTVIKEFVAK VIDIWPDLTR  120
RYAGPGNCSE CADSFIPVNR TFVIAGGRFR EPYYWDSFWI LEGLLRTGGA FTEISKNMIE   180
NFLDFVETIG HIPNGARIYY LNRSQPPLLA GMVKNYVDYT NDTSILERAL PLLIKEYEFW   240
TNNRTVQVTA SDGKTYTLHR YVNNNQPRPE SYREDWITAN NASYYAASG IIYPVKTPLN    300
ESEKAALYSN LASGAESGWD YGTRFLMRPE DAARDIYFPL NHLNVRDMVT VDLNAILYQN   360
EVIISEYLEQ AGNNTEAERF ASAARQRSEA MYALMWNETL WSYFDYNLTS NSQYTFIPAD   420
VNATAAEKAN APEGQKVIFH IAQLYPFWTG AAPDQLKNNP LAVQKAYSRV AEMLDIKPGA   480
IPATNFITGQ QWDQPNVWPP LMHVLMAGLL NTPPTFGEDD PAYQAVQALA LRLGQRYLDS   540
TFCTWYATGG ETSQTPRLQG VSPDATGTMF EKYADNAINV AGGGGEYEVV EGFGWTNGVL   600
IWAADVFANG LKRPDCGNIT AAHTHNGAKR AVELHPRDAA WTKKFGKRAL KKRA          654

SEQ ID NO: 181          moltype = AA  length = 661
FEATURE                 Location/Qualifiers
source                  1..661
                        mol_type = protein
                        organism = Thielavia antarctica
SEQUENCE: 181
LYVNGSVTAP CDSPLYCQGE ILKAIELARP FADSKTFVDM PTLRPLDDVI AAFRKLSQPL    60
SNSSELNAFL AANFPAPAGGE LEEVPKSELR TKPAFLDKVE DVVIKEFVGK VIDIWPDLTR  120
RYAGPGNCTE CANSFIPVNR TFVVAGGRFR EPYYWDSYWI LEGLLRTGGD FTKISRNIIE   180
NFLDFVDTIG FVPNGARIYY LNRSQPPVLT LMVKTYVDYT NDTSILERAL PLLIKEHEFW   240
TTNRSVSVEV DGKTHTLNRY FVNNNQPRPE SYREDWITAN NASYYAASGI IYPVKTPLNG   300
TQQAELYANL ASGAESGWDY TSRWLKTPSD AARDYFPLR SLNVINTIPV DLNSILYQNE     360
VIISEYLEQA GNKSGAEKFS DAARQRSEAM YALMWNATNW SYFDYNLTSS GQNTHFPADA   420
DATAAETTSS PAGTQLLFSV SQLYPFWTGA APQQLKSNPL AVTQAYARVA AMLDAKAGAI   480
PATNLLTGQQ WDEPNVWPPL QHVLMQGLLN TPATFGADDP AYQATQALAL RLAQRYLDST   540
FCTWYATGGS TSATPRLAGV SAGAEGSMFE KYGDDSTNVA GGGGEYEVVE GFGWTNGVLI   600
WAADVFAGKL QRPECGDIEA AQTHGGAARR GLGMERRAIE LDPWDARWTK AFGKRALRRR   660
A                                                                  661
```

```
SEQ ID NO: 182          moltype = AA  length = 667
FEATURE                 Location/Qualifiers
source                  1..667
                        mol_type = protein
                        organism = Chaetomium sp.
SEQUENCE: 182
LYINGSVTAP CDSPLYCQGE ILKAIELARP FSDSKTFVDM PTIKPVDDVI AAFSRLSQPL   60
SNNSELNAFL AENFAPAGGE LEEVPESELE TDPAFLDKLE DTTIKEFVTK VIDIWPDLTR  120
RYAGPGNCSK CANSFIPVNR TFVVAGGRFR EPYYWDSYWI LEGLLRTGGA FTEISKNIIE  180
NFLDFVDTIG FIPNGARIYY LNRSQPPLLT LMVKTYVDYT NDTSILERAL PLLIKEHEFW  240
TNNRSVAITA ADGKKYTLQR YYVNNNQPRP ESFREDYITA NNASYYAASG IIYPVKTPLN  300
ETEKAELYSN LASGAEAGWD YTARWLKTPN DAARDVYFPL RSLNVIGMVP VDLNSILYQN  360
EVIIAEYLQQ AGNSSEARRF ATAAEKRSEA MYALMWNSTH WSYFDYNLTS NSQRIFVPTD  420
ADADPVDQTN APPGHQVLFD IAQLYPFWTG AAPASLKNNP LAVQLAYARV AHMLDTKAGA  480
IPGTNFRTGQ QWDQPNVWPP LQHVLMKGLL NTPPTFGEAD PAYQEVQRLA LRLAQRYLDS  540
TFCTWYATGG STSDMPQLQG VNPGATGTMF EKYADNATNV AGGGGEYEVV EGFGWTNGVL  600
IWAADVFGEG LTRPDCGNIT AAHTSGAKR GLDGGEGGAG GLWGRRAVEL DPWDARWTKM  660
FGRRKRE                                                            667

SEQ ID NO: 183          moltype = AA  length = 671
FEATURE                 Location/Qualifiers
source                  1..671
                        mol_type = protein
                        organism = Chaetomium nigricolor
SEQUENCE: 183
LYINGSVTAP CDSPLYCQGE ILRAIELARP FSDSKTFVDM PTIKPLEEVI AAFNQLTQPL   60
SNNSELNTFL AENFAPAGGE LEEVPKDELN TDPGFLDKLN DTTIREFVAK VIDIWPDLTR  120
RYAGGGNCSE CANSFIPVNR TFVVAGGRFR EPYYWDSYWI LEGLLRTGGA FIEISKNIIE  180
NFLDFVETIG FIPNGARIYY LNRSQPPLLT LMVKTYVDYT NDTSILERAL PLLIKEHEFW  240
VNNRSVEITA ANGQTYTLNR YHVNNNQPRP ESYREDYITA NNGSYYAASG IIYPVRTPLN  300
ETEKAELYAN LASGAESGWD YTARWLKTPN DAANDVYFPL RSLNVRGLVP VDLNSILYQN  360
EVIIAEYLQQ AGNLSLAQRF AEAAEQRSEA MYALMWNATY WSYFDYNLTS NSQRIFVPLD  420
ADSRTIETVG APPGHQVLFD IAQLYPFWTG AAPANLKNNP LAVQQAYSRV ASMLDAKAGA  480
IPATNFRTGQ QWDQPNVWPP LQHILMQGLL NTPPTFGDSD PAYQHVRDLA LRLAQRYLDS  540
TFCTWYATGG STSDMPQLQG VSPDATGTMF EKYADNATNV AGGGGEYEVV EGFGWTNGVL  600
IWAADVFGDA LKRPDCGDIE AAHTQAKKR DVEGLERRAV ELDPWDAAWT KMFGRSKLRK  660
RGAGGQKRWV S                                                       671

SEQ ID NO: 184          moltype = AA  length = 666
FEATURE                 Location/Qualifiers
source                  1..666
                        mol_type = protein
                        organism = Chaetomium jodhpurense
SEQUENCE: 184
LYFNGSVIAP CDSPLYCQGE ILKAIELARP FSDSKTFVDM PTIKPVDEVI AAFNRLSQPL   60
TNNSELNAFL AENFAPAGGE LEEVPKDELN TDPKFLDKLE DATIKEFVAK VIDIWPDLTR  120
RYAGASNCSE CANSFIPVNR TFVIAGGRFR EPYYWDSYWI LEGLLRTGGA YTQISRNMLE  180
NFLDFVETIG FIPNGARIYY LNRSQPPLLA MMIKNYVDYT NDTSILDRAL PLLIKEHEFW  240
INNRSVSITA ADGKQYTLHR YNVNNNQPRP ESYREDYITA NNASYYAASG IIYPVKTPLN  300
ESEKAELYAN LATGAESGWD YTARWLKTPN DAAKDVYFPL RSLNVRGMVS VDLNSILYQN  360
EVIIAEYLER AGNISEAERF AAMAQQRSEA MYALMWNSTH WSYFDYNLTS NSQRIFVPLD  420
DDSSTAEQAN SPPGHQVLFD IAQLYPFWTG AAPESLKSNP LAVQLAYSRV ARMLDTKAGA  480
IPATNFRTGQ QWDQPNVWPP LQHVLMAGLL NTPPTFGESD PAYQNVRALA LRLAQRYLDS  540
TFCTWYATGG ETSQTPRLQG VSPDATGTMF EKYADNATNV AGGGGEYEVV EGFGWTNGVL  600
IWAADVFADG LKKPDCGNIT AAHTSAKRG LERRAVELDP WDAAWTKMFG RSKLRKREEG  660
RKRWLS                                                             666

SEQ ID NO: 185          moltype = AA  length = 670
FEATURE                 Location/Qualifiers
source                  1..670
                        mol_type = protein
                        organism = Chaetomium piluliferum
SEQUENCE: 185
LYINGSVIAP CDSPLYCHGE ILKAIELARP FSDSKTFVDM PTIKPLDEVI AAFSQLSQPL   60
SNNSELNAFL AENFAPAGGE LEEVSKDELQ TDPTFLDKLD DTTIKEFVSK VIDIWPELTR  120
RYVGSSDCSG CANSFIPINR TFVVAGGRFR EPYYWDSYWI LEGLLRTGGA FVDISRNIIE  180
NFLDFVETIG FVPNGARIYY LNRSQPPLLT LMVKTYVDYT NDTSILERAL PLLVKEHEFW  240
TTNRSVSITA NGKEYTLNRY SVNNNQPRPE SYREDYITAS NESYYAESGI IYPVRTPLNE  300
TEKAELYSNL ASGAESGWDY TSRWLKTPND AANDVYFPLR SLNVLGLVPV DLNSILYQNE  360
VILAEYFEQA GNSSEAERFA AAAEQRSEAM YDLMWNATHW SYFDYNLTSS SQRIFVPLDD  420
GASTQEQSTS PPGYQVLFDV AQLYPFWTGA APAALKSNPL AVQHAYSRVA DMLNTKAGAI  480
PATNFRTGQQ WDQPNVWPPL QHIIMQGLLN TPPTFGESDP AYENTQSLAL RLAQRYLDST  540
FCTWYATGGS TSDMPPLQGV SAGATGTMFE KYADDATNVA GGGGEYEVVE GFGWTNGVLI  600
WAADVFGDAL KRPDCGNITA ASTHEGATKR DLRGLGRRAV ELDPWDAAWT KMFGRAKLRK  660
REQGRETWVN                                                         670

SEQ ID NO: 186          moltype = AA  length = 674
FEATURE                 Location/Qualifiers
```

```
source                  1..674
                        mol_type = protein
                        organism = Myceliophthora hinnulea
SEQUENCE: 186
LYINGSVTAP CDSPIYCHGE LLKGVELAHP FVDSKTFVDM PTLKPVDEVL AAFSKLRQPL    60
SNNSELNNFL AEYFAPAGHE LEEVPDSELQ TDPKFLDKLE DRTIKEFVSK VIDIWPDLTR   120
RYAGPGDCSD CANSFIPVNR TFVVAGGRFR EPYYWDSYWI LEGLLRTGGA FTQISKNIIE   180
NFLDFIDTIG FIPNGARIYY LNRSQPPLLT RMVKSYVDYT NDTSILERAL PLLIKEHDFF   240
TNNRSVSVTA SNGKTYTLHR YHVENNQPRP ESYREDYITA NNGSYYAASG IIYPVKTPLN   300
ETEKAVLYSN LASGAESGWD YTARWLRVPD DAARDVYFPL RSLNVREIVP VDLNSILYEN   360
EVIIAGYLEK AGNSSEAKRF ASAAKQRSEA MYNLMWNATH WSYFDYNLTS NAQNIFIPAD   420
EDTAPFDRTA APPGKQVLFH IAQLYPFWTG AAPAHLKSNP LAVQKAYARV SRMLDSKKGA   480
IAATNYRTGQ QWDQPNVWPP LQHVLMQGLL NTPATFGESD PAYQGVQKLA LRLAQRYLDS   540
TFCTWYATGG STSDFPQLQG VSPDATGIMF EKYADSAINV AGSGGEYEVV EGFGWTNGVL   600
IWAADVFGNK LKRPDCGNIT AAHTHSEAKR SLGDGGLARR AVELDPWDAA WTKMFGRSKL   660
RRREAEDVRK RWSS                                                    674

SEQ ID NO: 187          moltype = AA length = 659
FEATURE                 Location/Qualifiers
source                  1..659
                        mol_type = protein
                        organism = Chloridium virescens
SEQUENCE: 187
LYINGSVIAP CDSPLYCQGD ILKAIQLAQP FSDKTFVDM PTTQPVDQVI AAFNQLPQPV     60
SNNSGLQNFL STYFAPAGGE LTEVPKDQLQ TNPMFLNKLN DTVIREFVTA VIDIWPDLTR   120
TYTGASNCTG CSDSFIPVNR TFVVAGGRFR EPYYWDSFWI LQGLLRTGGA FTQISKNIIE   180
NFLDLVDQFG FVPNGARVYY LNRSQPPVLS EMVRTYVAYT NDTSILARAI PTLIKEHNFW   240
MQNRTVNITG ADGNTYTLNQ YHVENTQPRP ESYTEDYITA NNHSYYATSG IIYPETKPLN   300
DSEIANLYAN LASGAESGWD YGSRYLARPN DAAQDVYFPL RSLNVLNIVP LDLNSLLYQS   360
EQNIALFLQA TGNSSEAEQW TSLAAQRQTA IHALMWNETL WSYFDYNLTS NGQNIYVPAD   420
KDATPADTAS APPGYQVLFD VAQFYPFWTG AATDELRRNP LAVRQAFTRV DAYLTAKAGG   480
IPATNLMTGQ QWDQPNVWPP LMHVLMQSLL DTPATFGAAD PSYAALQGLA LRLAQRYLDM   540
TFCTWYATGS STSQTPKLQG LGPDAVGTMF EKYADNATNI AGSGGEYTVV EGFGWTNGVL   600
IWAADTFGAQ LTRPNCGNIT AAHVTPGKRS VGLGRRAVEL HESDARWVKM FGSRAWRNA   659

SEQ ID NO: 188          moltype = AA length = 662
FEATURE                 Location/Qualifiers
source                  1..662
                        mol_type = protein
                        organism = Gelasinospora cratophora
SEQUENCE: 188
LYVNGSVTAP CDSPIYCYGE LLHQVELARP FSDKTFVDM PTIKPVDEVL EAFSKLTLPL     60
SNNSELHEFL NTYFGPAGGE LEAVPTDQLH VSPTFLDNVS DDVVKQFVNS VINIWPDLTR   120
KYVGAGEICT GCANSFIPVN RTFVVAGGRF REPYYWDSFW ILEGLLRTGG AFTEISKNTI   180
ENFLDLVEQI GFVPNGARLY YLNRSQPPLL TQMVRIYVEH TNDTSILERA VPILKKEWEW   240
WITNRTVEVT ADGKTYSLQR YHVDNNQPRP ESYSEDYITA NNNSYYATSG IIYPETTPLN   300
DTQKAQLYAN LASGAESGWD YSTRWLKNPN DAARDVYFPL RSLNVLEIVP VDLNSILYQN   360
EVTIGKFLAQ QGNKDEAEEW AKKAEQRSEA MYKLMWNSTL WSYFDYNLTS SSQNIYVPAD   420
PQVFPPEKPS GTPEGYQVLF SINQMFPFWT GAAPDQLKAN PLAVKLTFDR VKNYLDNKAG   480
GIPATNFVTG QQWDEPNVWP PLMHVLMDGL LNTPATFGED DPAYQETQNL ALRLAQRYVD   540
STFCTWWATG GSTSETPKLQ GLGSDAKGIM FEKYADNSTN VAGGGGEYEV VEGFGWTNGV   600
LIWAADKFGD KLKRPNCGDL TPANVGKRAV ELDAFDAKFT KKFARKGKLE KLKAKFKRRA   660
AI                                                                 662

SEQ ID NO: 189          moltype = AA length = 543
FEATURE                 Location/Qualifiers
source                  1..543
                        mol_type = protein
                        organism = Acidobacteriaceae bacterium
SEQUENCE: 189
QTTTTSAGLH DTLAYIKRTW HTLERSNKTL LKSADDVKVG QAGTLTLYVS QDVKPQAVNA    60
SLRRELPPAD KKRIVVRQLP EHPEAVEPAG LLYLPYPYVV PGGRFNEMYG WDSYFILLGL   120
VHDDELALAK NMTDNFIYEI EHYGMILNAN RTYYLTRSQP PFLTQMILEV YRRTGDGKWL   180
ASTLPAIEKY YAYWMREPHL TPETGLSRYW GGADTPAPEV VHGEKDAAGH NQYDRVREYY   240
RTHNVTAYDV SQYYDKATDR LKPLFYIADR AMRESGFDPS SRYGPFSADI IHYDPVCLNS   300
LLYRMESDTA TILKQLNRTS EARVWEKRAT QRAELVNRLM WNEEKGLYFD YDFITRRQSN   360
YHFVTTFYPL WAGIASRQQA DRVRKNLSIF ERAGGLQTSD YISGSQWDAP FGWAPLQIMT   420
VEGLRRYGFN EDADRISRKF INMVVRDFEE HGTIKEKYDV VIGKSDLAAG LKFGYTSNEA   480
GFGWTNAAVV LFIEELAGER PLAASLDRES MPMLRQRHLS PQPSVWPPFS PQAPQYRRRD   540
PYR                                                                543

SEQ ID NO: 190          moltype = AA length = 532
FEATURE                 Location/Qualifiers
source                  1..532
                        mol_type = protein
                        organism = Acidobacterium capsulatum
SEQUENCE: 190
GARSSLSPHA VAGPQPIDAY IHTAWSTLTR SMSDCKSVAD PKLKSTPVLY LPRDLAVPAN    60
VAAMQKCHV RVLRLPIVIT HFDQIRESQI ATPGLLYLPH PYVVPGGRFN EMYGWDSFFI   120
```

```
LKGLLDDHHI ALARGIVENF FFEIAHYGGI LNANRTYYFT RSQPPFLSSM IRAIYAAEVA    180
EGHTQAAHAW LVEAYPYAVR DHALWMSPIH QAGNTGLARY FDTGQGPVPE MADDSTYYQD    240
VIRWLLAHPG LHTGYLMHGS PHLDAAARER LAQLSCDPTL SKVCARAHVH GYWLTRSFYK    300
GDRAMRESGF DTTFRFGPFS GSTQHFAPVG LNALLYKYER DLAWMAAQLG KPGEAAKWNS    360
EAETRRAEMN HYLWNAQKKM YFDYNFETHR QSSYAFITTF YPLWAGAADK AQQQGVIASL    420
PLFEHPGGLA ISNHDSGVQW DLPYGWAPTE WMAVQGLLRA DDQHDARRIA SEFNRTVRTT    480
YQHDHAIYEK YDVVNRSNDF RVTAGYTQNV VGFGWTNAVY LEFQSLLAHP GQ            532

SEQ ID NO: 191         moltype = AA   length = 568
FEATURE                Location/Qualifiers
source                 1..568
                       mol_type = protein
                       organism = Acidovorax wautersii
SEQUENCE: 191
AAAVSSGLRI SERHPAYSTN PARVQVPGAP GAPPSDHCTP ADRYQELFVA VQSQQIFEDS    60
KTFVDCGPIG EPEDILAAYR AEHAQPDFDL ARFVAQHFTA PQVAANDYVG APGMALAEHI    120
DALWPVLTRK PEDHPVRGSA LPLAHPYVVP GGRFAELYYW DSYFTMLGLA ATGRSELVQC    180
MTDNFARLID AFGFVPNGTR TYYLSRSQPP LFAAMAELGA LVGGPPVSHY LPQLLQEHAW    240
WMDGLHVLHP GEARRVVAL PGGEILNRYW DDRDTPREES WREDIETASA VDRPSADVYR     300
DLRAAAESGW DFSTRWLRAP DAANPASLHL SQICTTDLLP VDLNAFLYRM EVSIAKASQS    360
AGDRATATHF HDLAAHRREA VNRLMWNEAE GAYFDYDWRR GELRGCLTAA TVVPLYAGMA    420
TEAQAAAVAR AVRTHLLAAG GLATTVCSSD QQWDRPNGWA PLQWMAVRGL ERYGHKDLAL    480
EVRQRWIETV RSVYQREGKL VEKYAVGNGD GAPLCGGGGG EYPLQDGFGW TNGVVQCWLD    540
PRYDTYAAAQ TVYYGPTDDG TADSLPEA                                      568

SEQ ID NO: 192         moltype = AA   length = 529
FEATURE                Location/Qualifiers
source                 1..529
                       mol_type = protein
                       organism = Xanthomonas arboricola
SEQUENCE: 192
APMDTPVVNA PAATPPTPDL AYPELFQAVQ SGELFDDQKH FVDFLPLRDP ALINADYLAQ    60
HDHPGFDLRK FVDANFEESP PVQTDAIRQD TALREHIDEL WPKLVRSQTH VPPYSSLLAL    120
PHPYVVPGGR FREVYYWDSY FTMLGLVKSG ETTLSRQMLD NFAYLIDTYG HIPNGNRSYY    180
LSRSQPPFFS YMVELQAGVE GEAVYQRYLP QLRKEYAYWM QGSEDLQPGQ AARHVVRLAD    240
GSLLNRYWDE RDTPRPEAWL HDTRTAAEAG DRPAAEVYRD LRAGAESGWD YTSRWLADGQ    300
NLRTIRTTAI VPIDLNSLLY HLERTLAQAC AQPGAECAQD YAALALRRKQ AIDAHLWNAA    360
GYYADYDWQT RKLSDQVTAA ALYPLFTGLA TDAHAKRTSA TVRARLLRPG GLATTAVKTG    420
QQWDEPNGWA PLQWVAVDGL RRYGEDALAR TIGERFLTQV QALFAREHKL VEKYGLEADA    480
AGGGGGEYAL QDGFGWTNGV TLMLLNLYPD TATKPAPAKR ARKPEAAAR                529

SEQ ID NO: 193         moltype = AA   length = 540
FEATURE                Location/Qualifiers
source                 1..540
                       mol_type = protein
                       organism = Kosakonia sacchari
SEQUENCE: 193
AEAQNTPQPP DILLGPLFSD VQTAKLFPDQ KTFADAVPKG DPLMILADYR MQRMQTSFDL    60
RHFVDVNFTL PKEGEKYVPP EGQNLREHID GLWPVLTRTT DSAGKWDSLL PLPKPYVVPG    120
GRFREVYYWD SYFTMLGLAE SGHWDKIEDM VTNFAHEIDT WGHIPNGNRS YYLSRSQPPF    180
FSLMHDGEAL KTW LPQMEKEYQY WMEGADTLQP GQANKRVVKL SDGSVLNRYW           240
DDRDTPRPES WLDDVTTAKN NPNRPATEIY RDLRSAAASG WDFSSRWMDD PNQLGTIRTT    300
SIVPVDLNAL MFKMEKMLAR GYQAAGDSAK ASQYDALANA RQKGIEANLW NEKEGWYADY    360
DLKTKKVRNQ LTAAALYPLF VNAAAKDRAD KVASAAKERL LKPGGIATTT VNSGQQWDAP    420
NGWAPLQWVA TAGLQNYDQQ KLAMEVSWRF LTNVQHTYDR EKKLVEKYDV STTGTGGGG     480
EYPLQDGFGW TNGVTLKMLD QICPKEKPCD SVPQTQPAQQ PAAKVEPTSQ PSKQQQAVAQ    540

SEQ ID NO: 194         moltype = AA   length = 532
FEATURE                Location/Qualifiers
source                 1..532
                       mol_type = protein
                       organism = Enterobacter sp.
SEQUENCE: 194
DEQPAFQKNS PDILLGPLFN DVQSAKLFPD QKTFADAVPK SDPLMILADY RMQHTQSSFD    60
LRHFVEMNFT LPAEGEKYVP PAGQSLREHI DDLWPVLTRT TDKASNKWDS LLPLPKPYVV    120
PGGRFREVYY WDSYFTMLGL AESGHWDKIS DMVDNFAWEI DTFGHIPNGN RSYYLSRSQP    180
PFFSMMVELL ATHDSDALKK YRPQMEKEYA YWMEGVDSLQ PGQANQRVVK LDDGSVLNRY    240
WDDRDTPRPE SWLDDVNTAK NNPNRPATEI YRDLRSAAAS GWDFSSRWMD DPQKLGTIRT    300
TSIVPVDLNA LMFKMEKLLA RASQEAGDSA AASKYEALAT ARQKAIENHL WNDKEGWYAD    360
YDLKSKKVRN QLTAAALFPL YVKAASQERA DKVAAATSAR LLKPGGITTT TINSGQQWDA    420
PNGWAPLQWV ATEGLQNYGQ NKVAMDVTWR FLKNVQHTYD REKKLVEKYD VSTTGTGGGG    480
GEYPLQDGFG WSNGVTLKML DLVCPKEKPC DSVPENQPAA NDEAAPVKAS AQ            532

SEQ ID NO: 195         moltype = AA   length = 720
FEATURE                Location/Qualifiers
source                 1..720
                       mol_type = protein
                       organism = Saitozyma flava
SEQUENCE: 195
```

```
QNPASSSSFS PTPVTTMVPS PTAALNATVP GQGVYPPLQA WCNNGGNDTF CPGVLLQDVQ    60
LSGIFPDSKT FVDKPTRGTL NETLRTFASL GNNLTVGQIE GFVNNSFKGE GLELSQVALE   120
GFNPNPAFLD TISDPIYQGW MSVVNSYWTL LIRETNRSAL CNGDCESSLI PLNNTIVVPG   180
GRYREIYYWD SYWILIGLLE SELTAYATDL ISNFMDFIQT YGFIPNGGRK YYLNRSQPPV   240
FTQMLNTYVQ RTGNTSILAR GLPLAHQELV WWENNRVISV TSPYSNITRR VAHFAVNNTA   300
PRPEGYVEDY ETAFGASPAL NETARGQLYS DLAAGAESGW DYSSRWCKQP VINLTDNFPA   360
LRTINTAKII PVDLNSLLAG DHTLLANLYE LYGNSSNANT SVTSNSSQLV PYHRQLAKNY   420
SDAVLDLHWD AQKAWFYDFN LTANARADIY HPGGTFALWQ NITPPAVASN ETYALEVVSG   480
ARFLLGKYTS IPSVSTLIET GLNWDFPNSW PPHVYSSIKA FETLGRAFPN ASVLSNISIP   540
FSDVQKNQLG LDESAIPAQP ASTIGNSTSQ IAEAQGKPWP QALSIEYANR YMQAAFCSWY   600
STGGSIDGLL TQLPLSELNM TGTFQAGTTG VMFEKFNVTD LDAAGGGGEY KVQIGFWTN    660
GVALWLGANF GQYLPQPTCP LIPIIEVQNG MNSSVYQNGT MTNSTKTQSY IFQGHRIPRK   720

SEQ ID NO: 196          moltype = AA  length = 723
FEATURE                 Location/Qualifiers
source                  1..723
                        mol_type = protein
                        organism = Phaeotremella skinneri
SEQUENCE: 196
QTPTSSSSSS FSATPVSTSV PSPTVPLNSS VIGQGLYPPA QAWCNGGMND TFCPGVLLQD    60
VELSGIFADS KTFPDKPTVG TLNSTLQAFA ALPANVTVGE IETFVNQYFK GEGLELEQVA   120
IEGFVANPAI LNNITDPVFK GWVSTVNGYW QLLIRQTNES SLCNETSCAS SLIPLNHTIV   180
VPGGRYREIY YWDSFWILQG LLKSELYTYS WDLLQNFMDL IETYGFLPNG GRKYYLNRSQ   240
PPVFIQMLDA YIKVTGNSSI LARALPIATT ELAWWSSNRT IPVTSPYTGI THLVAHYAVT   300
NSAPRPEGYV EDFTTAMGAS PALNDSARAE LYSELASGAE TGWDYSSRWC RQPLLNLTDN   360
NPALRTLNVK AIIPVDLNSL LAGDHALLAN LYDLYSNSSS SNSTSNSSSI SNSSSQAAYH   420
RQAAQNLTAA ILDLHWSPSK SFFYDFNTSS NSQSDIYTPA SLFPLWQNIT PPALVGNETA   480
ALQLVSGVRY LLGKYAGIPS VATLLATGLN WDFPNSWPPH VYTSIKAFQT LYRVNPNATV   540
LSNLTLSFAQ VQAGQLGLSE TGFQIQPAST VGNTSLETAE AKGKPWPVAL GIEYANRYMQ   600
SAFCSWYSTG GEISGVLTQL PLSDLNSTGT FTAGQTGVMF EKFNVTDPDA AGGGGEYTVQ   660
TGFGWTNGVV LWVAGEFGSL LPAPTCPLIP IIEISGSSNS SIYANGTVTN STALYRGYKI   720
PRK                                                                 723

SEQ ID NO: 197          moltype = AA  length = 663
FEATURE                 Location/Qualifiers
source                  1..663
                        mol_type = protein
                        organism = Trichoderma asperellum
SEQUENCE: 197
LYTNGSVIAP CDSPIYCHGD ILQDIQLAHP FSDSKTFVDM PAKRPLREIQ SAFNNLSKPL    60
TNDSSLQVFL ETYFADAGGE LVEVPRSSLT TNPAFLNKIN DTVIREFVTK VIDIWPDLTR   120
RYSGAVGNCS TCPNSFIPVN RTFVVAGGRF REPYYWDSYW IIEGLLRTGG AFVGIAKNTI   180
ENFLDFIDRF GFIPNGARLY YLNRSQPPLL SQMVRIYIEH TNDTSILKRA LPLLVKEHDF   240
WIRNRTISVN IANKTYTLQQ YAVQNTQPRP ESFLEDYVTA NNRSYYATSG IIYPENKHLN   300
STEMADLYAN LATGAESGND YTSRWLANPS DAINDVYFPL RSLNNKEIVP VDLNSILYGN   360
ELTISQFYNR TGDATAARAW AERAANRSAA IQAVFWNETL FSYFDYNLTS SSQYVYVPAD   420
KDTISLDRQT APSGKQVFFH VGQFYPFWTG AAPDYVKNNP YAVTRAYDRV TGYLDAQPGG   480
IPASNVQTGQ QWDPNVWPP HMHILMQGLN NVPATFTAQD PSYQDIQNLS LRLGQRYLDF   540
TFCTWLATGG STSETPKLHG LSDQDVGIMF EKYDDNSTNA AGGGGEYEVV EGFGWTNGVL   600
LWTADTFGNK LKRPQCGNIT AGHPAPASSS SKRSAVQLDA WDARRVKKFG KRTEGRVKRP   660
FLF                                                                 663

SEQ ID NO: 198          moltype = AA  length = 674
FEATURE                 Location/Qualifiers
source                  1..674
                        mol_type = protein
                        organism = Corynascus sepedonium
SEQUENCE: 198
LYINGSVTAP CDSPIYCQGE LLKAVELARP FVDSKTFVDM PTIKPVDEVL AAFSKLSLPL    60
SNNSELNAFL YENFAQAGHE LEEVPDSELE TDAKFLDKLE DRTIKEFVGK VIDIWPDLTR   120
RYAGPSNCTE CANSFIPVNR TFVVAGGRFR EGYYWDSYWI VEGLLRTGGA FTHISKNIIE   180
NFLDFVDTIG FIPNGARIYY LNRSQPPLLT LMVKSYVDYT NDTSILDRAL PLLIKEHEFF   240
MNNRTVSITG SNGKEYTLNR YHVENNQPRP ESFREDYIIA NNGSYYASSG IIYPVKTPLN   300
ETEKAALYSN LATGAESGWD YTSRWLGVPS DAARDVYFPL RSLNVRDIVP VDLNSILYQN   360
EVIIAEYLEK AGNSSAAKRF ATAAEQRSEA MYSLMWNATH WSYFDYNLTD NTQHIFVPAD   420
EDTAPQDRIE APPGQQVFFH IAQLYPFWTG AAPASLKANP LAVQQAYARV ARMLDIKKGA   480
IPATNYRTGQ QWDPNVWPP LQHILMKGLL NTPATFGKSD PAYQSVQNLA LRLAQRYLDS   540
TFCTWYATGG STSDFPQLEG VTPGATGVMF EKYADNATNV AGTGGEYEVV EGFGWTNGVL   600
IWAADVFGNK LKRPDCGNIT AAHTSSSAKR GLEENKLPRR AVELDPWDAA WTKMFGRSKL   660
RRREAEDVRK RWMS                                                     674

SEQ ID NO: 199          moltype = AA  length = 674
FEATURE                 Location/Qualifiers
source                  1..674
                        mol_type = protein
                        organism = Myceliophthora thermophila
SEQUENCE: 199
LYINGSVTAP CDSPIYCHGE LLKGVELAHP FVDSKTFVDM PTLKPVDEVL AAFSKLRQPL    60
SNNSELNNFL AEYFAPAGHE LEEVPKGELQ IDPKFLNKLE DRTIKEFVSK VIDIWPDLTR   120
```

```
RYAGPGDCSG CANSFIPVNR TFVVAGGRFR EPYYWDSYWI LEGLLRTGGA FTQISKNIIE     180
NFLDFIDTIG FIPNGARIYY LNRSQPPLLT RMVKSYVDYT NDTSILERAL PLLIKEHDFF     240
TNNRSVSVTA SNGKTYTLHR YHVENNQPRP ESYREDYITA NNGSYYAASG IIYPVKTPLN     300
ETEKAVLYSN LASGAESGWD YTARWLRVPD DAARDVYFPL RSLNVREMVP VDLNSILYEN     360
EVIIAEYLEK AGNSSEAKRF ASAAKQRSEA MYNLMWNATH WSYFDYNLTS NAQNIFVPAD     420
EDTASFDRYA APPGQQVLFH VAQLYPFWTG AAPAHLKSNP LAVQKAYARV SRRLDTKKGA     480
IAATNYRTGQ QWDQPNVWPP LQHVLMQGLL NTPATFGESD PAYQGVQKLA LRLAQRYLDS     540
TFCTWYATGG STSDFPQLQG VSPDATGIMF EKYADSATNV AGGGGEYEVV EGFGWTNGVL     600
IWAADVFGNK LKRPDCGNIT AAHTSEAKR  SLGDGGLARR AVELDPWDAA WTKMFGRSKL     660
RRREAEDVRK RWSS                                                      674

SEQ ID NO: 200          moltype = AA  length = 661
FEATURE                 Location/Qualifiers
source                  1..661
                        mol_type = protein
                        organism = reesei GH37
SEQUENCE: 200
LYINGSVIAP CDSPIYCHGD ILREIELAHP FSDSKTFVDM PAKRPLSEIQ TAFANLPKPL      60
RNDSSLQTFL ASYFADAGGE LIQVPRANLT TNPTFLSKIN DTVIEQFVTQ VIDIWPDLTR     120
RYAGDAAVKN CSSCPNSFIP VNRTFVVAGG RFREPYYWDS YWIVEGLLRT GGAFVGIARN     180
TIDNFLDFIE RFGFVPNGAR LYYLNRSQPP LLSRMVKVYI DHTNDTAILR RALPLLVKEH     240
EFWTRNRTVD VRVNNKTYVL NQYAVQNTQP RPESFREDFQ TANNRSYYAA SGIIYPATKP     300
LNESQIEELY ANLASGAESG NDYTARWLAD PSDAMRDVYF PLRSLNNKDI VPVDLNSILY     360
GNELAIAQFY NQTGNTTAAR EWSSLAANRS ASIQAVFWNE TLFSYFDYNL TSSSQNIYVP     420
LDKDAVALDR QTAPPGKQVL FHVGQFYPFW TGAAPEYLRN NPFAVTRIFD RVKSYLDTRP     480
GGIPASNVNT GQQWDQPNVW PPHMHILMES LNSVPATFSE ADPAYQDVRN LSLRLGQRYL     540
DFTFCTWRAT GGSTSETPKL QGLTDQDVGI MFEKYNDNST NAAGGGGEYQ VVEGFGWTNG     600
VLLWTADTFG SQLKRPQCGN IMAGHPAPSK RSAVQLDMWD ASRVKKFGRR AEGRMGTLHA     660
W                                                                    661

SEQ ID NO: 201          moltype = AA  length = 670
FEATURE                 Location/Qualifiers
source                  1..670
                        mol_type = protein
                        organism = Chaetomium virescens
SEQUENCE: 201
LYINGSVTAP CDSPLYCQGE ILKAIELARP FSDSKTFVDM PTIKPLEEVI AAFGRLKQPL      60
SNNSELTAFL AENFAPAGGE LEEVPKSELH TDPVFLNKLD DAVVKEFVGK VIDIWPDLTR     120
RYAGPGNCSN CENSFIPVNR TFVVAGGRFR EPYYWDSYWI VEGLLRTGGA FVGITKNILE     180
NFLDFIETIG FVPNGARIYY LNRSQPPLLT KMIKIYVDHT KDTSILQRAL PLLIKEHEWW     240
TNNRSVTVTG PNGKTYTLNR YHVNNNQPRP ESFREDYITA NNGSYYATSG IIYPVKSPLN     300
ETEKDETYAN LATGAESGWD YTARWLRTPN DAAKDVYFPL RSLNVRNMIP VDLNSILYQN     360
EVIIGEYLEQ AGNKSEAQRW FQAANQRSEA MYALMWNATH WSYFDYNLTS NSQYIFIAND     420
EDATTAEQAN SPPGQQVLFS ISQLYPFWTG AAPDQLKKNP LAVQQAYYRI ERMLNEKAGA     480
IPSTNFRTGQ QWDEPNVWPP LQHILMQGLL NTPATFGTAD PAYAAVQNLA LRLAQRYLDS     540
TFCTWYATGG STSQTPQLQG VSPGATGIMF EKYADNATNV AGSGGEYEVV EGFGWTNGVL     600
IWAAETFGNK LKRPDCGDIQ AAHTDKKK   RWSVDGEVRA RERMAVELDP WDAKWTKMFG     660
QAKGRVGRRS                                                           670

SEQ ID NO: 202          moltype = AA  length = 508
FEATURE                 Location/Qualifiers
source                  1..508
                        mol_type = protein
                        organism = Rhodothermus marinus
SEQUENCE: 202
QDRVACQVPL PSVERIEAVR AYIRQSWDVL TRSHRDLLAA VQDPKIEHEP GTPWPLYIAA      60
TEDSVAVWHR LQQELPDSVL QQIVLRVLPE DPVAHLDEIH PHGLLYLPEP YVVPGGRFNE     120
MYGWDSYFIV VGLLRDGRVD LAKAMTDNHL YQVRHYGKVL NANRTYYLTR SQPPFLSAMV     180
LAVYAHTQDR DWLAAAVPLI ERYYAYWTTP PHLAGETGLS RYYDLGEGPA PEVVAGERDA     240
QGRTHYDRVR EYYRMHEVTA YDESLYYAE  ADSLTPLFYK GDRSMRESGF DPSNRFGPFS     300
VDIIHYAPVG LNALLYRMET DLARIHEILG DTAAAAAWRA RAEARRERVD RYLWDSERGL     360
YFDYNFRTGR RSDYVFATTF YPLWVGMASP EQAARVAANL YLLEAPGGLL TSTHISGSQW     420
DAPYGWAPLY LIAVEGLRRY GYDEAADRLT AKFVSMIVED FERTGVILEK YDVVQRRSDV     480
ALRYGYTSNE IGFGWTNAVF AELLAQMD                                       508

SEQ ID NO: 203          moltype = AA  length = 674
FEATURE                 Location/Qualifiers
source                  1..674
                        mol_type = protein
                        organism = Myceliophthora sepedonium
SEQUENCE: 203
LYINGSVTAP CDSPIYCQGE LLKAVELARP FVDSKTFVDM PTIKPVDEVL AAFSKLSLPL      60
SNNSELNAFL YENFAQAGHE LEEVPDSELE TDAKFLDKLE DRTIKEFVGK VIDIWPDLTR     120
RYAGPSNCTE CANSFIPVNR TFVVAGGRFR EPYYWDSYWI VEGLLRTGGA FTHISKNIIE     180
NFLDFVDTIG FIPNGARIYY LNRSQPPLLT LMVKSYVDYT NDTSILDRAL PLLIKEHEFF     240
MNNRTVSITG SNGKEYTLNR YHVENNQPRP ESFREDYITA NNGSYYASSG IIYPVKTPLN     300
ETEKAALYSN LATGAESGWD YTSRWLGVPS DAARDVYFPL RSLNVRDIVP VDLNSILYQN     360
EVIIAEYLEK AGNSSAAKRF ATAAEQRSEA MYSLMWNATH WSYFDYNLTD NTQHIFVPAD     420
EDTAPQDRIE APPGQQVFFH IAQLYPFWTG AAPASLKANP LAVQQAYARV ARMLDIKKGA     480
```

```
IPATNYRTGQ QWDQPNVWPP LQHILMKGLL NTPATFGKSD PAYQSVQNLA LRLAQRYLDS    540
TFCTWYATGG STSDFPQLEG VTPGATGVMF EKYADNATNV AGGGGEYEVV EGFGWTNGVL    600
IWAADVFGNK LKRPDCGNIT AAHTSSSAKR GLEENKLPRR AVELDPWDAA WTKMFGRSKL    660
RRREAEDVRK RWMS                                                     674

SEQ ID NO: 204           moltype = AA   length = 657
FEATURE                  Location/Qualifiers
source                   1..657
                         mol_type = protein
                         organism = Moelleriella libera
SEQUENCE: 204
LHTNGSLIAP CDSPIYCYGD ILKQVELARP FADSKTFVDM PGVKPLAEIQ AAFDKLEKPL     60
RNNTALQDFL KTYFADAGQE LQEVPKSELK TDPQFLKTLN DTVIREFVTK VIDIWPDLTR    120
SYKGSNTNCT DCPNSFIPIN RTFVIAGGRF REPYYWDSYW ILEGLLRTRG SFTQIAKNTL    180
ENFLDFVEQF GFVPNGARIY FLNRSQPPML SQMVKLYIDH TNDTAILQRA LPLLVKEHAW    240
WMNNRTVDVQ VGGKTYKLNR YAVSNTEPRP ESYREDFETA SNSSYYAQSG IIYPETKKLN    300
DSQRAVLYAN MATGGENGWD FSSRWIANPS DSVRDVYFPL RTNNAQNVVP VCLNSILYGN    360
EMTIGGFFNS TGNTTAGQEW AAKAKARSEA MHATMWNETH FSYFDYNLTS SAQDVYTLAD    420
DDTSIYDNGT LTGAPPGYQV AFNGAQFYPF WQGAAPTYLK ENPQAVKTAY ARVAQYLKVR    480
KGGIPATNLK AREQWDQPNV WPPLMHILMQ GLLNTPPTFG SSDPSYKSVR SMALTLAQRY    540
LDSTFCTWYA TGGSTSETPK RPGLPEKDKG IMFEKYADNS IDIAGSGGEY EVVEGFGWTN    600
GVLIWAADTF ANELKRPDCG NGSSSSSTSS AAKRGLSAVE LHPADASRIK RFGSSKG       657

SEQ ID NO: 205           moltype = AA   length = 660
FEATURE                  Location/Qualifiers
source                   1..660
                         mol_type = protein
                         organism = Acremonium dichromosporum
SEQUENCE: 205
IYVDGNITAP CDSPVYCYGE MLHQIQLAKP FDDSKTFVDM PALKPLSQIQ AAFDRLDKPL     60
SNNSALNNFL DEFFADAGGE LSEVDKADLE TDPVFLDKID DEVVKEFTNK VIDIWPDLTR    120
RYSGAAASNC TNCPSSFIPL NRTFVVAGGR FREPYYWDTY WIIEGLLRTG GSFTDISRDI    180
IENFLDFVDQ FGFVPNGARI YYLNRSQPPV LSRMVQAYIE HTNDTDILDR ALPLLMKEHE    240
FFSENRTIDI EGPNGTTYTL NRYDVRNNQP RPESYSEDYE TATNTSYYSH DSGIIYPETE    300
PLNDTERANL YSALASGAES GWDYSSRWIA RPRDAAEDVY FPLRSLNTNN IVPVDLNSIM    360
YANEMAIAGF LNQTGNASAA AEWEELAYNR SEAIHALMWN ETYMSYFDYN LTSAAQHIYV    420
PADDDVSTLE SSTAPEGHMV LFSVSQFYPF WTGAAPSYIK NNPFAIAQIY KRVETLLDTR    480
KGGIPATNFR TGQQWDQPSV WPPLMHILMA GLQNTPATFG EDDPAYQHVH EIALRIGQRY    540
LDSTFCTWRA TGGATSETPQ LEGFTDRDVG IMFEKYADNS TNIAGGGGEY EVVEGFGWTN    600
GVLIWTVDEF GNELKRPDCG DLEAADTTER RKRSALQLAP RDAQRTKKFG KRAVERQPWF    660

SEQ ID NO: 206           moltype = AA   length = 667
FEATURE                  Location/Qualifiers
source                   1..667
                         mol_type = protein
                         organism = Fusarium sambucinum
SEQUENCE: 206
LYVNGTVVAP CDSPIYCHGD ILEQVELARP FSDSKTFVDM PAIRPLSEIQ KAFDELDKPL     60
RNNSALADFL SENFADAGNE LEEVPEDELK TDPKFLDNIN DTVIREFTEK VIDIWPDLTR    120
RYDQDSKNCS DCPNSFIPVN RSFVVAGGRF REPYYWDSYW IIEGLLRTGG SFVNIAKNTI    180
ENFLDFIEEY GFVPNGARIY YLNRSQPPLL SQMVKIYIDH TNDTDILERA LPLLVKEHEF    240
FMKNRSVPVY INDETYMLNT YNVSNTQPRP ESYREDYITA TNKSYYSTSG EVYSGGEELS    300
FKQKETLYGN LASGAESGLD YTSKWIARPE NAIRDNYFPL RYLNTRNIIP VDLNSILYGN    360
EIAIADFYEQ TGNSSASEQW REVAANRSYA MHAFMWNETL WSYFDYNLTS KAQQIYFPAD    420
NNTVSVDTED APKGQQVFFS PTQFYPFPWLG AAPDYLKNAY YAVLSAYKRV ATYLDKREGG    480
IPASNIETGQ QWDQPNVWPP MMHILMAGLE KVPATFGIMD PSFIEIRKLA LRLGQRYLDS    540
TFCTWYATGG STSETPKLES VSDKEDGIMF EKYADNATNT AGGGGEYEVV EGFGWTNGVL    600
IWAVEEFGNR LTRPKCKNLE TAHSSDKRDT SAVMLHARDA KHVKKFGRRK RAEEKAAKKR    660
SSRLFHF                                                             667

SEQ ID NO: 207           moltype = AA   length = 660
FEATURE                  Location/Qualifiers
source                   1..660
                         mol_type = protein
                         organism = Phoma sp.
SEQUENCE: 207
LYQNGSIIAP CDSPIYCYGD LLREIELAQP FSDSKTFVDL PTIRPLDEVL RAFNNLTKPI     60
QNNTELNNFL TTYFGEAGSE LDALPKDQLE TQPDFLDNNN SSVIVNFTSQ VIDIWPDLTR    120
RYVGAGNCTG CVSSFIPVNR TFVVAGGRFR EPYYWDSFWI IEGLLRTKGS FTQIAENIIE    180
NFMDLVEELG FVPNGARRYY ENRSQPPLLT QMVRVYEYT QNYTLLERAL PVLEQEYEFW    240
VNNRSVTLER GGKNYTLHHY NVSNTQPRPE SYREDYITAN NLTYYNENGE QFNASHPLND    300
TQKALLYAEL ASGAETGWDY SSRWLANPSD AVNDDFFPLR SLNVINTIPV DLNSILYYNE    360
ITIAEFHRRE GNYCAARQWA ELARNRSEAM TALLWNAEYY SYPDYNLTSS AQNIYTLADN    420
TSTPLSLAGA PAGYGVGFQL SQLYPFWTGA APDSIKGDPT AIRRAFARVE EALDTEAGAV    480
SATNLFTGQQ WDEPNVWPPL QYIAIQGLLN TPLEVSEDDD EQTAEDYVWT QNLALRLAQR    540
YTDSLFCTWR STGGATEEEP QLPGATGNGT IFEKYSDEAI NARGGGGEYT VVEGFGWSNG    600
VLIWAVDNFG QKLTTPDCGN ITAAAPPSTA SKRKRSAVEI HQRDAAWIKG TKENKMFGKK    660

SEQ ID NO: 208           moltype = AA   length = 737
```

```
FEATURE                 Location/Qualifiers
source                  1..737
                        mol_type = protein
                        organism = Lentinus similis
SEQUENCE: 208
LPQAVTPSST SVSSQTVSTA VPSPTASLTS TLPSQIPLPP KQDWCPSEIF CAGELLQTVN    60
VAQLYPDPKT FVDKPTARKS QQVVSNFQNI GGNSSNVTVG AIEDFVNSNF KGEGLELEPI   120
AFANFNPTPA FLNNVSDPLV KAWSQIVHGY WTQLTRSTND SALCPEGTES GSCESSLIPL   180
NHTFVVPGGR FREQYYWDSY WIVQGLLVSE LYDIVNDTLQ NFMDELEHIG FIPNGGRIYY   240
LNRSQPPLFI HMLTSYVQAS GDTSILKRAL PLAEKELAWW SANRSVQKS PYTNATHNVY    300
RYHVTNTAPR PESYYTDYIT ANDPTLQTPL TEQQRADLYA ELATGAESGW DYSSRWLKEP   360
LAGGSNNTSP ALRSLNIRSL VPVDLNSILY KAHLNLAALY NNESHSAAAS NHTQAAIALR   420
EAILDLHWDA NKRAFYDFNI TSNARNDIFS AATFYPLWSG IIPDEILSDG SGATAFGAFA   480
AVNMVLNRYN GTFPVTFLET GLQWDAPNAW PPHQFIIIEA LRNLPSNITN TPLPSAPSGN   540
STYALIPAGQ VGIAEGDLPG QILSPGQNAT KTGPAADINT LNGTVVNGGN ATSGEGWAAV   600
LQRELANRYI ASALCSWHAT GGEVPNLLPR LSDSQLQITQ SQNNTGNMFE KFSINDIDSA   660
GRGGEYTVQA GFGWTNGVVL YLTHVFGDKL VAPSCPNLVA LSSNTATTSG AVAQMTLPSS   720
LAVTVGAVVL GFVGLVL                                                 737

SEQ ID NO: 209          moltype = AA  length = 683
FEATURE                 Location/Qualifiers
source                  1..683
                        mol_type = protein
                        organism = Diaporthe nobilis
SEQUENCE: 209
QTLDGIYYDG DNIAPCSSAL YCYGDILDSI QRAKPFADSK TFVDMPTRVP LEEVRAAYDQ    60
LTKPLQNNTE LLDFLSNNFG PAGQEVVPVD PGSLGVNASF LGGIANAVNR EFTEAVIDLW   120
PNLTRWVNES AVCAECDNSL LSIKRPFIVA GGRFREPYYW DSYWILHGLL RSGGNFTRIA   180
RNQIENFLDF VEDYGFVPNG ARVYYLNRSQ PPLLAQMVRI YIEQTGDATI LDRAIPLLIR   240
EHDFFMSNRT VHVSVGSRNY TLNRYNVANT EPPRESYYED YTQVNNASYY ANDGRVFPTR   300
NTTQAEKDLQ YKNLASGAES GWDFSTRFMR DPTIAANDTY FPLASYNIIN IIPVELNSIL   360
YWNEVTIAAF LRQQQQQVPN ATAEADADAW DARAASRSEA MYSVMWNETL GGYFDFNLTS   420
GSQDVFWARD ADSLPTEQAG TEPGQQVVFN IGQLSPFWTG AAPRSLAGDP AAVRRAFSRV   480
DEYLGSRKGG IAPTNFVSGQ QWDQPSVWPP HMHILMEALL RTAEAGGESE GGSEDWAWAQ   540
DLALRLGQRY FDSAYCTWRA TGGGTPSSPP LANPPQDLGG QMFEKYSDQS LNEAGSGGEY   600
VVVVGFGWSN GVLIWADTF RDRLQTPACG DLTTRGEAGK MREKRMSENG RHGDGSNAIS    660
AVKLDYFDAA WTSENVGGLH GVR                                          683

SEQ ID NO: 210          moltype = AA  length = 763
FEATURE                 Location/Qualifiers
source                  1..763
                        mol_type = protein
                        organism = Solicoccozyma terricola
SEQUENCE: 210
QGNSSMSASN ATSSSTGTGT SSSAAAVMTA VPMPTAPLSS PVEMLPLPPV QPWCNGGENA    60
TYCPGSLMQL VQLSGIYNDS KTFPDKPTQY NASVTYQAFD ALPVNATVGD VETFVEKYFK   120
GEGQELETVQ IQNFTQNPTF LNVIDDELYK GFVSTVNGYW SLLVRQTNES ALCTNGACES   180
SLIPLNRSFI VPGGRYREIY YWDSFWILEG LLKSELYLYA YNLLENFMDL IEKFGFLPNG   240
GRSYYLNRSQ PPVFVQMLNA YIQVTGNVSI LTRALPIAET ELQWWRTNRT ISVTSPYTGT   300
NYSVARYFVT NSAPRPEGYV EDITTAFGGN PALNESARSA LYAELASGAE TGWDYSSRWC   360
KQPLLNLTDN DPALRTLNVR QQIPVDLNSL LCGDHVLLAN LYEFYMNSTI GGGSGISSGG   420
GNSTIGMGAW ANSTSGSNMT SNSTSSSNMT GLVQSHRMIA KEFEAAINDL MWDKQKLWWY   480
DFNMTANARA DVYHPGGLFP LWQNITPSDI VGNDTAAFGV FAGVRYMVGM YPGPPAPASL   540
IQTGLNWDAP NVWPPHVYTG IKALETVLRI NPNSSVVPNI TLTDFTRIPT GQLGLNQSQL   600
PPQPASALGN GTADLDQAIA QMQKGKPWPT ALAIEFANRY LGSAFCSWYS TGGSIPGLLQ   660
QLSPQELNLT GSLTTGSQAM GNIFEKFNLT NVDAAGGGGE YTVQIGFGWS NGVILHTAGE   720
YGQYLVQPSC PLIAIHETAN ATSTNATKSN NTMVFSGYRL PHD                    763

SEQ ID NO: 211          moltype = AA  length = 734
FEATURE                 Location/Qualifiers
source                  1..734
                        mol_type = protein
                        organism = Dioszegia cryoxerica
SEQUENCE: 211
QSSSSSSFSP TPVTTAVPSA TAALNQTVSG QGVYPPLQPW CNAGENATYC PGVILQDVQL    60
SGLFPDSKTF VDKPTNGTQN ATQQAFQQLG NNITLGQLAQ FVNTSFRGEG LELSQVPING   120
FVANPAAVNK VSNPLYRGWV STVNSYWSLL IRETNQSAVC TTQCESSLIP LNYTIVVPGG   180
RYREIYYWDT FWILEGLLKS ELYTYAWDVL QNFMDFVDVY GFIPNGGRKY YLNRSQPPVF   240
IQMLDAYVKA TGNVTILERA LPLASEEMRW WINNRTTQVT SPFTGITRRV YVFNVTNSAP   300
RPEGYVEDYE AAFGAQPPLT EAQRGALYAE LATGAESGWD YSSRWCKQPV INVTDNLPAL   360
RTLNGRSIVP VDLNSLQAGN HALLARLYEV YINASTTSNT TAAQTIRANA TQEIALHKTL   420
ANDYSQAVLD LHWDPARAWF YDFNLTSNSR ESLYTPAGTF ALWQNITPPG LEGNDTAALR   480
IASGARYLLG RYGGIQGVSS LLVTGLNWDF PNSWPPHTYT SIKAFQTLGR LVGNASIVGN   540
ATIPFSQVAT NQLGLNETQL PPQDPALQGN ASLTVPSARN VSWPLALEIE YASRYMQGAF   600
CSWYSTGGSI SGLLTQLPVS QLNATGTYQA GQTGQMFEKF NATDIDAAGG GGEYTVQIGF   660
GWTNGVVLWL ADNFGQYLPQ PTCPLVVLSL TNLNSTTAGN STNGTSPAAP GNATSLVAVS   720
ELQGIWEGQR VSRD                                                    734

SEQ ID NO: 212          moltype = AA  length = 1020
```

```
FEATURE                 Location/Qualifiers
source                  1..1020
                        mol_type = protein
                        organism = Talaromyces funiculosus
SEQUENCE: 212
LPFNERVDQV LRSYEVTSKL DSRSTKPSKH GHTYQTQFLG VTWDQRNWRL QSTVLDQGHY    60
ESRGSIANGY IGLNVAGAGP LFELDSPVDG DVINGWPLFS RRQTFAGLAG FYDLQPRTNG   120
TNFPWLSQYG DDSAISGVPH WGGMVLDLGD GEYLDATVDN STISDYTTTY DYKAGVLSWD   180
YKWTPKNANG SFGISYKIFA NKLDVNQAVV QLSITPSTNG SASVVNVIDG YAAVRTDFVS   240
SGNESDVVYT AVKPNGVTNV TAWIYTALDG DDAFDISSAA LVNDKPYVHQ NDSSIAQSVN   300
VTFTAGTTIT INKFVGAAST DAFPDPQSTA REAALSARRR GFDDLFRSHI SEWAQVMPDD   360
SVDDFTLANG TLPNDTFIIE SAVMAVVNPY YLLQNTVGPN ALRRVNNAPV NDWSIPVGGL   420
TSDSYAGQIF WDADVWMQPG LVAAFPESAK RITNYRAAKY SQALENAKTA YTSSQNQTWF   480
SPDAAIYSWT SGRVGNCTAT GPCWDYEYHL NGDIGISLVN EWVVSGDNET FKNKHFPIYN   540
SIATLYGDLL KKNGSYYTLT NMTDPDEYAN NVDAGGYTMT LISQTLSNAN AFRKQFGMNE   600
NTTWTEMADN ILLIRENDVT LEYTTMNNSV AVKQADVILS TFPLDYTKNY TTSAALNDLD   660
YYALKQSPDG PGMTYAIFSI VANDVSPSGC SAYTYAQYSY DPYIRGPFFQ FSEQLLDDYT   720
INGGTHPAFP FLTGHGGANQ VVLYGYLGLR LLPDDMLHID PNLPPQIPSI KYRTFYWRGW   780
PIQAASNYTH TTIQRATTVA PLSTADPTYA NKSIHVSVGH NTVNSTTYSL SANGSALVVP   840
NRQIGSINTV AGNVVQCKSV LSTDAYQKGQ YPISAVDGAA STKWQPEFAA NISSLTVDLT   900
GSNVSSVSGF YFDWAQAPPT NITVLLHNSS SAALASSGDK PGSSAVTLNI TISNPYNAST   960
YNANIIALPS SNSTNYTFPA PVPKPRYATL FVQGNQALDE TDTKSGNGTG ATVAEWAILS  1020

SEQ ID NO: 213          moltype = AA  length = 1063
FEATURE                 Location/Qualifiers
source                  1..1063
                        mol_type = protein
                        organism = Hamigera avellanea
SEQUENCE: 213
ASPKSRINQC LKKHAGQGSH DDETSSNVYQ TRFPGVTWDE DNWSLTTSVL DQGHYQSRGS    60
VANGYLGINV ASVGPFFELD IPLNGDVING WPLYSRRQTF ATISGFFDSQ PETNGTNFGW   120
LNQYGGESVI SGVPHWSGLI LDLGDGTYLD STVDNATLSG FTSSYDFKAG VLSWSYQWTP   180
EGKHGSYDIT YRLFTNKLYV NQAVVDMEIV PTVAGKASVV NVIEGSSAVR TDFVESGEDD   240
GAIFSAVRPW GISNVTAYFY ANLTVSDNVD LSSRTLVSNK PYVSTNESSI AQSVDVQFIP   300
GKSVRITKFV GAASTDAFAN PQETAKRAAS TAQTNGYLKS LNSHIAEWAS VMPDDSVEDF   360
SLPETGKLPA DEHIIESAII SVTNTYYLLQ NTVGKNAIKA SSDAALNMDS ISVGGLTSDS   420
YAGLIFWDAD IWMQPGLVAS HPEAAEVFTN YRVAKYPQAV KNIETAFASS KNQTNFSPSA   480
AAYPWTSGRY GNCTGTGPCF DYQYHLNGDI GLSMINQWVV SGDTQTFREK HPPIYDSAAT   540
FFSNLVERNG STWTLTNMTD PDEYANHIDA GGYTMPLIAE TLLYANSFRK QFGVEPNETW   600
NEIAENVLVL RTNGVTLEFT SMNGSAPVKQ ADVVLVTYPL DYNNNYSPED SLNDLDYYAN   660
KQSEDGPAMT WAIFSVVANE ASPSGCSAYT YAQYAYYPYA RAPFFQLSEQ MIDDASINGG   720
THPAYPPLTG HGGANQVNLM GYLGLRLLPD NVIHVDPNLP PQIPHLKYRT FYWRGWPMSA   780
ASNYTHTTIQ RAVNVPALST ADQKFANVSI PVHVGPETNA TVYRLPVNGT LTIPNRQIAS   840
KNTVAGNLIQ CRPVESQNDF QPGQFPISVV DGASSTRWQP KHADNVSAVT VTFADEEVGS   900
LVSGFYFDWA QAPPVDAAVI FHNSSLENPA SAFSFASNSS SSEYSVITTL KNVEQSDPYD   960
PESDKLDIIA IPTGNTTKVT LPSAVPAARY ATLFITGNQA LGPEDIAAKN GTGATVAEWA  1020
IVGQTSSATS KRSIQTRKLQ VRSGAALSGL GFAQRRRQSA EMY                    1063

SEQ ID NO: 214          moltype = AA  length = 1020
FEATURE                 Location/Qualifiers
source                  1..1020
                        mol_type = protein
                        organism = Talaromyces ruber
SEQUENCE: 214
LPFNERVDHV LRSHDLTSRL HSRSAKPSNH GGTYQTQFTG VTWDQRNWRL QSNVLDQGHY    60
ESRGSIANGY IGLNVAGAGP FFELDTAVDG DVINGWPLFS RRQTFAGLAG FYDLQPTTNG   120
SNFPWLDQYG DDSVISGVPH WGGLVLDLGN GEYLDATVDN STISDYSTTY DYKAGVLSWH   180
YKWTPKNANG SFEIKYKIFA NKLDVNQAVV QLSITPSANG SASVANVIDG YSAVRTEFVA   240
SGNESDAIFT AVKPVGVSNV TAWIYAALDG DDAFDFSSAA LVNDKPYVHQ NDSSIAQSVN   300
VTFTAGTTIT INKFVGAAST DAFPDPQSTA REAALKARRR GFDDLFRSHI SEWAQVMPDD   360
SVDDFTLANG TLPNDPFIIE SAVMAVVNPY YLLQNTVGPN ALRRVNNAPV NDWSIPVGGL   420
TSDSYAGQVF WDADVWMQPG LVAAFPESAK RITNYRTAIY SQALENAKTA YTSSQNQTSF   480
SSDAAIYSWT SGRYGNCTAT GPCWDYEYHL NGDIGISLVN QWVVSGDNDT FKNTHFPIYN   540
SIATLYGDLL KKNGSYYTLT NMTDPDEYAN NVDAGGYTMT LISQTLSNAN AFRKQFGMDE   600
NTTWTDMADN VLLIRENDVT LEYTTMNNSV AVKQADVILS TYPLDYTKNY TTSAALNDLD   660
YYALKQSPDG PGMTYAIFSI VANDVSPSGC SAYTYAQYSY DPYIRGPFFQ FSEQLLDDYT   720
ANGGTHPAFP FLTGHGGANQ VVLYGYLGLR LLPDNVLHID PNLPPQIPSV KYRTFYWRGW   780
PIQAASNYTH TTIQRATSVA PLSTADQTYA NRSISVQVGQ NTVNSTTYSL PANGSAIVVP   840
NRQIGSINTV AGNIAQCKSV LSTDAYQPGQ YPISAVDGAA STKWQPEFAA NISSLTVDLT   900
SSNASTVSGF YFDWAQAPPT NITVLLHNSS NAPLTSSNSN GGNSTVSLNV TISNPYDASA   960
YNANVITLSS SNTTNYTFPA PVSKPRYATL FVQGNQALDE TDLKAGNGTG ATVAEWAVLS  1020

SEQ ID NO: 215          moltype = AA  length = 1055
FEATURE                 Location/Qualifiers
source                  1..1055
                        mol_type = protein
                        organism = Trichoderma lixii
SEQUENCE: 215
ATSNNRVSEC LGRNGGSSTG VHFSKNVYKT DFAGVTWDED NWLLSTTELK QGAFESRGSI    60
```

```
ANGYLGINVA SVGPFFELDT EENGDVISGW PLFSRRQSFA TIAGFWDSQP VMNGTNFPWI    120
SQYGSDTAIS GIPHWSGLIL DLGGNTYLDA TVDNRTISNF RSTYDYKAGV LSWSYKWTPK    180
GNKGSFDISY RIFANKLYVN QAVVDLQVTA SKNVEASIVN VIDGFAAVRT DFVESGEDGN    240
AIFSAVRPNG VANVTAYVYA DITGSGGVDL SSRKIVHNKP YVHANASSIA QAVPVKFSAG    300
RAVRVTKFVG GASSDAFKNP KQIAKSAAAT ALKNGYSKSL NSHVTEWAAV MPESSVDSFA    360
DPKTGKLPND NYIIDSAIIA VVNTYYLLQN TVGKNGSKAA NGAPVNVDSI SVGGLTSDSY    420
AGQVFWDADL WMQPGLLAAH PEAAERIINY RLARYGQAKE NVKTSYAGSQ NETFFSASAA    480
VFPWTSGRYG NCTATGPCWD YEYHLNGDIG LALVNQWVVN GDTKDFEKNL FPVYDSIAQL    540
YGNLLKPNGT AWTLTNMTDP DEYANHVDAG GYTMPFIAET LQNANTFRKQ FGIEQNKTWN    600
DMASNALVLR ENGVTLEFTT MNGSAVVKQA DVIMVTFPLS YTTNYTTEDA LNDLDYYANK    660
QSPDGPAMTY AFFSIVANEI SPSGCSAYTY AQYAFKPYVR APFYQLSEQI IDDSSINGGT    720
HPAYPFLTGH GGANQVVLFG YLGLRLVPDD FIHIEPNLPP QIPYLRYRTF YWRGWPISAW    780
SNYTHTTISR ASGVAALDGA DQRFAGKTIT IHSGPEESPK AYHLPVKGSV VVPNKQIGSQ    840
QTYAGNLVQC HAASSPSDYV PGQFPIAAVD GATSTKWQPA SADKLSSITV SLDQEDVGSL    900
VSGFHFDWAQ APPVNATIIF HNEAINDPAT VLKSQKHNSN YKVVSSLTNI KQSNPYIKTT    960
DLDIIAIPIG NTTNVTLSQP VAASRYASLV IVGNQGLDHA DVVGKNGTGA TVAEWAIIGH   1020
SKGHTGAPGH HGKRKLNLRA AAAMSDPDSF ARRRQ                             1055

SEQ ID NO: 216          moltype = AA  length = 1056
FEATURE                 Location/Qualifiers
source                  1..1056
                        mol_type = protein
                        organism = Aspergillus cervinus
SEQUENCE: 216
STFSHKNDRI LKGLKRHGDH YSRKSNTNST DVYQTKFDGV TWDDDNWLLT TTALDQGDFR    60
SRGSIANGYL GINVASVGPF FELDTAENGD VISGWPLFSR RQTFATIAGF FDSQPTTNGS   120
NFPWLYQYGG DSVISGVPHW SGLVLDLGND TYLDSTVDNQ TIENFTSMYD YKSGVLSWSY   180
TWVPAGNKGS FDIVYRLFAH KLNVNQAVVD MEITPSLSFN ATVVNILDGY SAVRTDFVES   240
GNDNGAIFTA VRPWGISNVT AYVYANLTGT PNVDLSSRTI VANKPYVHTN ASSIAQAVNV   300
SCSPNETVRI TKFVGAASSD AFENPQETAR QAVSSAAIGA YLRSLGTHIA EWASIFPDDS   360
VDRFTDPATG KLPANKHIIN SAIIAVTNTY YLLQNTVGKN AIQAVSGAPV NIDSISVGGL   420
TSDSYAGQVF WDADVWMQPG LAASHPEAAQ RITNFRAAKY PQALANIETA FTSSKNQTSF   480
SPSAAAFPWT SGRFGNCTAT GPCWDYEYHL NGDIGLSLMY QWIASGDTQT FRETHFPIYD   540
SIATMYSNIV ERNGSYWTLK NMTDPDEYAN QIDAGGFTMP LISQTLNYAN AFRQQFGLDV   600
NQTWSEIANN VLVLNDNGVT LEYTTMNGST VVKQADVVLD TYPLVYSNNY TSQNSLDDLD   660
YYANQQSPDG PAMTWAIFSI VANDVSPSGC SAFTYHQYSY DPYARAPFFQ LSEQLIDDAS   720
TNGGTHPAFP FLTGHGGANQ VVIFGYLGLR LLPDEAIHID PNLPPQIPHV AYRTFYWRGW   780
PISAQSNSTH TTISRAMNAS PLDTADSRFA NVSIPIYVGT ESNATVFQLP PTGPLTILNR   840
QNGFNNTIPG NVAQCRPVYS PDDYAPGQFP IAAVDGATST RWQPSSANTS SVTVTLPDTQ   900
INSPVSGFYF NWWQLPPVNA TVIFHDDLLE NPAATISSSG NSSSYRVVMT LTNIQQSSPY   960
NAQIAALDEI TIPTGNTTTV QLTNHAQTSR YATLLISGNQ GLGDTQDGVG ATVAEWVILG  1020
QGQGSSSSNS NGKRKLGARS AAALSNGWTE RRRRLI                           1056

SEQ ID NO: 217          moltype = AA  length = 1053
FEATURE                 Location/Qualifiers
source                  1..1053
                        mol_type = protein
                        organism = Rasamsonia brevistipitata
SEQUENCE: 217
LRSEARVAQV VRAYSSSTGV EAGHGNATQY ETRFPGVTWD QRHWRLKSTV LDQGHFQSRG    60
SIANGYVGIN VASAGPFFEL DTPVDGDVIN GWPLFSRRQT FATIAGFYDE QPRTNGSNFD   120
WLYQDGGESV ISGVPHWSGL ILDLGDGTYL DATVDDSTIS DYSTVYDYKA GILSWSYKWT   180
PKSSKGSFKI SYRLFAHKLN INQAVVRMEI TPSADTDATV VNVLDGYSAV RTDFVGSGKD   240
GDAVYSAVSP WEVQNVTAYV YAVLDGSDGV DLSTLSLVNG KPYVHTNESS IAQSVNVRFR   300
AGKTVTVTKF VGAASTDAFP DPQQTAREAA LAAKEEGYDA LLRSHVAEWA AVMPEESVDS   360
FTYHNGTLPG DDFIVESAIM AVVNPYYLLQ NTVGENALRE VSHAPVNEWS ISVGGLTSDS   420
YAGLIFWDAD LWMHPGLAVA FPQAATRITN YRVAKYEQAR QNAKTSFTGS KNQTWFSDSA   480
AVYPWTSGRY GNCTGTGPCW DYEYHLNGDI GLSLINEWVA SGDTKTFQES YFPIYDSIAT   540
LYADLLQQNG SHWTLTNMTD PDEYANAVDA GGYTMPLIAQ TLLYANSFRQ QFGAQPNSTW   600
TEMASNILFL RENDITLEYT TMNNSVQVKQ ADVVLTYPL EYTTNYNAGN ALTDLDYYAL   660
KQSPDGPAMT YAIFSIVANE VSPSGCSVYT YAQYSYDPYV RPPFFQLSEQ LVDDYTLNGG   720
THPAYPFLTG HGGANQVVIF GYLGLRLLPD NVIHIDPNLP PQIPQVKYRT FYWRGWPIQA   780
YSNYTHTTIG RAADVLALDT ADQRFANTTI PVQVGSGSNA ESNATVQLPIDGV LTVANRQVAS   840
TNTVAGNLAQ CQPVDSSDSY VPGQYPLAAV DGAASTKWQP SFAANVSSVT VSLPESESGT   900
LVSGFYFDWA QAPPVNATVV FHNNTVENPT RYMSSPTFVT HIDNITLSSP YNAEANPAAT   960
ILLPSSNTTN VTLAHPMPVP RYATLFITGN QALSESEVQA QNGTGATVAE WAILASNPET  1020
GSSKRNLQLR GVGRSALAGL PRRANRKERR TDV                              1053

SEQ ID NO: 218          moltype = AA  length = 1034
FEATURE                 Location/Qualifiers
source                  1..1034
                        mol_type = protein
                        organism = Acremonium curvulum
SEQUENCE: 218
LEERVSQTLN RHGVRSSYNR RADNGDQNRI SNTSHPYIYQ TSFEGVTWDS RNWRLQGTVL    60
DQGHYQSRGS IANGYFGINV ASAGPFFELD TPVDGDVING WPLFSRRQTF AGLAGFWATQ   120
PTTNGTNFPW LYQYGDESPI SGIPHWGGLV LDLGDDVYLD ATVDNKTIKN YRTTFDYKAG   180
VLTWDYTWSP KKRSGSFDI TYSLFANKLD INQAAVRLSI RPSRDTKAKV VNVLEGYAAV   240
RTDFVDSGKD GDAIYSAVRP VGVNNVTAYV YAVLDADSAV DLSSAKVIDD APYLYTNKST   300
```

```
IAQSVNVEFK ANQNVTITKF VGIASTDAFP KPRDVAKQAA FAGKRRGYDD ALRSHVSEWA    360
QVMPDDSVDD FSSDNGTLPD DGFIIESSIM AVVNPFYLLQ NTVGANALRR VNNAAVNDYS    420
ISVGGLTSDS YAGLVFWDAD IWMQPGLAAA FPEAAQRITN YRVALYPQAK RNIKTAFQSS    480
KNKTRFSDDA ALYPWTSGRW GNCTASGPCF DYEYHLNGDI GIAFVNEWIT SGDEKAFEEK    540
YPPIYDSIAT AFANLLQKNG TQWTLTNMTD PDEYANHVDA GGFTMPLISQ TLTYANLFRK    600
KFGKEENDTW ADMAENVLIL RENDVTLEYT AMNNSVEVKQ ADVVLNTFPL DYTRDYAPSA    660
ALNDLDYYAL KQSPDGPAMT YAIFSIVANE VSPSGCSAYT YAQYSYSPYL RGPFHQLSEQ    720
LTDDFTTNGG THPAYPFLTG HGGANQVVLF GYLGLRIVPD DKIHVDPNLP PQIPQVKYRT    780
FYWHGWPIAA KSNYTHTTIS RATTIKELDT ANKKYANASI QVVVGSGKSA KTYKLPANGS    840
SIVVANRKIG TVNTLEGNMI QCQPAQSFDT FVPGQFPISI NDGAASTKWQ PEFANNISAV    900
TVTVPASKSK KISGFYFDWA QAPPTNATVV LHDEKMDNPT MVLLPVSKDD DKKGSVARVN    960
VTISEPWSAK DKSNFVIGLQ GGNTTNFTFS EPVAAKRYAT LFIQGNQALD KVDIKYKNGT   1020
GATVAEWGIL SDDA                                                    1034

SEQ ID NO: 219          moltype = AA   length = 1015
FEATURE                 Location/Qualifiers
source                  1..1015
                        mol_type = protein
                        organism = Talaromyces piceae
SEQUENCE: 219
ARVDQVLQAR DTHHPSLHSS SSYQTRFDGV TWDQRNWRLQ SRVLDQGHYQ SRGSVANGYL     60
GINVASAGPF FELDTPVDGD VINGWPLFSR RQTFAGLAGF YDRQPTTNST NYGWLNQYGD    120
ESVISGIPHW SGLVLDLGDG HYLDATVDSS TISDYTTTYD FKAGVLSWDY NWAPRQHGGG    180
NSSFHISYQL FAHKLDINQA VVKLSITPSA SGNASVVNVI DGYSAVRTEF VKSGTDGDAV    240
YSAVSPVGVS NVTAWVYTVL DGDEAFNLSS AQLVTGKPYV YQNDSSIAQS VNVEFRAGET    300
VTITKFVGAA STDAFADPRQ TARDAALLAK KKGFDDLLRS HVSEWAQVMP DGSVDDFTRE    360
DGTLPDDEFI IESAVTAVVN PFYLLQNTVG KNALQRVSNA PVNDWSIPVG GLSSDSYAGL    420
IFWDADVWMQ PGLVAAFPES AQRITNYRAA MYRQARANIQ SAFASSQNKT VFSPDGAIYP    480
WTSGRYGNCT GTGPCFDYEY HLNGDIAISL VNQWVVSGDT ETFKNEHFPI YDSIATMYAD    540
VLKKNGSFYT LTNMTDPDEY ANNKDAGGFT MPLIAKTLLN ANDFRKQFNM EENSTWNEKA    600
ASVQILREND VTLEYTTMNN SVAVKQADVV LMTFPLDYTA NYSSSSALND LDYYALKQSP    660
DGPGMTYAIF SIVANQVSPS GCSAYTYAQY SYYPYARAPF FQLSEQLLDD YTANGGTHPA    720
YPPFLTGHGGA NQVVLYGYLG LRLVPDETLY IDPNLPPQIP QVKYRTFYWR GWPIQAASNY    780
THTTIRRATT VAPLDTADEK YTDEAITLHV GQQSDGNKYQ LPADGTPVTV ANRRVSSVNT    840
VKGNMIQCQP VQSTASIQPG QFPIAAVDGA ASTKWQPEFA ANASSLTVEI PSSGKKRKTV    900
SGFFFDWAEA PPTNATVVLH NNPVSEPTLS SFEAGKDGVV LRAFDIEISS PYNASTYADE    960
IIIPQGNSTN YTFSHPVPAP RFATLFVQGN QALDKVDVEN KNGTGPMVAE WVILE        1015

SEQ ID NO: 220          moltype = AA   length = 1022
FEATURE                 Location/Qualifiers
source                  1..1022
                        mol_type = protein
                        organism = Penicillium sp.
SEQUENCE: 220
LPLEERVDRV LRSYSVGSGL EARHSKYTYQ TQFDGVTWDQ QNWRLESTVL DQGHYSSRGS     60
IANGYIGLNV AGAGPFFELD APVDGDVING WPLFSRRQTF AGLSGFYDVQ PTTNGSNYPW    120
LDQYGFDSVI SGIPHWGGLV LDLGNGDYLD ATVDNSTISD YTTTFDYKAG VLSWDYNWTP    180
KNTSFGISYK IFSSKLDINQ AVVQLSITPS ANGTASVANV IDGYAAVRTE FVTSGNDSDA    240
LFTAVKPTGI NNVTAWIYAV LDGDDAFDFS SATLVNNKPY INQNDSSIAQ AVDVEFTADS    300
TVTITKFVGA ASTDAFADPQ KTAKDAALAA RIKGFEDLLR SHVSEWAQVM PDDSVDDFSL    360
ADGTLPDDIF IIESSMVAVV NPYYLLQNTV GENALRRVND APVNIWSIPV GGLTSDSYAG    420
QIFWDADLWM QPGLVAAFPE SAKRISNYRV AKYPEALANT NTSFAGSQNH TTFSSDAAIY    480
SWTSGRYGNC TATGPCWDYE YHLNGDIGIS LVNQWVTSGD TETFQNDLFP IYNSVATLYA    540
DLLKLNGSYY TLTNMTDPDE YANNVDAGGY TMTLISKTLS NANAFRKHFG LDQNSTWTEM    600
AENVLVIREN DVTLEYTTMN NSVAVKQADV VLSTFPLDYT MNYTTSDAVN DLDYYALKQA    660
SDGPGMTYAI FSIVADKVSK SGCSAYTYAQ YSFDPYIRSP FFQFSEQLDD DYTTNGGTHP    720
AFPPFLTGHGG ANQVVLYGYL GLRLLPDNVL HIDPNLPPQI PSVKYRTFYW HGWPIQANSN    780
YTHTTIRRAT TTAPLSTADQ TYSNTSITVQ VGTSNGTTYS LRVDGTPLTI KNRRIGSVQT    840
ISGNIAQCQP VQSPDSYEPG QYPLSVVDGA SSTKWQPESA ANISSVTVTL GSSYSPGNSS    900
NATASSILGF YFNWAQAPPD NITVVLHNAS IPYLNASLSS LSNTTTTTSL NITVSNPYDS    960
SADEKIIVLP SSNTTNYTFP SPVPVPRFAT LFIQGNQGLD QTDLEYGNGT GATVAEWAIL   1020
SA                                                                 1022

SEQ ID NO: 221          moltype = AA   length = 1020
FEATURE                 Location/Qualifiers
source                  1..1020
                        mol_type = protein
                        organism = Talaromyces aurantiacus
SEQUENCE: 221
LPFQDRVDQV LRSYSAKTLD IRSAKSSSKH GNTYETQFPG VTWDQRNWRL QSTVLDQGHY     60
ESRGSIANGY IGLNVAGAGP FFELDTPVDG DVINGWPLFS RRQTFAGLAG FYDLQPTTNG    120
SNFPWLDQYG DDSAISGVPH WGGLVLDLGD GQYLDATVDN STVSDYKTTY DFKAGVLSWD    180
YKWTPKSSNV SFGISYKVFA NKLDVNQAVV QLSITPSANG SASVVNVIDG YSAVRTDFVS    240
SGNESDAIYT AVKPLGVSNV TAWIYATLDG DDAFDFSSAT IVNNKPVYHQ NDSSIAQSVN    300
VTFTAGTTVT INKFVGAAST DAFPDPRSTA KEAALAGRRR GYDDSFRAHI SEWAQVMPDD    360
SVDDFTLANG TLPNDTFIIE SAVMAVVNPY YLLQNTVGPN ALRRVNNAPV NDWSISVGGL    420
TSDSYAGQVF WDADVWMQPG LVAAFPESAK RITNYRAAIY SQALANAKTA YTSSQNQTSF    480
SSDAAIYSWT SGRYGNCTAT GPCWDYEYHL NGDIGISLVN QWVASGDNET FKNTHFPIYN    540
SIATLYGDLL KKNGSYYTLT NMTDPDEYAN NVDAGGYTMT LISQTLSNAN AFRKQFGMDE    600
```

```
NTTWTEMADN VLLIRENDIT LEYTTMNNSV AVKQADVILS TYPLDYTKNY TTSAALNDLD    660
YYALKQSPDG PGMTYAIFSI VANDVSPSGC SAYTYAQYSY DPYIRGPFFQ FSEQLLDDYT    720
ANGGTHPAFP FLTGHGGANQ VVLYGYLGLR LVPDDKLHID PNLPPQIPSV KYRTFYWRGW    780
PIQAASNYTH TTIQRATRVA PLSTADMTYA NKSISVQVGQ NTANSTTYSL PVNGSALVIS    840
NRQIGSINTV QGNIAQCKSV QSMNGYQPGQ YPISAVDGAA STKWQPEFAA NVSSLTVDLT    900
SSNASSVSGF YFDWAQAPPV NVTVVLHNST SASLTSSAAQ NGSSTVSLNI TISNPYNASS    960
YDANVIELSS SNTTNYRFPA PVPKPRYATL FVQGSQALDE TDMKAGNGTG ATVAEWAILS   1020

SEQ ID NO: 222          moltype = AA   length = 1016
FEATURE                 Location/Qualifiers
source                  1..1016
                        mol_type = protein
                        organism = Talaromyces pinophilus
SEQUENCE: 222
LPFNERVDQV LRSYSPKNLE SRSTKHGNSY QTQFSGVTWD QRNWRLQSTV LDQGHYESRG     60
SIANGYIGLN VAGAGPFFEL DTAVDGDVIN GWPLFSRRQT FAGLAGFYDL QPTTNGSNFP    120
WLSQYGDDSA ISGVPHWGGL ILDLGDGEYL DATVDNSTIS DYTTTYDYKA GVLSWDYKWT    180
PKNSKASFGI NYKIFANKLD VNQAVVQLSI TPSANGSGSV VNVIDGYSAV RTDFVSSGNE    240
SDVIYTAVKP VGVNNVTAWI YAALDGDEAF DFSSAELVND KPYVHQNDSS IAQSVNVAFT    300
AGTTITINKF VGAASTDAFP DPQSTAREAA MTARRRGFDD LFRSHVSEWA QVMPDDSVDD    360
FTLANGTLPN DTFIIESAVM AVVNPYYLLQ NTVGANALRR VNNAPVNDWS IPVGGLTSDS    420
YAGQIFWDAD VWMQPGLVAA FPESAKRITN YRTAKYSQAI ENAKTAYTSS QNQTSFSSDA    480
AIYSWTSGRY GNCTATGPCW DYEYHLNGDI GISLVNQWVV SGDNETFKNT HFPIYNSIAT    540
LYGDLLKKNG SYYTLNMTD PDEYANNVDA GGYTMTLISQ TLSNANAFRK QFGMDENTTW    600
TEMADNILLI RENDVTLEYT TMNNSVAVKQ ADVILSTFPL DYTKNYTTSA ALNDLDYYAL    660
KQSPDGPGMT YAIFSIVAND VSPSGCSAYT YAQYSYDPYI RGPFFQFSEQ LLDDYTANGG    720
THPAFPFLTG HGGANQVVLY GYLGLRLLPD DMLHIDPNLP PQIPSVKYRT FYWRGWPIQA    780
ASNYTHTTIQ RATSVAPLST ADPAYANTSI SVSVGQNTAN STTYSLPVNG SAIVVPNRQI    840
GSINTVAGNI AQCSVSLSTD AYQPGQYPIS AVDGAASTKW QPEFAANVSS LTVDLTSSNA    900
SSVSGFYFDW AQAPPPTNITV LLHNSSSAAL TSSSTHGGSS SVSLNITISN PYDASSYDAN    960
VIALSSSNTT NYTFSAPVAK PRYATLFVQG NQALDETDTK AGNGTGATVA EWAILS       1016

SEQ ID NO: 223          moltype = AA   length = 1069
FEATURE                 Location/Qualifiers
source                  1..1069
                        mol_type = protein
                        organism = Talaromyces leycettanus
SEQUENCE: 223
TSANARINRC VKKHAGGKTP SGPSNNTYQT RFPGVTWDQD NWCLSTTTLD QGHYESRGSV     60
ANGYLGINVA SVGPFFEFDT PVDGDVINGW PLFDRRMSFA TISGFWDQQP TTNGSNFPWL    120
YQYGGESVIS GVPHWSGLIL DLGDNTYLDA TVDSRTISGF STTYDFKSGV LSWSYQWTPA    180
GNMGSYNITY RLFAHKLYVN QAVVDMEVVS STEAKATVVN VIDGSAVRT DFVESGQDDG    240
AIYTAVRPWG IANVTAYIYA NITGSDNVDM RSRALVTNKP YVNGNASSIT QAVNVHFPTG    300
KSVRITKFVG GASSDAFSNP QQIAKQCACST AQANGYVKSL RSHVAEWASV MPDDSVDDFT    360
FPSNGTLPAD EYIIESQIIS VANTYYLLQN TVGKNAINAS SSTELNKDSI AVGGLTSESY    420
AGMIFWDADV WMQPGLVASH PEAAQRITNY RVAKYPQAKA NVATAYQSSK NQTNFSPDAA    480
VYSWTSARYG NCTATGPCWD YEYHLNGDIG LSIINQYVAS GDTQTFKEKL FPVFDSVATL    540
YSNIVQKNGS SWTLTNMTDP DEYANQVDAG GYTMPLIAQT LLYANSFRQQ FGLETNDTWN    600
EIAQDVLVIR ENGVTLEFTT MNGSAVVKQA DVVLDTYPLG YTHNYGPTDA LNDLDYYANR    660
QSPDGPAMTW AIFSVVANQI SPSGCSAYTY AQYAFSPYAR APFYQLSEQL IDDASLNGGT    720
HPAYPPFLTGH GGALQVNLFG YLGFRYLPDN VIHIDPNLPP QIPHITYRTF YWRGWPITAA    780
STYTHTTLSR AWNVSSLDSA DPKFANASIP VHVGLESNVT VYRLPVNGTL TVPNRMVGSK    840
NTLAGNMVQC RPVQSMDGYQ PGQFPISVVD GASSTKWQPL YSANVSSVTV TLSSSAVGKS    900
VNGFYFDWAQ NPPVNAAVVF HNSSFAQNPA TTFSFDNPSA SGNLYSVVSV LKDIQLSDPY    960
DPATTDLDVI AIPKGNTTNV TLSSPVPAAR YATLFIQGNQ ANSPAEVAAK NGTGATVAEW   1020
AILGQEVQNN GYGDQIEARR LDVRGAAALS GMGSFTQRRK RKMILPRFD              1069

SEQ ID NO: 224          moltype = AA   length = 1016
FEATURE                 Location/Qualifiers
source                  1..1016
                        mol_type = protein
                        organism = Talaromyces variabilis
SEQUENCE: 224
ALSPGARVNQ VLRAHNSLPP SLTDNSTGSS YKTRFDGVTW DQRNWRLQSR VLDQGHYEAR     60
GSVANGYIGI NVASAGPFFE LDTPVDGDVI NGWPLFSRRQ TFAGLAGFYD LQPTTNSTNY    120
GWLNQYGDES VISGIPHWAG LVLDLGNGDY LDATVDNSTI SDYTTTYDYK AGILSWDYKW    180
TPRQNSSSFR ISYQLFANKL DINQAVVKLS ITPSKSGNAS VVNVIDGYSA VRTDFVKSGS    240
DGNAIYTAVS PVGVSNVTAW VYAVLDGDKA FDLSSPSRVT GKPYIHQNES SIAQAVNVEF    300
SAGKTVTIAK FVGAASTDAF SNPQKKAKTA ALDGKKKGFE DLLRSHVSEW AQVMPDDSVD    360
DFTLANGTLP DDSFIIEQAV TAVVNPYYLL QNTVGKNALQ RVNNAPVNDW SIPVGGLSSD    420
SYAGMIFWDA DVWMQPGLVA AFPESAKRIT NYRAAKYQQA IANVKTAYSS SQNETVFSPN    480
AAIFPWTSGR YGNCTGTGPC WDYEYHLNGD IAISLVNQWV VSGDTETFQN EHFPIYNSIA    540
TVYGDLLKKN GSYYTLTNMT DPDEYANNKD AGGYTMPLIA NTLIKANEFR RQFGMAENAT    600
WNEMAENVLI IRENDVTLEY TTMNNSVAVK QADVVLRTFP LDYTNYSSA AALNDLDYYA    660
LKQSPDGPGM TYAIFSIVAN EVSPSGCSAY TYAQYSYDPY ARAPFFQLSE QLIDDYTTNG    720
GTHPAYPFLT GHGGANQVVL YGYLGLRVLA DEILHIDPNL PPQIPQVTYR TFYWRGWPIQ    780
AASNYTHTTI HRATTVAPLD SAEKKYAKSA ISVQVGQQAN STTYKLPADG TPLTVANRKV    840
GSTNTIKGNI AQCQSVQSVD SYQPGQYALA AVDGAASTKW QPEFAANVSS LTVSIPSGKT    900
SVSGFYFDWA QAPPSNATVV FHNNSVSNPT FSSFGSRKGA RITHIDVKLS NPYNASSNAD    960
```

```
AIVIPSGNTT NFTFSNPVPA PRFATLFVQG NQGLDKVDVQ NGNGTGATVA EWAILE              1016

SEQ ID NO: 225            moltype = AA   length = 1050
FEATURE                   Location/Qualifiers
source                    1..1050
                          mol_type = protein
                          organism = Aspergillus niger
SEQUENCE: 225
LPGKNARISA SLKRHAGRDV PQTALNSTNV YQTKFSGVTW DEDHWLLTTT TPDQGHYQSR            60
GSVANGYLGI NVANIGPFFE LDEPVNGDVI NGWPLYSRRQ SFATISGFWD RQAHTNGSNF           120
PWLSQYGDDS VISGVPHWSG LILDLGDDTY LDATVDNRTI SNFKSTYDFK SGVLSWSYTW           180
TPQGNKGSYA ITYRLFAHKL YVNRAVVDME ITPLTNGNAT VVNVLDGYAA VRTDFVASGQ           240
EEGAIFSAVR PWGVNNVTAY VYATLDGSDS VDLSSRRIVT DKPYVSTNSS SVAQAVDVMF           300
TANETVRITK FVGGATTDYF LATQETAKAA CLAGLADGYV KSLQSHVGEW ATIMHDHSVD           360
RFTDPATGKL PEDSHIVDSA IIAVTNTYYL LQNTAGTNAI VAAGGIPVNV DSCAPGGLTS           420
DSYGGQIFWD ADLWMQPGLV ASHPESAQRF TNYRIALHYQ AQANIETAFT GSKNQTSFSS           480
SAAIYPWTSG RFGNCTATGP CWDYQYHLNG DIGLAMINQW VASGDTAWFK NYLFPIYDAA           540
ATLYSELVER NGSSWTLTNM TDPDEYANSI NAGGYTMPLI AETLQNANKL RKQFGLEPNE           600
TWDEIAEDVL ILRENGVTLE YTSMNGSAVV KQADIVLNTF PLTYESDNYT ATNSLTDLDY           660
YANKQSADGP AMTYAIFAIV ASDVSPSGCS AFTYHQYSYA PYARGPWYQL SEQMIDDASI           720
NGGTHPAFPF LTGHGGANQV ALYGYLGLRL HPDDTIYIDP NLPPQIPHIT YRTFYWHGWP           780
ISAWSNYTHT TIQRDSSLAP LASADLLFSN VSIKVQVGQS TASADEATIY YLPLSGALTV           840
PNRMIGSVNT TPGNQVQCHP VYSPDAYEPG QFPISAVDGA TSTKWQPSTS DLTSLTVTLS           900
TTAEAGAEEV SGFYFDWSQA PPENLTVIFH DSPIGNPSTV FAAAGSNSTG YRVITSMSNI           960
VQSKPYNAIS AEELNVVSIP TANTTTITLD APVQKARYAT LLIAGNQANE TAGATVAEWV          1020
ILGQNSTSSS SAQAKRKMSA RSKATLAQLS                                          1050

SEQ ID NO: 226            moltype = AA   length = 1056
FEATURE                   Location/Qualifiers
source                    1..1056
                          mol_type = protein
                          organism = Trichoderma reesei
SEQUENCE: 226
TTLVDRVTKC LSRHDGSDAE SHFSKNVYKT DFAGVTWDED NWLLSTTQLK QGAFEARGSV            60
ANGYLGINVA SVGPFFEVDT EEDGDVISGW PLFSRRQSFA TVAGFWDAQP QMNGTNFPWL           120
SQYGSDTAIS GIPHWSGLVL DLGGGTYLDA TVSNKTISHF RSTYDKAGV LSWSYKWTPK            180
GNKGSFDISY RLFANKLHVN QAVVDMQVTA SKNVQASIVN VLDGFAAVRT DFVESGEDGS           240
AIFAAVRPNG VANVTAYVYA DITGSGGVNL SSRKIVHNKP YVHANASSIA QAVPVKFAAG           300
RTVRVTKFVG AASSDAFKNP KQVAKKAAAA GLSNGYTKSL KAHVEEWATV MPESSVDSFA           360
DPKTGKLPAD SHIVDSAIIA VTNTYYLLQN TVGKNGIKAV DGAPVNVDSI SVGGLTSDSY           420
AGQIFWDADL WMQPGLVAAH PEAAERITNY RLARYGQAKE NVKTAYAGSQ NETFFSASAA           480
VFPWTSGRYG NCTATGPCWD YEYHLNGDIG ISLVNQWVYN GDTKDFEKNL FPVYDSVAQL           540
YGNLLRPNKT SWTLTNMTDP DEYANHVDAG GYTMPLIAET LQKANSFRQQ FGIEQNKTWN           600
DMASNVLVLR ENGVTLEFTA MNGTAVVKQA DVIMLTYPLS YGTNYSAQDA LNDLDYYANK           660
QSPDGPAMTY AFFSIVANEI SPSGCSAYTY AQNAFKPYVR APFYQISEQL IDDASVNGGT           720
HPAYPFLTGH GGAHQVVLFG YLGLRLVPDD VIHIEPNLPP QIPYLRYRTF YWRGWPISAW           780
SNYTHTTLSR AAGVAALEGA DQRFARKPIT IHAGPEQDPT AYRLPVKGSV VIPNKQIGSQ           840
QTYAGNLVQC HAASSPNDYV PGQFPIAAVD GATSTKWQPA SADKVSSITV SLDKEDVGSL           900
VSGFHFDWAQ APPVNATVIF HDEALADPAT ALASAHKHNS KYTTVTSLTN IELSDPYVST           960
KDLNAIAIPI GNTTNVTLSH PVAASRYASL LIVGNQGLDP VDVKAKNGTG ATVAEWAIFG          1020
HGKEHSGKPS SHSKRRLNVR TAATLSNPRS FMRRRL                                   1056

SEQ ID NO: 227            moltype = AA   length = 19
FEATURE                   Location/Qualifiers
source                    1..19
                          mol_type = protein
                          organism = Saccharomyces cerevisiae
SEQUENCE: 227
MLSLKTLLCT LLTVSSVLA                                                        19

SEQ ID NO: 228            moltype = DNA   length = 185
FEATURE                   Location/Qualifiers
source                    1..185
                          mol_type = genomic DNA
                          organism = Saccharomyces cerevisiae
SEQUENCE: 228
agtgctttta actaagaatt attagtcttt tctgcttatt ttttcatcat agtttagaac            60
actttatatt aacgaatagt ttatgaatct atttaggttt aaaaattgat acagttttat           120
aagttacttt ttcaaagact cgtgctgtct attgcataat gcactggaag gggaaaaaaa           180
aggtg                                                                      185

SEQ ID NO: 229            moltype = AA   length = 555
FEATURE                   Location/Qualifiers
source                    1..555
                          mol_type = protein
                          organism = Pycnoporus sanguineus glucoamylase
SEQUENCE: 229
QSSAVDAYVA SESPIAKQGV LNNIGPNGSK AHGAKAGIVV ASPSTENPDY LYTWTRDSSL            60
VFKLLIDQFT SGDDTSLRGL IDDFTSAEAI LQQVSNPSGT VSTGGLGEPK FNIDETAFTG           120
```

```
AWGRPQRDGP ALRATSIIRY ANWLLDNGNT TYVSNTLWPV IQLDLDYVAD NWNQSTFDLW    180
EEVDSSSFFT TAVQHRALRE GATFASRIGQ SSVVSGYTTQ ADNLLCFLQS YWNPSGGYVT    240
ANTGGGRSGK DSNTVLTSIH TFDPAAGCDA ATFQPCSDKA LSNLKVYVDA FRSIYTINNG    300
IASNAAVATG RYPEDSYMGG NPWYLTTSAV AEQLYDALYV WDQLGGLNVT STSLAFFQQF    360
ASGLSTGTYS ASSSTYATLT SAIRSFADGF LAINAKYTPA DGGLAEQYSR NDGTPLSAVD    420
LTWSYAAALT AFAAREGKTY GSWGAAGLTV PASCSGGGGA TVAVTFNVQA TTVFGENIYI    480
TGSVAALQNW SPDNALILSA ANYPTWSITV NLPANTVVQY KYIRKFNGQV TWESDPNNQI    540
TTPSGGSFTQ NDVWR                                                    555

SEQ ID NO: 230          moltype = AA  length = 599
FEATURE                 Location/Qualifiers
source                  1..599
                        mol_type = protein
                        organism = Trichoderma reesei
SEQUENCE: 230
SVDDFISTET PIALNNLLCN VGPDGCRAFG TSAGAVIASP STIDPDYYYM WTRDSALVFK    60
NLIDRFTETY DAGLQRRIEQ YITAQVTLQG LSNPSGSLAD GSGLGEPKFE LTLKPFTGNW    120
GRPQRDGPAL RAIALIGYSK WLINNNYQST VSNVIWPIVR NDLNYVAQYW NQTGFDLWEE    180
VNGSSFFTVA NQHRALVEGA TLAATLGQSG SAYSSVAPQV LCFLQRFWVS SGGYVDSNIN    240
TNEGRTGKDV NSVLTSIHTF DPNLGCDAGT FQPCSDKALS NLKVVVDSFR SIYGVNKGIP    300
AGAAVAIGRY AEDVYYNGNP WYLATFAAAE QLYDAIYVWK KTGSITVTAT SLAFFQELVP    360
GVTAGTYSSS SSTFTNIINA VSTYADGFLS EAAKYVPADG SLAEQFDRNS GTPLSAVHLT    420
WSYASFLTAA ARRAGIVPPS WANSSASTIP STCSGASVVG SYSRPTATSF PPSQTPKPGV    480
PSGTPYTPLP CATPTSVAVT FHELVSTQFG HTVKVAGNAA ALGNWSTSAA VALDAVNYRD    540
NHPLWIGTVN LEAGDVVEYK YIIVGQDGSV TWESDPNHTY TVPAVACVTQ VVKEDTWQS     599

SEQ ID NO: 231          moltype = AA  length = 633
FEATURE                 Location/Qualifiers
source                  1..633
                        mol_type = protein
                        organism = Bacillus amyloliquefaciens
SEQUENCE: 231
GPAAANAETA NKSNKVTASS VKNGTILHAW NWSFNTLTQN MKDIRDAGYA AIQTSPINQV    60
KEGNQGDKSM RNWYWLYQPT SYQIGNRYLG TEQEFKDMCA AAEKYGVKVI VDAVINHTTS    120
DYGAISDEIK RIPNWTHGNT QIKNWSDRWD VTQNSLLGLY DWNTQNTEVQ VYLKRFLERA    180
LNDGADGFRY DAAKHIELPD DGNYGSQFWP NITNTSAEFQ YGEILQDSAS RDTAYANYMN    240
VTASNYGHSI RSALKNRNLS VSNISHYASD VSADKLVTWV ESHDTYANDD EESTWMSDDD    300
IRLGWAVIGS RSGSTPLFFS RPEGGGNGVR FPGKSQIGDR GSALFKDQAI TAVNTFHNVM    360
AGQPEELSNP NGNNQVFMNQ RGSKGVVLAN AGSSSVTINT SAKLPDGRYD NRAGAGSFQV    420
ANGKLTGTIN ARSAAVLYPD DIGNAPHVFL ENYQTGAVHS FNDQLTVTLR ANAKTTKAVY    480
QINNGQQTAF KDGDRLTIGK GDPIGTTYNI KLTGTNGEGA ARTQEYTFVK KDPSQTNIIG    540
YQNPDHWGQV NAYIYKHDGG RAIELTGSWP GKAMTKNANG MYTLTLPENT DTANAKVIFN    600
NGSAQVPGQN QPGFDYVQNG LYNNSGLNGY LPH                                633

SEQ ID NO: 232          moltype = DNA  length = 700
FEATURE                 Location/Qualifiers
source                  1..700
                        mol_type = genomic DNA
                        organism = Saccharomyces cerevisiae
SEQUENCE: 232
cacccatgaa ccacacggtt agtccaaaag gggcagttca gattccagat gcgggaatta    60
gcttgctgcc accctcacct cactaacgct gcggtgtgcg gatacttcat gctatttata    120
gacgcgcgtg tcggaatcag cacgcgcaag aaccaaatgg gaaaatcgga atgggtccag    180
aactgctttg agtgctggct attggcgtct gatttccgtt ttgggaatcc tttgccgcgc    240
gccctctca aaactccgca caagtcccag aaagcgggca agaaataaaa cgccaccaaa    300
aaaaaaaaaa taaaagccaa tcctcgaagc gtgggtggta ggccctggat tatcccgtac    360
aagtatttct caggagtaaa aaaaccgttt gttttggaat ttcccatttc gcggccacct    420
acgccgctat ctttgcaaca actatctgcg ataactcagc aaattttgca tattcgtgtt    480
gcagtattgc gataatggga gtcttacttc caacataacg gcagaaagaa atgtgagaaa    540
attttgcatc ctttgcctcc gttcaagtat ataaagtcgg catgcttgat aatctttctt    600
tccatcctac attgttctaa ttattcttat tctcctttat tctttcctaa cataccaaga    660
aattaatctt ctgtcattcg cttaaacact atatcaataa                         700

SEQ ID NO: 233          moltype = DNA  length = 240
FEATURE                 Location/Qualifiers
source                  1..240
                        mol_type = genomic DNA
                        organism = Saccharomyces cerevisiae
SEQUENCE: 233
tcagtactga caataaaaag attcttgttt tcaagaactt gtcatttgta tagttttttt    60
atattgtagt tgttctattt taatcaaatg ttagcgtgat ttatatttt tttgccctcg    120
acatcatctg cccagatgcg aagttaagtg cgcagaaagt aatatcatgc gtcaatcgta    180
tgtgaatgct ggtcgctata ctgctgtcga ttcgatacta acgccgccat ccagtgtcga    240

SEQ ID NO: 234          moltype = AA  length = 18
FEATURE                 Location/Qualifiers
source                  1..18
                        mol_type = protein
                        organism = Saccharomyces cerevisiae
```

```
SEQUENCE: 234
MQLLRCFSIF SVIASVLA                                                       18

SEQ ID NO: 235          moltype = DNA  length = 47
FEATURE                 Location/Qualifiers
misc_feature            1..47
                        note = ARTIFICIAL DNA PRIMER
source                  1..47
                        mol_type = other DNA
                        organism = synthetic construct
SEQUENCE: 235
atgatgaaaa aataagcaga aaagactaat aattcttagt taaaagc                       47

SEQ ID NO: 236          moltype = DNA  length = 26
FEATURE                 Location/Qualifiers
misc_feature            1..26
                        note = ARTIFICIAL DNA PRIMER
source                  1..26
                        mol_type = other DNA
                        organism = synthetic construct
SEQUENCE: 236
atgctttcgc ttaaaacgtt actgtg                                              26
```